United States Patent
Tong et al.

(10) Patent No.: US 12,359,068 B2
(45) Date of Patent: Jul. 15, 2025

(54) RHODAMINE FLUORESCENT COMPOUNDS AND PRODUCTION METHODS THEREOF

(71) Applicant: Singular Genomics Systems, Inc., San Diego, CA (US)

(72) Inventors: Ada Tong, San Diego, CA (US); Megha Cila, San Diego, CA (US); Ronald Graham, Carlsbad, CA (US)

(73) Assignee: Singular Genomics Systems, Inc., San Diego, CA (US)

(*) Notice: Subject to any disclaimer, the term of this patent is extended or adjusted under 35 U.S.C. 154(b) by 0 days.

(21) Appl. No.: 18/435,635

(22) Filed: Feb. 7, 2024

(65) Prior Publication Data
US 2024/0294764 A1    Sep. 5, 2024

Related U.S. Application Data

(60) Provisional application No. 63/444,848, filed on Feb. 10, 2023.

(51) Int. Cl.
  *C09B 11/24*    (2006.01)
  *A61K 49/00*    (2006.01)
  *C07H 19/20*    (2006.01)
  *C12Q 1/6869*   (2018.01)

(52) U.S. Cl.
  CPC ......... *C09B 11/24* (2013.01); *A61K 49/0041* (2013.01); *A61K 49/0054* (2013.01); *C07H 19/20* (2013.01); *C12Q 1/6869* (2013.01)

(58) Field of Classification Search
  CPC . C09B 11/24; A61K 49/0041; A61K 49/0054; C07H 19/20; C12Q 1/6869
  USPC ............................................................. 8/648
  See application file for complete search history.

(56) References Cited

U.S. PATENT DOCUMENTS

| | | | |
|---|---|---|---|
| 4,622,400 A | 11/1986 | Hammond | |
| 5,034,506 A | 7/1991 | Summerton et al. | |
| 5,235,033 A | 8/1993 | Summerton et al. | |
| 5,268,486 A | 12/1993 | Waggoner et al. | |
| 5,686,261 A | 11/1997 | Zhang et al. | |
| 5,728,529 A | 3/1998 | Metzker et al. | |
| 6,130,101 A * | 10/2000 | Mao | C09B 11/08 544/70 |
| 6,191,278 B1 * | 2/2001 | Lee | C07H 19/207 546/41 |
| 6,372,907 B1 * | 4/2002 | Lee | C07D 491/04 546/41 |
| 6,605,434 B1 * | 8/2003 | Ferrie | C12Q 1/6806 204/461 |
| 6,664,079 B2 | 12/2003 | Ju et al. | |

(Continued)

FOREIGN PATENT DOCUMENTS

CN     105263918 A  *  1/2016  ............ C09B 11/24
EP     3461815 A1      4/2019

(Continued)

OTHER PUBLICATIONS

STIC Search Report dated Mar. 4, 2025.*

(Continued)

*Primary Examiner* — Eisa B Elhilo
(74) *Attorney, Agent, or Firm* — Mintz, Levin, Cohn, Ferris, Glovsky and Popeo, P.C.; Zachary Terranova

(57) ABSTRACT

Disclosed herein, inter alia, are fluorescent compounds and methods of making and using thereof.

20 Claims, 1 Drawing Sheet

(56) References Cited

U.S. PATENT DOCUMENTS

| | | | |
|---|---|---|---|
| 8,754,244 B1* | 6/2014 | Romanov | C12Q 1/6869 |
| | | | 549/381 |
| 9,139,868 B2 | 9/2015 | Zhou et al. | |
| 9,649,389 B2 | 5/2017 | Groves et al. | |
| 9,714,260 B2 | 7/2017 | Nagano et al. | |
| 9,933,417 B2* | 4/2018 | Lavis | C07D 401/14 |
| 10,087,199 B2 | 10/2018 | Erdmann et al. | |
| 10,564,164 B2 | 2/2020 | Majima et al. | |
| 10,738,072 B1 | 8/2020 | Graham et al. | |
| 11,697,736 B2 | 7/2023 | Graham et al. | |
| 2002/0058272 A1* | 5/2002 | Lee | C07H 21/00 |
| | | | 435/6.12 |
| 2004/0096825 A1 | 5/2004 | Chenna et al. | |
| 2010/0009353 A1* | 1/2010 | Barnes | C09B 11/24 |
| | | | 435/6.12 |
| 2014/0272990 A1 | 9/2014 | Zhou et al. | |
| 2014/0342384 A1 | 11/2014 | Nagano et al. | |
| 2015/0353585 A1 | 12/2015 | Nagano et al. | |
| 2016/0115180 A1 | 4/2016 | Erdmann et al. | |
| 2017/0363636 A1 | 12/2017 | Majima et al. | |
| 2019/0100653 A1* | 4/2019 | Kemnitzer | C09B 5/42 |
| 2019/0352508 A1 | 11/2019 | Graham et al. | |
| 2022/0332752 A2 | 10/2022 | Graham et al. | |
| 2023/0295437 A1 | 9/2023 | Graham et al. | |

FOREIGN PATENT DOCUMENTS

| | | | |
|---|---|---|---|
| WO | WO 0132783 A1 * | 5/2001 | C09B 11/24 |
| WO | WO-2006/132588 A1 | 12/2006 | |
| WO | WO-2009/108905 A2 | 9/2009 | |
| WO | WO 2011123820 A2 * | 10/2011 | C09B 11/24 |
| WO | WO-2016/061555 A2 | 4/2016 | |
| WO | WO-2019/222653 A1 | 11/2019 | |
| WO | WO-2020/132487 A1 | 6/2020 | |

OTHER PUBLICATIONS

Bentley, D. R. et al. (Nov. 6, 2008). "Accurate whole human genome sequencing using reversible terminator chemistry," *Nature* 456(7218): 53-59.

Berlier, J. E. et al. (Dec. 2003). "Quantitative comparison of long-wavelength Alexa Fluor dyes to Cy dyes: fluorescence of the dyes and their bioconjugates," *J Histochem Cytochem* 51 (12): 1699-1712.

Best, Q. A., et al. (Jan. 15, 2016, e-published Nov. 25, 2016). "Environmentally robust rhodamine reporters for probe-based cellular detection of the cancer-linked oxidoreductase hNQO1," *ACS Chemical Biology* 11(1): 231-240.

Birtalan, E. et al. (Mar. 1, 2011). "Investigating rhodamine B-labeled peptides: Scopes and limitations of its applications," *Peptide Science* 96(5): 694-701.

Brauch, S. et al. (Oct. 25, 2011). "Fast and efficient MCR-based synthesis of clickable rhodamine tags for protein profiling," *Organic & biomolecular chemistry* 10(5): 958-965.

Chevalier, A. et al. (Jan. 2015, e-published Nov. 5, 2014). "Rapid Synthesis of Unsymmetrical Sulforhodamines Through Nucleophilic Amination of a Monobrominated Sulfoxanthene Dye," *European Journal of Organic Chemistry* 2015(1): 152.

Extended European Search Report mailed on Jan. 31, 2022, for EP Patent Application No. EP19803002.5, 9 pages.

Goldstein, S. W. et al. (Sep. 12, 2017, e-published Jul. 28, 2017). "Nucleophilic aromatic substitution-addition and identification of an amine," *J Chem Educ* 94(9): 1388-1390.

Grimm, J. B. et al. (Sep. 27, 2017, e-published Aug. 9, 2017). "General Synthetic Method for Si-Fluoresceins and Si-Rhodamines," *ACS Cent Sci* 3(9): 975-985.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27): 9145-9150.

Hutter, D. et al. (Nov. 2010, e-published Dec. 1, 2010). "Labeled nucleoside triphosphates with reversibly terminating aminoalkoxyl groups," *Nucleosides Nucleotides Nucleic Acids* 29(11): 879-895.

International Search Report and Written Opinion mailed on Oct. 24, 2019, for PCT Application No. PCT/US2019/032907, filed May 17, 2019, 9 pages.

Jadhav, A. G. et al. (Mar. 2017, e-published Nov. 19, 2016). "Red emitting triphenylamine based rhodamine analogous with enhanced Stokes shift and viscosity sensitive emission," *Dyes and Pigments* 138: 56.

Ju, J. et al. (Dec. 26, 2006, e-published Dec. 14, 2006). "Four-color DNA sequencing by synthesis using cleavable fluorescent nucleotide reversible terminators," *PNAS USA* 103(52): 19635-19640.

Kim, T. G. et al. (Jan. 1, 2006, e-published Dec. 7, 2005). "Correlations of structure and rates of energy transfer for through-bond energy-transfer cassettes," *The Journal of Physical Chemistry A* 110(1): 20-27.

Koide, Y. et al. (Mar. 21, 2012, e-published Mar. 7, 2012). "Development of NIR fluorescent dyes based on Si-rhodamine for in vivo imaging," *Journal of the American Chemical Society* 134(11): 5029-5031.

Kolmakov, K. et al. (Sep. 14, 2015, e-published Aug. 13, 2015) "Far-Red Emitting Fluorescent Dyes for Optical Nanoscopy: Fluorinated Silicon-Rhodamines (SiRF Dyes) and Phosphorylated Oxazines," *Chemistry—A European Journal* 21(38): 13344-13356.

Kvach, M. V. et al. (Aug. 19, 2009, e-published Jul. 16, 2009). "Practical synthesis of isomerically pure 5-and 6-carboxytetramethylrhodamines, useful dyes for DNA probes," *Bioconjugate chemistry* 20(8): 1673-1682.

Leicher, T. et al. (Dec. 25, 1998). "Coexpression of the KCNA3B gene product with Kv1.5 leads to a novel A-type potassium channel," *J Biol Chem* 273(52): 35095-35101.

Li, M. et al. (Jan. 16, 2020). "Asymmetric Si-rhodamine scaffolds: rational design of pH- durable protease-activated NIR probes in vivo," *Chemical Communications* 56(16): 2455-2458.

Lin, Z. et al. (Aug. 28, 2019), "Photoswitchable ultrahigh-brightness red fluorescent polymeric nanoparticles for information encryption, anti-counterfeiting and bioimaging," *Journal of Materials Chemistry C* 7(37): 11515-11521.

Marcaccini, S. et al. (Mar. 2007, e-published Mar. 22, 2007). "The use of the Ugi four-component condensation," *Nature Protocols* 2(3): 632-639.

Mathews, A. S. et al. (Aug. 9, 2016). "Photo-cleavable nucleotides for primer free enzyme mediated DNA synthesis," *Organic & Biomolecular Chemistry* 14(35): 8278-8288.

Needleman, S. B. et al. (Mar. 28, 1970, e-published Oct. 28, 2004). "A general method applicable to the search for similarities in the amino acid sequence of two proteins," *J Mol Biol* 48(3): 443-453.

Pearson, W. R. et al. (Apr. 1, 1988). "Improved tools for biological sequence comparison," *PNAS USA* 85(8): 2444-2448.

Randolph, J. B. et al. (Jul. 1, 1997). "Stability, specificity and fluorescence brightness of multiply-labeled fluorescent DNA probes," *Nucleic Acids Res* 25(14): 2923-2929.

Rosenblum, B.B. et al. (Nov. 1, 1997). "New dye-labeled terminators for improved DNA sequencing patterns," *Nucleic Acids Res* 25(22): 4500-4504.

Ruparel, H. et al. (Apr. 26, 2005, e-published Apr. 13, 2005). "Design and synthesis of a 3'-0-allyl photocleavable fluorescent nucleotide as a reversible terminator for DNA sequencing by synthesis," *PNAS USA* 102(17): 5932-5937.

Shen, S. et al. (Feb. 9, 2017). "Near-infrared probes based on fluorinated Si-rhodamine for live cell imaging," *RSC advances* 7(18): 10922-10927.

Smith T. F. et al. (Dec. 1981, e-published Sep. 3, 2004). "Comparison of biosequences," *Adv Appl Math* 2(4): 482-489.

Szepesi Kovács, D. et al. (Jun. 27, 2023, e-published Jun. 14, 2023). "Synthesis and Application of Two-Photon Active Fluorescent Rhodol Dyes for Antibody Conjugation and In Vitro Cell Imaging," *ACS omega* 8(25): 22836-22843.

Wu, J. et al. (Oct. 16, 2007, e-published Oct. 8, 2007). "3'-O-modified nucleotides as reversible terminators for pyrosequencing," *PNAS USA* 104(42): 16462-16467.

(56) References Cited

OTHER PUBLICATIONS

Xu, H. et al. (May 19, 2016). "Cellular thermal shift and clickable chemical probe assays for the determination of drug-target engagement in live cells," *Organic & Biomolecular Chemistry* 14(26): 6179-6183.

Zhu, Z. et al. (Aug. 25, 1994). "Directly labeled DNA probes using fluorescent nucleotides with different length linkers," *Nucleic Acids Res* 22(16): 3418-3422.

* cited by examiner

RHODAMINE FLUORESCENT COMPOUNDS AND PRODUCTION METHODS THEREOF

CROSS-REFERENCES TO RELATED APPLICATIONS

This application claims the benefit of U.S. Provisional Application No. 63/444,848, filed Feb. 10, 2023, which is incorporated herein by reference in its entirety and for all purposes.

BACKGROUND

Rhodamine dyes are a group of fluorescent compounds that are used extensively in a wide range of applications, such as in fluorescence microscopy, flow cytometry, and in DNA sequencing. The synthesis of rhodamine dyes is a challenging process, as they are highly reactive compounds and require special conditions and techniques to produce. This makes them costly to produce, and efforts have been made to find ways to make them more cost effective. Disclosed herein, inter alia, are solutions to these and other problems in the art.

BRIEF SUMMARY

In an aspect is provided a method of making a compound, or salt thereof, of formula I,

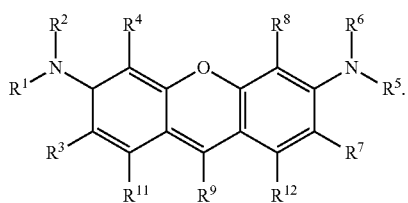

(I)

In embodiments, the method includes mixing compound A and compound B together in a reaction vessel at a first temperature to form a dye-intermediate, and adding oleum to the reaction vessel at a second temperature, wherein compound A has the formula:

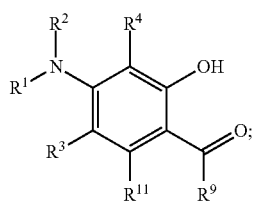

(A)

and compound B has the formula:

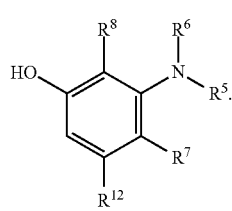

(B)

$R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, at least one of $R^1$, $R^2$, $R^5$, or $R^6$ is hydrogen (e.g., wherein $R^1$, $R^2$, $R^5$, or $R^6$ is hydrogen). $R^1$ and $R^2$ substituents bonded to the same nitrogen atom may optionally be joined to form a substituted or unsubstituted heterocycloalkyl, or substituted or unsubstituted heteroaryl. $R^5$ and $R^6$ substituents bonded to the same nitrogen atom may optionally be joined to form a substituted or unsubstituted heterocycloalkyl, or substituted or unsubstituted heteroaryl. $R^2$ and $R^4$ substituents may optionally be joined to form a substituted or unsubstituted heterocycloalkyl, or substituted or unsubstituted heteroaryl. $R^1$ and $R^3$ substituents may optionally be joined to form a substituted or unsubstituted heterocycloalkyl, or substituted or unsubstituted heteroaryl. $R^6$ and $R^8$ substituents may optionally be joined to form a substituted or unsubstituted heterocycloalkyl, or substituted or unsubstituted heteroaryl. $R^5$ and $R^7$ substituents may optionally be joined to form a substituted or unsubstituted heterocycloalkyl, or substituted or unsubstituted heteroaryl. $R^3$, $R^4$, $R^7$, $R^8$, $R^{11}$, and $R^{12}$ are independently hydrogen, $-PO_3H$, "\*MERGEFORMAT\*MERGEFORMAT   $-PO_4H$, $-SO_2NH_2$, $-SO_3H$, $-SO_4H$, substituted or unsubstituted alkyl, or substituted or unsubstituted heteroalkyl; wherein $R^3$, $R^4$, $R^7$, or $R^8$ is $-SO_3H$ (e.g., at least one of the aforementioned substituents is $-SO_3H$). $R^9$ is substituted or unsubstituted aryl.

DETAILED DESCRIPTION

Figure 1A:
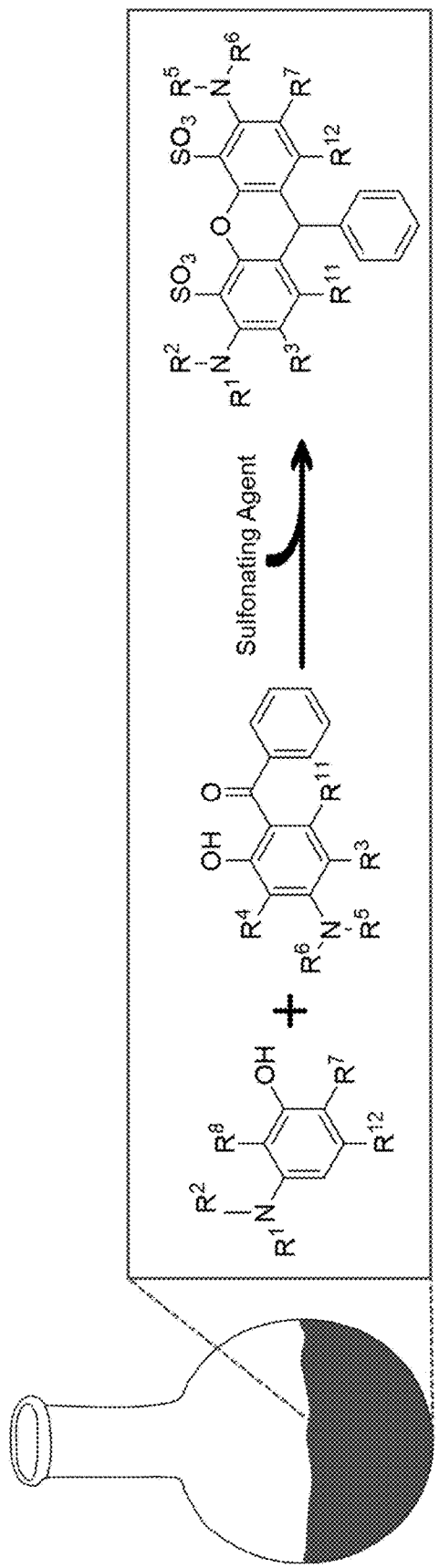
FIG. 1A shows a reaction scheme for generating an asymmetrical rhodamine compound as described herein. The scheme depicts a one-pot method using an aminophenol (e.g., Compound A) in the presence of a benzophenone substituted with hydroxyl and amine moieties (e.g., Compound B) and a sulfonating agent to provide an asymmetrical rhodamine with sulfonate moieties installed adjacent to the carbons bearing the amine moieties.

The aspects and embodiments described herein relate to fluorescent compounds and methods for making such compounds.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, "\*MERGEFORMAT\*MERGEFORMAT —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. An alkenylene includes one or more double bonds. An alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to:

"\*MERGEFORMAT\*MERGEFORMAT —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$,

"\*MERGEFORMAT\*MERGEFORMAT —$CH_2$—S—$CH_2$, —S(O)—$CH_3$, —$CH_2$—$CH_2$—S(O)$_2$—$CH_3$, —CH=CHO—$CH_3$, —Si($CH_3$)$_3$,

"\*MERGEFORMAT\*MERGEFORMAT —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as "\*MERGEFORMAT\*MERGEFORMAT —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, a bicyclic or multicyclic cycloalkenyl ring system refers to multiple rings fused together or multiple spirocyclic rings wherein at least one of the fused or spirocyclic rings is a cycloalkenyl ring and wherein the multiple rings are attached to the parent molecular moiety through any carbon atom contained within a cycloalkenyl ring of the multiple rings.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⌇⌇⌇" denotes the point of attachment of a chemical moiety to the remainder of a molecule or chemical formula.

The term "oxo," as used herein, means an oxygen that is double bonded to a carbon atom.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R',
"\*MERGEFORMAT\*MERGEFORMAT —C(O)R', —CO$_2$R', —CONR'R", —OC(O)NR'R", —NR"C(O)R', —NR'—C(O)NR"R'", —NR"C(O)$_2$R',
"\*MERGEFORMAT\*MERGEFORMAT —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R",
"\*MERGEFORMAT\*MERGEFORMAT —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', halogen,
"\*MERGEFORMAT\*MERGEFORMAT —SiR'R"R", —OC(O)R', —C(O)R', —CO$_2$R', —CONR'R", —OC(O)NR'R", —NR"C(O)R',
"\*MERGEFORMAT\*MERGEFORMAT —NR'—C(O)NR"R'", —NR"C(O)$_2$R', —NR—C(NR'R"R'")=NR"", —NR—C(NR'R")=NR'", —S(O)R',
"\*MERGEFORMAT\*MERGEFORMAT —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R",
"\*MERGEFORMAT\*MERGEFORMAT —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., C$_6$-C$_{10}$ aryl, C$_{10}$ aryl, or phenyl), heteroaryl (e.g., 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., C$_1$-C$_8$ alkyl, C$_1$-C$_6$ alkyl, or C$_1$-C$_4$ alkyl), heteroalkyl (e.g., 2 to 8 membered heteroalkyl, 2 to 6 membered heteroalkyl, or 2 to 4 membered heteroalkyl), cycloalkyl (e.g., C$_3$-C$_8$ cycloalkyl, C$_3$-C$_6$ cycloalkyl, or C$_5$-C$_6$ cycloalkyl), heterocycloalkyl (e.g., 3 to 8 membered heterocycloalkyl, 3 to 6 membered heterocycloalkyl, or 5 to 6 membered heterocycloalkyl), aryl (e.g., $C_6$-$C_{10}$ aryl, $C_{10}$ aryl, or phenyl), heteroaryl (e.g., 5 to 10 membered heteroaryl, 5 to 9 membered heteroaryl, or 5 to 6 membered heteroaryl), substituted with at least one substituent selected from: oxo, halogen, —CCl$_3$, —CBr$_3$, —CF$_3$, —CI$_3$, —CH$_2$Cl, —CH$_2$Br, —CH$_2$F, —CH$_2$I, —CHCl$_2$, —CHBr$_2$, —CHF$_2$, —CHI$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —PO$_3$H, —PO$_4$H, —N$_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound (e.g., nucleotide analogue) is a chemical species set forth in the Examples section, claims, embodiments, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Where a moiety is substituted (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene), the moiety is substituted with at least one substituent (e.g., a substituent group, a size-limited substituent group, or lower substituent group) and each substituent is optionally different. Additionally, where multiple substituents are present on a moiety, each substituent may be optionally different.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure. The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," "analogue" or "derivative" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{10}$ substituents are present, each $R^{10}$ substituent may be distinguished as $R^{10.1}$, $R^{10.2}$, $R^{10.3}$, $R^{10.4}$, etc., wherein each of $R^{10.1}$, $R^{10.2}$, $R^{10.3}$, $R^{10.4}$, etc. is defined within the scope of the definition of $R^{10}$ and optionally differently.

Descriptions of the compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art. The neutral forms of the compounds are preferably regenerated by contacting the salt with a base or acid and isolating the parent compound in the conventional manner. The parent form of the compound may differ from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Contacting" is used in accordance with its plain ordinary meaning and refers to the process of allowing at least two distinct species (e.g., chemical compounds including biomolecules or cells, or bioconjugate reactive moieties) to become sufficiently proximal to react, interact or physically touch. It should be appreciated, however, that the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound as described herein and a nucleotide, linker, protein, or enzyme.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Nucleic acid" or "oligonucleotide" or "polynucleotide" or grammatical equivalents used herein means at least two nucleotides covalently linked together. The term "nucleic acid" includes single-, double-, or multiple-stranded DNA, RNA and analogs (derivatives) thereof. Oligonucleotides are typically from about 5, 6, 7, 8, 9, 10, 12, 15, 25, 30, 40, 50 or more nucleotides in length, up to about 100 nucleotides in length. Nucleic acids and polynucleotides are polymers of any length, including longer lengths, e.g., 200, 300, 500, 1000, 2000, 3000, 5000, 7000, 10,000, etc. In certain embodiments the nucleic acids herein contain phosphodiester bonds. In other embodiments, nucleic acid analogs are included that may have alternate backbones, comprising, e.g., phosphoramidate, phosphorothioate, phosphorodithioate, or O-methylphosphoroamidite linkages (see, Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. A residue of a nucleic acid, as referred to herein, is a monomer of the nucleic acid (e.g., a nucleotide).

"Nucleotide," as used herein, refers to a nucleoside-5'-polyphosphate compound, or a structural analog thereof, which can be incorporated (e.g., partially incorporated as a nucleoside-5'-monophosphate or derivative thereof) by a nucleic acid polymerase to extend a growing nucleic acid chain (such as a primer). Nucleotides may include bases such as guanine (G), adenine (A), thymine, (T), uracil (U), cytosine (C), or analogues thereof, and may comprise 2, 3, 4, 5, 6, 7, 8, or more phosphates in the phosphate group. Nucleotides may be modified at one or more of the base, sugar, or phosphate group. A nucleotide may have a label or tag attached (a "labeled nucleotide" or "tagged nucleotide"). In embodiments, the nucleotide is a modified nucleotide which terminates primer extension reversibly. In embodiments, nucleotides may further include a polymerase-compatible cleavable moiety covalently bound to the 3' oxygen.

A "nucleoside" is structurally similar to a nucleotide but lacks the phosphate moieties. An example of a nucleoside analog would be one in which the label is linked to the base and there is no phosphate group attached to the sugar molecule.

The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g., phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

In embodiments, "nucleotide analogue," "nucleotide analog," or "nucleotide derivative" shall mean an analogue of A, G, C, T or U (that is, an analogue or derivative of a nucleotide comprising the base A, G, C, T or U), including a phosphate group, which may be recognized by DNA or RNA polymerase (whichever is applicable) and may be incorporated into a strand of DNA or RNA (whichever is appropriate). Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

The term "bioconjugate group" or "bioconjugate reactive moiety" or "bioconjugate reactive group" refers to a chemical moiety which participates in a reaction to form bioconjugate linker (e.g., covalent linker). Non-limiting examples of bioconjugate groups include —NH$_2$, "\*MERGEFORMAT\*MERGEFORMAT    —COOH, —COOCH$_3$, —N-hydroxysuccinimide, -maleimide,

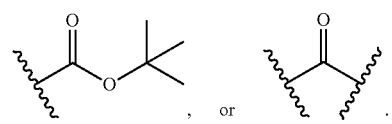

, or    .

In embodiments, the bioconjugate reactive group may be protected (e.g., with a protecting group). In embodiments, the bioconjugate reactive moiety is

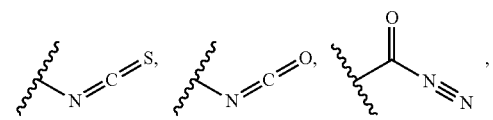

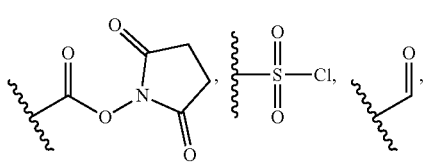

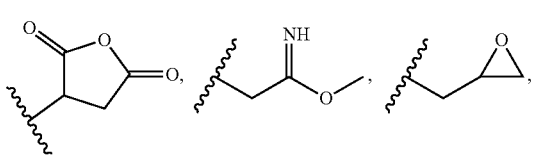

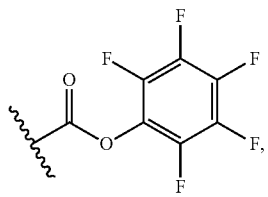

or —NH$_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., "\*MERGEFORMAT\*MERGEFORMAT —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIO-CONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., "\*MERGEFORMAT\*MERGEFORMAT -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g., 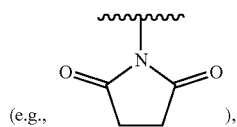 [SMILES: *N1C(=O)CCC1=O] ), thereby forming a bioconjugate (e.g., 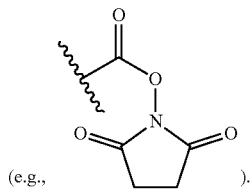 [SMILES: *C(=O)ON1C(=O)CCC1=O] ).

In embodiments, the first bioconjugate reactive group (e.g., —NH$_2$) is covalently attached to the second bioconjugate reactive group (e.g., 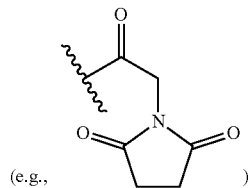 [SMILES: *C(=O)CN1C(=O)CCC1=O] )

thereby forming a bioconjugate (e.g., 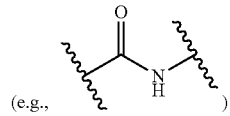 [SMILES: *NC(*)=O] )

In embodiments, the first bioconjugate reactive group (e.g., a coupling reagent) is covalently attached to the second bioconjugate reactive group (e.g., 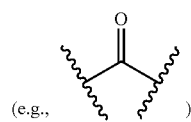 [SMILES: *C(*)=O] )

thereby forming a bioconjugate (e.g., 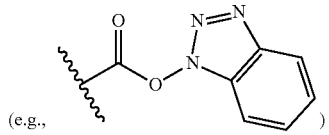 [SMILES: *C(=O)On1nnc2ccccc21] )

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc. (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite (Na$_2$S$_2$O$_4$), or hydrazine (N$_2$H$_4$)). In embodiments, a chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation).

A photocleavable linker (e.g., including or consisting of an o-nitrobenzyl group) refers to a linker which is capable of being split in response to photo-irradiation (e.g., ultraviolet radiation). An acid-cleavable linker refers to a linker which is capable of being split in response to a change in the pH (e.g., increased acidity). A base-cleavable linker refers to a linker which is capable of being split in response to a change in the pH (e.g., decreased acidity). An oxidant-cleavable linker refers to a linker which is capable of being split in response to the presence of an oxidizing agent. A reductant-cleavable linker refers to a linker which is capable of being split in response to the presence of an reducing agent (e.g., Tris(3-hydroxypropyl)phosphine). In embodiments, the cleavable linker is a dialkylketal linker, an azo linker, an allyl linker, a cyanoethyl linker, a 1-(4,4-dimethyl-2,6-dioxocyclohex-1-ylidene)ethyl linker, or a nitrobenzyl linker.

The term "orthogonally cleavable linker" or "orthogonal cleavable linker" as used herein refer to a cleavable linker that is cleaved by a first cleaving agent (e.g., enzyme, nucleophilic/basic reagent, reducing agent, photo-irradiation, electrophilic/acidic reagent, organometallic and metal reagent, oxidizing reagent) in a mixture of two or more different cleaving agents and is not cleaved by any other different cleaving agent in the mixture of two or more cleaving agents. For example, two different cleavable linkers are both orthogonal cleavable linkers when a mixture of the two different cleavable linkers are reacted with two different cleaving agents and each cleavable linker is cleaved by only one of the cleaving agents and not the other cleaving agent. In embodiments, an orthogonally cleavable linker is a cleavable linker that, following cleavage (e.g., following exposure to a cleaving agent), the two separated entities (e.g., fluorescent dye, bioconjugate reactive group) do not further react and form a new orthogonally cleavable linker.

The term "polymer" refers to a molecule including repeating subunits (e.g., polymerized monomers). For example, polymeric molecules may be based upon polyethylene glycol (PEG), tetraethylene glycol (TEG), polyvinylpyrrolidone (PVP), poly(xylene), or poly(p-xylylene). The term "polymerizable monomer" is used in accordance with its meaning in the art of polymer chemistry and refers to a compound that may covalently bind chemically to other monomer molecules (such as other polymerizable monomers that are the same or different) to form a polymer. In embodiments, polymer refers to PEG, having the formula:

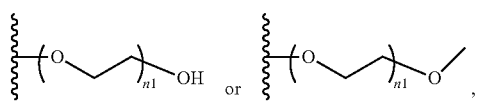

wherein n1 is an integer from 1 to 30.

The term "solution" is used in accordance with its plain ordinary meaning in the arts and refers to a liquid mixture in which the minor component (e.g., a solute or compound) is distributed (e.g., uniformly distributed) within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

As used herein, the term "salt" refers to acid or base salts of the compounds described herein. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. In embodiments, compounds may be presented with a positive charge, for example

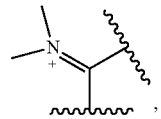

and it is understood an appropriate counter-ion (e.g., chloride ion, fluoride ion, or acetate ion) may also be present, though not explicitly shown. Likewise, for compounds having a negative charge (e.g., 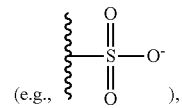), it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g., 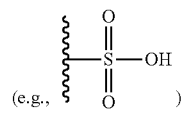 )

or an ionic state (e.g., 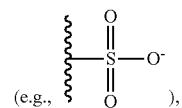 ), and it is understood these are interchangable. In embodiments, the counter-ion is represented by the symbol M (e.g., $M^+$ or $M^-$).

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In embodiments the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In embodiments the protecting group is an amine protecting group. Non-limiting examples of amine protecting groups include carbobenzyloxy (Cbz), tert-butyloxycarbonyl (BOC), 9-Fluorenylmethyloxycarbonyl (FMOC), acetyl, benzoyl, benzyl, carbamate, p-methoxybenzyl ether (PMB), and tosyl (Ts).

The term "polymerase-compatible cleavable moiety" or a "reversible terminator moiety" as used herein refers to a cleavable moiety which does not interfere with the function of a polymerase (e.g., DNA polymerase, modified DNA polymerase) in incorporating the nucleotide to which the polymerase-compatible moiety is attached to the 3' end of the newly formed nucleotide strand. The polymerase-compatible moiety does, however, interfere with the polymerase function by preventing the addition of another nucleotide to the 3' oxygen of the nucleotide to which the polymerase-compatible moiety is attached. Methods for determining the function of a polymerase contemplated herein are described in B. Rosenblum et al. (Nucleic Acids Res. 1997 Nov. 15; 25(22): 4500-4504); and Z. Zhu et al. (Nucleic Acids Res. 1994 Aug. 25; 22(16): 3418-3422), which are incorporated by reference herein in their entirety for all purposes. In embodiments, the polymerase-compatible cleavable moiety does not decrease the function of a polymerase relative to the absence of the polymerase-compatible cleavable moiety. In embodiments, the polymerase-compatible cleavable moiety does not negatively affect DNA polymerase recognition. In embodiments, the polymerase-compatible cleavable moiety does not negatively affect (e.g., limit) the read length of the DNA polymerase. Additional examples of a polymerase-compatible cleavable moiety may be found in U.S. Pat. No. 6,664,079, Ju J. et al. (2006) Proc Natl Acad Sci USA 103(52):19635-19640; Ruparel H. et al. (2005) Proc Natl Acad Sci USA 102(17):5932-5937; Wu J. et al. (2007) Proc Natl Acad Sci USA 104(104):16462-16467; Guo J. et al. (2008) Proc Natl Acad Sci USA 105(27): 9145-9150 Bentley D. R. et al. (2008) Nature 456(7218):53-59; or Hutter D. et al. (2010) Nucleosides Nucleotides & Nucleic Acids 29:879-895, which are incorporated herein by reference in their entirety for all purposes. In embodiments, a polymerase-compatible moiety includes hydrogen, $-N_3$, $-CN$, or halogen. In embodiments, a polymerase-compatible cleavable moiety includes an azido moiety or a dithiol linking moiety. In embodiments, the polymerase-compatible cleavable moiety is independently $-NH_2$, $-CN$, $-CH_3$, $C_2-C_6$ allyl (e.g., $-CH_2-CH=CH_2$), methoxyalkyl (e.g., $-CH_2-O-CH_3$), or "\*MERGEFORMAT\*MERGEFORMAT $-CH_2N_3$. In embodiments, the polymerase-compatible cleavable moiety comprises a disulfide moiety. In embodiments, a polymerase-compatible cleavable moiety is a cleavable moiety on a nucleotide, nucleobase, nucleoside, or nucleic acid that does not interfere with the function of a polymerase (e.g., DNA polymerase, modified DNA polymerase). In embodiments, the reversible terminator moiety is

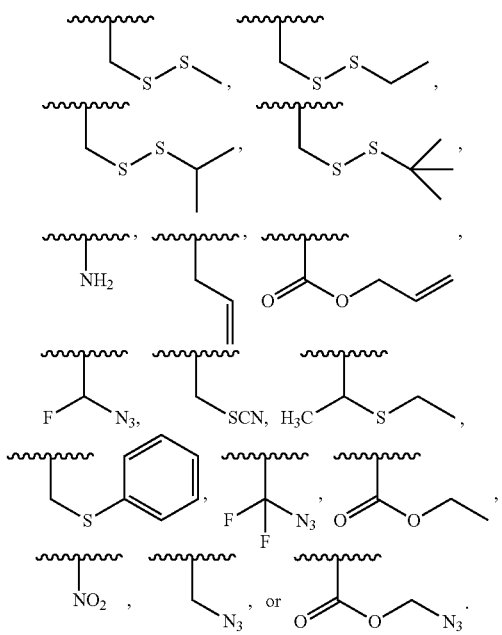

In embodiments, the reversible terminator moiety is

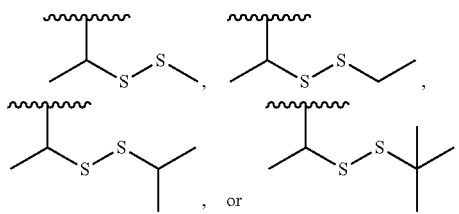

The term "allyl" as described herein refers to an unsubstituted methylene attached to a vinyl group (i.e., $-CH=CH_2$), having the formula

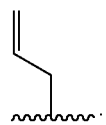

An "allyl linker" refers to a divalent unsubstituted methylene attached to a vinyl group, having the formula

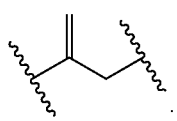 [SMILES: *CC(*)=C]

The terms "DNA polymerase" and "nucleic acid polymerase" are used in accordance with their plain ordinary meaning and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Taq polymerase, Terminator γ, 9°N polymerase (exo-), Terminator II, Terminator III, or Terminator IX).

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH$_3$). Likewise, for a linker variable (e.g., L$^1$, L$^2$, L$^3$, or L$^4$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "leaving group" is used in accordance with its ordinary meaning in chemistry and refers to a moiety (e.g., atom, functional group, or molecule) that separates from the molecule following a chemical reaction (e.g., bond formation, reductive elimination, condensation, or cross-coupling reaction) involving an atom or chemical moiety to which the leaving group is attached, also referred to herein as the "leaving group reactive moiety", and a complementary reactive moiety (i.e., a chemical moiety that reacts with the leaving group reactive moiety) to form a new bond between the remnants of the leaving groups reactive moiety and the complementary reactive moiety. Thus, the leaving group reactive moiety and the complementary reactive moiety form a complementary reactive group pair. Non limiting examples of leaving groups include hydrogen, hydroxide, halogen (e.g., Br), perfluoroalkylsulfonates (e.g., triflate), tosylates, mesylates, water, alcohols, nitrate, phosphate, thioether, amines, ammonia, fluoride, carboxylate, phenoxides, boronic acid, boronate esters, substituted or unsubstituted piperazinyl, and alkoxides. In embodiments, two molecules are allowed to contact, wherein at least one of the molecules has a leaving group, and upon a reaction and/or bond formation (e.g., acyloin condensation, aldol condensation, Claisen condensation, or Stille reaction) the leaving group(s) separate from the respective molecule. In embodiments, a leaving group is a bioconjugate reactive moiety. In embodiments, the leaving groups is designed to facilitate the reaction. In embodiments, the leaving group is a substituent group.

The terms "detect" and "detecting" as used herein refer to the act of viewing (e.g., imaging, indicating the presence of, quantifying, or measuring (e.g., spectroscopic measurement), an agent based on an identifiable characteristic of the agent, for example, the light emitted from the present compounds. For example, the compound described herein can be bound to an agent, and, upon being exposed to an absorption light, will emit an emission light. The presence of an emission light can indicate the presence of the agent. Likewise, the quantification of the emitted light intensity can be used to measure the concentration of the agent.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

The terms "fluorophore" or "fluorescent agent" are used interchangeably and refer to a substance, compound, agent, or composition (e.g., compound) that can absorb light at one or more wavelengths and re-emit light at one or more longer wavelengths, relative to the one or more wavelengths of absorbed light. Examples of fluorophores that may be included in the compounds and compositions described herein include fluorescent proteins, xanthene derivatives (e.g., fluorescein, rhodamine, Oregon Green®, eosin, or Texas Red®), cyanine and derivatives (e.g., cyanine, indocarbocyanine, oxacarbocyanine, thiacarbocyanine, or merocyanine), napththalene derivatives (e.g., dansyl or prodan derivatives), coumarin and derivatives, oxadiazole derivatives (e.g., pyridyloxazole, nitrobenzoxadiazole or benzoxadiazole), anthracene derivatives (e.g., anthraquinones, DRAQ5™, DRAQ7™, or CyTRAK Orange™), pyrene derivatives (e.g., Cascade® Blue and derivatives), oxazine derivatives (e.g., Nile red, Nile blue, cresyl violet, or oxazine 170), acridine derivatives (e.g., proflavin, acridine orange, acridine yellow), arylmethine derivatives (e.g., auramine, crystal violet, or malachite green), tetrapyrrole derivatives (e.g., porphin, phthalocyanine, bilirubin), CF® dye, DRAQ™, CyTRAK™, BODIPY™, Alexa Fluor™, DyLight®, Atto™, Tracy™, FluoProbes™, Abberior Dyes™, DY™ dyes, MegaStokes Dyes™, Sulfo Cy™ dyes, Seta dyes, SeTau dyes, Square dyes, Quasar™ dyes, Cal Fluor™ dyes, SureLight™ dyes, PerCP™, PBXL™ (phycobillisome-based fluorophores), APC, APCXL™, R-PE (R-phycoerythrin), and/or B-PE (B-phycoerythrin). A fluorescent moiety is a radical of a fluorescent agent. The emission from the fluorophores can be detected by any number of methods, including but not limited to, fluorescence spectroscopy, fluorescence microscopy, fluorimeters, fluorescent plate readers, infrared scanner analysis, laser scanning confocal microscopy, automated confocal nanoscanning, laser spectrophotometers, fluorescent-activated cell sorters (FACS), image-based analyzers and fluorescent scanners (e.g., gel/membrane scanners).

The term "rhodamine" as is used in accordance with its ordinary meaning in the art and refers to a detectable moiety including a xanthene backbone. Structurally, rhodamine is a family of related polycyclic dyes with a xanthene core, i.e.,

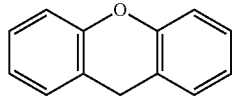 [SMILES: c1ccc2c(c1)Cc1ccccc1O2]

(xanthene). Generally speaking, functional groups on the conjugated moiety of the xanthene core have the ability to fine tune the fluorescent colors. Non-limiting examples of rhodamine dyes include Rhodamine B, Rhodamine 6G, Rhodamine 123, and Rhodamine WH. Rhodamine derivatives have also been disclosed, such as in PCT Int. Appl, WO 2009108905; U.S. Pat. Nos. 5,728,529; 5,686,261; and by Kim et al. (Journal of Physical Chemistry A (2006), 110(1), 20-27)).

The term "oleum" is used in accordance with its ordinary meaning in chemistry, and refers to solutions of sulfur trioxide in sulfuric acid. Alternative names for oleum may include fuming sulfuric acid, disulfuric acid, or pyrosulfuric acid. Oleum is identified by the CAS number 8014-95-7. Oleums can be described by the formula $\{X\}SO_3 \cdot H_2O$ where $\{X\}$ is the total molar mass of sulfur trioxide. Oleum is made by dissolving sulfur trioxide ($SO_3$) in concentrated sulfuric acid ($H_2SO_4$); for example to make 20% fuming sulfuric acid, add 100 ml of sulfuric acid to 80 ml of sulfur trioxide.

The term "dye-intermediate" is used in accordance with its ordinary meaning in chemistry, and refers to a chemical dye molecule that is produced during a chemical reaction but is not necessarily isolated from the reaction.

The term "Lewis acid" is used in accordance with its ordinary meaning in chemistry, and refers to an ion or molecule that is capable of acting as an electron acceptor. Examples of Lewis acids include but are not limited to $AlCl_3$, $BF_3$, and $SnCl_4$.

The term "monovalent compound" is used in accordance with its plain and ordinary meaning and refers to a compound capable of forming one covalent bond. In embodiments, the monovalent compound is covalently attached to an agent described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions & Kits

In an aspect is provided a compound, or salt thereof, having the formula (I):

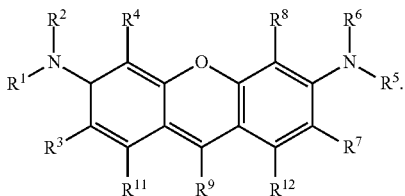

In embodiments, the compound made using any one of methods described herein. $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$, $R^2$, $R^5$, or $R^6$ is hydrogen. $R^1$ and $R^2$ substituents bonded to the same nitrogen atom may optionally be joined to form a substituted or unsubstituted heterocycloalkyl, or substituted or unsubstituted heteroaryl. $R^5$ and $R^6$ substituents bonded to the same nitrogen atom may optionally be joined to form a substituted or unsubstituted heterocycloalkyl, or substituted or unsubstituted heteroaryl. $R^2$ and $R^4$ substituents may optionally be joined to form a substituted or unsubstituted heterocycloalkyl, or substituted or unsubstituted heteroaryl. $R^1$ and $R^3$ substituents may optionally be joined to form a substituted or unsubstituted heterocycloalkyl, or substituted or unsubstituted heteroaryl. $R^6$ and $R^8$ substituents may optionally be joined to form a substituted or unsubstituted heterocycloalkyl, or substituted or unsubstituted heteroaryl. $R^5$ and $R^7$ substituents may optionally be joined to form a substituted or unsubstituted heterocycloalkyl, or substituted or unsubstituted heteroaryl. $R^3$, $R^4$, $R^7$, $R^8$, $R^{11}$, and $R^{12}$ are independently hydrogen, $-PO_3H$, $-PO_4H$, $-SO_2NH_2$, $-SO_3H$, $-SO_4H$, substituted or unsubstituted alkyl, or substituted or unsubstituted heteroalkyl; wherein $R^3$, $R^4$, $R^7$, or $R^8$ is $-SO_3H$. $R^9$ is substituted or unsubstituted aryl. In embodiments, the compound is synthesized according to the methods provided herein.

In an aspect is provided a compound, or salt thereof, having the formula (I):

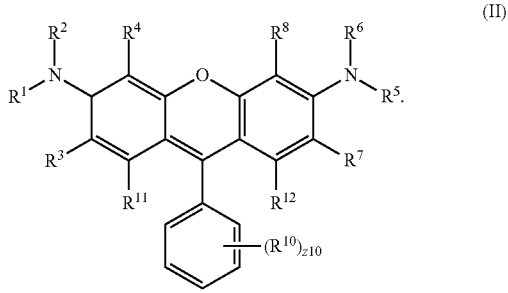

(II)

R¹ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R² is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R⁵ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R⁶ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R¹, R², R⁵, or R⁶ is hydrogen. R¹ and R² substituents bonded to the same nitrogen atom may optionally be joined to form a substituted or unsubstituted heterocycloalkyl, or substituted or unsubstituted heteroaryl. R⁵ and R⁶ substituents bonded to the same nitrogen atom may optionally be joined to form a substituted or unsubstituted heterocycloalkyl, or substituted or unsubstituted heteroaryl. R² and R⁴ substituents may optionally be joined to form a substituted or unsubstituted heterocycloalkyl, or substituted or unsubstituted heteroaryl. R¹ and R³ substituents may optionally be joined to form a substituted or unsubstituted heterocycloalkyl, or substituted or unsubstituted heteroaryl. R⁶ and R⁸ substituents may optionally be joined to form a substituted or unsubstituted heterocycloalkyl, or substituted or unsubstituted heteroaryl. R⁵ and R⁷ substituents may optionally be joined to form a substituted or unsubstituted heterocycloalkyl, or substituted or unsubstituted heteroaryl. R³, R⁴, R⁷, R⁸, R¹¹, and R¹² are independently hydrogen, —PO₃H, —PO₄H, —SO₂NH₂, —SO₃H, —SO₄H, substituted or unsubstituted alkyl, or substituted or unsubstituted heteroalkyl; wherein R³, R⁴, R⁷, or R⁸ is —SO₃H. R¹⁰ is hydrogen, halogen, —CCl₃, —CBr₃, —CF₃, —CI₃, —CHCl₂, —CHBr₂, "\*MERGEFORMAT\*MERGEFORMAT —CHF₂, —CHI₂, —CH₂Cl, —CH₂Br, —CH₂F, —CH₂I, —CN, —OH, —NH₂, —COOH, —CONH₂, —NO₂, "\*MERGEFORMAT\*MERGEFORMAT —SH, —SO₃H, —SO₄H, —SO₂NH₂, —NHNH₂, —ONH₂, —NHC(O)NHNH₂, —NHC(O)NH₂, "\*MERGEFORMAT\*MERGEFORMAT —NHSO₂H, —NHC(O)H, —NHC(O)OH, —NHOH, —OCCl₃, —OCF₃, —OCBr₃, —O CI₃, —OCHCl₂, "\*MERGEFORMAT\*MERGEFORMAT —OCHBr₂, —OCHI₂, —OCHF₂, —OCH₂Cl, —OCH₂Br, —OCH₂I, —OCH₂F, —N₃, —S F₅, —SO₂Cl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -L¹-R¹³; and z10 is an integer from 1 to 5. R¹³ is a bioconjugate reactive moiety, a monovalent nucleotide, a monovalent nucleoside, or a nucleic acid. L¹ is a covalent linker or a bond. In embodiments, the compound is synthesized according to the methods provided herein.

Fluorescent compounds absorb light and then emit light instantaneously at a different wavelength, typically at a longer wavelength. Fluorescent compounds convert all or part of the light (depending on the absorbance coefficient and quantum yield of the molecule) absorbed in a certain energy interval to radiate it at longer wavelengths. This approach is used to fabricate or modify light sources that emit in the visible spectral range (light wavelengths between 400 and 800 nm). These latter sources are used in lighting devices that produce visible light. Examples of such lighting devices are fluorescent tubes, fluorescent compact lamps, or ultraviolet-based white light emitting diodes, where the ultraviolet radiation, invisible to the human eye, is converted by fluorescent materials into visible light (longer than UV) with a spectral distribution between 400 and 800 nm. Described herein are fluorescent compounds.

In embodiments, the compound has a maximum excitation wavelength between 350-400 nm, between 400-450 nm, between 450-500 nm, between 500-550 nm, between 550-600 nm, between 600-650 nm, between 650-700 nm, 700-750 nm, or between 750-800 nm. In embodiments, the compound has a maximum excitation wavelength of about 325 nm, 343 nm, 350 nm, 353 nm, 359 nm, 360 nm, 395 nm, 400 nm, 401 nm, 402 nm, 403 nm, 425 nm, 434 nm, 440 nm, 466 nm, 480 nm, 485 nm, 489 nm, 490 nm, 492 nm, 493 nm, 494 nm, 495 nm, 496 nm, 498 nm, 499 nm, 500 nm, 502 nm, 503 nm, 505 nm, 517 nm, 518 nm, 520 nm, 525 nm, 528 nm, 530 nm, 531 nm, 535 nm, 542 nm, 544 nm, 547 nm, 550 nm, 553 nm, 554 nm, 558 nm, 560 nm, 561 nm, 562 nm, 565 nm, 567 nm, 570 nm, 572 nm, 579 nm, 581 nm, 589 nm, 590 nm, 591 nm, 593 nm, 596 nm, 610 nm, 631 nm, 632 nm, 638 nm, 650 nm, 652 nm, 654 nm, 663 nm, 675 nm, 680 nm, 692 nm, 696 nm, 743 nm, 752 nm, 777 nm, or 782 nm.

In embodiments, the compound has a maximum emission wavelength between 400-450 nm, between 450-500 nm, between 500-550 nm, between 550-600 nm, between 600-650 nm, between 650-700 nm, between 700-750 nm, between 750-800 nm, or between 800-850 nm. In embodiments, the compound has a maximum emission of about 410 nm, 420 nm, 421 nm, 423 nm, 432 nm, 442 nm, 445 nm, 455 nm, 506 nm, 512 nm, 514 nm, 517 nm, 518 nm, 519 nm, 520 nm, 521 nm, 523 nm, 525 nm, 528 nm, 533 nm, 537 nm, 539 nm, 540 nm, 542 nm, 548 nm, 550 nm, 551 nm, 554 nm, 555 nm, 556 nm, 565 nm, 568 nm, 570 nm, 572 nm, 573 nm, 574 nm, 575 nm, 576 nm, 578 nm, 580 nm, 590 nm, 591 nm, 594 nm, 595 nm, 596 nm, 603 nm, 605 nm, 613 nm, 615 nm, 617 nm, 618 nm, 619 nm, 620 nm, 629 nm, 630 nm, 640 nm, 647 nm, 648 nm, 658 nm, 660 nm, 668 nm, 670 nm, 673 nm, 675 nm, 691 nm, 694 nm, 695 nm, 702 nm, 712 nm, 719 nm, 767 nm, 776 nm, 778 nm, 794 nm, or 804 nm.

In embodiments, the compound has the formula:
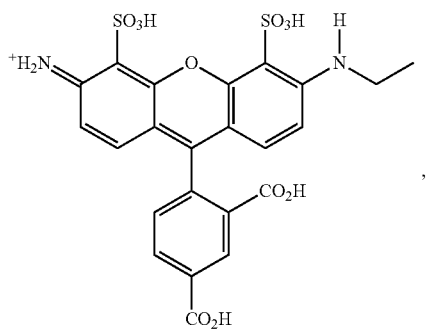
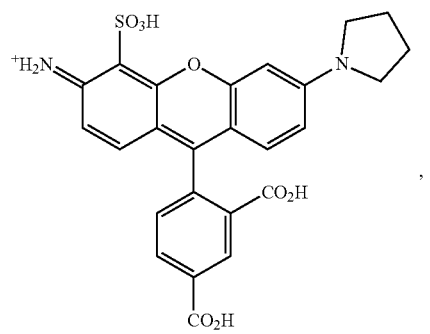
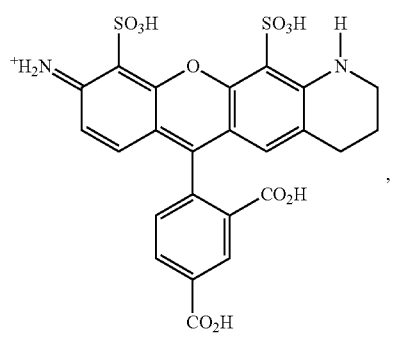
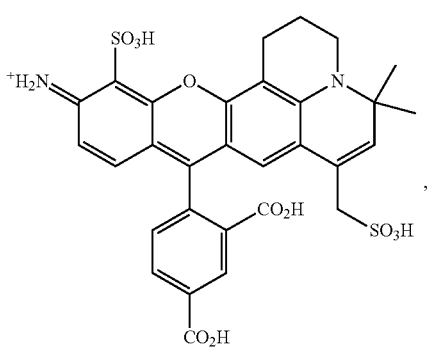
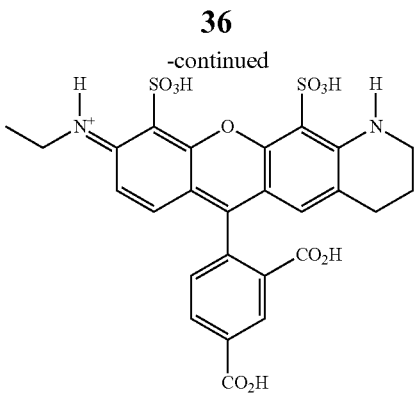
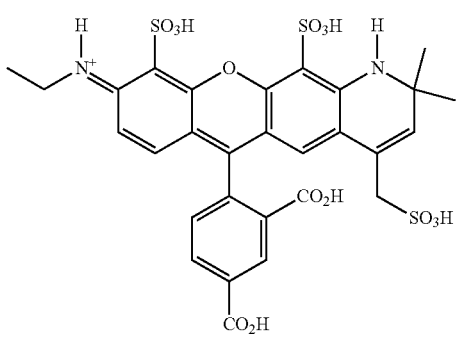
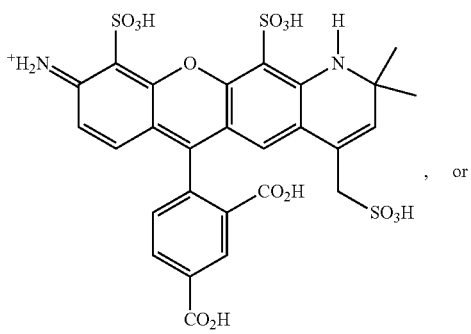, or
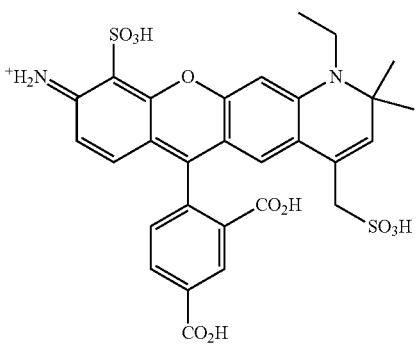

In an aspect is provided a compound having the formula:
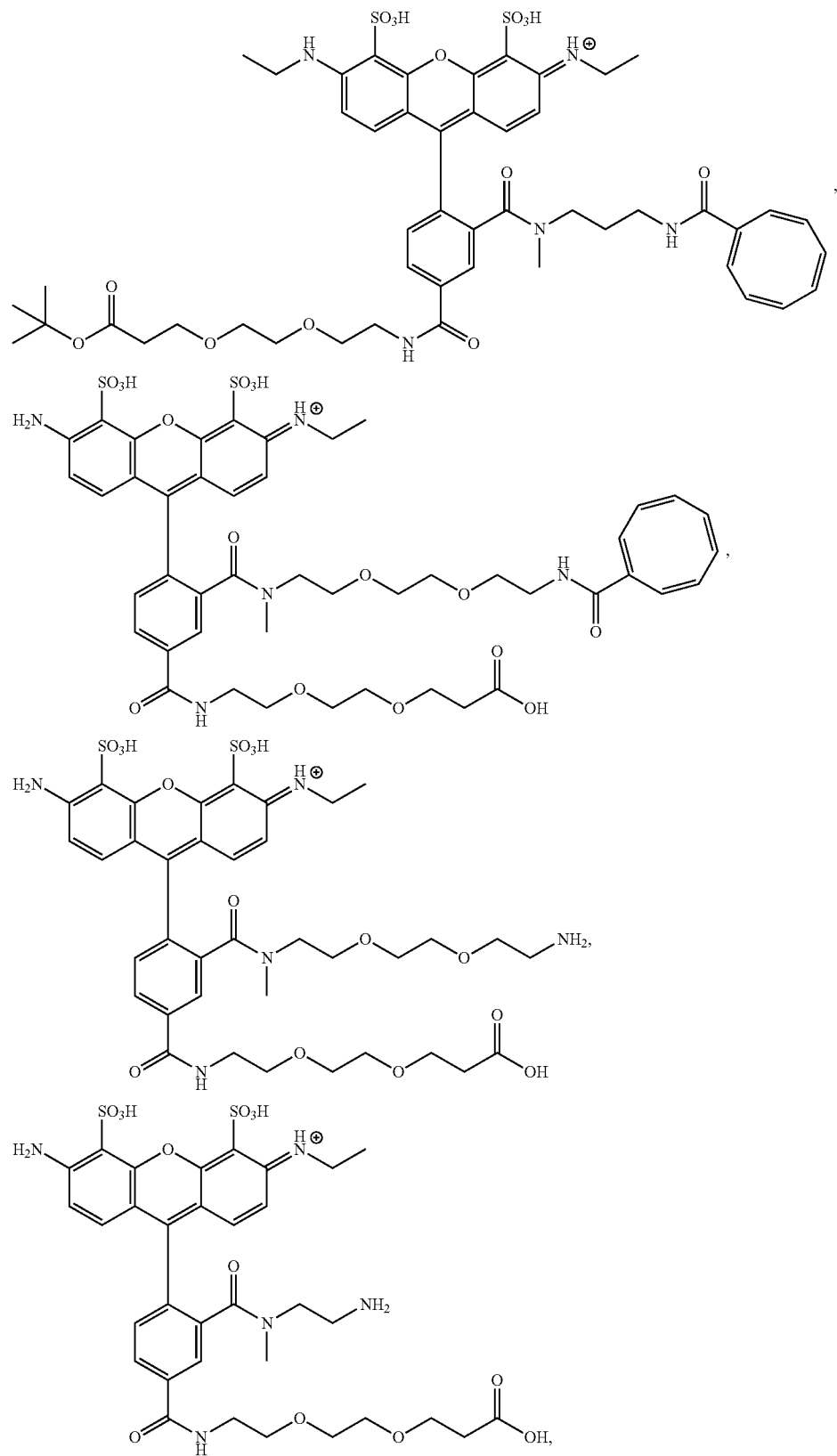

-continued
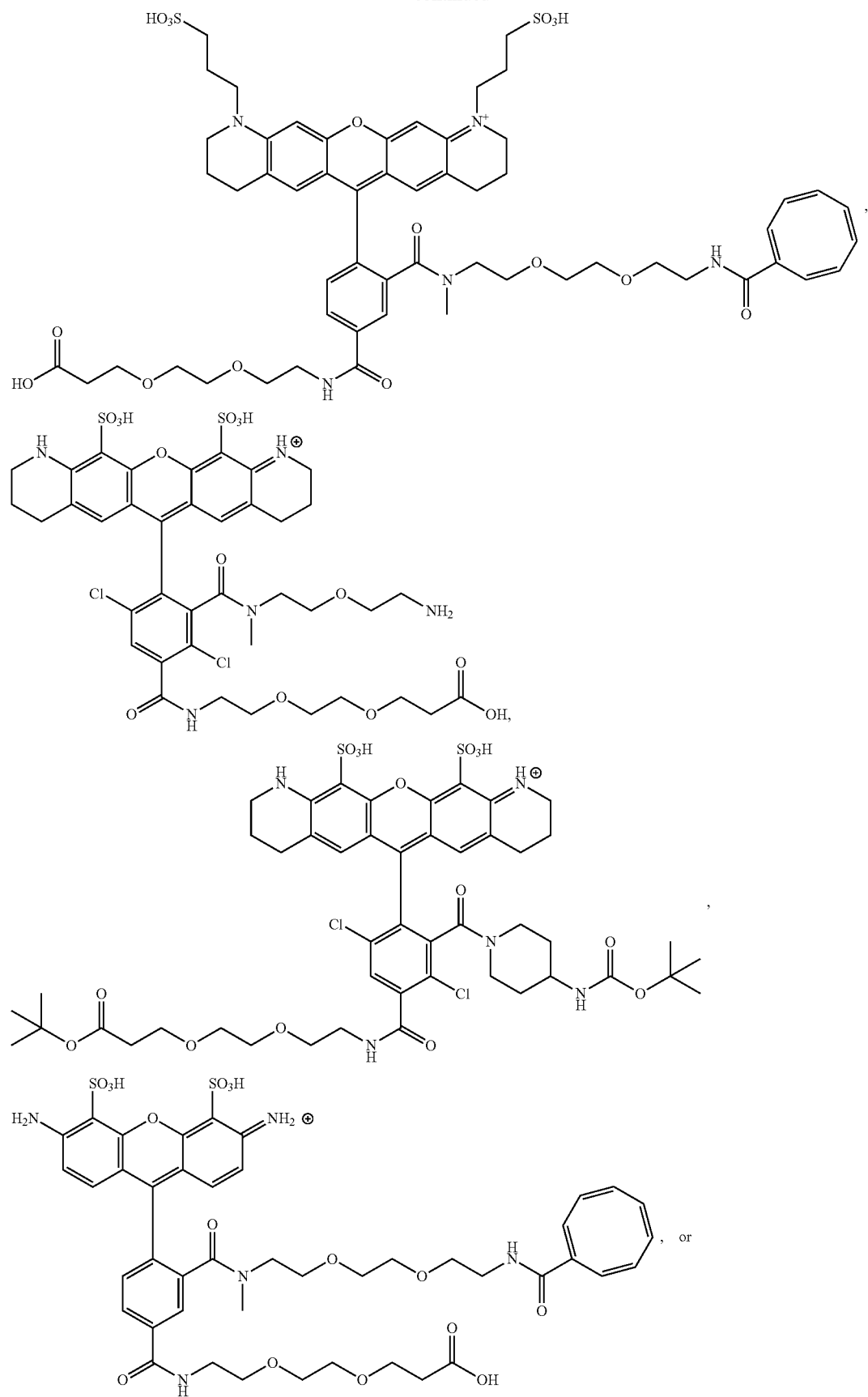

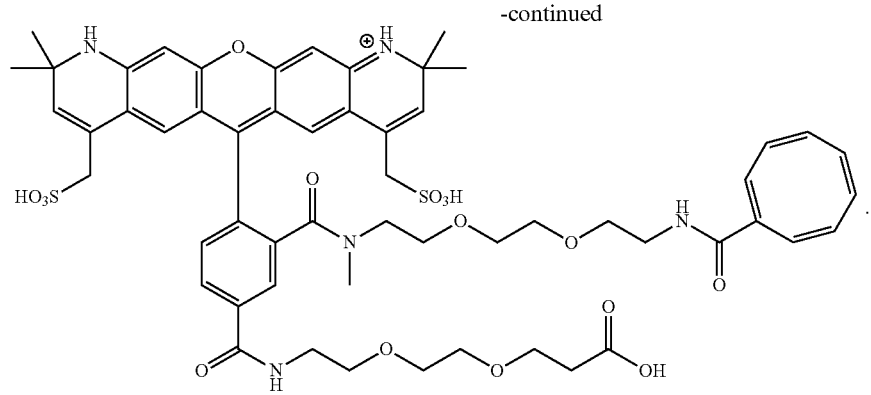
In embodiments, the compound is
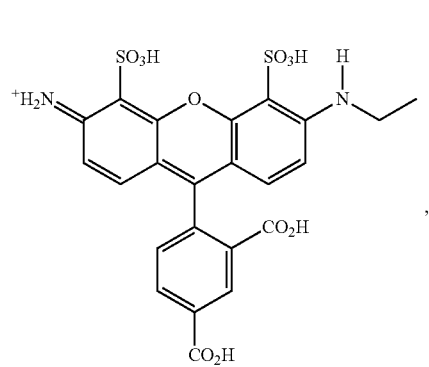
,
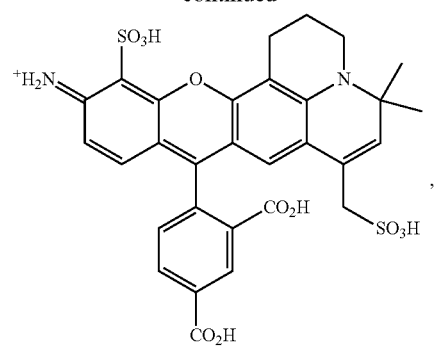
,
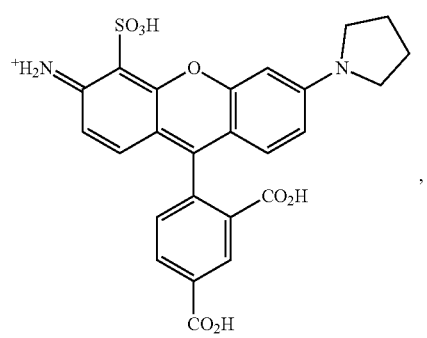
,
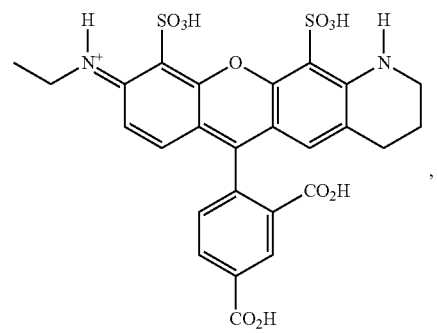
,
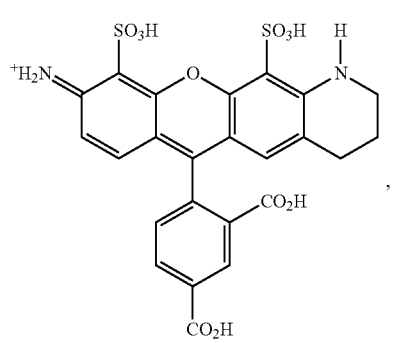
,
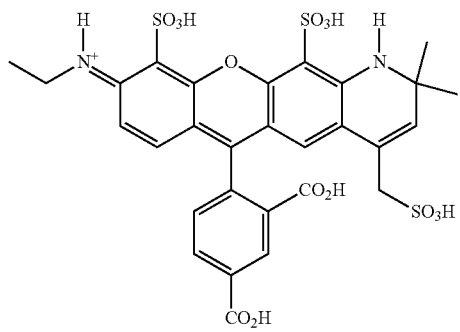
, 43
-continued
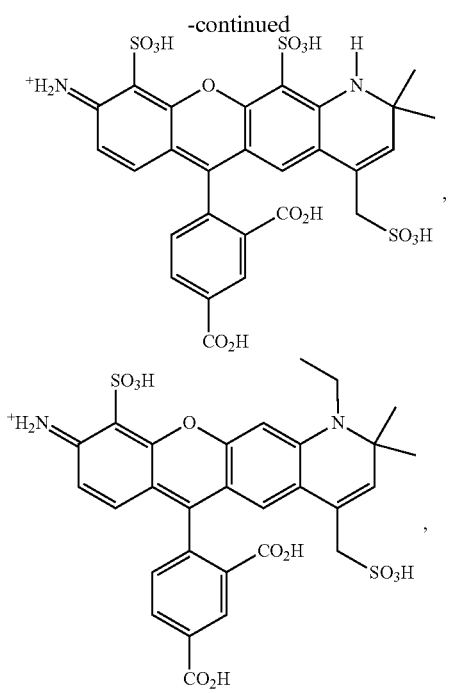
, or
44
-continued
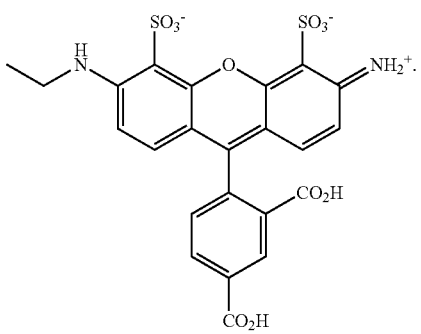
In embodiments, the compound is
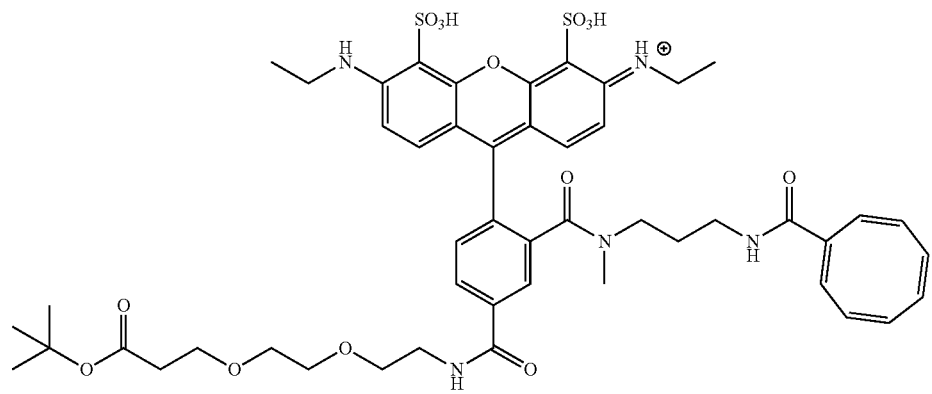
In embodiments, the compound is
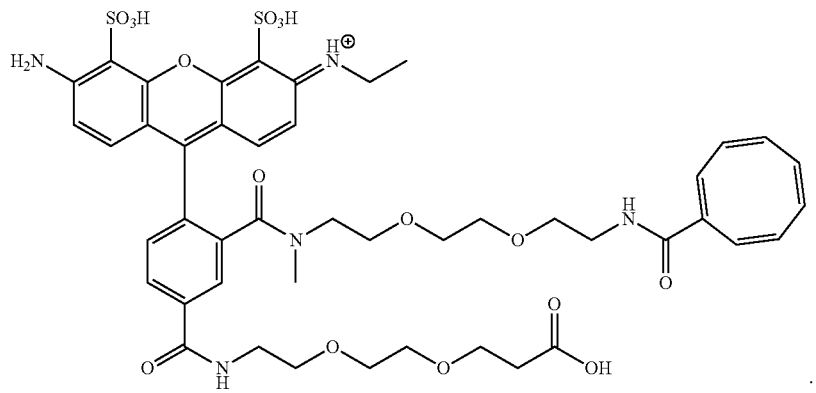

45
In embodiments, the compound is
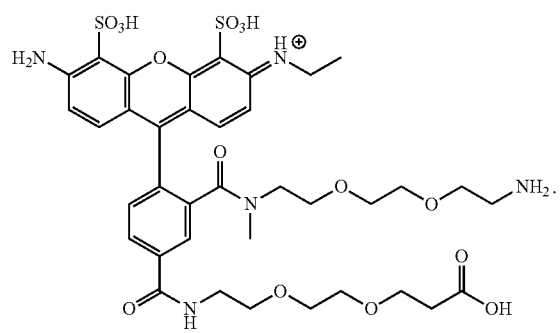
46
In embodiments, the compound is
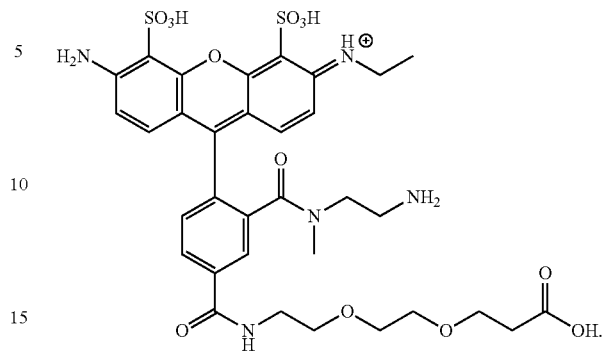
In embodiments, the compound is
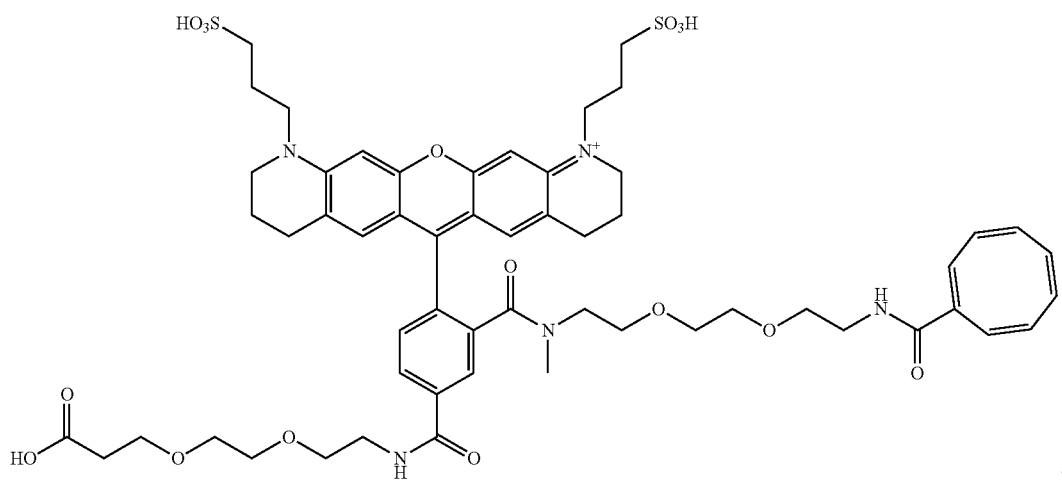 [SMILES: CN(CCOCCOCCNC(=O)C1=C/C=C\C=C/C=C\1)C(=O)c1cc(C(=O)NCCOCCOCCC(=O)O)ccc1C1=c2cc3c(cc2Oc2cc4c(cc21)CCCN4CCCS(=O)(=O)O)=[N+](CCCS(=O)(=O)O)CCC3]
In embodiments, the compound is
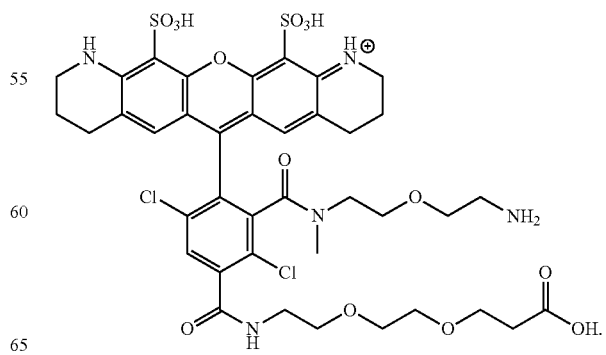

In embodiments, the compound is
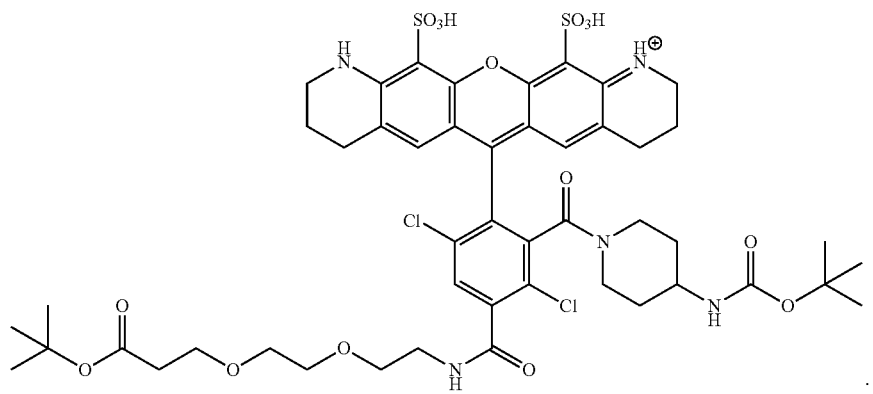
20
In embodiments, the compound is
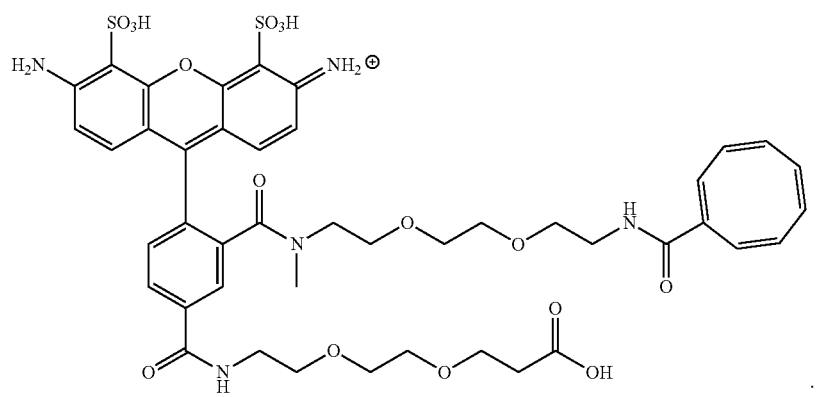 [SMILES: CN(CCOCCOCCNC(=O)C1=C/C=C\C=C/C=C\1)C(=O)c1cc(C(=O)NCCOCCOCCC(=O)O)ccc1-c1c2ccc(=[NH2+])c(S(=O)(=O)O)c-2oc2c(S(=O)(=O)O)c(N)ccc12]
In embodiments, the compound is
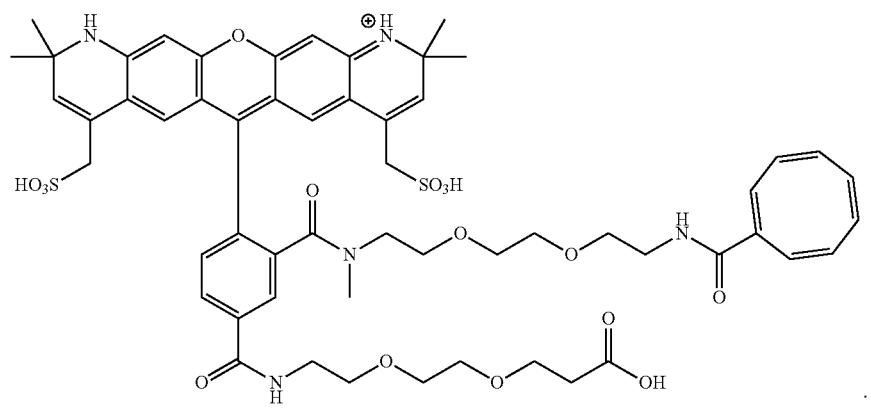

In embodiments, the compound is the compound is
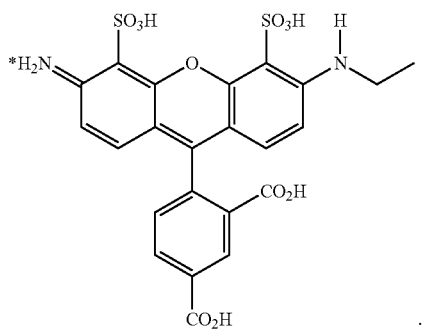
In embodiments, the compound is
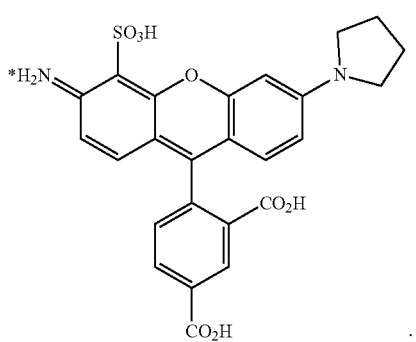
In embodiments, the compound is
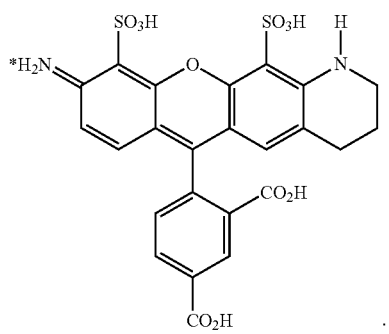
In embodiments, the compound is
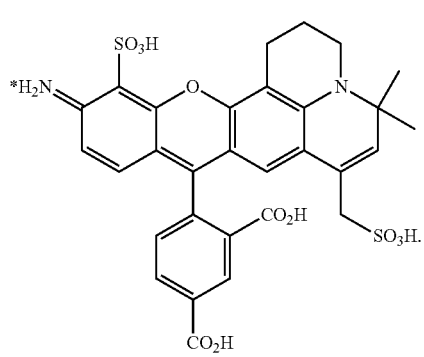
In embodiments, the compound is
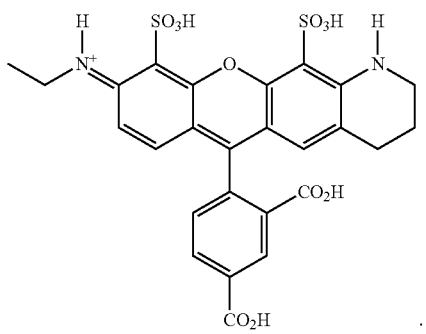 [SMILES: CC/[NH+]=c1\ccc2c(-c3ccc(C(=O)O)cc3C(=O)O)c3cc4c(c(S(=O)(=O)O)c3oc-2c1S(=O)(=O)O)NCCC4]
In embodiments, the compound is
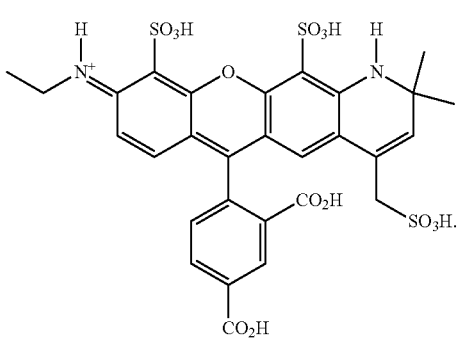
In embodiments, the compound is
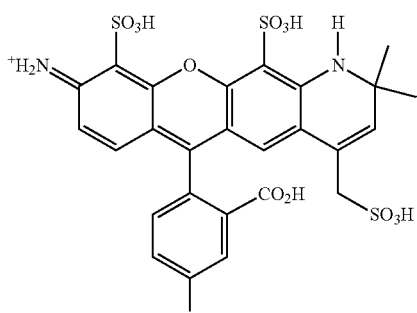
In embodiments, the compound is
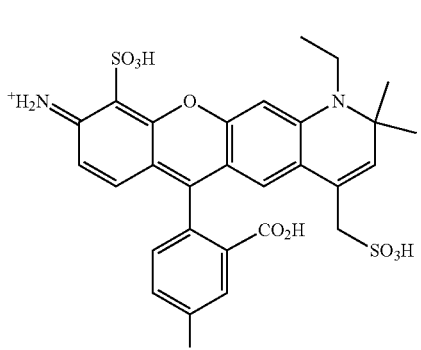

In embodiments, the compound is or

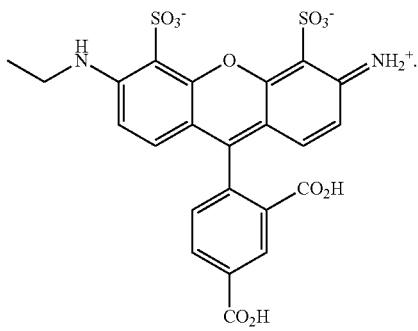

In embodiments, the compound is

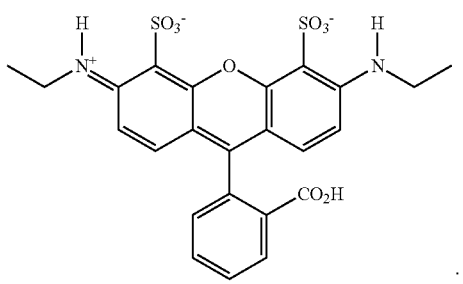

In embodiments, the compound is

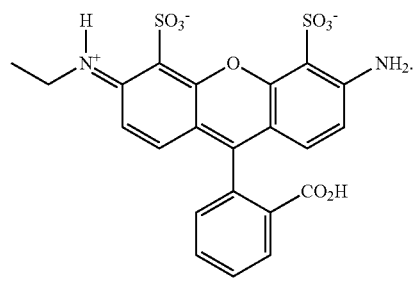

In embodiments, the compound is

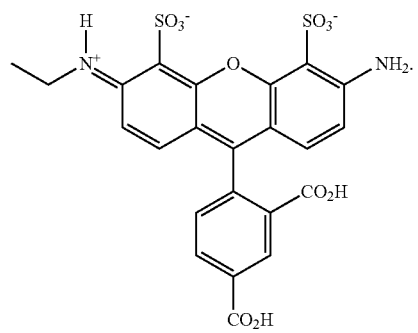

In embodiments, the compound is

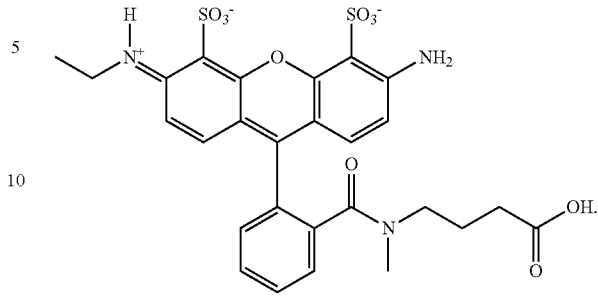

In embodiments, the compound is

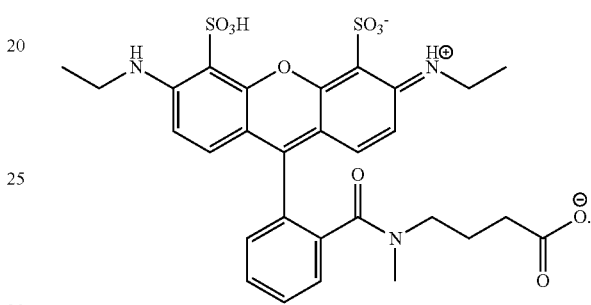

In an aspect is provided a compound having the formula

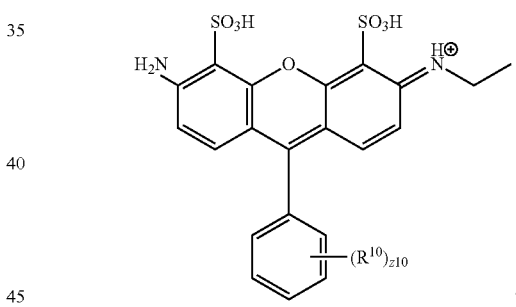

$R^{10}$ is independently hydrogen, halogen, —CCl$_3$, —CBr$_3$, —CF$_3$, —CI$_3$, —CHCl$_2$, —CHBr$_2$,
"\*MERGEFORMAT\*MERGEFORMAT —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$,
"\*MERGEFORMAT\*MERGEFORMAT —SH, —SO$_3$H, —SO$_4$H, —SO$_2$NH$_2$, —NHNH$_2$, —ONH$_2$, —NHC(O)NHNH$_2$, —NHC(O)NH$_2$,
"\*MERGEFORMAT\*MERGEFORMAT —NHSO$_2$H, —NHC(O)H, —NHC(O)OH, —NHOH, —OCCl$_3$, —OCF$_3$, —OCBr$_3$, —O CI$_3$, —OCHCl$_2$,
"\*MERGEFORMAT\*MERGEFORMAT —OCHBr$_2$, —OCHI$_2$, —OCHF$_2$, —OCH$_2$Cl, —OCH$_2$Br, —OCH$_2$I, —OCH$_2$F, —N$_3$, —S F$_5$, —SO$_2$Cl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or -L$^1$-R$^{13}$; and z10 is an integer from 1 to 5. In embodiments, z10 is 1. In embodiments, z10 is 2. In embodiments, z10 is 3. In embodiments, z10 is 4. In embodiments, z10 is 5. $R^{13}$ is a bioconjugate reactive moiety, a monovalent nucleotide, a monovalent nucleoside, or a nucleic acid. $L^1$ is a covalent linker or a bond.

In embodiments, $R^{10}$ is halogen. In embodiments, $R^{10}$ is hydrogen. In embodiments, $R^{10}$ is —$CCl_3$. In embodiments, $R^{10}$ is —$CBr_3$. In embodiments, $R^{10}$ is —$CF_3$. In embodiments, $R^{10}$ is "\*MERGEFORMAT\*MERGEFORMAT —$CI_3$. In embodiments, $R^{10}$ is —$CHCl_2$. In embodiments, $R^{10}$ is —$CHBr_2$. In embodiments, $R^{10}$ is —$CHF_2$. In embodiments, $R^{10}$ is $CHI_2$. In embodiments, $R^{10}$ is —$CH_2Cl$. In embodiments, $R^{10}$ is "\*MERGEFORMAT\*MERGEFORMAT —$CH_2Br$. In embodiments, $R^{10}$ is —$CH_2F$. In embodiments, $R^{10}$ is —$CH_2I$. In embodiments, $R^{10}$ is "\*MERGEFORMAT\*MERGEFORMAT —CN. In embodiments, $R^{10}$ is —OH. In embodiments, $R^{10}$ is —$NH_2$. In embodiments, $R^{10}$ is —COOH. In embodiments, $R^{10}$ is —$CONH_2$. In embodiments, $R^{10}$ is —$NO_2$. In embodiments, $R^{10}$ is —SH. In embodiments, $R^{10}$ is —$SO_3H$. In embodiments, $R^{10}$ is —$SO_4H$. In embodiments, $R^{10}$ is —$SO_2NH_2$. In embodiments, $R^{10}$ is —$NHNH_2$. In embodiments, $R^{10}$ is —$ONH_2$. In embodiments, $R^{10}$ is —NHC(O)$NHNH_2$. In embodiments, $R^{10}$ is —NHC(O)$NH_2$. In embodiments, $R^{10}$ is —$NHSO_2H$. In embodiments, $R^{10}$ is —NHC(O)H. In embodiments, $R^{10}$ is —NHC(O)OH. In embodiments, $R^{10}$ is —NHOH. In embodiments, $R^{10}$ is —$OCCl_3$. In embodiments, $R^{10}$ is —$OCF_3$. In embodiments, $R^{10}$ is —$OCBr_3$. In embodiments, $R^{10}$ is —$OCI_3$. In embodiments, $R^{10}$ is —$OCHCl_2$. In embodiments, $R^{10}$ is —$OCHBr_2$. In embodiments, $R^{10}$ is —$OCHI_2$. In embodiments, $R^{10}$ is —$OCHF_2$. In embodiments, $R^{10}$ is —$OCH_2Cl$. In embodiments, $R^{10}$ is —$OCH_2Br$. In embodiments, $R^{10}$ is —$OCH_2I$. In embodiments, $R^{10}$ is —$OCH_2F$. In embodiments, $R^{10}$ is —$N_3$. In embodiments, $R^{10}$ is —$SF_5$. In embodiments, $R^{10}$ is —$SO_2Cl$.

In embodiments, $R^{10}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10}$ is hydrogen. In embodiments, $R^{10}$ is $R^{10A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{10A}$-substituted or unsubstituted cycloalkyl (e.g., $C_3$-$C_8$, $C_3$-$C_6$, or $C_5$-$C_6$), $R^{10A}$-substituted or unsubstituted heterocycloalkyl (e.g., 3 to 8 membered, 3 to 6 membered, or 5 to 6 membered), $R^{10A}$-substituted or unsubstituted aryl (e.g., $C_6$-$C_{10}$, $C_{10}$, or phenyl), $R^{10A}$-substituted or unsubstituted heteroaryl (e.g., 5 to 10 membered, 5 to 9 membered, or 5 to 6 membered).

$R^{10A}$ is oxo, halogen, —$CCl_3$, —$CBr_3$, —$CF_3$, —$CI_3$, —$CHCl_2$, —$CHBr_2$, —$CHF_2$, —$CHI_2$, "\*MERGEFORMAT\*MERGEFORMAT —$CH_2Cl$, —$CH_2Br$, —$CH_2F$, —$CH_2I$, —CN, —OH, —$NH_2$, —COOH, —$CONH_2$, —$NO_2$, —SH, —$SO_2NH_2$, "\*MERGEFORMAT\*MERGEFORMAT —$NHNH_2$, —$ONH_2$, —NHC(O)$NHNH_2$, —NHC(O)$NH_2$, —$NHSO_2H$, —NHC(O)H, —NHC(O)OH, "\*MERGEFORMAT\*MERGEFORMAT —NHOH, —$OCCl_3$, —$OCF_3$, —$OCBr_3$, —$OCI_3$, —$OCHCl_2$, —$OCHBr_2$, —$OCHI_2$, —O $CHF_2$, —$OCH_2Cl$, "\*MERGEFORMAT\*MERGEFORMAT —$OCH_2Br$, —$OCH_2I$, —$OCH_2F$, —$N_3$, —$SF_5$, —$PO_3H$, —$PO_4H$, —$SO_2NH_2$, —$SO_3H$, —S $O_4H$, $R^{10B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{10B}$-substituted or unsubstituted cycloalkyl (e.g., $C_3$-$C_8$, $C_3$-$C_6$, or $C_5$-$C_6$), $R^{10B}$-substituted or unsubstituted heterocycloalkyl (e.g., 3 to 8 membered, 3 to 6 membered, or 5 to 6 membered), $R^{10B}$-substituted or unsubstituted aryl (e.g., $C_6$-$C_{10}$, $C_{10}$, or phenyl), or $R^{10B}$-substituted or unsubstituted heteroaryl (e.g., 5 to 10 membered, 5 to 9 membered, or 5 to 6 membered). In embodiments, $R^{10A}$ is unsubstituted phenyl.

$R^{10B}$ is oxo, halogen, —$CCl_3$, —$CBr_3$, —$CF_3$, —$CI_3$, —$CHCl_2$, —$CHBr_2$, —$CHF_2$, —$CHI_2$, "\*MERGEFORMAT\*MERGEFORMAT —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, "\*MERGEFORMAT\*MERGEFORMAT —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, "\*MERGEFORMAT\*MERGEFORMAT —$OCH_2Cl$, —$OCH_2Br$, —$OCH_2I$, —$OCH_2F$, —$N_3$, —$SF_5$, —$PO_3H$, —$PO_4H$, —$SO_2NH_2$, —$SO_3H$, —$SO_4H$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^9$ is substituted with multiple, independent $R^{10}$ substituents. When multiple $R^{10}$ substituents are present, each $R^{10}$ substituent may be distinguished as $R^{10.1}$, $R^{10.2}$, $R^{10.3}$, $R^{10.4}$, etc., wherein each of $R^{10.1}$, $R^{10.2}$, $R^{10.3}$, $R^{10.4}$, etc. is defined within the scope of the definition of $R^{10}$ and optionally differently. For example, $R^9$ may have the formula:

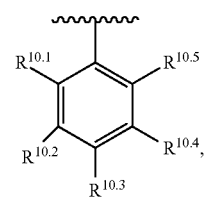

wherein $R^{10.1}$, $R^{10.2}$, $R^{10.3}$, $R^{10.4}$, and $R^{10.5}$ are each defined within the scope of the definition of $R^{10}$ and optionally differently.

In embodiments, the compound has the formula:

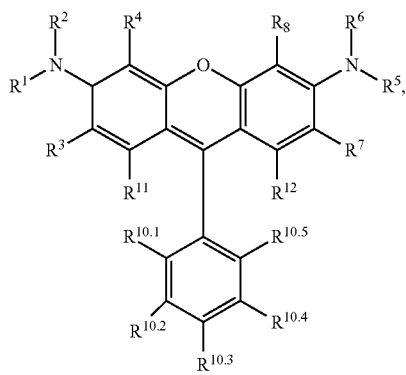

wherein $R^1$, $R^2$, $R^3$, $R^4$, $R^5$, $R^6$, $R^7$, $R^8$, $R^{11}$, $R^{12}$, are described herein and $R^{10.1}$, $R^{10.2}$, $R^{10.3}$, $R^{10.4}$, and $R^{10.5}$ are each defined within the scope of the definition of $R^{10}$ and optionally differently. In embodiments, $R^{10.1}$, $R^{10.2}$, $R^{10.3}$, $R^{10.4}$, or $R^{10.5}$ is $L^1$-$R^{13}$. In embodiments, when $R^{10.1}$ is $L^1$-$R^{13}$, $R^{10.2}$, $R^{10.3}$, $R^{10.4}$, and $R^{10.5}$ are not $L^1$-$R^{13}$. In embodiments, when $R^{10.2}$ is $L^1$-$R^{13}$, $R^{10.1}$, $R^{10.3}$, $R^{10.4}$, and $R^{10.5}$ are not $L^1$-$R^{13}$. In embodiments, when $R^{10.3}$ is $L^1$-$R^{13}$, $R^{10.1}$, $R^{10.2}$, $R^{10.4}$, and $R^{10.5}$ are not $L^1$-$R^{13}$. In embodiments, when $R^{10.4}$ is $L^1$-$R^{13}$, $R^{10.1}$, $R^{10.2}$, $R^{10.3}$, and $R^{10.5}$ are not $L^1$-$R^{13}$. In embodiments, when $R^{10.5}$ is $L^1$-$R^{13}$, $R^{10.2}$, $R^{10.3}$, $R^{10.4}$, and $R^{10.1}$ are not $L^1$-$R^{13}$.

In embodiments, $R^{13}$ is

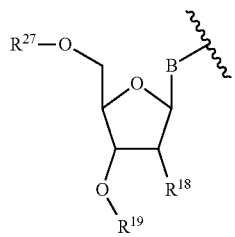

B is a divalent base. $R^{27}$ is independently a 5'-nucleoside protecting group, monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite). $R^{18}$ is hydrogen or —$OR^{18A}$. $R^{18A}$ and $R^{19}$ are each independently hydrogen, or a reversible terminator moiety. In embodiments, $R^{13}$ is

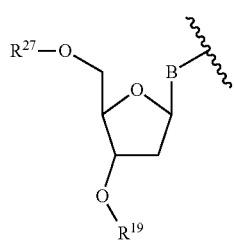

In embodiments, $R^{18}$ is hydrogen. In embodiments, $R^{18}$ is —$OR^{18A}$. In embodiments, $R^{18}$ is —OH. In embodiments, $R^{18}$ is hydrogen or —OH.

In embodiments, $R^{18A}$ is hydrogen. In embodiments, $R^{18A}$ is a reversible terminator moiety. In embodiments, $R^{18A}$ is

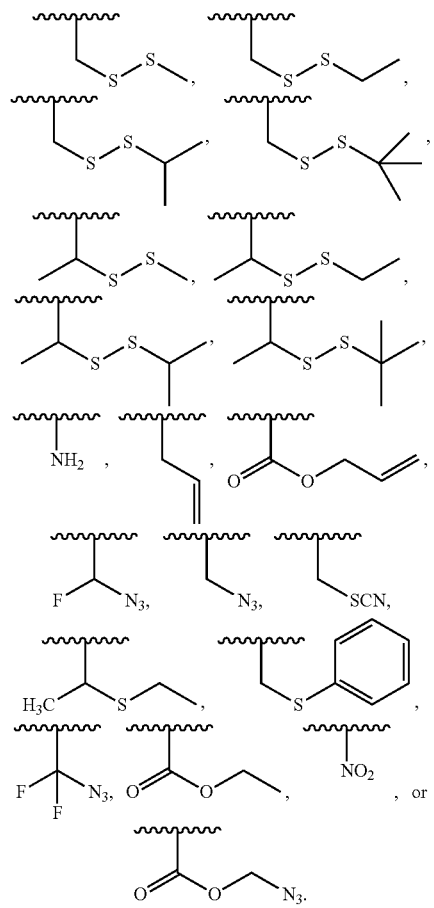

In embodiments, $R^{18A}$ is

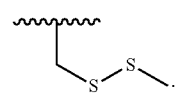 [SMILES: *CSSC]

In embodiments $R^{18A}$ is

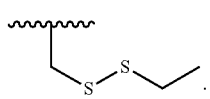

In embodiments, $R^{18A}$ is

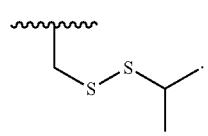

In embodiments, $R^{18A}$ is

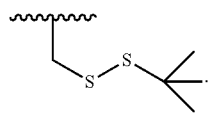

In embodiments $R^{18A}$ is

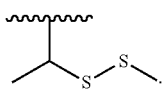

In embodiments, $R^{18A}$ is

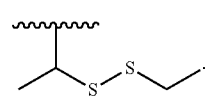

In embodiments, $R^{18A}$ is

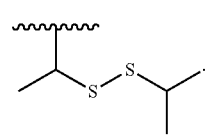

In embodiments, $R^{18A}$ is

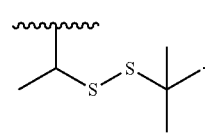

In embodiments, $R^{18A}$ is

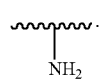

In embodiments, $R^{18A}$ is

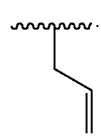

In embodiments, $R^{18A}$ is

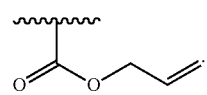

In embodiments, $R^{18A}$ is

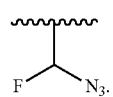

In embodiments, $R^{18A}$ is

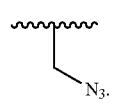

In embodiments, $R^{18A}$ is

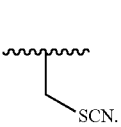

In embodiments, $R^{18A}$ is

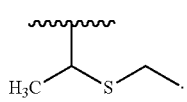

In embodiments, $R^{18A}$ is

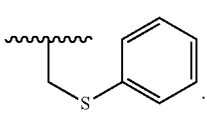 [SMILES: *CSc1ccccc1]

In embodiments, $R^{18A}$ is

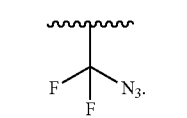

In embodiments, $R^{18A}$ is

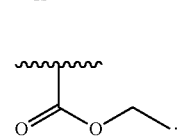 [SMILES: *C(=O)OCC]

In embodiments, $R^{18A}$ is

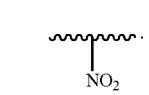

In embodiments, $R^{18A}$ is
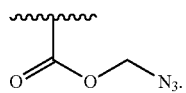
In embodiments, $R^{19}$ is hydrogen. In embodiments, $R^{19}$ is a reversible terminator moiety.
In embodiments, the reversible terminator moiety is:
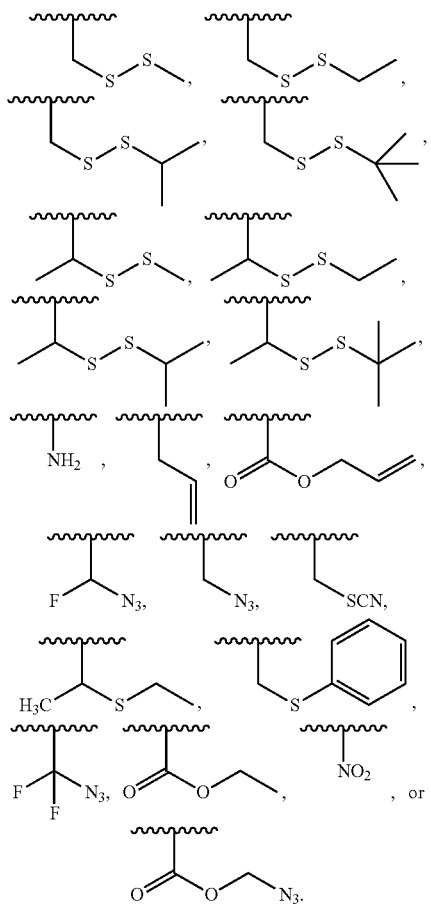
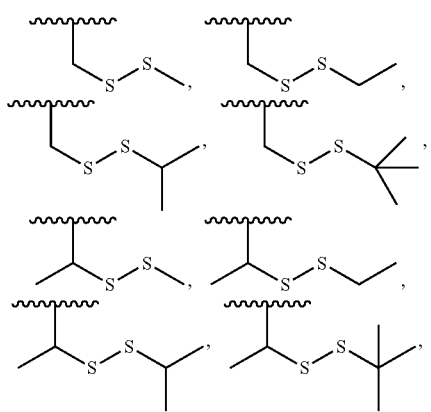
In embodiments, $R^{19}$ is
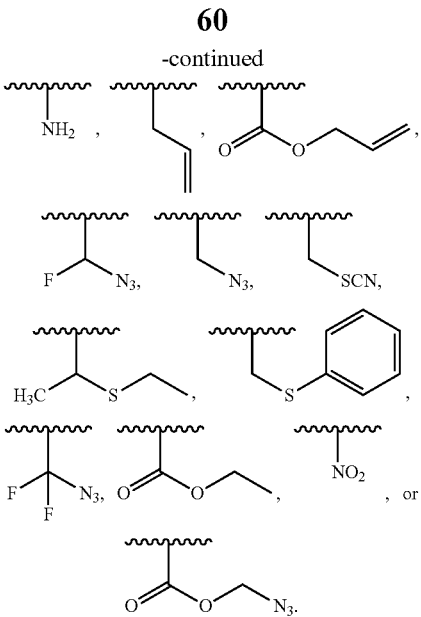
In embodiments, $R^{19}$ is
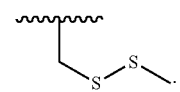 [SMILES: *CSSC]
In embodiments, $R^{19}$ is
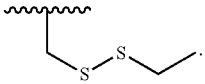 [SMILES: *CSSCC]
In embodiments, $R^{19}$ is
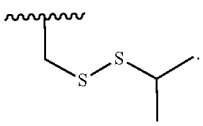 [SMILES: *CSSC(C)C]
In embodiments, $R^{19}$ is
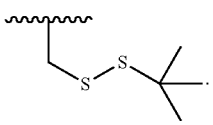 [SMILES: *CSSC(C)(C)C]
In embodiments, $R^{19}$ is
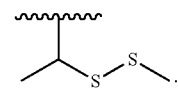 [SMILES: *C(C)SSC]

In embodiments, $R^{19}$ is

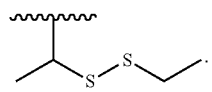 [SMILES: *C(C)SSCC]

In embodiments, $R^{19}$ is

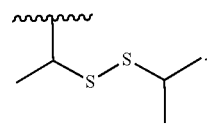 [SMILES: *C(C)SSC(C)C]

In embodiments, $R^{19}$ is

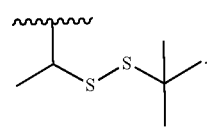 [SMILES: *C(C)SSC(C)(C)C]

In embodiments, $R^{19}$ is

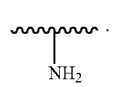

In embodiments, $R^{19}$ is

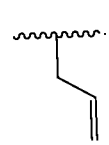 [SMILES: *CC=C]

In embodiments, $R^{19}$ is

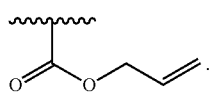 [SMILES: *C(=O)OCC=C]

In embodiments, $R^{19}$ is

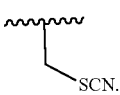

In embodiments, $R^{19}$ is

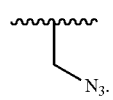

In embodiments, $R^{19}$ is

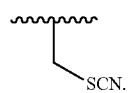

In embodiments, $R^{19}$ is

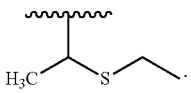

In embodiments, $R^{19}$ is

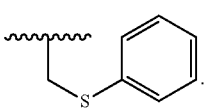

In embodiments, $R^{19}$ is

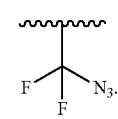

In embodiments, $R^{19}$ is

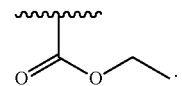 [SMILES: *C(=O)OCC]

In embodiments, $R^{19}$ is

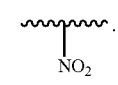

In embodiments, $R^{19}$ is

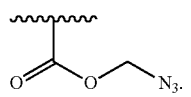

In embodiments, $R^{27}$ is a triphosphate moiety. In embodiments, $R^{27}$ is a 5'-nucleoside protecting group. In embodiments, $R^{27}$ is monophosphate moiety. In embodiments, $R^{27}$ is polyphosphate moiety. In embodiments, $R^{27}$ is nucleic acid moiety. In embodiments, $R^{27}$ is a monophosphate moiety or derivative thereof (e.g., phosphoramidate moiety, phosphorothioate moiety, phosphorodithioate moiety, or O-methylphosphoroamidite moiety), polyphosphate moiety or derivative thereof (e.g., including a phosphoramidate, phosphorothioate, phosphorodithioate, or O-methylphosphoroamidite), or nucleic acid moiety or derivative thereof (e.g., including a phosphoramidate, phosphorothioate, phosphorodithioate, or O-methylphosphoroamidite).

In embodiments, $L^1$ is a covalent linker. In embodiments, $L^1$ is a bond. In embodiments, $L^1$ is a divalent polymer.

In embodiments, $L^1$ is —S(O)$_2$—, —S(O)$_2$NH—, —NHS(O)$_2$—, —NH—, —O—, —S—, —C(O)—, "\*MERGEFORMAT\*MERGEFORMAT —C(O)NH—, —NHC(O)—, —NHC(O)NH—, —C(O)O—, or —OC(O)—. In embodiments, $L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, or a polymer.

In embodiments, $L^1$ is independently a bond, —S(O)$_2$—, —S(O)$_2$NH—, —NHS(O)$_2$—, —NH—, "\*MERGEFORMAT\*MERGEFORMAT —O—, —S—, —C(O)—, —C(O)NH—, —NHC(O)—, —NHC(O)NH—, —C(O)O—, —OC(O)—, $R^{51}$-substituted or unsubstituted alkylene, $R^{51}$-substituted or unsubstituted heteroalkylene, $R^{51}$-substituted or unsubstituted cycloalkylene, $R^{51}$-substituted or unsubstituted heterocycloalkylene, $R^{51}$-substituted or unsubstituted arylene, $R^{51}$-substituted or unsubstituted heteroarylene, or a divalent polymer. In embodiments, $L^1$ is independently a divalent polymer. In embodiments, $L^1$ is independently divalent polyethylene glycol (PEG). In embodiments, $L^1$ is independently a bond, —C(O)—, —C(O)NH—, —NHC(O)—, —NHC(O)NH—, —C(O)O—, —OC(O)—, substituted or unsubstituted $C_1$-$C_6$ alkylene. In embodiments, $L^1$ is independently substituted or unsubstituted $C_1$-$C_6$ alkylene.

In embodiments, $L^1$ is independently a bond, —S(O)$_2$—, —NH—, —O—, —S—, —C(O)—, "\*MERGEFORMAT\*MERGEFORMAT —C(O)NH—, —NHC(O)—, —NHC(O)NH—, —C(O)O—, —OC(O)—, $R^{51}$-substituted or unsubstituted alkylene, $R^{51}$-substituted or unsubstituted heteroalkylene, $R^{51}$-substituted or unsubstituted cycloalkylene, $R^{51}$-substituted or unsubstituted heterocycloalkylene, $R^{51}$-substituted or unsubstituted arylene, $R^{51}$-substituted or unsubstituted heteroarylene, or a divalent polymer.

$R^{51}$ is independently oxo, halogen, —CF$_3$, —CCl$_3$, —CI$_3$, —CBr$_3$, —CHF$_2$, —CHCl$_2$, —CHI$_2$, "\*MERGEFORMAT\*MERGEFORMAT —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, "\*MERGEFORMAT\*MERGEFORMAT —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, "\*MERGEFORMAT\*MERGEFORMAT —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^1$ is a bond, —C(O)—, —C(O)NH—, —NHC(O)—, —NHC(O)NH—, "\*MERGEFORMAT\*MERGEFORMAT —C(O)O—, —OC(O)—, or substituted or unsubstituted alkylene. In embodiments, $L^1$ is a bond, —C(O)—, —C(O)NH—, —NHC(O)—, —NHC(O)NH—, —C(O)O—, —OC(O)—, or substituted or unsubstituted $C_1$-$C_6$ alkylene. In embodiments, $L^1$ is a bond, —C(O)—, —C(O)NH—, —NHC(O)—, "\*MERGEFORMAT\*MERGEFORMAT —NHC(O)NH—, —C(O)O—, —OC(O)—, or substituted $C_1$-$C_6$ alkylene. In embodiments, $L^1$ is a bond, —C(O)—, —C(O)NH—, —NHC(O)—, —NHC(O)NH—, —C(O)O—, —OC(O)—, or unsubstituted $C_1$-$C_6$ alkylene. In embodiments, $L^1$ is a substituted or unsubstituted $C_1$-$C_6$ alkylene. In embodiments, $L^1$ is a substituted $C_1$-$C_6$ alkylene. In embodiments, $L^1$ is an unsubstituted $C_1$-$C_6$ alkylene.

In embodiments, $L^1$ is a bond, —C(O)—, —C(O)NH—, —NHC(O)—, —NHC(O)NH—, "\*MERGEFORMAT\*MERGEFORMAT —C(O)O—, —OC(O)—, or $R^{51}$-substituted or unsubstituted alkylene. In embodiments, $L^1$ is a bond, —C(O)—, —C(O)NH—, —NHC(O)—, —NHC(O)NH—, —C(O)O—, —OC(O)—, or $R^{51}$-substituted or unsubstituted $C_1$-$C_6$ alkylene. In embodiments, $L^1$ is a bond, —C(O)—, —C(O)NH—, —NHC(O)—, "\*MERGEFORMAT\*MERGEFORMAT —NHC(O)NH—, —C(O)O—, —OC(O)—, or $R^{11}$-substituted $C_1$-$C_6$ alkylene. In embodiments, $L^1$ is a bond, —C(O)—, —C(O)NH—, —NHC(O)—, —NHC(O)NH—, —C(O)O—, —OC(O)—, or unsubstituted $C_1$-$C_6$ alkylene. In embodiments, $L^1$ is a $R^{51}$-substituted or unsubstituted $C_1$-$C_6$ alkylene. In embodiments, $L^1$ is a $R^{51}$-substituted $C_1$-$C_6$ alkylene. In embodiments, $L^1$ is an unsubstituted $C_1$-$C_6$ alkylene.

In embodiments, $L^1$ is substituted or unsubstituted alkylene (e.g., $C_1$-$C_8$, $C_1$-$C_6$, $C_1$-$C_4$, or $C_1$-$C_2$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., $C_3$-$C_8$, $C_3$-$C_6$, $C_4$-$C_6$, or $C_5$-$C_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., $C_6$-$C_{10}$ or phenylene), or substituted or unsubstituted heteroarylene (e.g., 5 to 10 membered, 5 to 9 membered, or 5 to 6 membered).

In embodiments, $L^1$ is $R^{51}$-substituted or unsubstituted alkylene (e.g., $C_1$-$C_8$, $C_1$-$C_6$, $C_1$-$C_4$, or $C_1$-$C_2$), $R^{51}$-substituted or unsubstituted heteroalkylene (e.g., 2 to 8 membered, 2 to 6 membered, 4 to 6 membered, 2 to 3 membered, or 4 to 5 membered), $R^{51}$-substituted or unsubstituted cycloalkylene (e.g., $C_3$-$C_8$, $C_3$-$C_6$, $C_4$-$C_6$, or $C_5$-$C_6$), $R^{51}$-substituted or unsubstituted heterocycloalkylene (e.g., 3 to 8 membered, 3 to 6 membered, 4 to 6 membered, 4 to 5 membered, or 5 to 6 membered), $R^{51}$-substituted or unsubstituted arylene (e.g., $C_6$-$C_{10}$ or phenylene), or $R^{51}$-substituted or unsubstituted heteroarylene (e.g., 5 to 10 membered, 5 to 9 membered, or 5 to 6 membered).

In embodiments, $L^1$ is substituted $C_1$-$C_8$ alkylene. In embodiments, $L^1$ is $R^{51}$-substituted $C_1$-$C_8$ alkylene. In embodiments, $L^1$ is unsubstituted $C_1$-$C_8$ alkylene. In embodiments, $L^1$ is substituted $C_1$-$C_6$ alkylene. In embodiments, $L^1$ is $R^{51}$-substituted $C_1$-$C_6$ alkylene. In embodiments, $L^1$ is unsubstituted $C_1$-$C_6$ alkylene. In embodiments, $L^1$ is substituted $C_1$-$C_4$ alkylene. In embodiments, $L^1$ is $R^{51}$-substituted $C_1$-$C_4$ alkylene. In embodiments, $L^1$ is unsubstituted $C_1$-$C_4$ alkylene. In embodiments, $L^1$ is substituted $C_1$-$C_2$ alkylene. In embodiments, $L^1$ is $R^{51}$-substituted $C_1$-$C_2$ alkylene. In embodiments, $L^1$ is unsubstituted $C_1$-$C_2$ alkylene.

In embodiments, $L^1$ is $L^{1A}$-$L^{1B}$-$L^{1C}$-$L^{1D}$-$L^{1E}$. $L^{1A}$, $L^{1B}$, $L^{1C}$, $L^{1D}$ and $L^{1E}$ are independently a bond, —SS—, —NN—, —NHC(O)—, —C(O)NH—, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., saturated heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{1A}$, $L^{1B}$, $L^{1C}$, $L^{1D}$, and $L^{1E}$ is not a bond.

In embodiments, $L^{1A}$, $L^{1B}$, $L^{1C}$, $L^{1D}$, and $L^{1E}$ are independently a bond, —NN—,
"\*MERGEFORMAT\*MERGEFORMAT —NHC(O)—, —C(O)NH—, substituted (e.g., substituted with a substituent group, size-limited substituent group, or lower substituent group) or unsubstituted alkylene (e.g., saturated alkylene, alkenylene, or alkynylene), substituted (e.g., substituted with a substituent group, size-limited substituent group, or lower substituent group) or unsubstituted heteroalkylene (e.g., saturated heteroalkylene, heteroalkenylene, or heteroalkynylene), substituted (e.g., substituted with a substituent group, size-limited substituent group, or lower substituent group) or unsubstituted cycloalkylene, substituted (e.g., substituted with a substituent group, size-limited substituent group, or lower substituent group) or unsubstituted heterocycloalkylene, substituted (e.g., substituted with a substituent group, size-limited substituent group, or lower substituent group) or unsubstituted arylene, or substituted (e.g., substituted with a substituent group, size-limited substituent group, or lower substituent group) or unsubstituted heteroarylene; wherein at least one of $L^{1A}$, $L^{1B}$ $L^{1C}$, $L^{1D}$, and $L^{1E}$ is not a bond.

In embodiments, $L^{1A}$ is independently a bond, —SS—, —NN—, —NHC(O)—, —C(O)NH—, $R^{51A}$-substituted or unsubstituted alkylene, $R^{51A}$-substituted or unsubstituted heteroalkylene, $R^{51A}$-substituted or unsubstituted cycloalkylene, $R^{51A}$-substituted or unsubstituted heterocycloalkylene, $R^{51A}$-substituted or unsubstituted arylene, or $R^{51A}$-substituted or unsubstituted heteroarylene.

In embodiments, $L^{1B}$ is independently a bond, —SS—, —NN—, —NHC(O)—, —C(O)NH—, $R^{51B}$-substituted or unsubstituted alkylene, $R^{51B}$-substituted or unsubstituted heteroalkylene, $R^{51B}$-substituted or unsubstituted cycloalkylene, $R^{51B}$-substituted or unsubstituted heterocycloalkylene, $R^{51B}$-substituted or unsubstituted arylene, or $R^{51B}$-substituted or unsubstituted heteroarylene.

In embodiments, $L^{1C}$ is independently a bond, —SS—, —NN—, —NHC(O)—, —C(O)NH—, $R^{51C}$-substituted or unsubstituted alkylene, $R^{51C}$-substituted or unsubstituted heteroalkylene, $R^{51C}$-substituted or unsubstituted cycloalkylene, $R^{51C}$-substituted or unsubstituted heterocycloalkylene, $R^{51C}$-substituted or unsubstituted arylene, or $R^{51C}$-substituted or unsubstituted heteroarylene.

In embodiments, $L^{1D}$ is independently a bond, —SS—, —NN—, —NHC(O)—, —C(O)NH—, $R^{51D}$-substituted or unsubstituted alkylene, $R^{51D}$-substituted or unsubstituted heteroalkylene, $R^{51D}$-substituted or unsubstituted cycloalkylene, $R^{51D}$-substituted or unsubstituted heterocycloalkylene, $R^{51D}$-substituted or unsubstituted arylene, or $R^{51D}$-substituted or unsubstituted heteroarylene.

In embodiments, $L^{1E}$ is independently a bond, —SS—, —NN—, —NHC(O)—, —C(O)NH—, $R^{51E}$-substituted or unsubstituted alkylene, $R^{51E}$-substituted or unsubstituted heteroalkylene, $R^{51E}$-substituted or unsubstituted cycloalkylene, $R^{51E}$ substituted or unsubstituted heterocycloalkylene, $R^{51E}$-substituted or unsubstituted arylene, or $R^{51E}$-substituted or unsubstituted heteroarylene.

$R^{51A}$, $R^{51B}$, $R^{51C}$, $R^{51D}$, and $R^{51E}$ are each independently oxo, halogen, —$CF_3$, —$CCl_3$,
"\*MERGEFORMAT\*MERGEFORMAT —$CI_3$, —$CBr_3$, —$CHF_2$, —$CHCl_2$, —$CHI_2$, —$CHBr_2$, —$CH_2F$, —$CH_2Cl$, —$CH_2I$, —$CH_2Br$, —$OCH_2F$,
"\*MERGEFORMAT\*MERGEFORMAT —$OCH_2Cl$, —$OCH_2I$, —$OCH_2Br$, —$OCHF_2$, —$OCHCl_2$, —$OCHI_2$, —$OCHBr_2$, —$OCF_3$, —$OCCl_3$, —$OCI_3$,
"\*MERGEFORMAT\*MERGEFORMAT —$OCBr_3$, —CN, —OH, —$NH_2$, —COOH, —$CONH_2$, —$NO_2$, —SH, —$SO_3H$, —$SO_4H$, —$SO_2NH_2$,
"\*MERGEFORMAT\*MERGEFORMAT —$NHNH_2$, —$ONH_2$, —NHC=(O)$NHNH_2$, —NHC=(O)$NH_2$, —$NHSO_2H$, —NHC=(O)H,
"\*MERGEFORMAT\*MERGEFORMAT —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $L^1$ includes an orthogonally cleavable linker, photocleavable linker, or cleavable linker. In embodiments, $L^1$ is an orthogonally cleavable linker, photocleavable linker, or cleavable linker. In embodiments, $L^1$ includes a bioconjugate linker. In embodiments, $L^1$ is a bioconjugate linker.

In embodiments, $L^1$ is independently a polymer. In embodiments, $L^1$ includes a polymer. In embodiments, $L^1$ includes PEG. In embodiments, $L^1$ includes the divalent moiety having the formula:

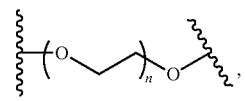

wherein n is an integer from 1 to 30. In embodiments, n is independently 1. In embodiments, n is independently 2. In embodiments, n is independently 3. In embodiments, n is independently an integer from 1 to 6.

In embodiments, L¹ is
—C(CH₃)₂CH₂NHC(O)—,
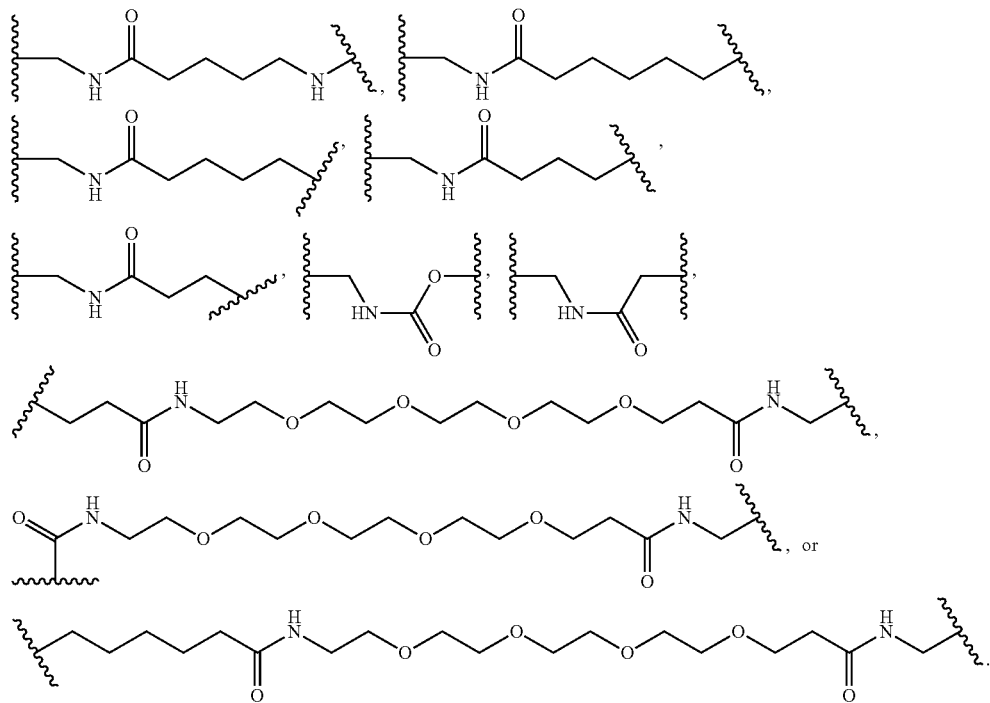
In embodiments, L¹ is
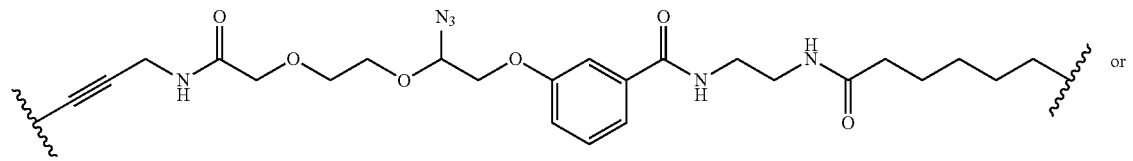
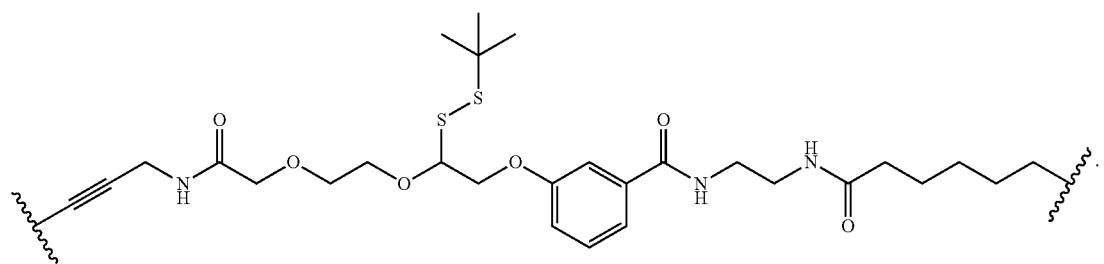
In embodiments, L¹ is,
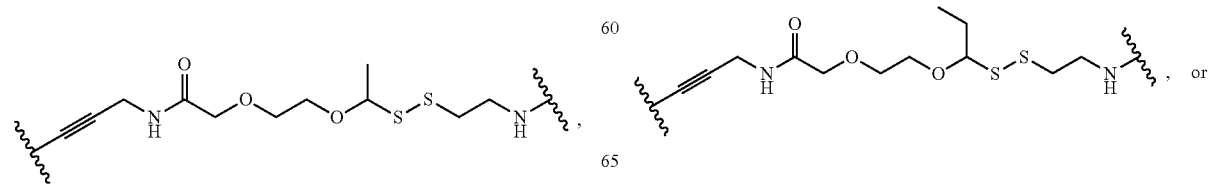

-continued

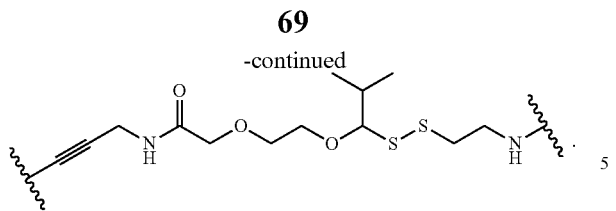

In embodiments, L¹ is

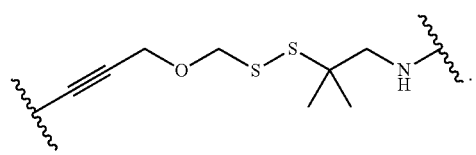 [SMILES: *C#CCOCSSC(C)(C)CN*]

In embodiments, R¹³ is a bioconjugate reactive moiety. In embodiments, R¹³ is a monovalent nucleotide. In embodiments, R¹³ is a monovalent nucleoside. In embodiments, R¹³ is a nucleic acid. In embodiments, R¹³ is a monovalent nucleic acid, or a monovalent nucleic acid analogue thereof.

In embodiments, R¹³ is —NH₂,

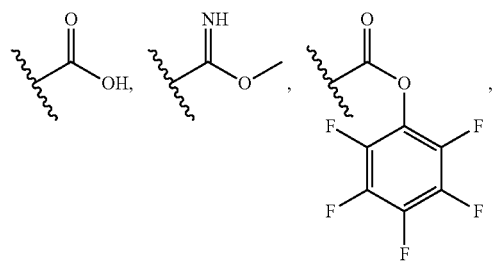

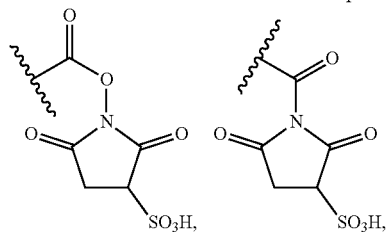

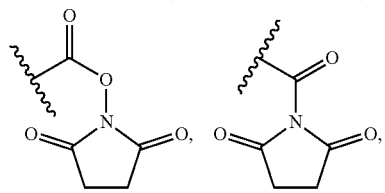

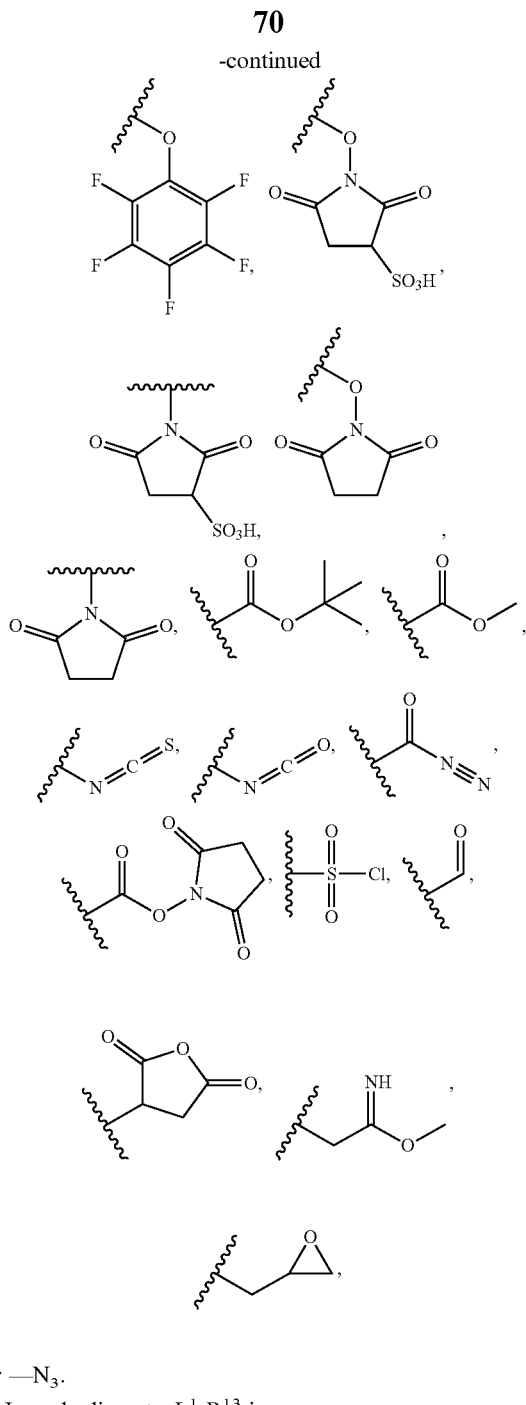

or —N₃.

In embodiments, L¹-R¹³ is

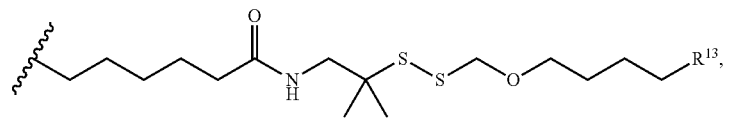

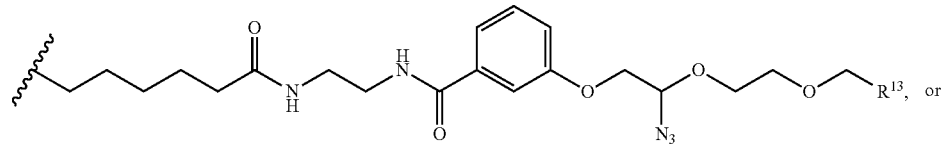

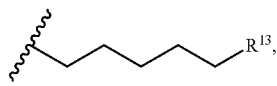
wherein $R^{13}$ is as described herein.
In embodiments, $L^1$-$R^{13}$ is
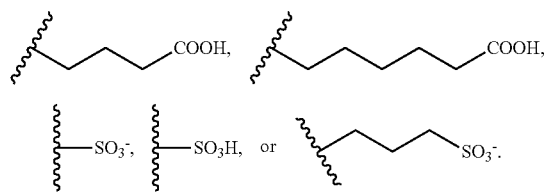
In embodiments, $L^1$-$R^{13}$ is
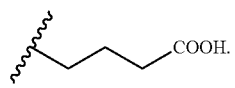
In embodiments, $L^1$-$R^{13}$ is
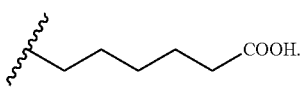 [SMILES: *CCCCCC(=O)O]
In embodiments, $L^1$-$R^{13}$ is
In embodiments, $L^1$-$R^{13}$ is
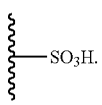
In embodiments, $L^1$-$R^{13}$ is
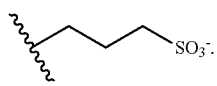
In embodiments, the compound is
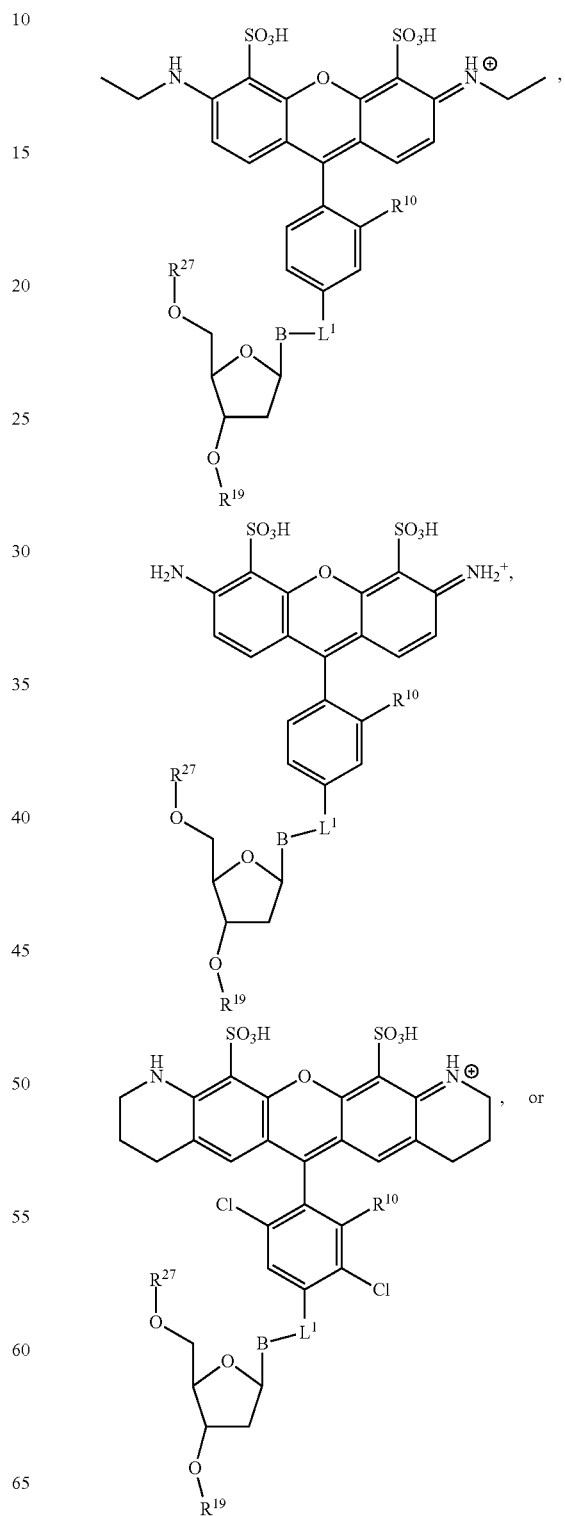

73
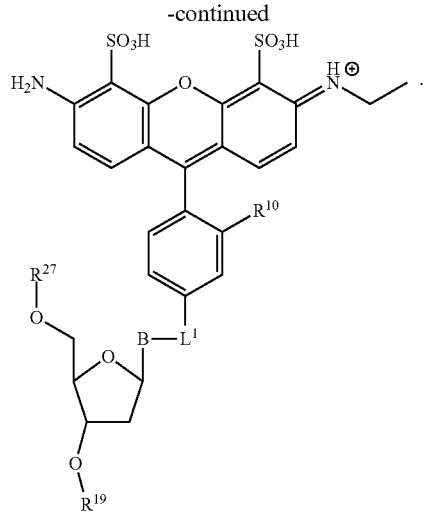
In embodiments, the compound is,
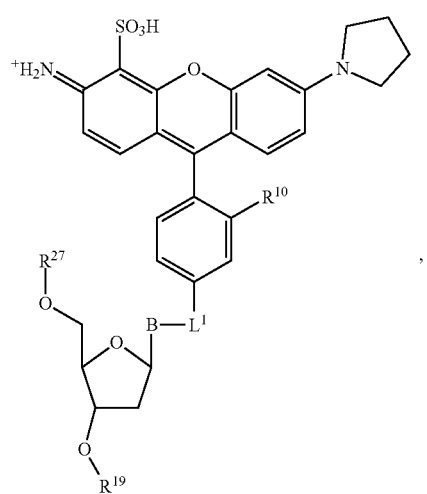
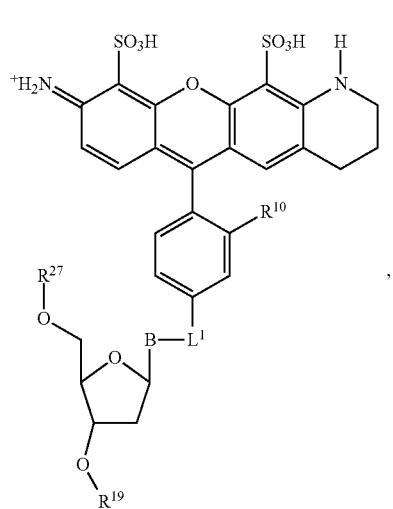
74
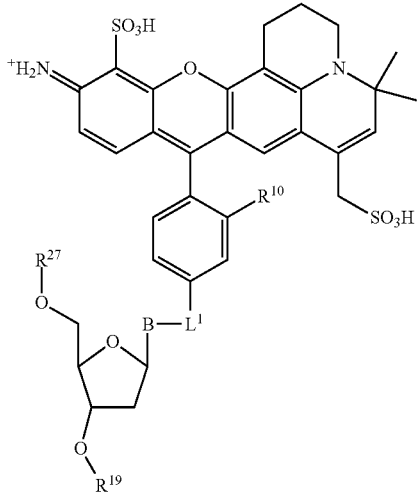
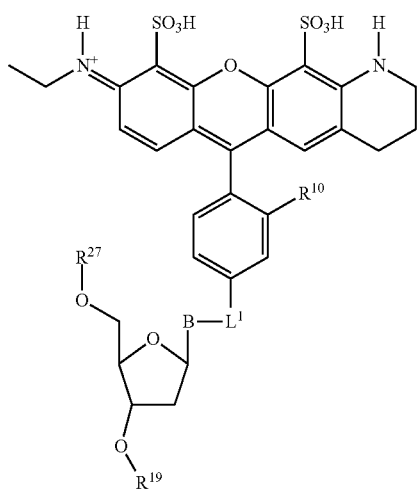
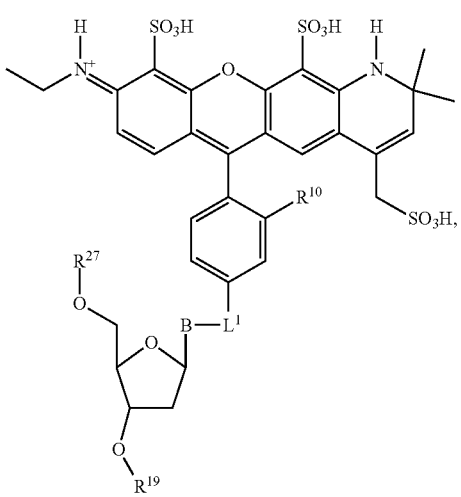

75
-continued
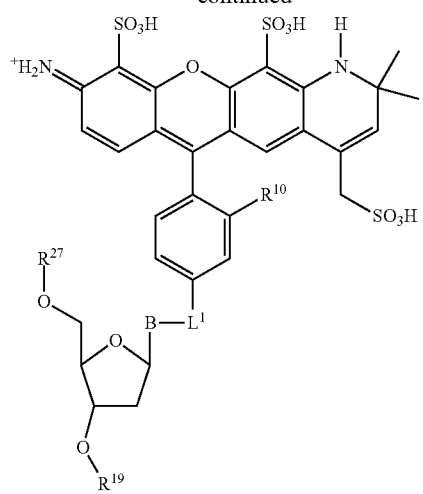
, or
76
-continued
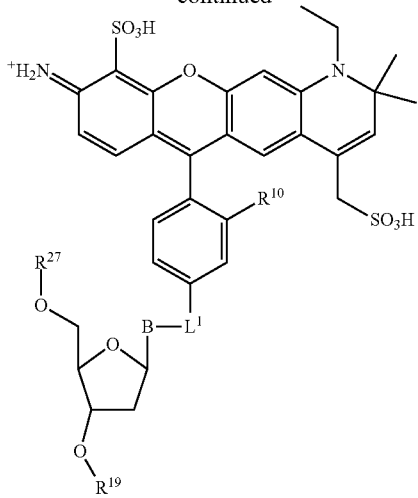
.
In embodiments, the compound is
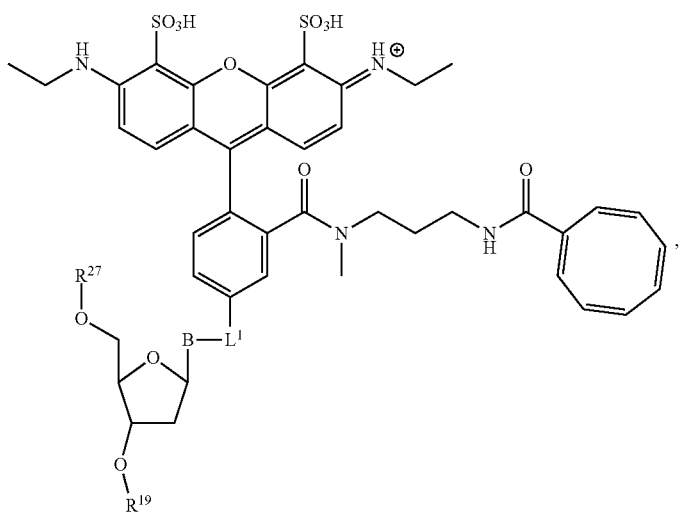
,
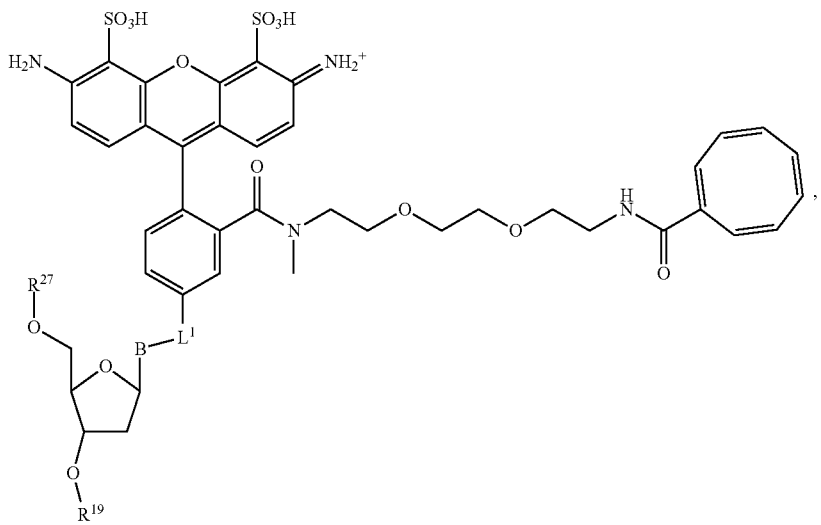
,

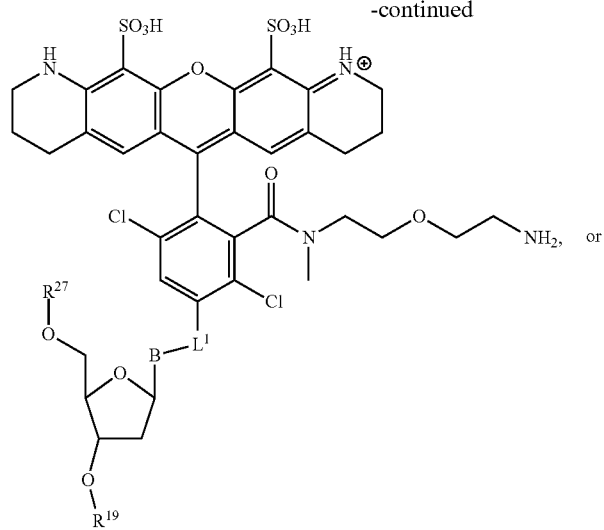
or
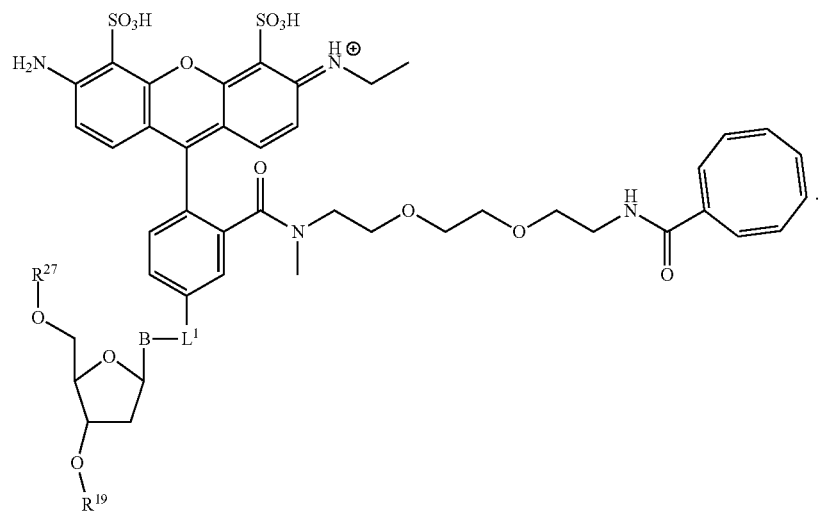
In embodiments, the compound is
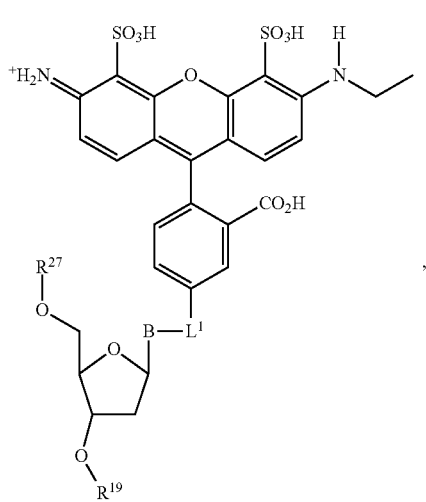
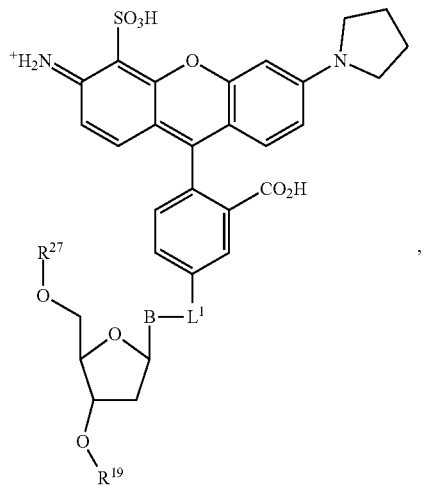

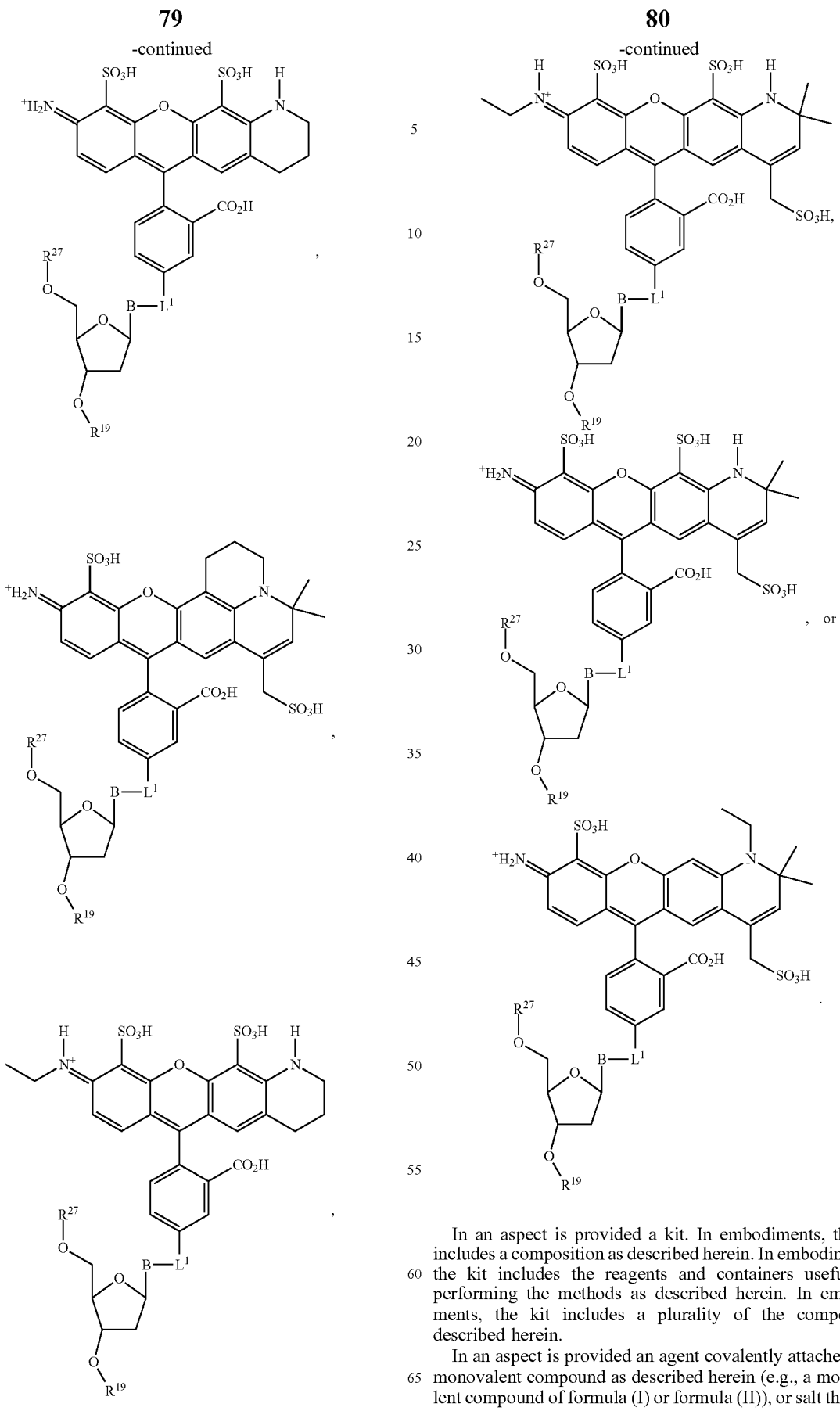

In an aspect is provided a kit. In embodiments, the kit includes a composition as described herein. In embodiments, the kit includes the reagents and containers useful for performing the methods as described herein. In embodiments, the kit includes a plurality of the compounds described herein.

In an aspect is provided an agent covalently attached to a monovalent compound as described herein (e.g., a monovalent compound of formula (I) or formula (II)), or salt thereof. In embodiments, the agent is covalently attached to the monovalent compound via a covalent linker. In embodiments, the covalent linker is a bioconjugate linker, where $R^{13}$ reacts to form part of the covalent linker.

In another aspect is provided a kit including a compound as described herein, or salt thereof, having formula (I):

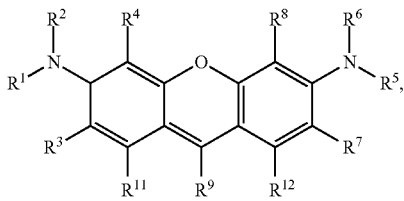

where $R^1$, $R^2$, $R^3$, $R^4$, $R^5$, $R^6$, $R^7$, $R^8$, $R^9$, $R^{11}$, and $R^{12}$ are described herein. In embodiments, the kit further includes a compound having formula:

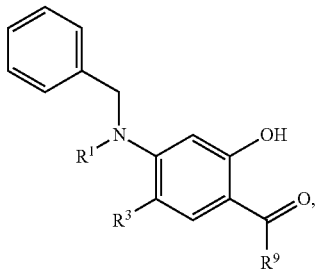

wherein $R^1$, $R^3$, and $R^9$ are as described herein. In embodiments, the kit further includes a compound having formula:

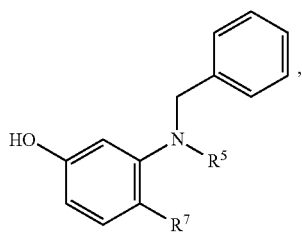

wherein $R^5$ and $R^7$ are as described herein. In embodiments, the kit includes an oleum as described herein. In embodiments, the kit includes a Lewis acid as described herein.

In embodiments, the kit further includes one or more sets of instructions. In embodiments, the kit includes nucleotides or nucleosides. Such kits will generally include at least one modified nucleotide or nucleoside, wherein the modified nucleotide or nucleoside is covalently bound to a compound described herein. In embodiments, the kit may include a modified nucleotide, wherein the modified nucleotide is covalently bound to a compound described herein, and a second modified nucleotide, wherein the second modified nucleotide or nucleoside is covalently bound to a different fluorophore. In embodiments, combinations of nucleotides may be provided as separate individual components or as nucleotide mixtures. In embodiments, the kit may further contain an unlabeled nucleotide. In embodiments, the kit includes a compound described herein covalently bound to a nucleotide (e.g., wherein the $R^{13}$ moiety of a compound described herein has reacted with a bioconjugate reactive group to form a bioconjugate linker thereby covalently bonding the compound described herein to the nucleotide). In embodiments, the kit includes a compound described herein covalently bound to a nucleoside (e.g., wherein the $R^{13}$ moiety of a compound described herein has reacted with a bioconjugate reactive group to form a bioconjugate linker thereby covalently bonding the compound described herein to the nucleoside).

In embodiments, the kit includes a plurality (e.g., two, three, or four) of modified nucleotides, wherein each modified nucleotide is covalently bound to a compound described herein. In embodiments, wherein the kit includes a plurality of modified nucleotides, the different nucleotides may be labelled (e.g., covalently bonded) with different compounds (e.g., compounds described herein) that are spectrally distinguishable compounds. As used herein, the term "spectrally distinguishable compounds" refers to compounds as described herein that emit fluorescent energy at wavelengths that can be distinguished by fluorescent detection equipment when two or more such compounds are present in one sample. In embodiments, when two modified nucleotides, each modified nucleotide covalently bound to a compound described herein, are supplied within a kit, the spectrally distinguishable compounds can be excited at the same wavelength, such as, for example by the same laser. In embodiments, when four modified nucleotides, each modified nucleotide covalently bound to a compound described herein, are supplied within a kit, two of the spectrally distinguishable compounds can both be excited at one wavelength and the other two spectrally distinguishable compounds can both be excited at another wavelength.

In embodiments, the kit may include a DNA polymerase enzyme capable of catalyzing incorporation of the modified nucleotides into a polynucleotide. In embodiments, the kit includes a buffer. In embodiments, the modified nucleotides may be provided in the kit in a concentrated form to be diluted prior to use. In such embodiments, a suitable dilution buffer may also be included.

III. Methods

In an aspect is provided a method of making a compound, or salt thereof, of formula I,

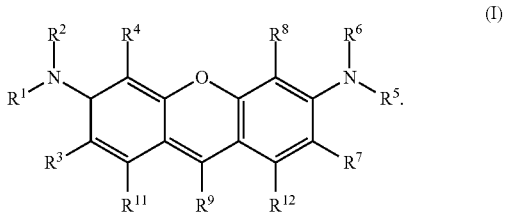

In embodiments, the method includes mixing compound A and compound B together in a reaction vessel at a first temperature to form a dye-intermediate, and adding oleum to the reaction vessel at a second temperature, wherein compound A has the formula:

83

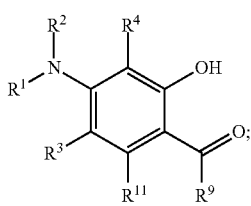

(A)

and compound B has the formula:

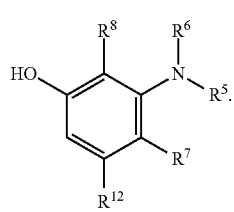

(B)

R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, at least one of R$^1$, R$^2$, R$^5$, or R$^6$ is hydrogen (e.g., wherein R$^1$, R$^2$, R$^5$, or R$^6$ is hydrogen). In embodiments, R$^1$, R$^2$, R$^5$, and R$^6$ are not hydrogen. R$^1$ and R$^2$ substituents bonded to the same nitrogen atom may optionally be joined to form a substituted or unsubstituted heterocycloalkyl, or substituted or unsubstituted heteroaryl. R$^5$ and R$^6$ substituents bonded to the same nitrogen atom may optionally be joined to form a substituted or unsubstituted heterocycloalkyl, or substituted or unsubstituted heteroaryl. R$^2$ and R$^4$ substituents may optionally be joined to form a substituted or unsubstituted heterocycloalkyl, or substituted or unsubstituted heteroaryl. R$^1$ and R$^3$ substituents may optionally be joined to form a substituted or unsubstituted heterocycloalkyl, or substituted or unsubstituted heteroaryl. R$^6$ and R$^8$ substituents may optionally be joined to form a substituted or unsubstituted heterocycloalkyl, or substituted or unsubstituted heteroaryl. R$^5$ and R$^7$ substituents may optionally be joined to form a substituted or unsubstituted heterocycloalkyl, or substituted or unsubstituted heteroaryl. R$^3$, R$^4$, R$^7$, R$^8$, R$^{11}$, and R$^{12}$ are independently hydrogen, —PO$_3$H, —PO$_4$H, —SO$_2$NH$_2$, —SO$_3$H, —SO$_4$H, substituted or unsubstituted alkyl, or substituted or unsubstituted heteroalkyl; wherein R$^3$, R$^4$, R$^7$, or R$^8$ is —SO$_3$H. R$^9$ is substituted or unsubstituted aryl.

In embodiments, compounds or salts herein may be presented with a positive charge, for example,

84

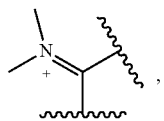

and it is understood an appropriate counter-ion (e.g., chloride ion, fluoride ion, or acetate ion) may also be present, though not explicitly shown. Likewise, for compounds having a negative charge (e.g., 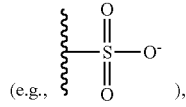 ), it is understood an appropriate counter-ion (e.g., a proton, sodium ion, potassium ion, or ammonium ion) may also be present, though not explicitly shown. The protonation state of the compound (e.g., a compound described herein) depends on the local environment (i.e., the pH of the environment), therefore, in embodiments, the compound may be described as having a moiety in a protonated state (e.g., 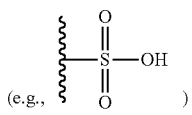 [SMILES: *S(=O)(=O)O] )

or an ionic state (e.g., 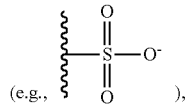 ), and it is understood these are interchangeable. In embodiments, the counter-ion is represented by the symbol M (e.g., M$^+$ or M$^-$). In embodiments, M$^+$ is H$^+$, K$^+$, Na$^+$, NH$_4^+$, Ag$^+$, Cu$^+$, Au$^+$, Li$^+$. In embodiments, M$^-$ is I$^-$, Br$^-$, Cl$^-$, F$^-$, OH$^-$, NO$_2^-$, NO$_3^-$, HCO$_3^-$, MnO$_4^-$, CN$^-$, or ClO$_3^-$.

In embodiments, the counterion is an anion. In embodiments, the anion is monovalent. In embodiments, the anion is polyvalent. In embodiments, the anion is a sulfate, chloride, bromide, iodide, perchlorate, nitrate, trifluoroacetate, hydroxide, hydrosulfide, sulfide, nitrite, carboxylate, dicarboxylate, sulfonate, tetraflouroborate hexaflourophosphate, hypophosphite, phosphate, phosphite, cyanate, cyanide, isocyanate, thiocyanate, tetralkylborate, tetraarylborate or chromate. In embodiments, non-limiting groups of carboxylate include formate, propionate, butyrate, lactate, pyruvate, tartrate, ascorbate, gluconate, glutamate, citrate, succinate, maleate, 4-pyridinecarboxylate, 2-hydroxypropanoate and glucoronate. In embodiments, non-limiting groups of sulfonate include mesylate, tosylate, ethanesulfonate, benzenesulfonate, and triflate. In embodiments, non-limiting groups of tetraalkylborates include tetramethylborate, trimethylethylborate and triethylbutylborate. In embodiments, non-limiting groups of tetraarylborates include tetrakis[3,5-bis(trifluoromethyl)phenyl]borate, tetrakis(4-chlorophenyl)borate, tetrakis(pentafluorophenyl)borate and tetrakis(4-fluorophenyl)borate.

In embodiments, the method further includes reacting the compound of formula (I) with an agent (e.g., an oligonucleotide, antibody, or nucleotide) to covalently attach the compound to the agent (e.g., forming the compound of formula (II)).

In embodiments, the dye-intermediate is not isolated or removed from the reaction vessel prior to adding oleum. In embodiments, the method is a one-pot synthetic protocol. A one-pot synthetic protocol is a chemical synthesis method in which all the steps of a multi-step reaction are combined into a single reaction vessel. This type of protocol can be used to quickly and efficiently synthesize a desired product, often with fewer steps and fewer hazardous byproducts than traditional multi-step protocols. In embodiments, the dye-intermediate has the formula:

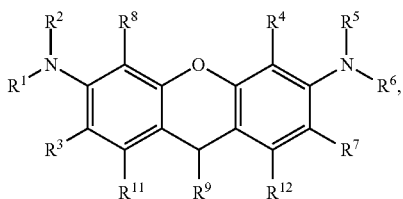

where $R^1$, $R^2$, $R^3$, $R^4$, $R^5$, $R^6$, $R^7$, $R^8$, $R^9$, $R^{11}$, and $R^{12}$ are described herein. In embodiments, the dye-intermediate has the formula:

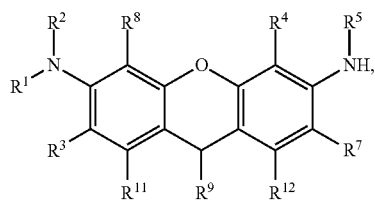

where $R^1$, $R^2$, $R^3$, $R^4$, $R^5$, $R^6$, $R^7$, $R^8$, $R^9$, $R^{11}$, and $R^{12}$ are described herein. In embodiments, the dye-intermediate has the formula:

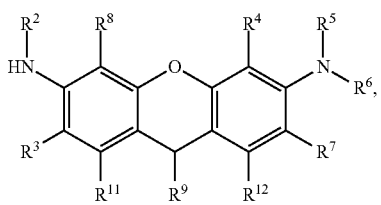

where $R^1$, $R^2$, $R^3$, $R^4$, $R^5$, $R^6$, $R^7$, $R^8$, $R^9$, $R^{11}$, and $R^{12}$ are described herein. In embodiments, the dye-intermediate has the formula:

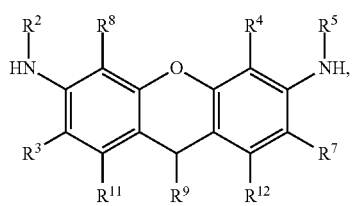

where $R^1$, $R^2$, $R^3$, $R^4$, $R^5$, $R^6$, $R^7$, $R^8$, $R^9$, $R^{11}$, and $R^{12}$ are described herein.

In embodiments, the reaction vessel includes a sulfonic acid (e.g., the reaction vessel includes ethane sulfonic acid, benzene sulfonic acid, toluene sulfonic acid, or methanesulfonic acid). In embodiments, the reaction vessel includes difluoroacetic acid, dichloroacetic acid, ethane sulfonic acid, benzene sulfonic acid, toluene sulfonic acid, methanesulfonic acid, dichlorobenzene, trifluoroacetic acid, polyphosphoric acid. In embodiments, the reaction vessel includes difluoroacetic acid. In embodiments, the reaction vessel includes dichloroacetic acid. In embodiments, the reaction vessel includes ethane sulfonic acid. In embodiments, the reaction vessel includes benzene sulfonic acid. In embodiments, the reaction vessel includes toluene sulfonic acid. In embodiments, the reaction vessel includes methanesulfonic acid. In embodiments, the reaction vessel includes dichlorobenzene. In embodiments, the reaction vessel includes trifluoroacetic acid. In embodiments, the reaction vessel includes polyphosphoric acid.

In embodiments, the reaction vessel includes a Lewis acid. In embodiments, the Lewis acid is aluminum chloride ($AlCl_3$), boron trifluoride ($BF_3$), iron(III) chloride ($FeCl_3$), magnesium chloride ($MgCl_2$), zinc chloride ($ZnCl_2$), chromic acid ($H_2CrO_4$), stannic chloride ($SnCl_4$), stannous chloride ($SnCl_2$), titanium(IV) chloride ($TiCl_4$), or bromotrifluoromethane ($CF_3Br$). In embodiments, the Lewis acid is phosphoryl chloride ($POCl_3$), boron trichloride ($BCl_3$), indium(III) chloride ($InCl_3$), boric acid ($B(OH)_3$), tris(pentafluorophenyl)borane (($C_6F_5)_3B$)), samarium(III) nitrate hexahydrate ($Sm(NO_3)_3$ $6H_2O$), molybdenum(V) chloride ($MoCl_5$), bismuth trichloride ($BiCl_3$), aluminum isopropoxide ($Al[OCH(CH_3)_2]_3$), zirconium tetrachloride ($ZrCl_4$), or lithium borofluoride ($LiBF_4$).

In embodiments, the oleum includes 20% fuming sulfuric acid. In embodiments, the oleum includes 10% fuming sulfuric acid. In embodiments, the oleum includes 30% fuming sulfuric acid. In embodiments, the oleum includes 40% fuming sulfuric acid. In embodiments, the oleum includes 50% fuming sulfuric acid. In embodiments, the oleum includes 60% fuming sulfuric acid. In embodiments, the oleum includes 70% fuming sulfuric acid. In embodiments, the oleum includes 80% fuming sulfuric acid.

In embodiments, the first temperature is about 80° C. to about 180° C. In embodiments, the first temperature is about 80° C. to about 130° C. In embodiments, the first temperature is about 95° C. to about 120° C. In embodiments, the first temperature is about 100° C. In embodiments, the first temperature is about 80° C., 90° C., 100° C., 110° C., 120° C., 130° C., 140° C., 150° C., 160° C., 170° C., or about 180° C.

In embodiments, the second temperature is about 10° C. to about 30° C. In embodiments, the second temperature is about 15° C. to about 25° C. In embodiments, the second temperature is about 20° C. In embodiments, the second temperature is about 15° C., 20° C., 25° C., 30° C., 35° C., or 40° C.

In embodiments, first temperature is about 80° C. to about 130° C., and said second temperature is about 10° C. to about 30° C. In embodiments, the first temperature is about 95° C. to about 120° C., and said second temperature is about 15° C. to about 25° C. In embodiments, the first temperature is about 100° C., and said second temperature is about 20° C.

In embodiments, the first temperature and the second temperature differ by about 50° C. In embodiments, the first temperature and the second temperature differ by about 100°

C. In embodiments, the first temperature and the second temperature differ by about 80° C. In embodiments, the first temperature and the second temperature differ by about 90° C. In embodiments, the first temperature and the second temperature differ by about 75° C. In embodiments, the first temperature and the second temperature differ by about 60° C. In embodiments, the decrease from the first temperature to the second temperature occurs at a controlled rate (i.e., or ΔT/Δt). For example, temperature may be decreased at a rate of about 0.1° C./s to about 5° C./s. In embodiments, temperature may be decreased at a rate of about 0.2° C./s. In embodiments, temperature may be decreased at a rate of about 0.3° C./s. In embodiments, temperature may be decreased at a rate of about 0.4° C./s. In embodiments, temperature may be decreased at a rate of about 0.5° C./s. In embodiments, temperature may be decreased at a rate of about 0.6° C./s. In embodiments, temperature may be decreased at a rate of about 0.75° C./s. In embodiments, temperature may be decreased at a rate of about 1° C./s. In embodiments, temperature may be decreased at a rate of about 1.25° C./s. In embodiments, temperature may be decreased at a rate of about 1.5° C./s. In embodiments, temperature may be decreased at a rate of about 1.75° C./s. In embodiments, temperature may be decreased at a rate of about 2° C./s. In embodiments, temperature may be decreased at a rate of about 2.25° C./s. In embodiments, temperature may be decreased at a rate of about 2.5° C./s. In embodiments, temperature may be decreased at a rate of about 2.75° C./s. In embodiments, temperature may be decreased at a rate of about 3° C./s. In embodiments, temperature may be decreased at a rate of about 3.25° C./s. In embodiments, temperature may be decreased at a rate of about 3.5° C./s. In embodiments, temperature may be decreased at a rate of about 3.75° C./s. In embodiments, temperature may be decreased at a rate of about 4° C./s. In embodiments, temperature may be decreased at a rate of about 4.25° C./s. In embodiments, temperature may be decreased at a rate of about 4.5° C./s. In embodiments, temperature may be decreased at a rate of about 4.75° C./s.

In embodiments, $R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^1$ is hydrogen. In embodiments, $R^1$ is not hydrogen. In embodiments, $R^1$ is $R^{1A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{1A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{1A}$-substituted or unsubstituted cycloalkyl (e.g., $C_3$-$C_8$, $C_3$-$C_6$, or $C_5$-$C_6$), $R^{1A}$-substituted or unsubstituted heterocycloalkyl (e.g., 3 to 8 membered, 3 to 6 membered, or 5 to 6 membered), $R^{1A}$-substituted or unsubstituted aryl (e.g., $C_6$-$C_{10}$, $C_{10}$, or phenyl), or $R^{1A}$-substituted or unsubstituted heteroaryl (e.g., 5 to 10 membered, 5 to 9 membered, or 5 to 6 membered).

$R^{1A}$ is oxo, halogen, —CCl$_3$, —CBr$_3$, —CF$_3$, —CI$_3$, —CHCl$_2$, —CHBr$_2$, —CHF$_2$, —CHI$_2$,
"\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_2$NH$_2$,
"\*MERGEFORMAT\*MERGEFORMAT —NHNH$_2$, —ONH$_2$, —NHC(O)NHNH$_2$, —NHC(O)NH$_2$, —NHSO$_2$H, —NHC(O)H, —NHC(O)OH,
"\*MERGEFORMAT\*MERGEFORMAT —NHOH, —OCCl$_3$, —OCF$_3$, —OCBr$_3$, —OCI$_3$, —OCHCl$_2$, —OCHBr$_2$, —OCHI$_2$, —O CHF$_2$, —OCH$_2$Cl,
"\*MERGEFORMAT\*MERGEFORMAT —OCH$_2$Br, —OCH$_2$I, —OCH$_2$F, —N$_3$, —SF$_5$, —PO$_3$H, —PO$_4$H, —SO$_2$NH$_2$, —SO$_3$H, —S O$_4$H, $R^{1B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{1B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{1B}$-substituted or unsubstituted cycloalkyl (e.g., $C_3$-$C_8$, $C_3$-$C_6$, or $C_5$-$C_6$), $R^{1B}$-substituted or unsubstituted heterocycloalkyl (e.g., 3 to 8 membered, 3 to 6 membered, or 5 to 6 membered), $R^{1B}$-substituted or unsubstituted aryl (e.g., $C_6$-$C_{10}$, $C_{10}$, or phenyl), or $R^{1B}$-substituted or unsubstituted heteroaryl (e.g., 5 to 10 membered, 5 to 9 membered, or 5 to 6 membered). In embodiments, $R^{1A}$ is unsubstituted phenyl.

$R^{1B}$ is oxo, halogen, —CCl$_3$, —CBr$_3$, —CF$_3$, —CI$_3$, —CHCl$_2$, —CHBr$_2$, —CHF$_2$, —CHI$_2$,
"\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H,
"\*MERGEFORMAT\*MERGEFORMAT —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$,
"\*MERGEFORMAT\*MERGEFORMAT —OCH$_2$Cl, —OCH$_2$Br, —OCH$_2$I, —OCH$_2$F, —N$_3$, —SF$_5$, —PO$_3$H, —PO$_4$H, —SO$_2$NH$_2$, —SO$_3$H, —SO$_4$H, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^1$ is hydrogen, or substituted or unsubstituted $C_1$-$C_6$ alkyl. In embodiments, $R^1$ is hydrogen. In embodiments, $R^1$ is substituted or unsubstituted $C_1$-$C_6$alkyl. In embodiments, $R^1$ is substituted or unsubstituted $C_1$ alkyl. In embodiments, $R^1$ is substituted or unsubstituted $C_2$ alkyl. In embodiments, $R^1$ is substituted or unsubstituted $C_3$ alkyl. In embodiments, $R^1$ is substituted or unsubstituted $C_4$ alkyl. In embodiments, $R^1$ is substituted or unsubstituted $C_5$ alkyl. In embodiments, $R^1$ is substituted or unsubstituted $C_6$ alkyl. In embodiments, $R^1$ is substituted $C_1$ alkyl. In embodiments, $R^1$ is substituted $C_2$ alkyl. In embodiments, $R^1$ is substituted $C_3$ alkyl. In embodiments, $R^1$ is substituted $C_4$ alkyl. In embodiments, $R^1$ is substituted $C_5$ alkyl. In embodiments, $R^1$ is substituted $C_6$ alkyl. In embodiments, $R^1$ is unsubstituted $C_1$ alkyl. In embodiments, $R^1$ is unsubstituted $C_2$ alkyl. In embodiments, $R^1$ is unsubstituted $C_3$ alkyl. In embodiments, $R^1$ is unsubstituted $C_4$ alkyl. In embodiments, $R^1$ is unsubstituted $C_5$ alkyl. In embodiments, $R^1$ is unsubstituted $C_6$ alkyl. In embodiments, $R^1$ is $R^{1A}$-substituted or unsubstituted alkyl (e.g., $C_1$-$C_6$ alkyl), wherein $R^{1A}$ is independently —PO$_3$H, —PO$_4$H, —SO$_2$NH$_2$, —SO$_3$H, or —SO$_4$H. In embodiments, $R^1$ is

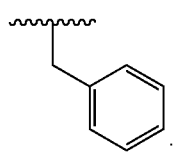 [SMILES: *Cc1ccccc1]

In embodiments, $R^1$ is hydrogen, substituted or unsubstituted $C_1$-$C_6$ alkyl, or substituted or unsubstituted 2 to 6 membered heteroalkyl. In embodiments, $R^1$ is substituted or unsubstituted $C_1$-$C_6$ alkyl. In embodiments, $R^1$ is substituted or unsubstituted 2 to 6 membered heteroalkyl.

In embodiments, $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^2$ is hydrogen. In embodiments, $R^2$ is $R^{2A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2A}$-substituted or unsubstituted heteroalkyl (e.g., 2 to membered, 8 to 20 membered, 2 to 10 membered, 2 to 8 membered, 2 to 6 membered, or 2 to 4 membered), $R^{2A}$-substituted or unsubstituted cycloalkyl (e.g., $C_3$-$C_8$, $C_3$-$C_6$, or $C_5$-$C_6$), $R^{2A}$-substituted or unsubstituted heterocycloalkyl (e.g., 3 to 8 membered, 3 to 6 membered, or 5 to 6 membered), $R^{2A}$-substituted or unsubstituted aryl (e.g., $C_6$-$C_{10}$, $C_{10}$, or phenyl), or $R^{2A}$-substituted or unsubstituted heteroaryl (e.g., 5 to 10 membered, 5 to 9 membered, or 5 to 6 membered).

$R^{2A}$ is oxo, halogen, —CCl$_3$, —CBr$_3$, —CF$_3$, —CI$_3$, —CHCl$_2$, —CHBr$_2$, —CHF$_2$, —CHI$_2$,
"\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_2$NH$_2$,
"\*MERGEFORMAT\*MERGEFORMAT —NHNH$_2$, —ONH$_2$, —NHC(O)NHNH$_2$, —NHC(O)NH$_2$, —NHSO$_2$H, —NHC(O)H, —NHC(O)OH,
"\*MERGEFORMAT\*MERGEFORMAT —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl,
"\*MERGEFORMAT\*MERGEFORMAT —OCH$_2$Br, —OCH$_2$I, —OCH$_2$F, —N$_3$, —SF$_5$, —PO$_3$H, —PO$_4$H, —SO$_2$NH$_2$, —SO$_3$H, —SO$_4$H, $R^{2B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{2B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{2B}$-substituted or unsubstituted cycloalkyl (e.g., $C_3$-$C_8$, $C_3$-$C_6$, or $C_5$-$C_6$), $R^{2B}$-substituted or unsubstituted heterocycloalkyl (e.g., 3 to 8 membered, 3 to 6 membered, or 5 to 6 membered), $R^{2B}$-substituted or unsubstituted aryl (e.g., $C_6$-$C_{10}$, $C_{10}$, or phenyl), or $R^{2B}$-substituted or unsubstituted heteroaryl (e.g., 5 to 10 membered, 5 to 9 membered, or 5 to 6 membered). In embodiments, $R^{23}$ is unsubstituted phenyl.

$R^{2B}$ is oxo, halogen, —CCl$_3$, —CBr$_3$, —CF$_3$, —CI$_3$, —CHCl$_2$, —CHBr$_2$, —CHF$_2$, —CHI$_2$,
"\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H,
"\*MERGEFORMAT\*MERGEFORMAT —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$,
"\*MERGEFORMAT\*MERGEFORMAT —OCH$_2$Cl, —OCH$_2$Br, —OCH$_2$I, —OCH$_2$F, —N$_3$, —SF$_5$, —PO$_3$H, —PO$_4$H, —SO$_2$NH$_2$, —SO$_3$H, —SO$_4$H, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^2$ is hydrogen, or substituted or unsubstituted $C_1$-$C_6$ alkyl. In embodiments, $R^2$ is hydrogen. In embodiments, $R^2$ is substituted or unsubstituted $C_1$-$C_6$ alkyl. In embodiments, $R^2$ is substituted or unsubstituted $C_1$ alkyl. In embodiments, $R^2$ is substituted or unsubstituted $C_2$ alkyl. In embodiments, $R^2$ is substituted or unsubstituted $C_3$ alkyl. In embodiments, $R^2$ is substituted or unsubstituted $C_4$ alkyl. In embodiments, $R^2$ is substituted or unsubstituted $C_5$ alkyl. In embodiments, $R^2$ is substituted or unsubstituted $C_6$ alkyl. In embodiments, $R^2$ is substituted $C_1$ alkyl. In embodiments, $R^2$ is substituted $C_2$ alkyl. In embodiments, $R^2$ is substituted $C_3$ alkyl. In embodiments, $R^2$ is substituted $C_4$ alkyl. In embodiments, $R^2$ is substituted $C_5$ alkyl. In embodiments, $R^2$ is substituted $C_6$ alkyl. In embodiments, $R^2$ is unsubstituted $C_1$ alkyl. In embodiments, $R^2$ is unsubstituted $C_2$ alkyl. In embodiments, $R^2$ is unsubstituted $C_3$ alkyl. In embodiments, $R^2$ is unsubstituted $C_4$ alkyl. In embodiments, $R^2$ is unsubstituted $C_5$ alkyl. In embodiments, $R^2$ is unsubstituted $C_6$ alkyl. In embodiments, $R^2$ is $R^{2A}$-substituted or unsubstituted alkyl (e.g., $C_1$-$C_6$ alkyl), wherein $R^{2A}$ is independently —PO$_3$H, —PO$_4$H, —SO$_2$NH$_2$, —SO$_3$H, or —SO$_4$H. In embodiments, $R^2$ is

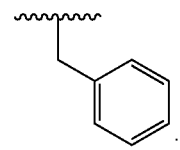

In embodiments, $R^2$ is hydrogen, substituted or unsubstituted $C_1$-$C_6$ alkyl, or substituted or unsubstituted 2 to 6 membered heteroalkyl. In embodiments, $R^2$ is substituted or unsubstituted $C_1$-$C_6$ alkyl. In embodiments, $R^2$ is substituted or unsubstituted 2 to 6 membered heteroalkyl.

In embodiments, $R^5$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^5$ is hydrogen. In embodiments, $R^5$ is $R^{5A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{5A}$-substituted or unsubstituted heteroalkyl (e.g., 2 to membered, 8 to 20 membered, 2 to 10 membered, 2 to 8 membered, 2 to 6 membered, or 2 to 4 membered), $R^{5A}$-substituted or unsubstituted cycloalkyl (e.g., $C_3$-$C_8$, $C_3$-$C_6$, or $C_5$-$C_6$), $R^{5A}$-substituted or unsubstituted heterocycloalkyl (e.g., 3 to 8 membered, 3 to 6 membered, or 5 to 6 membered), $R^{5A}$-substituted or unsubstituted aryl (e.g., $C_6$-$C_{10}$, $C_{10}$, or phenyl), $R^{5A}$-substituted or unsubstituted heteroaryl (e.g., 5 to 10 membered, 5 to 9 membered, or 5 to 6 membered).

$R^{5A}$ is oxo, halogen, —CCl$_3$, —CBr$_3$, —CF$_3$, —CI$_3$, —CHCl$_2$, —CHBr$_2$, —CHF$_2$, —CHI$_2$, "\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_2$NH$_2$, "\*MERGEFORMAT\*MERGEFORMAT —NHNH$_2$, —ONH$_2$, —NHC(O)NHNH$_2$, —NHC(O)NH$_2$, —NHSO$_2$H, —NHC(O)H, —NHC(O)OH, "\*MERGEFORMAT\*MERGEFORMAT —NHOH, —OCCl$_3$, —OCF$_3$, —OCBr$_3$, —OCI$_3$, —OCHCl$_2$, —OCHBr$_2$, —OCHI$_2$, —O CHF$_2$, —OCH$_2$Cl, "\*MERGEFORMAT\*MERGEFORMAT —OCH$_2$Br, —OCH$_2$I, —OCH$_2$F, —N$_3$, —SF$_5$, —PO$_3$H, —PO$_4$H, —SO$_2$NH$_2$, —SO$_3$H, —S O$_4$H, $R^{5B}$-substituted or unsubstituted alkyl (e.g., $C_1$-$C_{20}$, $C_1$-$C_{20}$, $C_1$-$C_8$, $C_1$-$C_6$, or $C_1$-$C_4$), $R^{5B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{5B}$-substituted or unsubstituted cycloalkyl (e.g., $C_3$-$C_8$, $C_3$-$C_6$, or $C_5$-$C_6$), $R^{5B}$-substituted or unsubstituted heterocycloalkyl (e.g., 3 to 8 membered, 3 to 6 membered, or 5 to 6 membered), $R^{5B}$-substituted or unsubstituted aryl (e.g., $C_6$-$C_{10}$, $C_{10}$, or phenyl), or $R^{5B}$-substituted or unsubstituted heteroaryl (e.g., 5 to 10 membered, 5 to 9 membered, or 5 to 6 membered). In embodiments, $R^{5A}$ is unsubstituted phenyl.

$R^{5B}$ is oxo, halogen, —CCl$_3$, —CBr$_3$, —CF$_3$, —CI$_3$, —CHCl$_2$, —CHBr$_2$, —CHF$_2$, —CHI$_2$, "\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, "\*MERGEFORMAT\*MERGEFORMAT —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, "\*MERGEFORMAT\*MERGEFORMAT —OCH$_2$Cl, —OCH$_2$Br, —OCH$_2$I, —OCH$_2$F, —N$_3$, —SF$_5$, —PO$_3$H, —PO$_4$H, —SO$_2$NH$_2$, —SO$_3$H, —SO$_4$H, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^5$ is hydrogen, or substituted or unsubstituted $C_1$-$C_6$ alkyl. In embodiments, $R^5$ is hydrogen. In embodiments, $R^5$ is substituted or unsubstituted $C_1$-$C_6$ alkyl. In embodiments, $R^5$ is substituted or unsubstituted $C_1$ alkyl. In embodiments, $R^5$ is substituted or unsubstituted $C_2$ alkyl. In embodiments, $R^5$ is substituted or unsubstituted $C_3$ alkyl. In embodiments, $R^5$ is substituted or unsubstituted $C_4$ alkyl. In embodiments, $R^5$ is substituted or unsubstituted $C_5$ alkyl. In embodiments, $R^5$ is substituted $C_1$ alkyl. In embodiments, $R^5$ is substituted $C_2$ alkyl. In embodiments, $R^5$ is substituted $C_3$ alkyl. In embodiments, $R^5$ is substituted $C_4$ alkyl. In embodiments, $R^5$ is substituted $C_5$ alkyl. In embodiments, $R^5$ is substituted $C_6$ alkyl. In embodiments, $R^5$ is unsubstituted $C_1$ alkyl. In embodiments, $R^5$ is unsubstituted $C_2$ alkyl. In embodiments, $R^5$ is unsubstituted $C_3$ alkyl. In embodiments, $R^5$ is unsubstituted $C_4$ alkyl. In embodiments, $R^5$ is unsubstituted $C_5$ alkyl. In embodiments, $R^5$ is unsubstituted $C_6$ alkyl. In embodiments, $R^5$ is $R^{5A}$-substituted or unsubstituted alkyl (e.g., $C_1$-$C_6$ alkyl), wherein $R^{5A}$ is independently —PO$_3$H, —PO$_4$H, —SO$_2$NH$_2$, —SO$_3$H, or —SO$_4$H. In embodiments, $R^5$ is

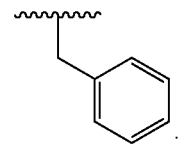

In embodiments, $R^5$ is hydrogen, substituted or unsubstituted $C_1$-$C_6$ alkyl, or substituted or unsubstituted 2 to 6 membered heteroalkyl. In embodiments, $R^5$ is substituted or unsubstituted $C_1$-$C_6$ alkyl. In embodiments, $R^5$ is substituted or unsubstituted 2 to 6 membered heteroalkyl.

In embodiments, $R^6$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^6$ is hydrogen. In embodiments, $R^6$ is $R^{6A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{6A}$-substituted or unsubstituted heteroalkyl (e.g., 2 to membered, 8 to 20 membered, 2 to 10 membered, 2 to 8 membered, 2 to 6 membered, or 2 to 4 membered), $R^{6A}$-substituted or unsubstituted cycloalkyl (e.g., $C_3$-$C_8$, $C_3$-$C_6$, or $C_5$-$C_6$), $R^{6A}$-substituted or unsubstituted heterocycloalkyl (e.g., 3 to 8 membered, 3 to 6 membered, or 5 to 6 membered), $R^{6A}$-substituted or unsubstituted aryl (e.g., $C_6$-$C_{10}$, $C_{10}$, or phenyl), $R^{6A}$-substituted or unsubstituted heteroaryl (e.g., 5 to 10 membered, 5 to 9 membered, or 5 to 6 membered).

$R^{6A}$ is oxo, halogen, —CCl$_3$, —CBr$_3$, —CF$_3$, —CI$_3$, —CHCl$_2$, —CHBr$_2$, —CHF$_2$, —CHI$_2$, "\*MERGEFORMAT\*MERGEFORMAT —CH$_2$Cl, —CH$_2$Br, —CH$_2$F, —CH$_2$I, —CN, —OH, —NH$_2$, —COOH, —CONH$_2$, —NO$_2$, —SH, —SO$_2$NH$_2$, "\*MERGEFORMAT\*MERGEFORMAT —NHNH$_2$, —ONH$_2$, —NHC(O)NHNH$_2$, —NHC(O)NH$_2$, —NHSO$_2$H, —NHC(O)H, —NHC(O)OH, "\*MERGEFORMAT\*MERGEFORMAT —NHOH, —OCCl$_3$, —OCF$_3$, —OCBr$_3$, —OCI$_3$, —OCHCl$_2$, —OCHBr$_2$, —OCHI$_2$, —O CHF$_2$, —OCH$_2$Cl, "\*MERGEFORMAT\*MERGEFORMAT —OCH$_2$Br, —OCH$_2$I, —OCH$_2$F, —N$_3$, —SF$_5$, —PO$_3$H, —PO$_4$H, —SO$_2$NH$_2$, —SO$_3$H, —S O$_4$H, $R^{6B}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{6B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{6B}$-substituted or unsubstituted cycloalkyl (e.g., $C_3$-$C_8$, $C_3$-$C_6$, or $C_5$-$C_6$), $R^{6B}$-substituted or unsubstituted heterocycloalkyl (e.g., 3 to 8 membered, 3 to 6 membered, or 5 to 6 membered), $R^{6B}$-substituted or unsubstituted aryl (e.g., $C_6$-$C_{10}$, $C_{10}$, or phenyl), or $R^{6B}$-substituted or unsubstituted heteroaryl (e.g., 5 to 10 membered, 5 to 9 membered, or 5 to 6 membered). In embodiments, $R^{6A}$ is unsubstituted phenyl.

$R^{6B}$ is oxo, halogen, $-CCl_3$, $-CBr_3$, $-CF_3$, $-CI_3$, $-CHCl_2$, $-CHBr_2$, $-CHF_2$, $-CHI_2$, "\*MERGEFORMAT\*MERGEFORMAT $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, "\*MERGEFORMAT\*MERGEFORMAT $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, "\*MERGEFORMAT\*MERGEFORMAT $-OCH_2Cl$, $-OCH_2Br$, $-OCH_2I$, $-OCH_2F$, $-N_3$, $-SF_5$, $-PO_3H$, $-PO_4H$, $-SO_2NH_2$, $-SO_3H$, $-SO_4H$, unsubstituted alkyl (e.g., $C_1-C_{20}$, $C_{10}-C_{20}$, $C_1-C_8$, $C_1-C_6$, or $C_1-C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3-C_5$, $C_3-C_6$, or $C_5-C_6$), unsubstituted heterocycloalkyl (e.g., 3 to 8 membered, 3 to 6 membered, or 5 to 6 membered), unsubstituted aryl (e.g., $C_6-C_{10}$, $C_{10}$, or phenyl), or unsubstituted heteroaryl (e.g., 5 to 10 membered, 5 to 9 membered, or 5 to 6 membered).

In embodiments, $R^6$ is hydrogen, or substituted or unsubstituted $C_1-C_6$ alkyl. In embodiments, $R^6$ is hydrogen. In embodiments, $R^6$ is substituted or unsubstituted $C_1-C_6$ alkyl. In embodiments, $R^6$ is substituted or unsubstituted $C_1$ alkyl. In embodiments, $R^6$ is substituted or unsubstituted $C_2$ alkyl. In embodiments, $R^6$ is substituted or unsubstituted $C_3$ alkyl. In embodiments, $R^6$ is substituted or unsubstituted $C_4$ alkyl. In embodiments, $R^6$ is substituted or unsubstituted $C_5$ alkyl. In embodiments, $R^6$ is substituted or unsubstituted $C_6$ alkyl. In embodiments, $R^6$ is substituted $C_1$ alkyl. In embodiments, $R^6$ is substituted $C_2$ alkyl. In embodiments, $R^6$ is substituted $C_3$ alkyl. In embodiments, $R^6$ is substituted $C_4$ alkyl. In embodiments, $R^6$ is substituted $C_5$ alkyl. In embodiments, $R^6$ is substituted $C_6$ alkyl. In embodiments, $R^6$ is unsubstituted $C_1$ alkyl. In embodiments, $R^6$ is unsubstituted $C_2$ alkyl. In embodiments, $R^6$ is unsubstituted $C_3$ alkyl. In embodiments, $R^6$ is unsubstituted $C_4$ alkyl. In embodiments, $R^6$ is unsubstituted $C_5$ alkyl. In embodiments, $R^6$ is unsubstituted $C_6$ alkyl. In embodiments, $R^6$ is $R^{6A}$-substituted or unsubstituted alkyl (e.g., $C_1-C_6$ alkyl), wherein $R^{6A}$ is independently $-PO_3H$, $-PO_4H$, $-SO_2NH_2$, $-SO_3H$, or $-SO_4H$. In embodiments, $R^6$ is

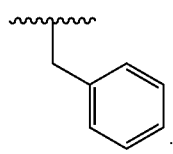 [SMILES: *Cc1ccccc1]

In embodiments, $R^6$ is hydrogen, substituted or unsubstituted $C_1-C_6$ alkyl, or substituted or unsubstituted 2 to 6 membered heteroalkyl. In embodiments, $R^6$ is substituted or unsubstituted $C_1-C_6$ alkyl. In embodiments, $R^6$ is substituted or unsubstituted 2 to 6 membered heteroalkyl.

In embodiments, at least one of $R^1$, $R^2$, $R^5$, or $R^6$ is hydrogen (e.g., wherein $R^1$, $R^2$, $R^5$, or $R^6$ is hydrogen). In embodiments, $R^1$ is hydrogen. In embodiments, $R^2$ is hydrogen. In embodiments, $R^5$ is hydrogen. In embodiments, $R^6$ is hydrogen. In embodiments, $R^1$ and $R^2$ are hydrogen. In embodiments, $R^1$ and $R^5$ are hydrogen. In embodiments, $R^1$ and $R^6$ are hydrogen. In embodiments, $R^2$ and $R^5$ are hydrogen. In embodiments, $R^2$ and $R^6$ are hydrogen. In embodiments, $R^5$ and $R^6$ are hydrogen. In embodiments, $R^1$ and $R^2$ are hydrogen and $R^5$ and $R^6$ are not hydrogen. In embodiments, $R^1$ and $R^5$ are hydrogen and $R^2$ and $R^6$ are not hydrogen. In embodiments, $R^1$ and $R^6$ are hydrogen and $R^2$ and $R^5$ are not hydrogen. In embodiments, $R^2$ and $R^5$ are hydrogen and $R^1$ and $R^6$ are not hydrogen. In embodiments, $R^2$ and $R^6$ are hydrogen and $R^1$ and $R^5$ are not hydrogen. In embodiments, $R^5$ and $R^6$ are hydrogen and $R^1$ and $R^2$ are not hydrogen. In embodiments, $R^1$ is not hydrogen. In embodiments, $R^2$ is not hydrogen. In embodiments, $R^5$ is not hydrogen. In embodiments, $R^6$ is not hydrogen. In embodiments, $R^1$, $R^2$, $R^5$, and $R^6$ are not hydrogen.

In embodiments, $R^1$ and $R^2$ substituents bonded to the same nitrogen atom may be joined to form a substituted or unsubstituted heterocycloalkyl, or substituted or unsubstituted heteroaryl. In embodiments, $R^1$ and $R^2$ substituents bonded to the same nitrogen atom may be joined to form a substituted or unsubstituted 3 to 6 membered heterocycloalkyl. In embodiments, $R^1$ and $R^2$ substituents bonded to the same nitrogen atom may be joined to form a substituted or unsubstituted 3 membered heterocycloalkyl. In embodiments, $R^1$ and $R^2$ substituents bonded to the same nitrogen atom may be joined to form a substituted or unsubstituted 4 membered heterocycloalkyl. In embodiments, $R^1$ and $R^2$ substituents bonded to the same nitrogen atom may be joined to form a substituted or unsubstituted 5 membered heterocycloalkyl. In embodiments, $R^1$ and $R^2$ substituents bonded to the same nitrogen atom may be joined to form a substituted or unsubstituted 6 membered heterocycloalkyl.

In embodiments, $R^1$ and $R^2$ substituents bonded to the same nitrogen atom may be joined to form a substituted or unsubstituted 3 to 6 membered heterocycloalkyl. In embodiments, $R^1$ and $R^2$ substituents bonded to the same nitrogen atom may be joined to form a substituted or unsubstituted 3 membered heterocycloalkyl. In embodiments, $R^1$ and $R^2$ substituents bonded to the same nitrogen atom may be joined to form a substituted or unsubstituted 4 membered heterocycloalkyl. In embodiments, $R^1$ and $R^2$ substituents bonded to the same nitrogen atom may be joined to form a substituted or unsubstituted 5 membered heterocycloalkyl. In embodiments, $R^1$ and $R^2$ substituents bonded to the same nitrogen atom may be joined to form a substituted or unsubstituted 6 membered heterocycloalkyl. In embodiments, $R^1$ and $R^2$ substituents bonded to the same nitrogen atom may be joined to form an unsubstituted 3 to 6 membered heterocycloalkyl. In embodiments, $R^1$ and $R^2$ substituents bonded to the same nitrogen atom may be joined to form an unsubstituted 3 membered heterocycloalkyl. In embodiments, $R^1$ and $R^2$ substituents bonded to the same nitrogen atom may be joined to form an unsubstituted 4 membered heterocycloalkyl. In embodiments, $R^1$ and $R^2$ substituents bonded to the same nitrogen atom may be joined to form an unsubstituted 5 membered heterocycloalkyl. In embodiments, $R^1$ and $R^2$ substituents bonded to the same nitrogen atom may be joined to form an unsubstituted 6 membered heterocycloalkyl. In embodiments, $R^1$ and $R^2$ substituents bonded to the same nitrogen atom may be joined to form a substituted 3 to 6 membered heterocycloalkyl. In embodiments, $R^1$ and $R^2$ substituents bonded to the same nitrogen atom may be joined to form a substituted 3 membered heterocycloalkyl. In embodiments, $R^1$ and $R^2$ substituents bonded to the same nitrogen atom may be joined to form a substituted 4 membered heterocycloalkyl. In embodiments, $R^1$ and $R^2$ substituents bonded to the same nitrogen atom may be joined to form a substituted 5 membered heterocycloalkyl. In embodiments, $R^1$ and $R^2$ substituents bonded to the same nitrogen atom may be joined to form a substituted 6 membered heterocycloalkyl.

In embodiments, $R^1$ and $R^2$ substituents bonded to the same nitrogen atom may be joined to form an $R^{1A}$-substituted or unsubstituted 3 to 6 membered heterocycloalkyl. In embodiments, $R^1$ and $R^2$ substituents bonded to the same nitrogen atom may be joined to form an $R^{1A}$-substituted or unsubstituted 3 membered heterocycloalkyl. In embodiments, $R^1$ and $R^2$ substituents bonded to the same nitrogen atom may be joined to form an $R^{1A}$-substituted or unsubstituted 4 membered heterocycloalkyl. In embodiments, $R^1$ and $R^2$ substituents bonded to the same nitrogen atom may be joined to form an $R^{1A}$-substituted or unsubstituted 5 membered heterocycloalkyl. In embodiments, $R^1$ and $R^2$ substituents bonded to the same nitrogen atom may be joined to form an $R^{1A}$-substituted or unsubstituted 6 membered heterocycloalkyl. In embodiments, $R^1$ and $R^2$ substituents bonded to the same nitrogen atom may be joined to form an $R^{1A}$-substituted 3 to 6 membered heterocycloalkyl. In embodiments, $R^1$ and $R^2$ substituents bonded to the same nitrogen atom may be joined to form an $R^{1A}$-substituted 3 membered heterocycloalkyl. In embodiments, $R^1$ and $R^2$ substituents bonded to the same nitrogen atom may be joined to form an $R^{1A}$-substituted 4 membered heterocycloalkyl. In embodiments, $R^1$ and $R^2$ substituents bonded to the same nitrogen atom may be joined to form an $R^{1A}$-substituted 5 membered heterocycloalkyl. In embodiments, $R^1$ and $R^2$ substituents bonded to the same nitrogen atom may be joined to form an $R^{1A}$-substituted 6 membered heterocycloalkyl.

In embodiments, $R^5$ and $R^6$ substituents bonded to the same nitrogen atom may be joined to form a substituted or unsubstituted heterocycloalkyl, or substituted or unsubstituted heteroaryl. In embodiments, $R^5$ and $R^6$ substituents bonded to the same nitrogen atom may be joined to form a substituted or unsubstituted 3 to 6 membered heterocycloalkyl. In embodiments, $R^5$ and $R^6$ substituents bonded to the same nitrogen atom may be joined to form a substituted or unsubstituted 3 membered heterocycloalkyl. In embodiments, $R^5$ and $R^6$ substituents bonded to the same nitrogen atom may be joined to form a substituted or unsubstituted 4 membered heterocycloalkyl. In embodiments, $R^5$ and $R^6$ substituents bonded to the same nitrogen atom may be joined to form a substituted or unsubstituted 5 membered heterocycloalkyl. In embodiments, $R^5$ and $R^6$ substituents bonded to the same nitrogen atom may be joined to form a substituted or unsubstituted 6 membered heterocycloalkyl. In embodiments, $R^5$ and $R^6$ substituents bonded to the same nitrogen atom may be joined to form a substituted or unsubstituted 3 to 6 membered heterocycloalkyl. In embodiments, $R^5$ and $R^6$ substituents bonded to the same nitrogen atom may be joined to form a substituted or unsubstituted 3 membered heterocycloalkyl. In embodiments, $R^5$ and $R^6$ substituents bonded to the same nitrogen atom may be joined to form a substituted or unsubstituted 4 membered heterocycloalkyl. In embodiments, $R^5$ and $R^6$ substituents bonded to the same nitrogen atom may be joined to form a substituted or unsubstituted 5 membered heterocycloalkyl. In embodiments, $R^5$ and $R^6$ substituents bonded to the same nitrogen atom may be joined to form a substituted or unsubstituted 6 membered heterocycloalkyl. In embodiments, $R^5$ and $R^6$ substituents bonded to the same nitrogen atom may be joined to form an unsubstituted 3 to 6 membered heterocycloalkyl. In embodiments, $R^5$ and $R^6$ substituents bonded to the same nitrogen atom may be joined to form an unsubstituted 3 membered heterocycloalkyl. In embodiments, $R^5$ and $R^6$ substituents bonded to the same nitrogen atom may be joined to form an unsubstituted 4 membered heterocycloalkyl. In embodiments, $R^5$ and $R^6$ substituents bonded to the same nitrogen atom may be joined to form an unsubstituted 5 membered heterocycloalkyl. In embodiments, $R^5$ and $R^6$ substituents bonded to the same nitrogen atom may be joined to form an unsubstituted 6 membered heterocycloalkyl. In embodiments, $R^5$ and $R^6$ substituents bonded to the same nitrogen atom may be joined to form a substituted 3 to 6 membered heterocycloalkyl. In embodiments, $R^5$ and $R^6$ substituents bonded to the same nitrogen atom may be joined to form a substituted 3 membered heterocycloalkyl. In embodiments, $R^5$ and $R^6$ substituents bonded to the same nitrogen atom may be joined to form a substituted 4 membered heterocycloalkyl. In embodiments, $R^5$ and $R^6$ substituents bonded to the same nitrogen atom may be joined to form a substituted 5 membered heterocycloalkyl. In embodiments, $R^5$ and $R^6$ substituents bonded to the same nitrogen atom may be joined to form a substituted 6 membered heterocycloalkyl.

In embodiments, $R^5$ and $R^6$ substituents bonded to the same nitrogen atom may be joined to form an $R^{5A}$-substituted or unsubstituted 3 to 6 membered heterocycloalkyl. In embodiments, $R^5$ and $R^6$ substituents bonded to the same nitrogen atom may be joined to form an $R^{5A}$-substituted or unsubstituted 3 membered heterocycloalkyl. In embodiments, $R^5$ and $R^6$ substituents bonded to the same nitrogen atom may be joined to form an $R^{5A}$-substituted or unsubstituted 4 membered heterocycloalkyl. In embodiments, $R^5$ and $R^6$ substituents bonded to the same nitrogen atom may be joined to form an $R^{5A}$-substituted or unsubstituted 5 membered heterocycloalkyl. In embodiments, $R^5$ and $R^6$ substituents bonded to the same nitrogen atom may be joined to form an $R^{5A}$-substituted or unsubstituted 6 membered heterocycloalkyl. In embodiments, $R^5$ and $R^6$ substituents bonded to the same nitrogen atom may be joined to form an $R^{5A}$-substituted 3 to 6 membered heterocycloalkyl. In embodiments, $R^5$ and $R^6$ substituents bonded to the same nitrogen atom may be joined to form an $R^{5A}$-substituted 3 membered heterocycloalkyl. In embodiments, $R^5$ and $R^6$ substituents bonded to the same nitrogen atom may be joined to form an $R^{5A}$-substituted 4 membered heterocycloalkyl. In embodiments, $R^5$ and $R^6$ substituents bonded to the same nitrogen atom may be joined to form an $R^{5A}$-substituted 5 membered heterocycloalkyl. In embodiments, $R^5$ and $R^6$ substituents bonded to the same nitrogen atom may be joined to form an $R^{5A}$-substituted 6 membered heterocycloalkyl.

In embodiments, $R^3$ is hydrogen, —$PO_3H$, —$PO_4H$, —$SO_2NH_2$, —$SO_3H$, —$SO_4H$, $R^{3A}$-substituted or unsubstituted alkyl (e.g., $C_1$-$C_8$, $C_1$-$C_6$, $C_1$-$C_4$, or $C_1$-$C_2$), or $R^{3A}$-substituted or unsubstituted heteroalkyl (e.g., 2 to 8 membered, 2 to 6 membered, 4 to 6 membered, 2 to 3 membered, or 4 to 5 membered). In embodiments, $R^3$ is hydrogen. In embodiments, $R^3$ is —$PO_3H$. In embodiments, $R^3$ is —$PO_4H$. In embodiments, $R^3$ is —$SO_2NH_2$. In embodiments, $R^3$ is —$SO_3H$. In embodiments, $R^3$ is —$SO_4H$. $R^{3A}$ is oxo, halogen, —$CF_3$, —$CCl_3$, —$CI_3$, —$CBr_3$, —$CHF_2$, —$CHCl_2$, —$CHI_2$, "\*MERGEFORMAT\*MERGEFORMAT —$CHBr_2$, —$CH_2F$, —$CH_2Cl$, —$CH_2I$, —$CH_2Br$, —$OCH_2F$, —$OCH_2Cl$, —$OCH_2I$, —$OC H_2Br$, —$OCHF_2$, "\*MERGEFORMAT\*MERGEFORMAT —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, "\*MERGEFORMAT\*MERGEFORMAT —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —PO$_4$H, —PO$_3$H, —OPO$_3$H, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). In embodiments, $R^{3A}$ is —PO$_3$H, —PO$_4$H, —SO$_2$NH$_2$, —SO$_3$H, or —SO$_4$H. In embodiments, $R^{3A}$ is —SO$_3$H. In embodiments, $R^{3A}$ is —PO$_3$H. In embodiments, $R^{3A}$ is —SO$_2$NH$_2$. In embodiments, $R^{3A}$ is —SO$_4$H. In embodiments, $R^{3A}$ is —NH$_2$. In embodiments, $R^{3A}$ is —COOH. In embodiments, $R^{3A}$ is —Br. In embodiments, $R^{3A}$ is —OH. In embodiments, $R^{3A}$ is —OPO$_3$H.

In embodiments, $R^3$ is $R^{3A}$-substituted or unsubstituted alkyl (e.g., C$_1$-C$_8$, C$_1$-C$_6$, C$_1$-C$_4$, or C$_1$-C$_2$). In embodiments, $R^3$ is $R^{3A}$-substituted alkyl (e.g., C$_1$-C$_8$, C$_1$-C$_6$, C$_1$-C$_4$, or C$_1$-C$_2$). In embodiments, $R^3$ is $R^{3A}$-substituted C$_1$ alkyl. In embodiments, $R^3$ is $R^{3A}$-substituted C$_2$ alkyl. In embodiments, $R^3$ is $R^{3A}$-substituted C$_3$ alkyl. In embodiments, $R^3$ is $R^{3A}$-substituted C$_4$ alkyl. In embodiments, $R^3$ is $R^{3A}$-substituted C$_5$ alkyl. In embodiments, $R^3$ is $R^{3A}$-substituted C$_6$ alkyl. In embodiments, $R^3$ is $R^{3A}$-substituted C$_7$ alkyl. In embodiments, $R^3$ is $R^{3A}$-substituted C$_8$ alkyl. In embodiments, $R^3$ is an unsubstituted alkyl (e.g., C$_1$-C$_8$, C$_1$-C$_6$, C$_1$-C$_4$, or C$_1$-C$_2$). In embodiments, $R^3$ is an unsubstituted C$_1$ alkyl. In embodiments, $R^3$ is an unsubstituted C$_2$ alkyl. In embodiments, $R^3$ is an unsubstituted C$_3$ alkyl. In embodiments, $R^3$ is an unsubstituted C$_4$ alkyl. In embodiments, $R^3$ is an unsubstituted C$_5$ alkyl. In embodiments, $R^3$ is an unsubstituted C$_6$ alkyl. In embodiments, $R^3$ is an unsubstituted C$_7$ alkyl. In embodiments, $R^3$ is an unsubstituted C$_8$ alkyl.

In embodiments, $R^3$ is $R^{3A}$-substituted or unsubstituted heteroalkyl (e.g., 2 to 8 membered, 2 to 6 membered, 4 to 6 membered, 2 to 3 membered, or 4 to 5 membered). In embodiments, $R^3$ is $R^{3A}$-substituted heteroalkyl (e.g., 2 to 8 membered, 2 to 6 membered, 4 to 6 membered, 2 to 3 membered, or 4 to 5 membered). In embodiments, $R^3$ is $R^{3A}$-substituted 2 membered heteroalkyl. In embodiments, $R^3$ is $R^{3A}$-substituted 3 membered heteroalkyl. In embodiments, $R^3$ is $R^{3A}$-substituted 4 membered heteroalkyl. In embodiments, $R^3$ is $R^{3A}$-substituted 5 membered heteroalkyl. In embodiments, $R^3$ is $R^{3A}$-substituted 6 membered heteroalkyl.

In embodiments, $R^1$ and $R^3$ substituents may be joined to form a substituted or unsubstituted heterocycloalkyl, or substituted or unsubstituted heteroaryl. In embodiments, $R^1$ and $R^3$ substituents may be joined to form a substituted or unsubstituted 3 to 8 membered heterocycloalkyl, or substituted or unsubstituted 5 to 6 membered heteroaryl. In embodiments, $R^1$ and $R^3$ substituents may be joined to form a substituted or unsubstituted 3 to 8 membered heterocycloalkyl. In embodiments, $R^1$ and $R^3$ substituents may be joined to form a substituted or unsubstituted 4 to 7 membered heterocycloalkyl. In embodiments, $R^1$ and $R^3$ substituents may be joined to form a substituted or unsubstituted 4 to 6 membered heterocycloalkyl.

In embodiments, $R^1$ and $R^3$ substituents may be joined to form a substituted or unsubstituted 3 membered heterocycloalkyl. In embodiments, $R^1$ and $R^3$ substituents may be joined to form a substituted or unsubstituted 4 membered heterocycloalkyl. In embodiments, $R^1$ and $R^3$ substituents may be joined to form a substituted or unsubstituted 5 membered heterocycloalkyl. In embodiments, $R^1$ and $R^3$ substituents may be joined to form a substituted or unsubstituted 6 membered heterocycloalkyl. In embodiments, $R^1$ and $R^3$ substituents may be joined to form a substituted or unsubstituted 7 membered heterocycloalkyl. In embodiments, $R^1$ and $R^3$ substituents may be joined to form a substituted or unsubstituted 8 membered heterocycloalkyl. In embodiments, $R^1$ and $R^3$ substituents may be joined to form a substituted 3 membered heterocycloalkyl. In embodiments, $R^1$ and $R^3$ substituents may be joined to form a substituted 4 membered heterocycloalkyl. In embodiments, $R^1$ and $R^3$ substituents may be joined to form a substituted 5 membered heterocycloalkyl. In embodiments, $R^1$ and $R^3$ substituents may be joined to form a substituted 6 membered heterocycloalkyl. In embodiments, $R^1$ and $R^3$ substituents may be joined to form a substituted 7 membered heterocycloalkyl. In embodiments, $R^1$ and $R^3$ substituents may be joined to form a substituted 8 membered heterocycloalkyl. In embodiments, $R^1$ and $R^3$ substituents may be joined to form an unsubstituted 3 membered heterocycloalkyl. In embodiments, $R^1$ and $R^3$ substituents may be joined to form an unsubstituted 4 membered heterocycloalkyl. In embodiments, $R^1$ and $R^3$ substituents may be joined to form an unsubstituted 5 membered heterocycloalkyl. In embodiments, $R^1$ and $R^3$ substituents may be joined to form an unsubstituted 6 membered heterocycloalkyl. In embodiments, $R^1$ and $R^3$ substituents may be joined to form an unsubstituted 7 membered heterocycloalkyl. In embodiments, $R^1$ and $R^3$ substituents may be joined to form an unsubstituted 8 membered heterocycloalkyl.

In embodiments, $R^1$ and $R^3$ substituents may be joined to form an $R^{14}$-substituted or unsubstituted 3 to 8 membered heterocycloalkyl, or $R^{14}$-substituted or unsubstituted 5 to 6 membered heteroaryl. In embodiments, $R^1$ and $R^3$ substituents may be joined to form an $R^{14}$-substituted or unsubstituted 3 membered heterocycloalkyl. In embodiments, $R^1$ and $R^3$ substituents may be joined to form an $R^{14}$-substituted or unsubstituted 4 membered heterocycloalkyl. In embodiments, $R^1$ and $R^3$ substituents may be joined to form an $R^{14}$-substituted or unsubstituted 5 membered heterocycloalkyl. In embodiments, $R^1$ and $R^3$ substituents may be joined to form an $R^{14}$-substituted or unsubstituted 6 membered heterocycloalkyl. In embodiments, $R^1$ and $R^3$ substituents may be joined to form an $R^{14}$-substituted or unsubstituted 7 membered heterocycloalkyl. In embodiments, $R^1$ and $R^3$ substituents may be joined to form an $R^{14}$-substituted or unsubstituted 8 membered heterocycloalkyl. In embodiments, $R^1$ and $R^3$ substituents may be joined to form an $R^{14}$-substituted 3 membered heterocycloalkyl. In embodiments, $R^1$ and $R^3$ substituents may be joined to form an $R^{14}$-substituted 4 membered heterocycloalkyl. In embodiments, $R^1$ and $R^3$ substituents may be joined to form an $R^{14}$-substituted 5 membered heterocycloalkyl. In embodiments, $R^1$ and $R^3$ substituents may be joined to form an $R^{14}$-substituted 6 membered heterocycloalkyl. In embodiments, $R^1$ and $R^3$ substituents may be joined to form an $R^{14}$-substituted 7 membered heterocycloalkyl. In embodiments, $R^1$ and $R^3$ substituents may be joined to form an $R^{14}$-substituted 8 membered heterocycloalkyl.

In embodiments, $R^4$ is hydrogen, $-PO_3H$, $-PO_4H$, $-SO_2NH_2$, $-SO_3H$, $-SO_4H$, $R^{4A}$-substituted or unsubstituted alkyl (e.g., $C_1$-$C_8$, $C_1$-$C_6$, $C_1$-$C_4$, or $C_1$-$C_2$), or $R^{4A}$-substituted or unsubstituted heteroalkyl (e.g., 2 to 8 membered, 2 to 6 membered, 4 to 6 membered, 2 to 3 membered, or 4 to 5 membered). In embodiments, $R^4$ is hydrogen. In embodiments, $R^4$ is $-PO_3H$. In embodiments, $R^4$ is $-PO_4H$. In embodiments, $R^4$ is $-SO_2NH_2$. In embodiments, $R^4$ is $-SO_3H$. In embodiments, $R^4$ is $-SO_4H$. $R^{4A}$ is oxo, halogen, $-CF_3$, $-CCl_3$, $-CI_3$, $-CBr_3$, $-CHF_2$, $-CHCl_2$, "\*MERGEFORMAT\*MERGEFORMAT $-CHI_2$, $-CHBr_2$, $-CH_2F$, $-CH_2Cl$, $-CH_2I$, $-CH_2Br$, $-OCH_2F$, $-OCH_2Cl$, $-OCH_2I$, $-OCH_2Br$, "\*MERGEFORMAT\*MERGEFORMAT $-OCHF_2$, $-OCHCl_2$, $-OCHI_2$, $-OCHBr_2$, $-OCF_3$, $-OCCl_3$, $-OCI_3$, $-OCBr_3$, $-CN$, $-OH$, $-NH_2$, "\*MERGEFORMAT\*MERGEFORMAT $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-PO_4H$, $-PO_3H$, $-OPO_3H$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{4A}$ is $-PO_3H$, $-PO_4H$, "\*MERGEFORMAT\*MERGEFORMAT $-SO_2NH_2$, $-SO_3H$, or $-SO_4H$. In embodiments, $R^{4A}$ is $-SO_3H$. In embodiments, $R^{4A}$ is $-PO_3H$. In embodiments, $R^{4A}$ is $-SO_2NH_2$. In embodiments, $R^{4A}$ is $-SO_4H$. In embodiments, $R^{4A}$ is $-NH_2$. In embodiments, $R^{4A}$ is $-COOH$. In embodiments, $R^{4A}$ is $-Br$. In embodiments, $R^{4A}$ is $-OH$. In embodiments, $R^{4A}$ is $-OPO_3H$.

In embodiments, $R^4$ is $R^{4A}$-substituted or unsubstituted alkyl (e.g., $C_1$-$C_8$, $C_1$-$C_6$, $C_1$-$C_4$, or $C_1$-$C_2$). In embodiments, $R^4$ is $R^{4A}$-substituted alkyl (e.g., $C_1$-$C_8$, $C_1$-$C_6$, $C_1$-$C_4$, or $C_1$-$C_2$). In embodiments, $R^4$ is $R^{4A}$-substituted $C_1$ alkyl. In embodiments, $R^4$ is $R^{4A}$-substituted $C_2$ alkyl. In embodiments, $R^4$ is $R^{4A}$-substituted $C_3$ alkyl. In embodiments, $R^4$ is $R^{4A}$-substituted $C_4$ alkyl. In embodiments, $R^4$ is $R^{4A}$-substituted $C_5$ alkyl. In embodiments, $R^4$ is $R^{4A}$-substituted $C_6$ alkyl. In embodiments, $R^4$ is $R^{4A}$-substituted $C_7$ alkyl. In embodiments, $R^4$ is $R^{4A}$-substituted $C_8$ alkyl. In embodiments, $R^4$ is an unsubstituted alkyl (e.g., $C_1$-$C_8$, $C_1$-$C_6$, $C_1$-$C_4$, or $C_1$-$C_2$). In embodiments, $R^4$ is an unsubstituted $C_1$ alkyl. In embodiments, $R^4$ is an unsubstituted $C_2$ alkyl. In embodiments, $R^4$ is an unsubstituted $C_3$ alkyl. In embodiments, $R^4$ is an unsubstituted $C_4$ alkyl. In embodiments, $R^4$ is an unsubstituted $C_5$ alkyl. In embodiments, $R^4$ is an unsubstituted $C_6$ alkyl. In embodiments, $R^4$ is an unsubstituted $C_7$ alkyl. In embodiments, $R^4$ is an unsubstituted $C_8$ alkyl.

In embodiments, $R^4$ is $R^{4A}$-substituted or unsubstituted heteroalkyl (e.g., 2 to 8 membered, 2 to 6 membered, 4 to 6 membered, 2 to 3 membered, or 4 to 5 membered). In embodiments, $R^4$ is $R^{4A}$-substituted heteroalkyl (e.g., 2 to 8 membered, 2 to 6 membered, 4 to 6 membered, 2 to 3 membered, or 4 to 5 membered). In embodiments, $R^4$ is $R^{4A}$-substituted 2 membered heteroalkyl. In embodiments, $R^4$ is $R^{4A}$-substituted 3 membered heteroalkyl. In embodiments, $R^4$ is $R^{4A}$-substituted 4 membered heteroalkyl. In embodiments, $R^4$ is $R^{4A}$-substituted 5 membered heteroalkyl. In embodiments, $R^4$ is $R^{4A}$-substituted 6 membered heteroalkyl.

In embodiments, $R^2$ and $R^4$ substituents may be joined to form a substituted or unsubstituted heterocycloalkyl, or substituted or unsubstituted heteroaryl. In embodiments, $R^2$ and $R^4$ substituents may be joined to form a substituted or unsubstituted 3 to 8 membered heterocycloalkyl, or substituted or unsubstituted 5 to 6 membered heteroaryl. In embodiments, $R^2$ and $R^4$ substituents may be joined to form a substituted or unsubstituted 3 to 8 membered heterocycloalkyl. In embodiments, $R^2$ and $R^4$ substituents may be joined to form a substituted or unsubstituted 4 to 7 membered heterocycloalkyl. In embodiments, $R^2$ and $R^4$ substituents may be joined to form a substituted or unsubstituted 4 to 6 membered heterocycloalkyl.

In embodiments, $R^2$ and $R^4$ substituents may be joined to form a substituted or unsubstituted 3 membered heterocycloalkyl. In embodiments, $R^2$ and $R^4$ substituents may be joined to form a substituted or unsubstituted 4 membered heterocycloalkyl. In embodiments, $R^2$ and $R^4$ substituents may be joined to form a substituted or unsubstituted 5 membered heterocycloalkyl. In embodiments, $R^2$ and $R^4$ substituents may be joined to form a substituted or unsubstituted 6 membered heterocycloalkyl. In embodiments, $R^2$ and $R^4$ substituents may be joined to form a substituted or unsubstituted 7 membered heterocycloalkyl. In embodiments, $R^2$ and $R^4$ substituents may be joined to form a substituted or unsubstituted 8 membered heterocycloalkyl. In embodiments, $R^2$ and $R^4$ substituents may be joined to form a substituted 3 membered heterocycloalkyl. In embodiments, $R^2$ and $R^4$ substituents may be joined to form a substituted 4 membered heterocycloalkyl. In embodiments, $R^2$ and $R^4$ substituents may be joined to form a substituted 5 membered heterocycloalkyl. In embodiments, $R^2$ and $R^4$ substituents may be joined to form a substituted 6 membered heterocycloalkyl. In embodiments, $R^2$ and $R^4$ substituents may be joined to form a substituted 7 membered heterocycloalkyl. In embodiments, $R^2$ and $R^4$ substituents may be joined to form a substituted 8 membered heterocycloalkyl. In embodiments, $R^2$ and $R^4$ substituents may be joined to form an unsubstituted 3 membered heterocycloalkyl. In embodiments, $R^2$ and $R^4$ substituents may be joined to form an unsubstituted 4 membered heterocycloalkyl. In embodiments, $R^2$ and $R^4$ substituents may be joined to form an unsubstituted 5 membered heterocycloalkyl. In embodiments, $R^2$ and $R^4$ substituents may be joined to form an unsubstituted 6 membered heterocycloalkyl. In embodiments, $R^2$ and $R^4$ substituents may be joined to form an unsubstituted 7 membered heterocycloalkyl. In embodiments, $R^2$ and $R^4$ substituents may be joined to form an unsubstituted 8 membered heterocycloalkyl.

In embodiments, $R^2$ and $R^4$ substituents may be joined to form an $R^{2A}$-substituted or unsubstituted 3 to 8 membered heterocycloalkyl, or $R^{2A}$-substituted or unsubstituted 5 to 6 membered heteroaryl. In embodiments, $R^2$ and $R^4$ substituents may be joined to form an $R^{2A}$-substituted or unsubstituted 3 membered heterocycloalkyl. In embodiments, $R^2$ and $R^4$ substituents may be joined to form an $R^{2A}$-substituted or unsubstituted 4 membered heterocycloalkyl. In embodiments, $R^2$ and $R^4$ substituents may be joined to form an $R^{2A}$-substituted or unsubstituted 5 membered heterocycloalkyl. In embodiments, $R^2$ and $R^4$ substituents may be joined to form an $R^{2A}$-substituted or unsubstituted 6 membered heterocycloalkyl. In embodiments, $R^2$ and $R^4$ substituents may be joined to form an $R^{2A}$-substituted or unsubstituted 7 membered heterocycloalkyl. In embodiments, $R^2$ and $R^4$ substituents may be joined to form an $R^{2A}$-substituted or unsubstituted 8 membered heterocycloalkyl. In embodiments, $R^2$ and $R^4$ substituents may be joined to form an $R^{2A}$-substituted 3 membered heterocycloalkyl. In embodiments, $R^2$ and $R^4$ substituents may be joined to form an $R^{2A}$-substituted 4 membered heterocycloalkyl. In embodiments, $R^2$ and $R^4$ substituents may be joined to form an $R^{2A}$-substituted 5 membered heterocycloalkyl. In embodiments, $R^2$ and $R^4$ substituents may be joined to form an $R^{2A}$-substituted 6 membered heterocycloalkyl. In embodiments, $R^2$ and $R^4$ substituents may be joined to form an $R^{2A}$-substituted 7 membered heterocycloalkyl. In embodiments, $R^2$ and $R^4$ substituents may be joined to form an $R^{2A}$-substituted 8 membered heterocycloalkyl.

In embodiments, $R^7$ is hydrogen, —$PO_3H$, —$PO_4H$, —$SO_2NH_2$, —$SO_3H$, —$SO_4H$, $R^{7A}$-substituted or unsubstituted alkyl (e.g., $C_1$-$C_8$, $C_1$-$C_6$, $C_1$-$C_4$, or $C_1$-$C_2$), or $R^{7A}$-substituted or unsubstituted heteroalkyl (e.g., 2 to 8 membered, 2 to 6 membered, 4 to 6 membered, 2 to 3 membered, or 4 to 5 membered). In embodiments, $R^7$ is hydrogen. In embodiments, $R^7$ is —$PO_3H$. In embodiments, $R^7$ is —$PO_4H$. In embodiments, $R^7$ is —$SO_2NH_2$. In embodiments, $R^7$ is —$SO_3H$. In embodiments, $R^7$ is —$SO_4H$. $R^{7A}$ is oxo, halogen, —$CF_3$, —$CCl_3$, —$CI_3$, —$CBBr_3$, —$CHF_2$, —$CHCl_2$, "\*MERGEFORMAT\*MERGEFORMAT —$CHI_2$, —$CHBr_2$, —$CH_2F$, —$CH_2Cl$, —$CH_2I$, —$CH_2Br$, —$OCH_2F$, —$OCH_2Cl$, —$OCH_2 I$, —$OCH_2Br$, "\*MERGEFORMAT\*MERGEFORMAT —$OCHF_2$, —$OCHCl_2$, —$OCHI_2$, —$OCHBr_2$, —$OCF_3$, —$OCCl_3$, —$OCI_3$, —$OCBr_3$, —C N, —OH, —$NH_2$, "\*MERGEFORMAT\*MERGEFORMAT —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$PO_4H$, —$PO_3H$, —$OPO_3H$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{7A}$ is —$PO_3H$, —$PO_4H$, "\*MERGEFORMAT\*MERGEFORMAT —$SO_2NH_2$, —$SO_3H$, or —$SO_4H$. In embodiments, $R^{7A}$ is —$SO_3H$. In embodiments, $R^{7A}$ is —$PO_3H$. In embodiments, $R^{7A}$ is —$SO_2NH_2$. In embodiments, $R^{7A}$ is —$SO_4H$. In embodiments, $R^{7A}$ is —$NH_2$. In embodiments, $R^{7A}$ is —COOH. In embodiments, $R^{7A}$ is —Br. In embodiments, $R^{7A}$ is —OH. In embodiments, $R^{7A}$ is —$OPO_3H$.

In embodiments, $R^7$ is $R^{7A}$-substituted or unsubstituted alkyl (e.g., $C_1$-$C_8$, $C_1$-$C_6$, $C_1$-$C_4$, or $C_1$-$C_2$). In embodiments, $R^7$ is $R^{7A}$-substituted alkyl (e.g., $C_1$-$C_8$, $C_1$-$C_6$, $C_1$-$C_4$, or $C_1$-$C_2$). In embodiments, $R^7$ is $R^{7A}$-substituted $C_1$ alkyl. In embodiments, $R^7$ is $R^{7A}$-substituted $C_2$ alkyl. In embodiments, $R^7$ is $R^{7A}$-substituted $C_3$ alkyl. In embodiments, $R^7$ is $R^{7A}$-substituted $C_4$ alkyl. In embodiments, $R^7$ is $R^{7A}$-substituted $C_5$ alkyl. In embodiments, $R^7$ is $R^{7A}$-substituted $C_6$ alkyl. In embodiments, $R^7$ is $R^{7A}$-substituted $C_7$ alkyl. In embodiments, $R^7$ is $R^{7A}$-substituted $C_8$ alkyl. In embodiments, $R^7$ is an unsubstituted alkyl (e.g., $C_1$-$C_8$, $C_1$-$C_6$, $C_1$-$C_4$, or $C_1$-$C_2$). In embodiments, $R^7$ is an unsubstituted $C_1$ alkyl. In embodiments, $R^7$ is an unsubstituted $C_2$ alkyl. In embodiments, $R^7$ is an unsubstituted $C_3$ alkyl. In embodiments, $R^7$ is an unsubstituted $C_4$ alkyl. In embodiments, $R^7$ is an unsubstituted $C_5$ alkyl. In embodiments, $R^7$ is an unsubstituted $C_6$ alkyl. In embodiments, $R^7$ is an unsubstituted $C_7$ alkyl. In embodiments, $R^7$ is an unsubstituted $C_8$ alkyl.

In embodiments, $R^7$ is $R^{7A}$-substituted or unsubstituted heteroalkyl (e.g., 2 to 8 membered, 2 to 6 membered, 4 to 6 membered, 2 to 3 membered, or 4 to 5 membered). In embodiments, $R^7$ is $R^{7A}$-substituted heteroalkyl (e.g., 2 to 8 membered, 2 to 6 membered, 4 to 6 membered, 2 to 3 membered, or 4 to 5 membered). In embodiments, $R^7$ is $R^{7A}$-substituted 2 membered heteroalkyl. In embodiments, $R^7$ is $R^{7A}$-substituted 3 membered heteroalkyl. In embodiments, $R^7$ is $R^{7A}$-substituted 4 membered heteroalkyl. In embodiments, $R^7$ is $R^{7A}$-substituted 5 membered heteroalkyl. In embodiments, $R^7$ is $R^{7A}$-substituted 6 membered heteroalkyl.

In embodiments, $R^5$ and $R^7$ substituents may be joined to form a substituted or unsubstituted heterocycloalkyl, or substituted or unsubstituted heteroaryl. In embodiments, $R^5$ and $R^7$ substituents may be joined to form a substituted or unsubstituted 3 to 8 membered heterocycloalkyl, or substituted or unsubstituted 5 to 6 membered heteroaryl. In embodiments, $R^5$ and $R^7$ substituents may be joined to form a substituted or unsubstituted 3 to 8 membered heterocycloalkyl. In embodiments, $R^5$ and $R^7$ substituents may be joined to form a substituted or unsubstituted 4 to 7 membered heterocycloalkyl. In embodiments, $R^5$ and $R^7$ substituents may be joined to form a substituted or unsubstituted 4 to 6 membered heterocycloalkyl.

In embodiments, $R^5$ and $R^7$ substituents may be joined to form a substituted or unsubstituted 3 membered heterocycloalkyl. In embodiments, $R^5$ and $R^7$ substituents may be joined to form a substituted or unsubstituted 4 membered heterocycloalkyl. In embodiments, $R^5$ and $R^7$ substituents may be joined to form a substituted or unsubstituted 5 membered heterocycloalkyl. In embodiments, $R^5$ and $R^7$ substituents may be joined to form a substituted or unsubstituted 6 membered heterocycloalkyl. In embodiments, $R^5$ and $R^7$ substituents may be joined to form a substituted or unsubstituted 7 membered heterocycloalkyl. In embodiments, $R^5$ and $R^7$ substituents may be joined to form a substituted or unsubstituted 8 membered heterocycloalkyl. In embodiments, $R^5$ and $R^7$ substituents may be joined to form a substituted 3 membered heterocycloalkyl. In embodiments, $R^5$ and $R^7$ substituents may be joined to form a substituted 4 membered heterocycloalkyl. In embodiments, $R^5$ and $R^7$ substituents may be joined to form a substituted 5 membered heterocycloalkyl. In embodiments, $R^5$ and $R^7$ substituents may be joined to form a substituted 6 membered heterocycloalkyl. In embodiments, $R^5$ and $R^7$ substituents may be joined to form a substituted 7 membered heterocycloalkyl. In embodiments, $R^5$ and $R^7$ substituents may be joined to form a substituted 8 membered heterocycloalkyl. In embodiments, $R^5$ and $R^7$ substituents may be joined to form an unsubstituted 3 membered heterocycloalkyl. In embodiments, $R^5$ and $R^7$ substituents may be joined to form an unsubstituted 4 membered heterocycloalkyl. In embodiments, $R^5$ and $R^7$ substituents may be joined to form an unsubstituted 5 membered heterocycloalkyl. In embodiments, $R^5$ and $R^7$ substituents may be joined to form an unsubstituted 6 membered heterocycloalkyl. In embodiments, $R^5$ and $R^7$ substituents may be joined to form an unsubstituted 7 membered heterocycloalkyl. In embodiments, $R^5$ and $R^7$ substituents may be joined to form an unsubstituted 8 membered heterocycloalkyl.

In embodiments, $R^5$ and $R^7$ substituents may be joined to form an $R^{5A}$-substituted or unsubstituted 3 to 8 membered heterocycloalkyl, or $R^{5A}$-substituted or unsubstituted 5 to 6 membered heteroaryl. In embodiments, $R^5$ and $R^7$ substituents may be joined to form an $R^{5A}$-substituted or unsubstituted 3 membered heterocycloalkyl. In embodiments, $R^5$ and $R^7$ substituents may be joined to form an $R^{5A}$-substituted or unsubstituted 4 membered heterocycloalkyl. In embodiments, $R^5$ and $R^7$ substituents may be joined to form an $R^{5A}$-substituted or unsubstituted 5 membered heterocycloalkyl. In embodiments, $R^5$ and $R^7$ substituents may be joined to form an $R^{5A}$-substituted or unsubstituted 6 membered heterocycloalkyl. In embodiments, $R^5$ and $R^7$ substituents may be joined to form an $R^{5A}$-substituted or unsubstituted 7 membered heterocycloalkyl. In embodiments, $R^5$ and $R^7$ substituents may be joined to form an $R^{5A}$-substituted or unsubstituted 8 membered heterocycloalkyl. In embodiments, $R^5$ and $R^7$ substituents may be joined to form an $R^{5A}$-substituted 3 membered heterocycloalkyl. In embodiments, $R^5$ and $R^7$ substituents may be joined to form an $R^{5A}$-substituted 4 membered heterocycloalkyl. In embodiments, $R^5$ and $R^7$ substituents may be joined to form an $R^{5A}$-substituted 5 membered heterocycloalkyl. In embodiments, $R^5$ and $R^7$ substituents may be joined to form an $R^{5A}$-substituted 6 membered heterocycloalkyl. In embodiments, $R^5$ and $R^7$ substituents may be joined to form an $R^{5A}$-substituted 7 membered heterocycloalkyl. In embodiments, $R^5$ and $R^7$ substituents may be joined to form an $R^{5A}$-substituted 8 membered heterocycloalkyl.

In embodiments, $R^8$ is hydrogen, $-PO_3H$, $-PO_4H$, $-SO_2NH_2$, $-SO_3H$, $-SO_4H$, $R^{8A}$-substituted or unsubstituted alkyl (e.g., $C_1$-$C_8$, $C_1$-$C_6$, $C_1$-$C_4$, or $C_1$-$C_2$), or $R^{8A}$-substituted or unsubstituted heteroalkyl (e.g., 2 to 8 membered, 2 to 6 membered, 4 to 6 membered, 2 to 3 membered, or 4 to 5 membered). In embodiments, $R^8$ is hydrogen. In embodiments, $R^8$ is $-PO_3H$. In embodiments, $R^8$ is $-PO_4H$. In embodiments, $R^8$ is $-SO_2NH_2$. In embodiments, $R^8$ is $-SO_3H$. In embodiments, $R^8$ is $-SO_4H$. $R^{8A}$ is oxo, halogen, $-CF_3$, $-CCl_3$, $-CI_3$, $-CBr_3$, $-CHF_2$, $-CHCl_2$, "\*MERGEFORMAT\*MERGEFORMAT $-CHI_2$, $-CHBr_2$, $-CH_2F$, $-CH_2Cl$, $-CH_2I$, $-CH_2Br$, $-OCH_2F$, $-OCH_2Cl$, $-OCH_2 I$, $-OCH_2Br$, "\*MERGEFORMAT\*MERGEFORMAT $-OCHF_2$, $-OCHCl_2$, $-OCHI_2$, $-OCHBr_2$, $-OCF_3$, $-OCCl_3$, $-OCI_3$, $-OCBr_3$, $-C$ N, $-OH$, $-NH_2$, "\*MERGEFORMAT\*MERGEFORMAT $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-PO_4H$, $-PO_3H$, $-OPO_3H$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{8A}$ is $-PO_3H$, $-PO_4H$, $-SO_2NH_2$, $-SO_3H$, or $-SO_4H$. In embodiments, $R^{8A}$ is $-SO_3H$. In embodiments, $R^{8A}$ is $-PO_3H$. In embodiments, $R^{8A}$ is $-SO_2NH_2$. In embodiments, $R^{8A}$ is $-SO_4H$. In embodiments, $R^{8A}$ is $-NH_2$. In embodiments, $R^{8A}$ is $-COOH$. In embodiments, $R^{8A}$ is $-Br$. In embodiments, $R^{8A}$ is $-OH$. In embodiments, $R^{8A}$ is $-OPO_3H$.

In embodiments, $R^8$ is $R^{8A}$-substituted or unsubstituted alkyl (e.g., $C_1$-$C_8$, $C_1$-$C_6$, $C_1$-$C_4$, or $C_1$-$C_2$). In embodiments, $R^8$ is $R^{8A}$-substituted alkyl (e.g., $C_1$-$C_8$, $C_1$-$C_6$, $C_1$-$C_4$, or $C_1$-$C_2$). In embodiments, $R^8$ is $R^{8A}$-substituted $C_1$ alkyl. In embodiments, $R^8$ is $R^{8A}$-substituted $C_2$ alkyl. In embodiments, $R^8$ is $R^{8A}$-substituted $C_3$ alkyl. In embodiments, $R^8$ is $R^{8A}$-substituted $C_4$ alkyl. In embodiments, $R^8$ is $R^{8A}$-substituted $C_5$ alkyl. In embodiments, $R^8$ is $R^{8A}$-substituted $C_6$ alkyl. In embodiments, $R^8$ is $R^{8A}$-substituted $C_7$ alkyl. In embodiments, $R^8$ is $R^{8A}$-substituted $C_8$ alkyl. In embodiments, $R^8$ is an unsubstituted alkyl (e.g., $C_1$-$C_8$, $C_1$-$C_6$, $C_1$-$C_4$, or $C_1$-$C_2$). In embodiments, $R^8$ is an unsubstituted $C_1$ alkyl. In embodiments, $R^8$ is an unsubstituted $C_2$ alkyl. In embodiments, $R^8$ is an unsubstituted $C_3$ alkyl. In embodiments, $R^8$ is an unsubstituted $C_4$ alkyl. In embodiments, $R^8$ is an unsubstituted $C_5$ alkyl. In embodiments, $R^8$ is an unsubstituted $C_6$ alkyl. In embodiments, $R^8$ is an unsubstituted $C_7$ alkyl. In embodiments, $R^8$ is an unsubstituted $C_8$ alkyl.

In embodiments, $R^8$ is $R^{8A}$-substituted or unsubstituted heteroalkyl (e.g., 2 to 8 membered, 2 to 6 membered, 4 to 6 membered, 2 to 3 membered, or 4 to 5 membered). In embodiments, $R^8$ is $R^{8A}$-substituted heteroalkyl (e.g., 2 to 8 membered, 2 to 6 membered, 4 to 6 membered, 2 to 3 membered, or 4 to 5 membered). In embodiments, $R^8$ is $R^{8A}$-substituted 2 membered heteroalkyl. In embodiments, $R^8$ is $R^{8A}$-substituted 3 membered heteroalkyl. In embodiments, $R^8$ is $R^{8A}$-substituted 4 membered heteroalkyl. In embodiments, $R^8$ is $R^{8A}$-substituted 5 membered heteroalkyl. In embodiments, $R^8$ is $R^{8A}$-substituted 6 membered heteroalkyl.

In embodiments, $R^6$ and $R^8$ substituents may be joined to form a substituted or unsubstituted heterocycloalkyl, or substituted or unsubstituted heteroaryl. In embodiments, $R^6$ and $R^8$ substituents may be joined to form a substituted or unsubstituted 3 to 8 membered heterocycloalkyl, or substituted or unsubstituted 5 to 6 membered heteroaryl. In embodiments, $R^6$ and $R^8$ substituents may be joined to form a substituted or unsubstituted 3 to 8 membered heterocycloalkyl. In embodiments, $R^6$ and $R^8$ substituents may be joined to form a substituted or unsubstituted 4 to 7 membered heterocycloalkyl. In embodiments, $R^6$ and $R^8$ substituents may be joined to form a substituted or unsubstituted 4 to 6 membered heterocycloalkyl.

In embodiments, $R^6$ and $R^8$ substituents may be joined to form a substituted or unsubstituted 3 membered heterocycloalkyl. In embodiments, $R^6$ and $R^8$ substituents may be joined to form a substituted or unsubstituted 4 membered heterocycloalkyl. In embodiments, $R^6$ and $R^8$ substituents may be joined to form a substituted or unsubstituted 5 membered heterocycloalkyl. In embodiments, $R^6$ and $R^8$ substituents may be joined to form a substituted or unsubstituted 6 membered heterocycloalkyl. In embodiments, $R^6$ and $R^8$ substituents may be joined to form a substituted or unsubstituted 7 membered heterocycloalkyl. In embodiments, $R^6$ and $R^8$ substituents may be joined to form a substituted or unsubstituted 8 membered heterocycloalkyl. In embodiments, $R^6$ and $R^8$ substituents may be joined to form a substituted 3 membered heterocycloalkyl. In embodiments, $R^6$ and $R^8$ substituents may be joined to form a substituted 4 membered heterocycloalkyl. In embodiments, $R^6$ and $R^8$ substituents may be joined to form a substituted 5 membered heterocycloalkyl. In embodiments, $R^6$ and $R^8$ substituents may be joined to form a substituted 6 membered heterocycloalkyl. In embodiments, $R^6$ and $R^8$ substituents may be joined to form a substituted 7 membered heterocycloalkyl. In embodiments, $R^6$ and $R^8$ substituents may be joined to form a substituted 8 membered heterocycloalkyl. In embodiments, $R^6$ and $R^8$ substituents may be joined to form an unsubstituted 3 membered heterocycloalkyl. In embodiments, $R^6$ and $R^8$ substituents may be joined to form an unsubstituted 4 membered heterocycloalkyl. In embodiments, $R^6$ and $R^8$ substituents may be joined to form an unsubstituted 5 membered heterocycloalkyl. In embodiments, $R^6$ and $R^8$ substituents may be joined to form an unsubstituted 6 membered heterocycloalkyl. In embodiments, $R^6$ and $R^8$ substituents may be joined to form an unsubstituted 7 membered heterocycloalkyl. In embodiments, $R^6$ and $R^8$ substituents may be joined to form an unsubstituted 8 membered heterocycloalkyl.

In embodiments, $R^6$ and $R^8$ substituents may be joined to form an $R^{6A}$-substituted or unsubstituted 3 to 8 membered heterocycloalkyl, or $R^{6A}$-substituted or unsubstituted 5 to 6 membered heteroaryl. In embodiments, $R^6$ and $R^8$ substituents may be joined to form an $R^{6A}$-substituted or unsubstituted 3 membered heterocycloalkyl. In embodiments, $R^6$ and $R^8$ substituents may be joined to form an $R^{6A}$-substituted or unsubstituted 4 membered heterocycloalkyl. In embodiments, $R^6$ and $R^8$ substituents may be joined to form an $R^{6A}$-substituted or unsubstituted 5 membered heterocycloalkyl. In embodiments, $R^6$ and $R^8$ substituents may be joined to form an $R^{6A}$-substituted or unsubstituted 6 membered heterocycloalkyl. In embodiments, $R^6$ and $R^8$ substituents may be joined to form an $R^{6A}$-substituted or unsubstituted 7 membered heterocycloalkyl. In embodiments, $R^6$ and $R^8$ substituents may be joined to form an $R^{6A}$-substituted or unsubstituted 8 membered heterocycloalkyl. In embodiments, $R^6$ and $R^8$ substituents may be joined to form an $R^{6A}$-substituted 3 membered heterocycloalkyl. In embodiments, $R^6$ and $R^8$ substituents may be joined to form an $R^{6A}$-substituted 4 membered heterocycloalkyl. In embodiments, $R^6$ and $R^8$ substituents may be joined to form an $R^{6A}$-substituted 5 membered heterocycloalkyl. In embodiments, $R^6$ and $R^8$ substituents may be joined to form an $R^{6A}$-substituted 6 membered heterocycloalkyl. In embodiments, $R^6$ and $R^8$ substituents may be joined to form an $R^{6A}$-substituted 7 membered heterocycloalkyl. In embodiments, $R^6$ and $R^8$ substituents may be joined to form an $R^{6A}$-substituted 8 membered heterocycloalkyl.

In embodiments, $R^{11}$ is hydrogen, —PO$_3$H, —PO$_4$H, —SO$_2$NH$_2$, —SO$_3$H, —SO$_4$H, $R^{11A}$-substituted or unsubstituted alkyl (e.g., $C_1$-$C_8$, $C_1$-$C_6$, $C_1$-$C_4$, or $C_1$-$C_2$), or $R^{11A}$-substituted or unsubstituted heteroalkyl (e.g., 2 to 8 membered, 2 to 6 membered, 4 to 6 membered, 2 to 3 membered, or 4 to 5 membered). In embodiments, $R^{11}$ is hydrogen. In embodiments, $R^{11}$ is —PO$_3$H. In embodiments, $R^{11}$ is —PO$_4$H. In embodiments, $R^{11}$ is —SO$_2$NH$_2$. In embodiments, $R^{11}$ is —SO$_3$H. In embodiments, $R^{11}$ is —SO$_4$H. $R^{11A}$ is oxo, halogen, —CF$_3$, —CCl$_3$, —CI$_3$, —CBr$_3$, "\*MERGEFORMAT\*MERGEFORMAT —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, "\*MERGEFORMAT\*MERGEFORMAT —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, "\*MERGEFORMAT\*MERGEFORMAT —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —PO$_4$H, "\*MERGEFORMAT\*MERGEFORMAT —PO$_3$H, —OPO$_3$H, —N$_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). In embodiments, $R^{11A}$ is —PO$_3$H, —PO$_4$H, —SO$_2$NH$_2$, —SO$_3$H, or —SO$_4$H. In embodiments, $R^{11A}$ is —SO$_3$H. In embodiments, $R^{11A}$ is —PO$_3$H. In embodiments, $R^{11A}$ is —SO$_2$NH$_2$. In embodiments, $R^{11A}$ is —SO$_4$H. In embodiments, $R^{11A}$ is —NH$_2$. In embodiments, $R^{11A}$ is —COOH. In embodiments, $R^{11A}$ is —Br. In embodiments, $R^{11A}$ is —OH. In embodiments, $R^{11A}$ is —OPO$_3$H.

In embodiments, $R^{11}$ is $R^{11A}$-substituted or unsubstituted alkyl (e.g., $C_1$-$C_8$, $C_1$-$C_6$, $C_1$-$C_4$, or $C_1$-$C_2$). In embodiments, $R^{11}$ is $R^{11A}$-substituted alkyl (e.g., $C_1$-$C_8$, $C_1$-$C_6$, $C_1$-$C_4$, or $C_1$-$C_2$). In embodiments, $R^{11}$ is $R^{11A}$-substituted $C_1$ alkyl. In embodiments, $R^{11}$ is $R^{11A}$-substituted $C_2$ alkyl. In embodiments, $R^{11}$ is $R^{11A}$-substituted $C_3$ alkyl. In embodiments, $R^{11}$ is $R^{11A}$-substituted $C_4$ alkyl. In embodiments, $R^{11}$ is $R^{11A}$-substituted $C_5$ alkyl. In embodiments, $R^{11}$ is $R^{11A}$-substituted $C_6$ alkyl. In embodiments, $R^{11}$ is $R^{11A}$-substituted $C_7$ alkyl. In embodiments, $R^{11}$ is $R^{11A}$-substituted $C_8$ alkyl. In embodiments, $R^{11}$ is an unsubstituted alkyl (e.g., $C_1$-$C_8$, $C_1$-$C_6$, $C_1$-$C_4$, or $C_1$-$C_2$). In embodiments, $R^{11}$ is an unsubstituted $C_1$ alkyl. In embodiments, $R^{11}$ is an unsubstituted $C_2$ alkyl. In embodiments, $R^{11}$ is an unsubstituted $C_3$ alkyl. In embodiments, $R^{11}$ is an unsubstituted $C_4$ alkyl. In embodiments, $R^{11}$ is an unsubstituted $C_5$ alkyl. In embodiments, $R^{11}$ is an unsubstituted $C_6$ alkyl. In embodiments, $R^{11}$ is an unsubstituted $C_7$ alkyl. In embodiments, $R^{11}$ is an unsubstituted $C_8$ alkyl.

In embodiments, $R^{11}$ is $R^{11A}$-substituted or unsubstituted heteroalkyl (e.g., 2 to 8 membered, 2 to 6 membered, 4 to 6 membered, 2 to 3 membered, or 4 to 5 membered). In embodiments, $R^{11}$ is $R^{11A}$-substituted heteroalkyl (e.g., 2 to 8 membered, 2 to 6 membered, 4 to 6 membered, 2 to 3 membered, or 4 to 5 membered). In embodiments, $R^{11}$ is $R^{11A}$-substituted 2 membered heteroalkyl. In embodiments, $R^{11}$ is $R^{11A}$-substituted 3 membered heteroalkyl. In embodiments, $R^{11}$ is $R^{11A}$-substituted 4 membered heteroalkyl. In embodiments, $R^{11}$ is $R^{11A}$-substituted 5 membered heteroalkyl. In embodiments, $R^{11}$ is $R^{11A}$-substituted 6 membered heteroalkyl.

In embodiments, $R^{12}$ is hydrogen, —PO$_3$H, —PO$_4$H, —SO$_2$NH$_2$, —SO$_3$H, —SO$_4$H, $R^{12A}$-substituted or unsubstituted alkyl (e.g., $C_1$-$C_8$, $C_1$-$C_6$, $C_1$-$C_4$, or $C_1$-$C_2$), or $R^{12A}$-substituted or unsubstituted heteroalkyl (e.g., 2 to 8 membered, 2 to 6 membered, 4 to 6 membered, 2 to 3 membered, or 4 to 5 membered). In embodiments, $R^{12}$ is hydrogen. In embodiments, $R^{12}$ is —PO$_3$H. In embodiments, $R^{12}$ is —PO$_4$H. In embodiments, $R^{12}$ is —SO$_2$NH$_2$. In embodiments, $R^{12}$ is —SO$_3$H. In embodiments, $R^{12}$ is —SO$_4$H. $R^{12A}$ is oxo, halogen, —CF$_3$, —CCl$_3$, —CI$_3$, —CBr$_3$, "\*MERGEFORMAT\*MERGEFORMAT —CHF$_2$, —CHCl$_2$, —CHI$_2$, —CHBr$_2$, —CH$_2$F, —CH$_2$Cl, —CH$_2$I, —CH$_2$Br, —OCH$_2$F, —OCH$_2$Cl, —OCH$_2$I, —OCH$_2$Br, —OCHF$_2$, —OCHCl$_2$, —OCHI$_2$, —OCHBr$_2$, —OCF$_3$, —OCCl$_3$, —OCI$_3$, —OCBr$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —PO$_4$H, —PO$_3$H, —OPO$_3$H, —N$_3$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 8 membered, 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). In embodiments, $R^{12A}$ is —PO$_3$H, —PO$_4$H, —SO$_2$NH$_2$, —SO$_3$H, or —SO$_4$H. In embodiments, $R^{12A}$ is —SO$_3$H. In embodiments, $R^{12A}$ is —PO$_3$H. In embodiments, $R^{12A}$ is —SO$_2$NH$_2$. In embodiments, $R^{12A}$ is —SO$_4$H. In embodiments, $R^{12A}$ is —NH$_2$. In embodiments, $R^{12A}$ is —COOH. In embodiments, $R^{12A}$ is —Br. In embodiments, $R^{12A}$ is —OH. In embodiments, $R^{12A}$ is —OPO$_3$H.

In embodiments, $R^{12}$ is $R^{12A}$-substituted or unsubstituted alkyl (e.g., C$_1$-C$_8$, C$_1$-C$_6$, C$_1$-C$_4$, or C$_1$-C$_2$). In embodiments, $R^{12}$ is $R^{12A}$-substituted alkyl (e.g., C$_1$-C$_8$, C$_1$-C$_6$, C$_1$-C$_4$, or C$_1$-C$_2$). In embodiments, $R^{12}$ is $R^{12A}$-substituted C$_1$ alkyl. In embodiments, $R^{12}$ is $R^{12A}$-substituted C$_2$ alkyl. In embodiments, $R^{12}$ is $R^{12A}$-substituted C$_3$ alkyl. In embodiments, $R^{12}$ is $R^{12A}$-substituted C$_4$ alkyl. In embodiments, $R^{12}$ is $R^{12A}$-substituted C$_5$ alkyl. In embodiments, $R^{12}$ is $R^{12A}$-substituted C$_6$ alkyl. In embodiments, $R^{12}$ is $R^{12A}$-substituted C$_7$ alkyl. In embodiments, $R^{12}$ is $R^{12A}$-substituted C$_8$ alkyl. In embodiments, $R^{12}$ is an unsubstituted alkyl (e.g., C$_1$-C$_8$, C$_1$-C$_6$, C$_1$-C$_4$, or C$_1$-C$_2$). In embodiments, $R^{12}$ is an unsubstituted C$_1$ alkyl. In embodiments, $R^{12}$ is an unsubstituted C$_2$ alkyl. In embodiments, $R^{12}$ is an unsubstituted C$_3$ alkyl. In embodiments, $R^{12}$ is an unsubstituted C$_4$ alkyl. In embodiments, $R^{12}$ is an unsubstituted C$_5$ alkyl. In embodiments, $R^{12}$ is an unsubstituted C$_6$ alkyl. In embodiments, $R^{12}$ is an unsubstituted C$_7$ alkyl. In embodiments, $R^{12}$ is an unsubstituted C$_8$ alkyl.

In embodiments, $R^{12}$ is $R^{12A}$-substituted or unsubstituted heteroalkyl (e.g., 2 to 8 membered, 2 to 6 membered, 4 to 6 membered, 2 to 3 membered, or 4 to 5 membered). In embodiments, $R^{12}$ is $R^{12A}$-substituted heteroalkyl (e.g., 2 to 8 membered, 2 to 6 membered, 4 to 6 membered, 2 to 3 membered, or 4 to 5 membered). In embodiments, $R^{12}$ is $R^{12A}$-substituted 2 membered heteroalkyl. In embodiments, $R^{12}$ is $R^{12A}$-substituted 3 membered heteroalkyl. In embodiments, $R^{12}$ is $R^{12A}$-substituted 4 membered heteroalkyl. In embodiments, $R^{12}$ is $R^{12A}$-substituted 5 membered heteroalkyl. In embodiments, $R^{12}$ is $R^{12A}$-substituted 6 membered heteroalkyl.

In embodiments, at least one of $R^3$, $R^4$, $R^7$, or $R^8$ is —SO$_3$H. In embodiments, $R^3$ is —SO$_3$H. In embodiments, $R^4$ is —SO$_3$H. In embodiments, $R^7$ is —SO$_3$H. In embodiments, $R^8$ is —SO$_3$H. In embodiments, $R^3$ and $R^4$ are —SO$_3$H. In embodiments, $R^3$ and $R^7$ are —SO$_3$H. In embodiments, $R^3$ and $R^8$ are —SO$_3$H. In embodiments, $R^4$ and $R^7$ are —SO$_3$H. In embodiments, $R^4$ and $R^8$ are —SO$_3$H. In embodiments, $R^7$ and $R^8$ are —SO$_3$H.

In embodiments, $R^9$ is substituted or unsubstituted aryl (e.g., C$_6$-C$_{10}$ or phenyl). In embodiments, $R^9$ is substituted phenyl. In embodiments, $R^9$ is unsubstituted phenyl. In embodiments, $R^9$ is $R^{10}$-substituted phenyl, having the formula:

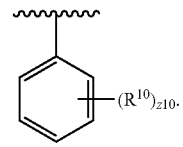

$R^{10}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —O CI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —S F$_5$, —SO$_2$Cl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and z10 is an integer from 1 to 5. In embodiments, z10 is 1. In embodiments, z10 is 2. In embodiments, z10 is 3. In embodiments, z10 is 4. In embodiments, z10 is 5.

In embodiments, $R^{10}$ is halogen. In embodiments, $R^{10}$ is hydrogen. In embodiments, $R^{10}$ is —CCl$_3$. In embodiments, $R^{10}$ is —CBr$_3$. In embodiments, $R^{10}$ is —CF$_3$. In embodiments, $R^{10}$ is —CI$_3$. In embodiments, $R^{10}$ is —CHCl$_2$. In embodiments, $R^{10}$ is —CHBr$_2$. In embodiments, $R^{10}$ is —CHF$_2$. In embodiments, $R^{10}$ is CHI$_2$. In embodiments, $R^{10}$ is —CH$_2$Cl. In embodiments, $R^{10}$ is —CH$_2$Br. In embodiments, $R^{10}$ is —CH$_2$F. In embodiments, $R^{10}$ is —CH$_2$I. In embodiments, $R^{10}$ is —CN. In embodiments, $R^{10}$ is —OH. In embodiments, $R^{10}$ is —NH$_2$. In embodiments, $R^{10}$ is —COOH. In embodiments, $R^{10}$ is —CONH$_2$. In embodiments, $R^{10}$ is —NO$_2$. In embodiments, $R^{10}$ is —SH. In embodiments, $R^{10}$ is —SO$_3$H. In embodiments, $R^{10}$ is —SO$_4$H. In embodiments, $R^{10}$ is —SO$_2$NH$_2$. In embodiments, $R^{10}$ is —NHNH$_2$. In embodiments, $R^{10}$ is —ONH$_2$. In embodiments, $R^{10}$ is —NHC(O)NHNH$_2$. In embodiments, $R^{10}$ is —NHC(O)NH$_2$. In embodiments, $R^{10}$ is —NHSO$_2$H. In embodiments, $R^{10}$ is —NHC(O)H. In embodiments, $R^{10}$ is —NHC(O)OH. In embodiments, $R^{10}$ is —NHOH. In embodiments, $R^{10}$ is —OCCl$_3$. In embodiments, $R^{10}$ is —OCF$_3$. In embodiments, $R^{10}$ is —OCBr$_3$. In embodiments, $R^{10}$ is —OCI$_3$. In embodiments, $R^{10}$ is —OCHCl$_2$. In embodiments, $R^{10}$ is —OCHBr$_2$. In embodiments, $R^{10}$ is —OCHI$_2$. In embodiments, $R^{10}$ is —OCHF$_2$. In embodiments, $R^{10}$ is —OCH$_2$Cl. In embodiments, $R^{10}$ is —OCH$_2$Br. In embodiments, $R^{10}$ is —OCH$_2$I. In embodiments, $R^{10}$ is —OCH$_2$F. In embodiments, $R^{10}$ is —N$_3$. In embodiments, $R^{10}$ is —SF$_5$. In embodiments, $R^{10}$ is —SO$_2$Cl.

In embodiments, $R^{10}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{10}$ is hydrogen. In embodiments, $R^{10}$ is $R^{10A}$-substituted or unsubstituted alkyl (e.g., $C_1$-$C_{20}$, $C_{10}$-$C_{20}$, $C_1$-$C_8$, $C_1$-$C_6$, or $C_1$-$C_4$), $R^{10A}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{10A}$-substituted or unsubstituted cycloalkyl (e.g., $C_3$-$C_8$, $C_3$-$C_6$, or $C_5$-$C_6$), $R^{10A}$-substituted or unsubstituted heterocycloalkyl (e.g., 3 to 8 membered, 3 to 6 membered, or 5 to 6 membered), $R^{10A}$-substituted or unsubstituted aryl (e.g., $C_6$-$C_{10}$, $C_{10}$, or phenyl), $R^{10A}$-substituted or unsubstituted heteroaryl (e.g., 5 to 10 membered, 5 to 9 membered, or 5 to 6 membered).

$R^{10A}$ is oxo, halogen, —$CCl_3$, —$CBr_3$, —$CF_3$, —$CI_3$, —$CHCl_2$, —$CHBr_2$, —$CHF_2$, —$CHI_2$,
"\*MERGEFORMAT\*MERGEFORMAT —$CH_2Cl$, —$CH_2Br$, —$CH_2F$, —$CH_2I$, —CN, —OH, —$NH_2$, —COOH, —$CONH_2$, —$NO_2$, —SH, —$SO_2NH_2$,
"\*MERGEFORMAT\*MERGEFORMAT —$NHNH_2$, —$ONH_2$, —NHC(O)$NHNH_2$, —NHC(O)$NH_2$, —$NHSO_2H$, —NHC(O)H, —NHC(O)OH,
"\*MERGEFORMAT\*MERGEFORMAT —NHOH, —$OCCl_3$, —$OCF_3$, —$OCBr_3$, —$OCI_3$, —$OCHCl_2$, —$OCHBr_2$, —$OCHI_2$, —O $CHF_2$, —$OCH_2Cl$,
"\*MERGEFORMAT\*MERGEFORMAT —$OCH_2Br$, —$OCH_2I$, —$OCH_2F$, —$N_3$, —$SF_5$, —$PO_3H$, —$PO_4H$, —$SO_2NH_2$, —$SO_3H$, —S $O_4H$, $R^{10B}$-substituted or unsubstituted alkyl (e.g., $C_1$-$C_{20}$, $C_1$-$C_{20}$, $C_1$-$C_8$, $C_1$-$C_6$, or $C_1$-$C_4$), $R^{10B}$-substituted or unsubstituted heteroalkyl (e.g., 2 to 20 membered, 8 to 20 membered, 2 to 10 membered, 2 to 8 membered, 2 to 6 membered, or 2 to 4 membered), $R^{10B}$-substituted or unsubstituted cycloalkyl (e.g., $C_3$-$C_8$, $C_3$-$C_6$, or $C_5$-$C_6$), $R^{10B}$-substituted or unsubstituted heterocycloalkyl (e.g., 3 to 8 membered, 3 to 6 membered, or 5 to 6 membered), $R^{10B}$-substituted or unsubstituted aryl (e.g., $C_6$-$C_{10}$, $C_{10}$, or phenyl), or $R^{10B}$-substituted or unsubstituted heteroaryl (e.g., 5 to 10 membered, 5 to 9 membered, or 5 to 6 membered). In embodiments, $R^{10A}$ is unsubstituted phenyl.

$R^{10B}$ is oxo, halogen, —$CCl_3$, —$CBr_3$, —$CF_3$, —$CI_3$, —$CHCl_2$, —$CHBr_2$, —$CHF_2$, —$CHI_2$,
"\*MERGEFORMAT\*MERGEFORMAT —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H,
"\*MERGEFORMAT\*MERGEFORMAT —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$,
"\*MERGEFORMAT\*MERGEFORMAT —$OCH_2Cl$, —$OCH_2Br$, —$OCH_2I$, —$OCH_2F$, —$N_3$, —$SF_5$, —$PO_3H$, —$PO_4H$, —$SO_2NH_2$, —$SO_3H$, —$SO_4H$, unsubstituted alkyl (e.g., $C_1$-$C_{20}$, $C_{10}$-$C_{20}$, $C_1$-$C_8$, $C_1$-$C_6$, or $C_1$-$C_4$), unsubstituted heteroalkyl (e.g., 2 to 20 membered, 8 to 20 membered, 2 to 10 membered, 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, $R^9$ is substituted with multiple, independent $R^{10}$ substituents. When multiple $R^{10}$ substituents are present, each $R^{10}$ substituent may be distinguished as $R^{10.1}$, $R^{10.2}$, $R^{10.3}$, $R^{10.4}$, etc., wherein each of $R^{10.1}$, $R^{10.2}$, $R^{10.3}$, $R^{10.4}$, etc. is defined within the scope of the definition of $R^{10}$ and optionally differently. For example $R^9$ may have the formula:

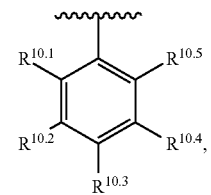

wherein $R^{10.1}$, $R^{10.2}$, $R^{10.3}$, $R^{10.4}$, and $R^{10.5}$ are each defined within the scope of the definition of $R^{10}$ and optionally differently.

In embodiments $R^{10}$ is halogen. In embodiments, $R^{10}$ is Cl. In embodiments, $R^{10}$ is

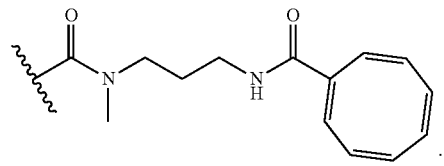 [SMILES: *C(=O)N(C)CCCNC(=O)C1=C/C=C\C=C/C=C\1]

In embodiments, $R^{10}$ is

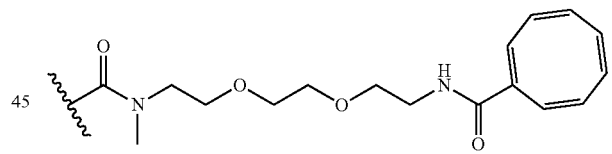

In embodiments, R10 is

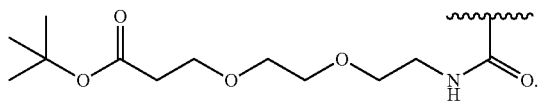 [SMILES: *C(=O)NCCOCCOCCC(=O)OC(C)(C)C]

In embodiments, $R^{10}$ is

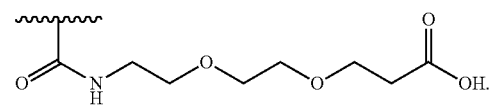 [SMILES: *C(=O)NCCOCCOCCC(=O)O]

In embodiments, $R^{10}$ is
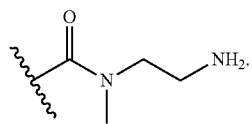 [SMILES: *C(=O)N(C)CCN]
In embodiments, $R^{10}$ is
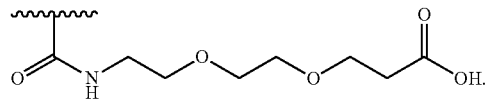 [SMILES: *C(=O)NCCOCCOCCC(=O)O]
In embodiments, $R^{10}$ is
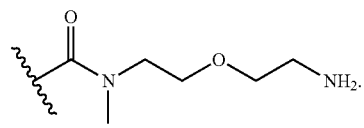 [SMILES: *C(=O)N(C)CCOCCN]
In embodiments, $R^{10}$ is
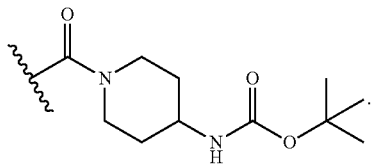 [SMILES: *C(=O)N1CCC(NC(=O)OC(C)(C)C)CC1]
In embodiments, $R^{10}$ is
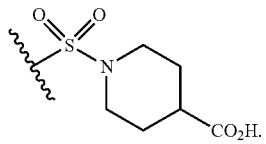
In embodiments, $R^9$ is:
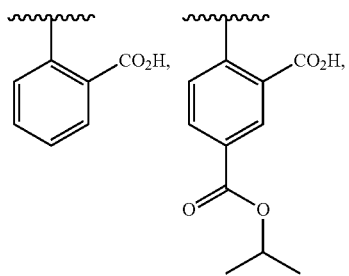
-continued
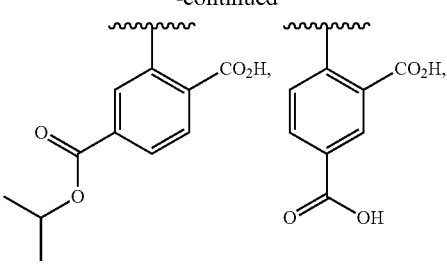
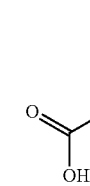 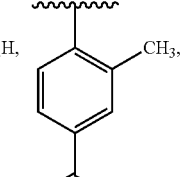
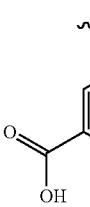 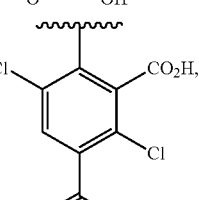
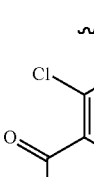 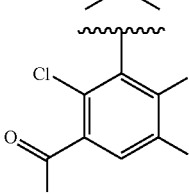
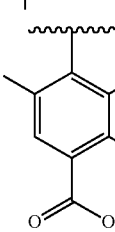 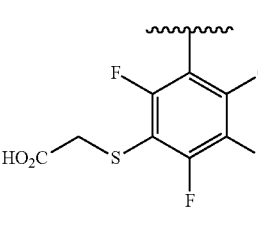
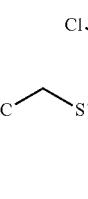 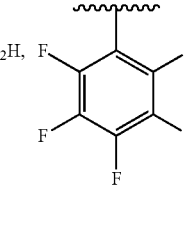
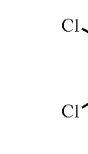 , 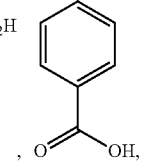

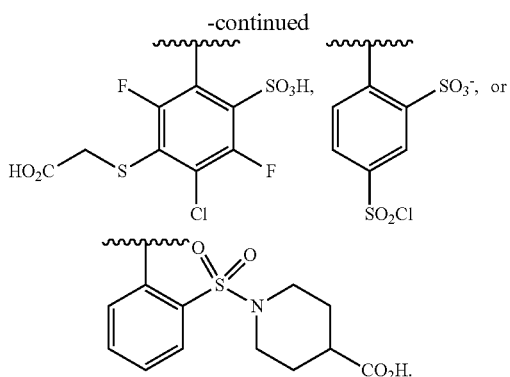
In embodiments, compound A has the formula:
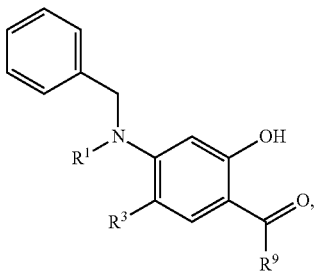
wherein $R^1$, $R^2$, and $R^9$ are as described herein.
In embodiments, compound A has the formula:
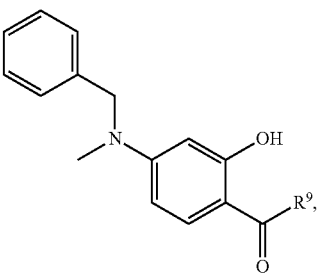
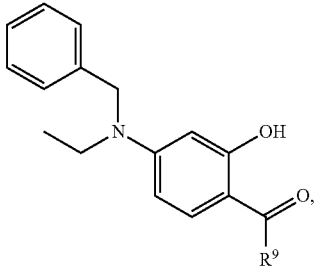
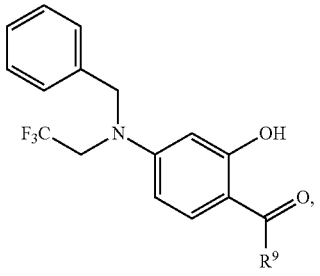
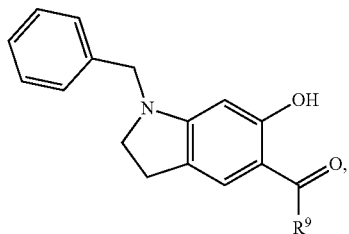
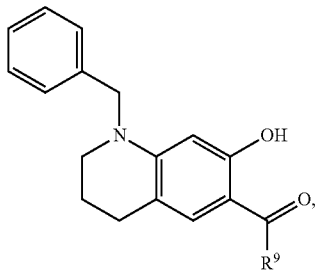
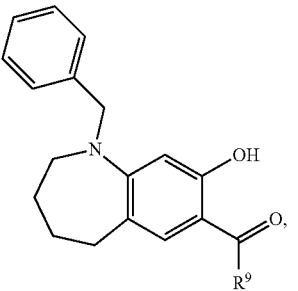
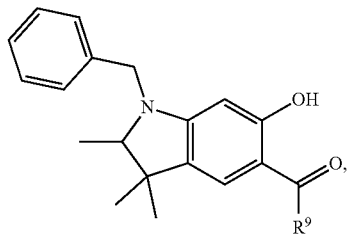
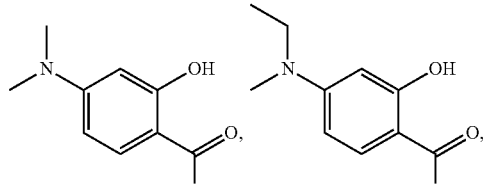
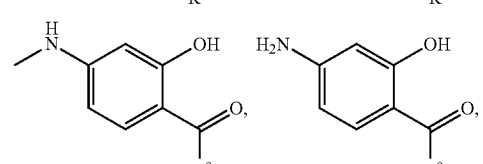
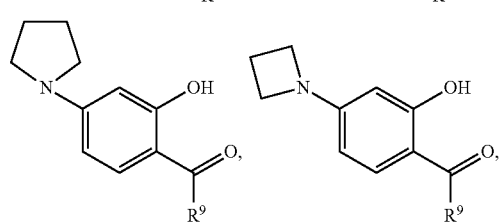

115
-continued
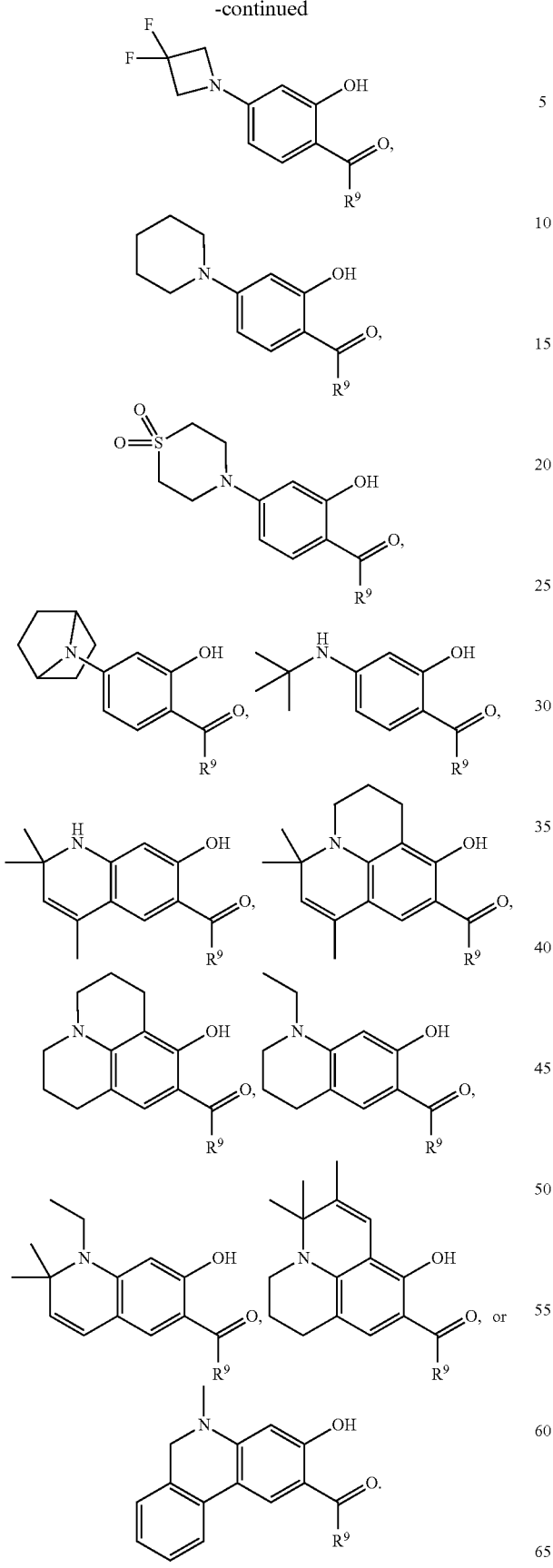
116
In embodiments, compound A has the formula:
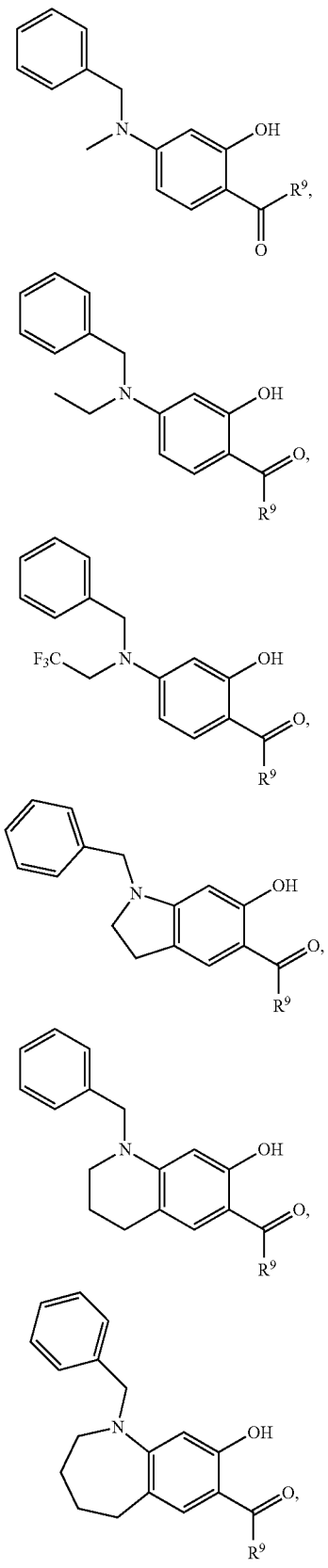

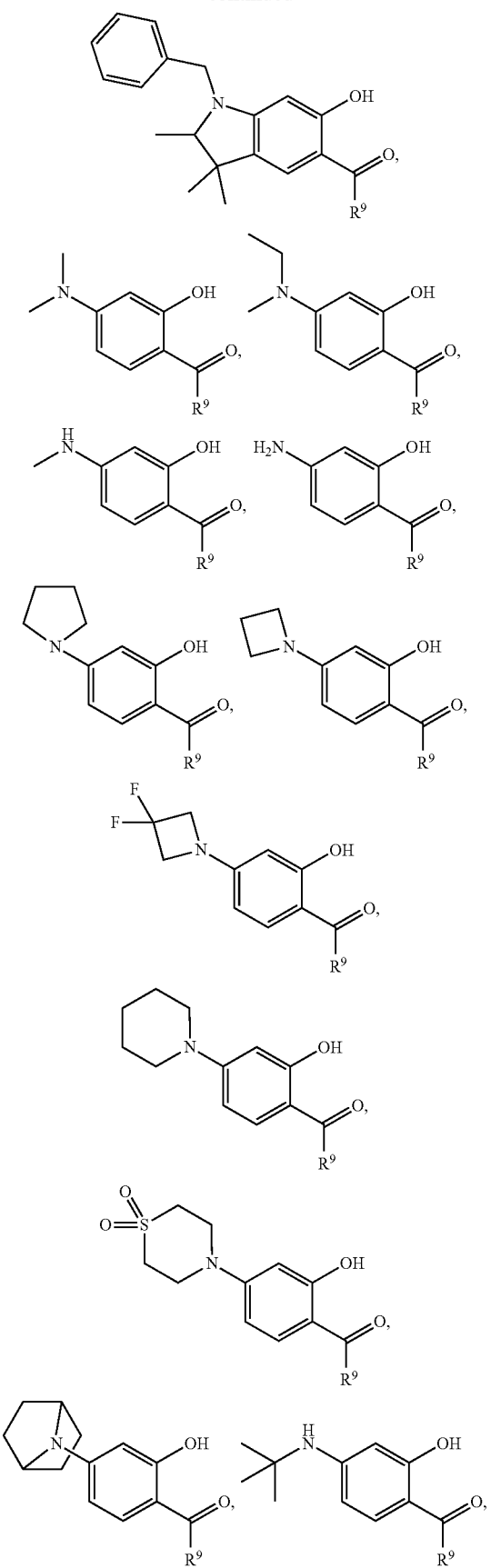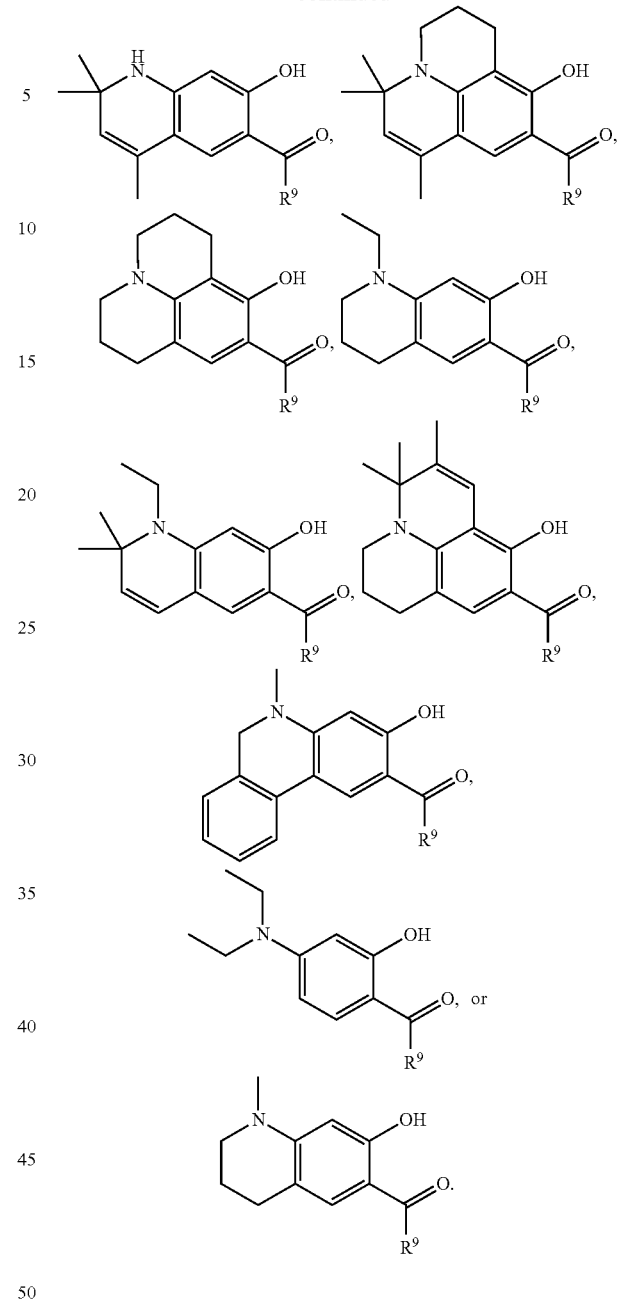
In embodiments, compound A has the formula:
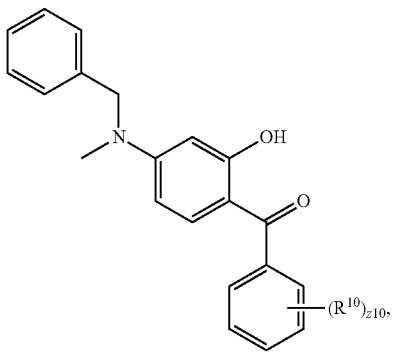

119
-continued
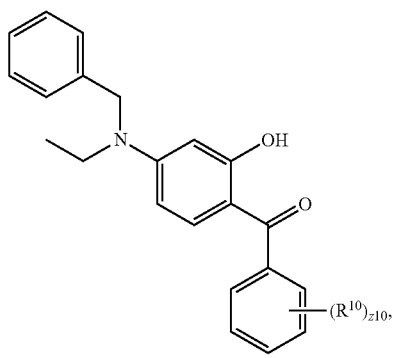
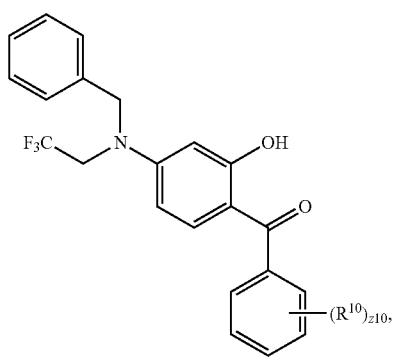
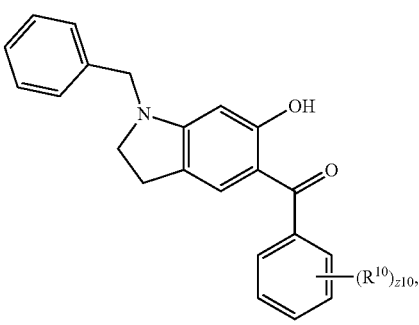
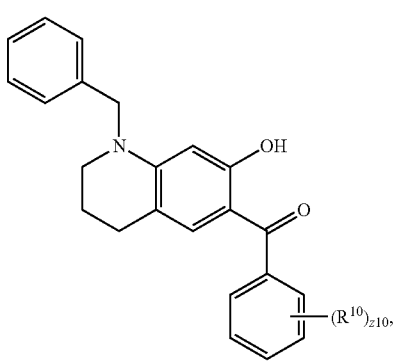
120
-continued
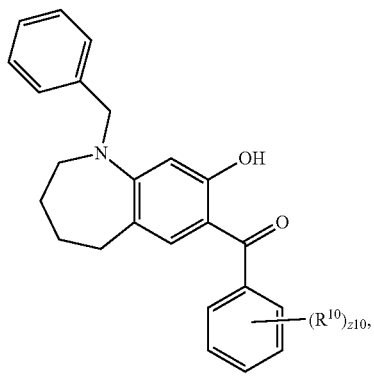
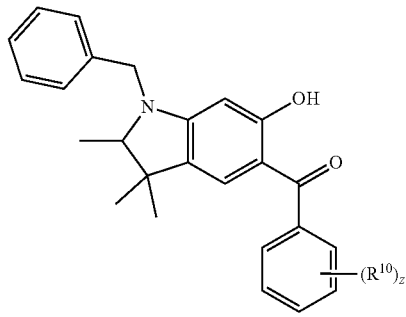
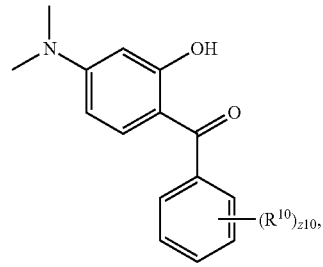
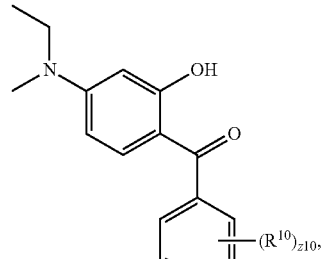
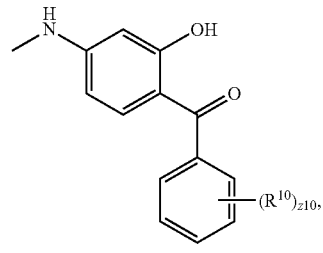
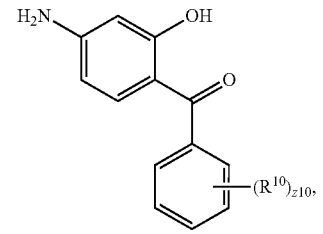

121
-continued
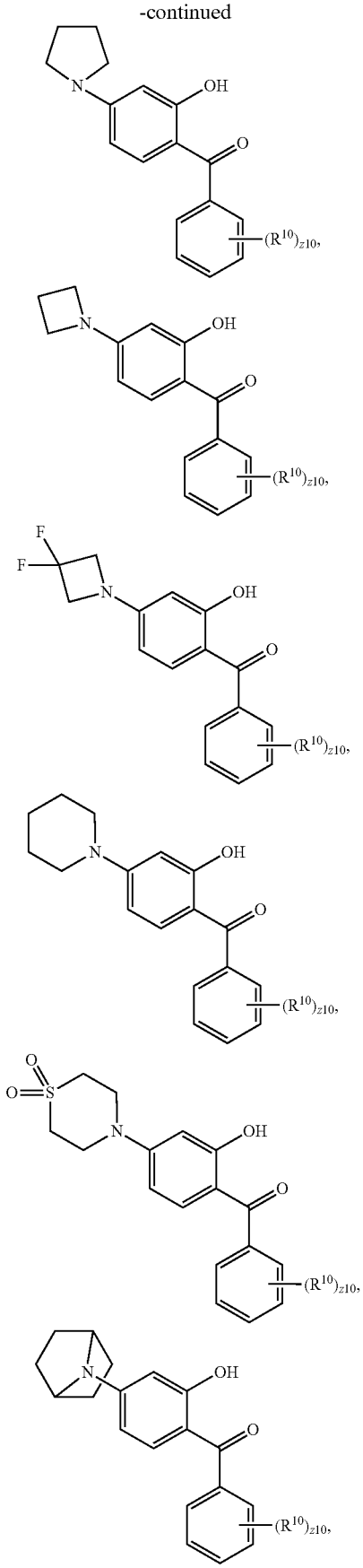
122
-continued
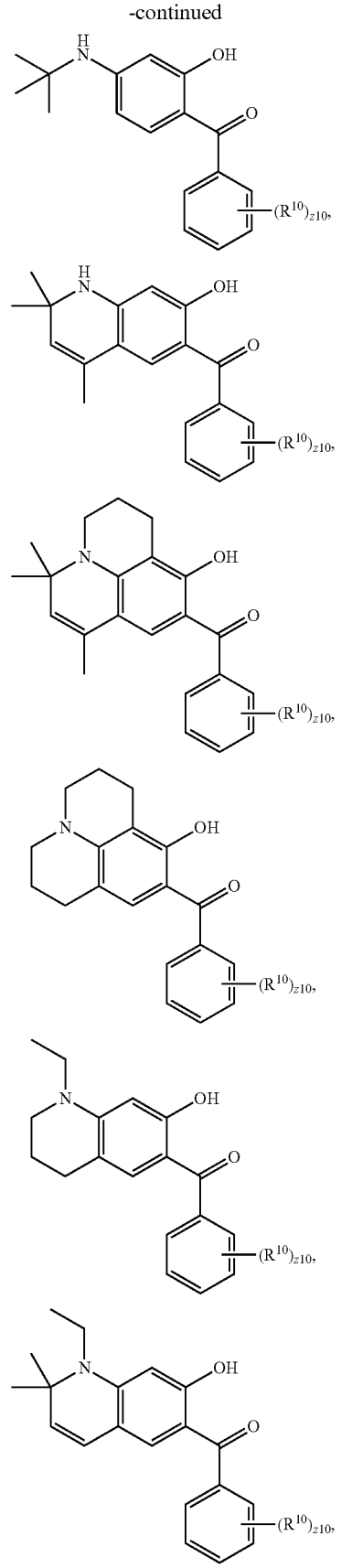

123
-continued
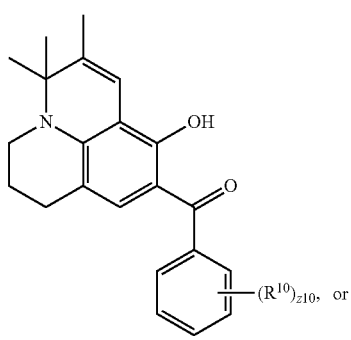
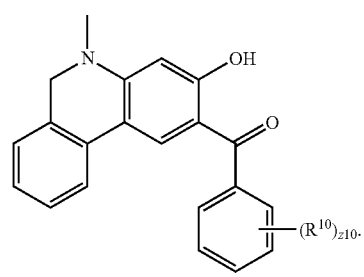
In embodiments, compound A has the formula:
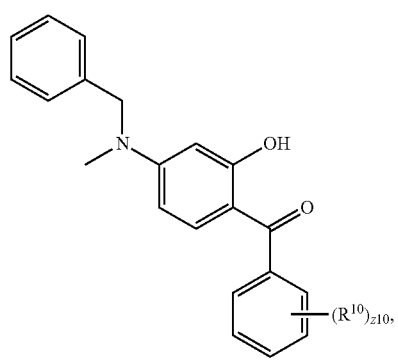
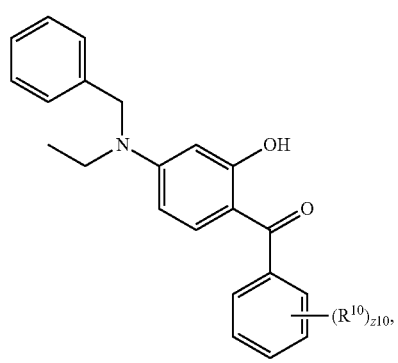
124
-continued
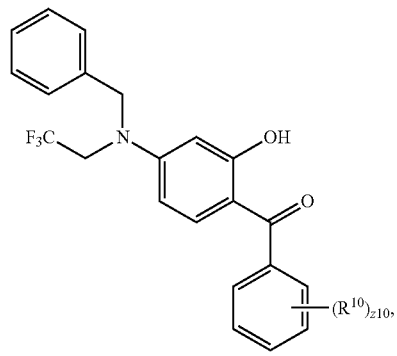
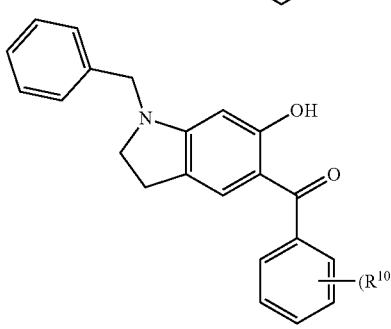
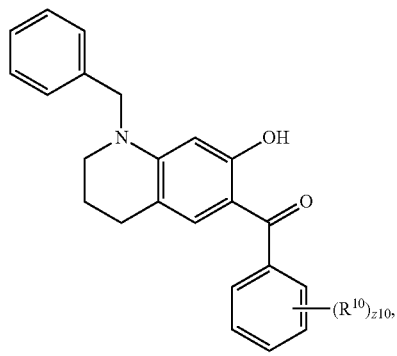
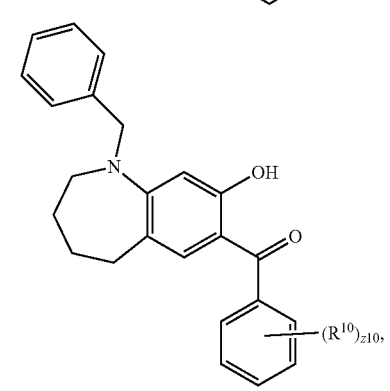
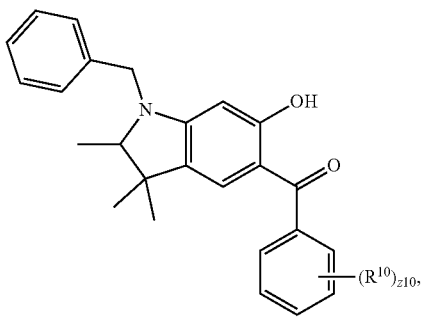

-continued
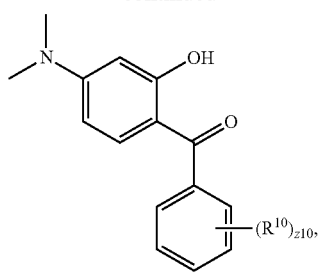
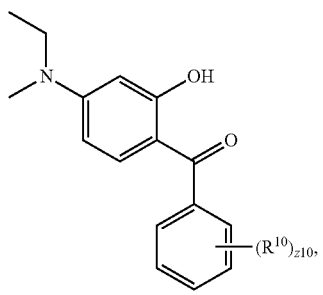
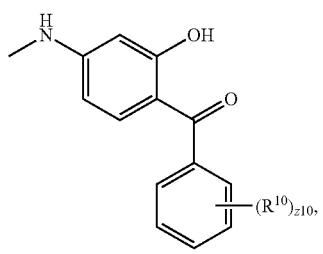
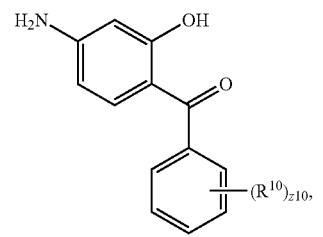
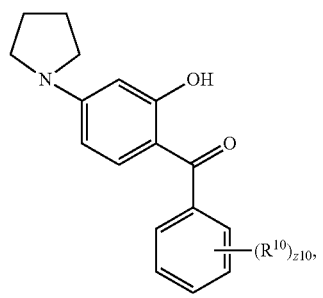
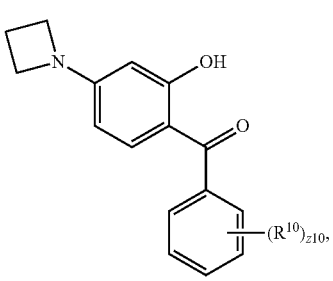
-continued
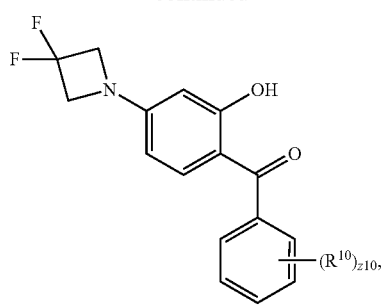
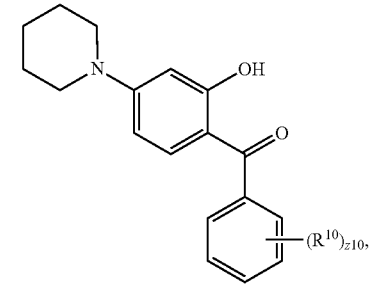
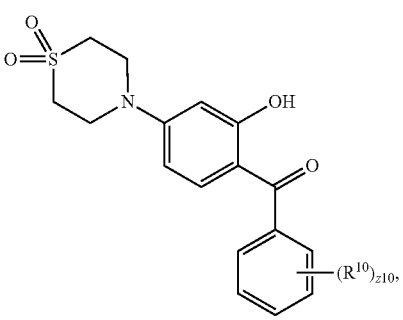
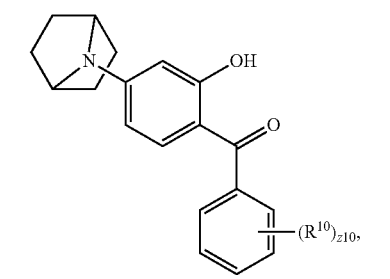
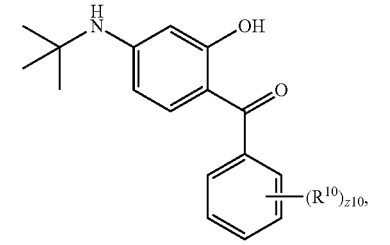
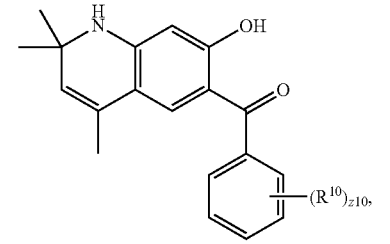

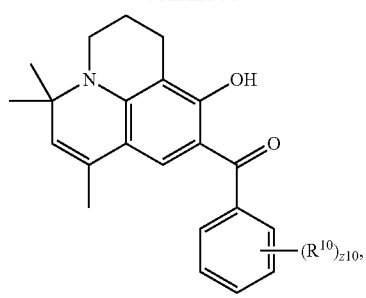
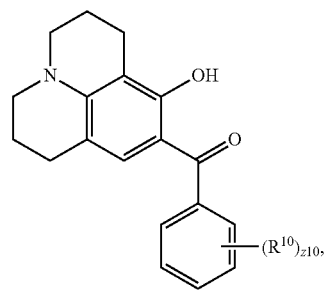
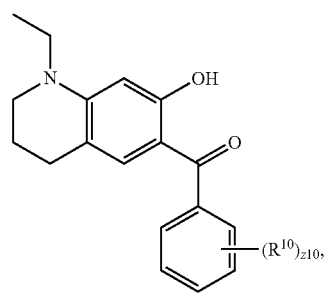
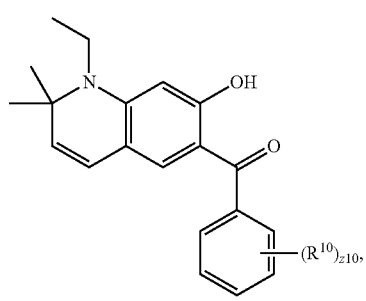
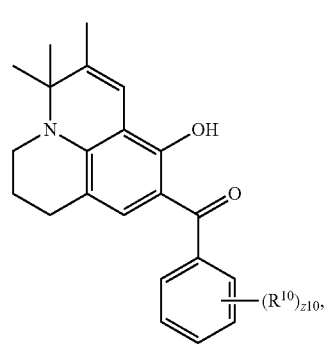
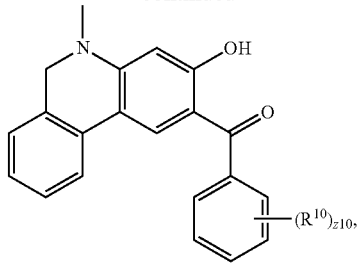
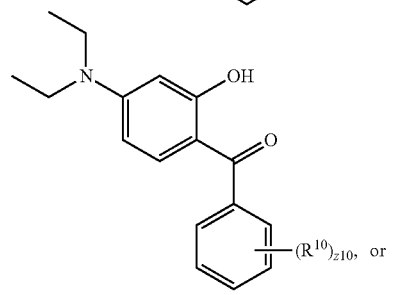
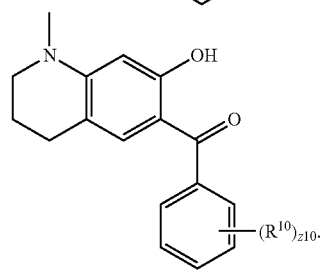
In embodiments, compound B has the formula:
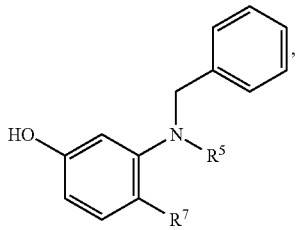
wherein $R^5$ and $R^7$ are as described herein.
In embodiments, compound B has the formula:
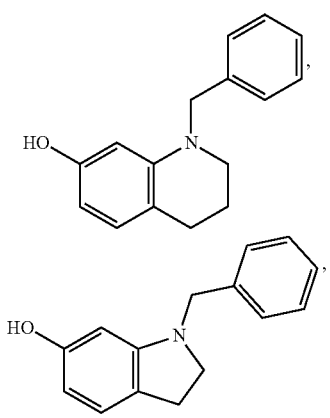

-continued
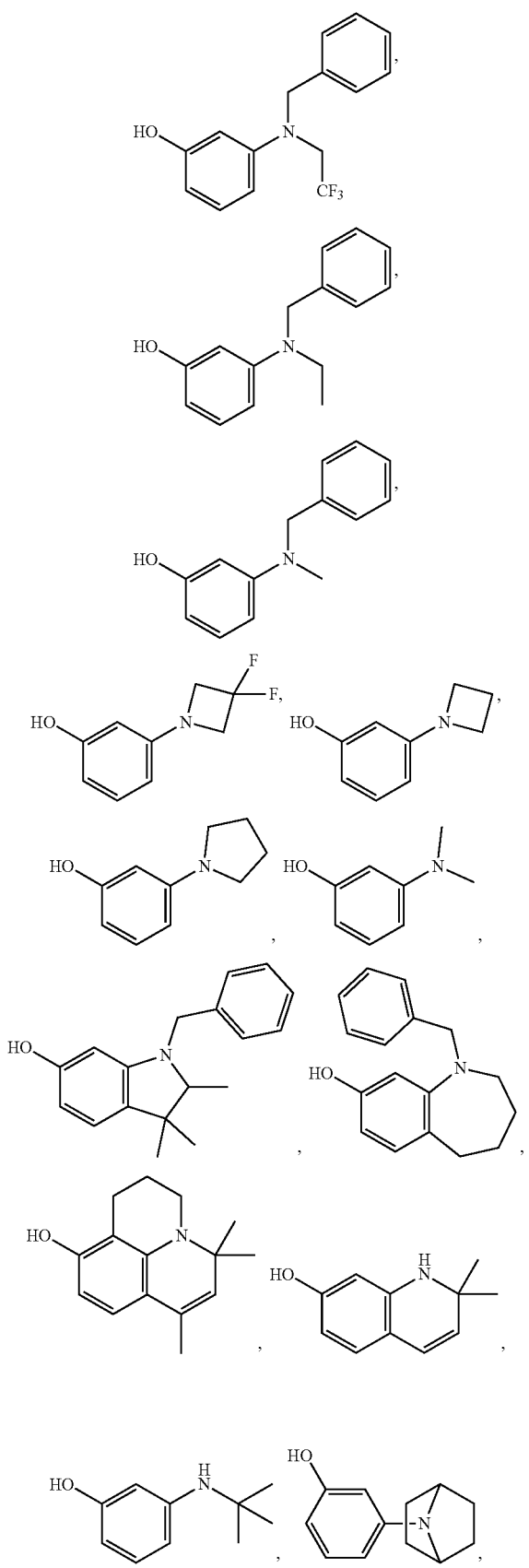
-continued
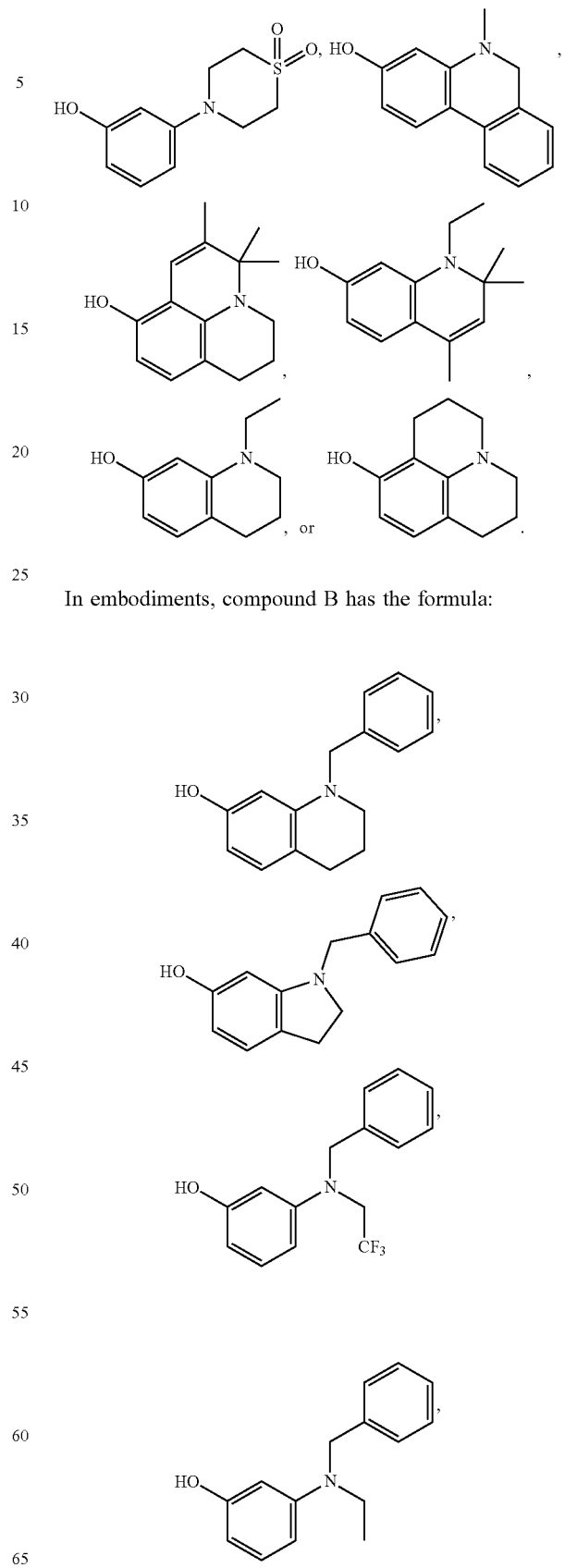
In embodiments, compound B has the formula:

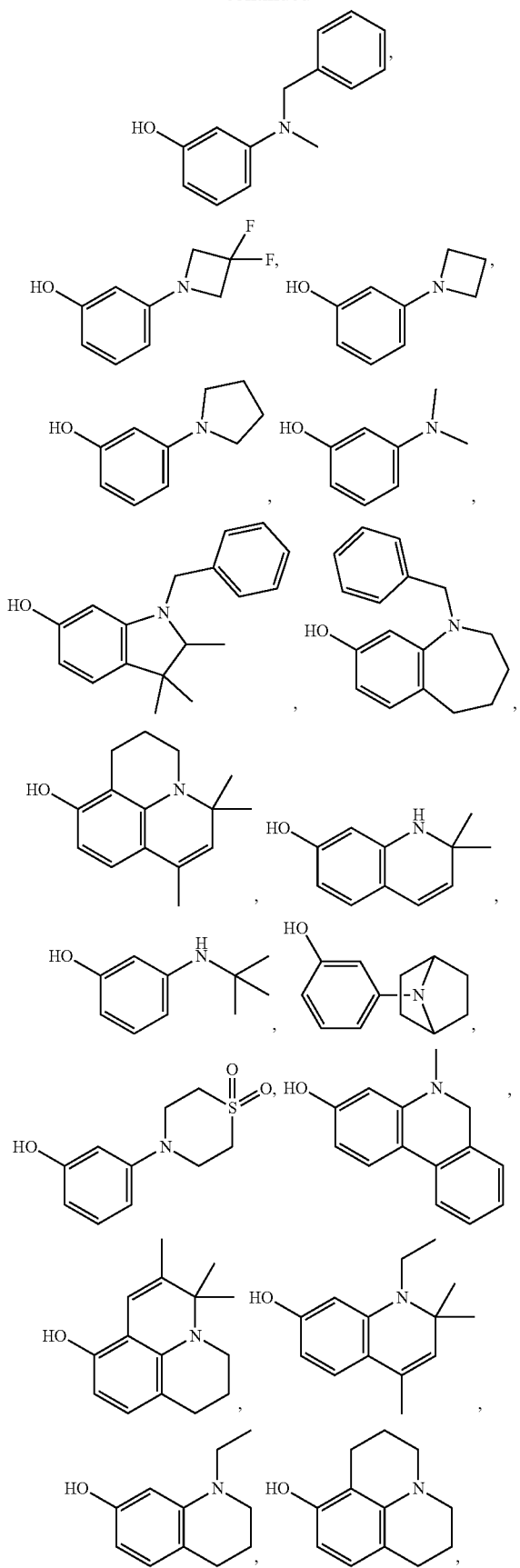
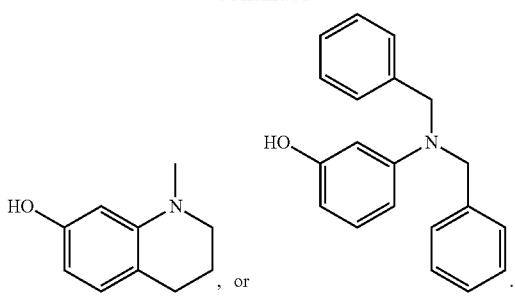, or 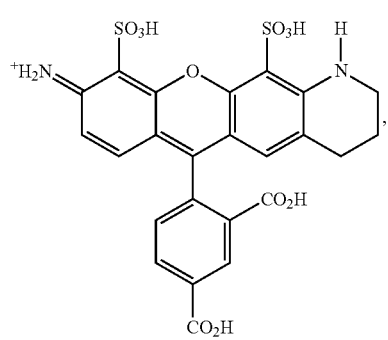.
In embodiments, the compound of formula I has the formula:
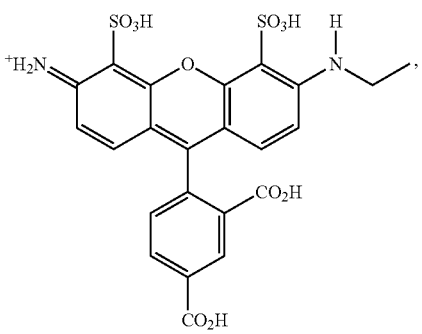
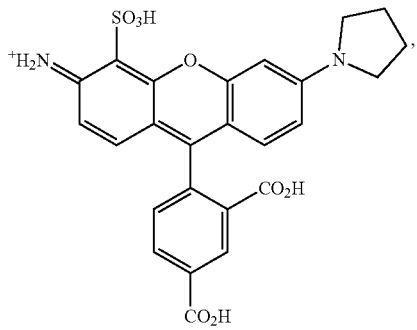

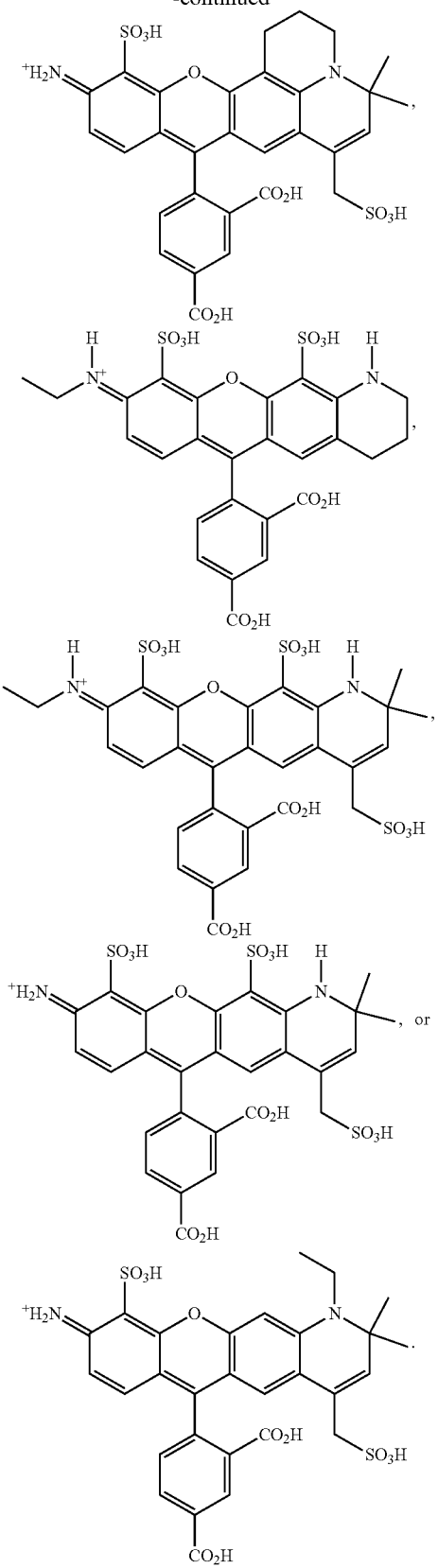

In an aspect is provided a method of detecting the presence of an agent, wherein the agent is covalently bound to a monovalent compound as described herein, wherein the agent is an oligonucleotide, protein, nucleotide, or compound. In embodiments, the agent is an oligonucleotide, protein, or compound. In embodiments, the agent is an oligonucleotide (e.g., DNA, RNA, or siRNA), protein (e.g., antibody or antibody fragment), or a compound. In embodiments, the method includes a spectroscopic measurement (e.g., measure the emission from the compound described herein bonded to the agent). In embodiments, the spectroscopic measurement is an ultraviolet-visible spectroscopy measurement. In embodiments, the spectroscopic measurement is an near-IR spectroscopy measurement. In embodiments, the compound is present in an effective amount. In embodiments, the agent is a nucleic acid. In embodiments, the agent is a nucleotide. In embodiments, the method includes detecting in vitro. In embodiments, the method includes detecting in a nucleic acid sequencing device. In embodiments, the agent is a protein, a carbohydrate, a polysaccharide, a glycoprotein, a hormone, a receptor, an antigen, an antibody, or a virus.

In embodiments, the agent is a cell. In embodiments, the agent is a cancer cell. In embodiments, the method of detecting includes identifying an agent. In embodiments, the method of detecting includes quantifying an agent. In embodiments, the agent is obtained from biological materials, such as, for example from a cell lysate, a buffer solution in which cells have been placed for evaluation, or physiological sources, e.g., blood, plasma, serum, or urine. In embodiments, the agent includes a plurality of cells. In embodiments, the agent is a single cell. In embodiments, when the agent includes cells, the cells may be lysed, e.g., a cell lysate, or whole cells. The cells may also be in an animal, i.e, the compounds as described herein may be used for in vivo imaging. In embodiments, the agent is present on or in a solid or semi-solid matrix. In embodiments, the matrix is an electrophoretic gel, such as those used for separating and characterizing nucleic acids or proteins, or a blot prepared by transfer from an electrophoretic gel to a membrane. In embodiments, the matrix is a silicon chip or glass slide, and the analyte of interest has been immobilized on the chip or slide in an array (e.g., the agent comprises proteins or nucleic acid polymers in a microarray). In embodiments, the matrix is a microwell plate or microfluidic chip, and the sample is analyzed by automated methods, typically by various methods of high-throughput screening, such as drug screening.

In embodiments, the agent is illuminated with a wavelength of light selected to give a detectable optical response and observed with a means for detecting the optical response. Equipment that is useful for illuminating the compound-agent complex includes, but is not limited to, ultraviolet lamps, mercury arc lamps, xenon lamps, lasers, and laser diodes. In embodiments the optical response is detected by visual inspection or by using one or more CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes.

In embodiments, the method includes detecting the presence of a nucleotide. In embodiments, the method includes detecting the presence of a polynucleotide. Such polynucleotides may be DNA or RNA comprised respectively of deoxyribonucleotides or ribonucleotides joined in phosphodiester linkage. In embodiments, the polynucleotides include naturally occurring nucleotides and/or non-naturally occurring (or modified) nucleotides, that is modified nucleotides other than the labelled nucleotides (e.g. nucleotides bound to a monovalent compound described herein), or any combination thereof, provided that at least one modified nucleotide is a nucleotide covalently bound to a compound described herein. Polynucleotides according to the invention may also include non-natural backbone linkages and/or non-nucleotide chemical modifications.

In embodiments, the method includes (i) incorporating one or more modified nucleotides into a polynucleotide, wherein the modified nucleotide is a nucleotide covalently bound to a compound described herein; and (ii) detecting the one or more modified nucleotide(s) incorporated into the polynucleotide by detecting or quantitatively measuring their fluorescence (e.g., fluorescence of the compound described herein that is included in the one or more modified nucleotide(s)). In embodiments, the modified nucleotide is incorporated into a polynucleotide by a DNA polymerase (e.g., a DNA polymerase described herein). In embodiments, step (i) includes incubating a template polynucleotide strand with a reaction mixture including modified nucleotides and a DNA polymerase under conditions that allow for the formation of a phosphodiester linkage between a free 3' hydroxyl group on a polynucleotide strand annealed to the template polynucleotide strand and a 5' phosphate group on the modified nucleotide. In embodiments, step (ii) may be carried out while the polynucleotide strand is annealed to a template strand, or after a denaturation step in which the two strands are separated.

In embodiments, the method includes exposing the compound described herein, which is bound to the agent, to electromagnetic radiation, wherein the electromagnetic radiation has a wavelength selected from 100 to 1000 nm. In embodiments, the electromagnetic radiation has a wavelength selected from about 500 nm to about 700 nm. In embodiments, the method includes detecting the emission wavelength of the compound described herein bound to the agent (e.g., detecting the emission wavelength of the compound following exposure to the electromagnetic radiation). In embodiments, the emission wavelength is about 500 nm to about 700 nm. In embodiments, the emission wavelength is about 500 nm to about 800 nm. In embodiments, the emission wavelength is about 600 nm to about 700 nm.

In another aspect is provided a method for detecting the presence of a nucleotide, wherein the nucleotide is covalently bound to a compound (e.g., a compound described herein) (i.e., detecting the presence of the compound and thereby detect the presence of the covalently bound nucleotide).

In embodiments the method includes use of the modified nucleotides or nucleosides labelled with compounds described herein in a method of nucleic acid sequencing, re-sequencing, whole genome sequencing, single nucleotide polymorphism scoring, any other application involving the detection of the modified nucleotide or nucleoside when incorporated into a polynucleotide, or any other application requiring the use of polynucleotides labelled with the modified nucleotides, wherein the modified nucleotide is a nucleotide covalently bound to a compound described herein.

In an aspect is provided a method of nucleic acid sequencing including incorporating a modified nucleotide (e.g., a nucleotide covalently bound to a compound described herein) into a polynucleotide. In embodiments, the covalent bond between the nucleotide and the compound described herein is cleavable (e.g., a cleavable linker).

EXAMPLES

Example 1. Rhodamine Compounds

Fluorescent dyes are widely used for labeling, detecting, and quantifying components in a sample. Analytical methods that utilize such dye reagents include fluorescence microscopy, fluorescence immunoassay, flow cytometric analysis of cells, nucleic acid sequencing, and various other applications. The choice of fluorescent dyes is particularly important in applications that utilize multiplex, multicolor analysis (e.g., nucleic acid sequencing technology). Currently available red- and near-infrared (NIR)-emitting fluorescent dyes, such as rhodamines and cyanines, suffer from low water-solubility, aggregation, and some derivatives suffer from poor photostability characteristics. For example, due to their hydrophobic nature, most commercially available rhodamine dyes are somewhat insoluble in water. Red-emitting cyanine dyes such as Cy5, although water-soluble, are photo unstable. Thus, available red-emitting rhodamine and cyanine dyes are not well-suited for many aqueous-based biological applications, such as cell staining or nucleic acid sequencing. In particular, for nucleic acid sequencing applications, the fluorophore needs to have relatively narrow excitation and emission bands to facilitate multiplex optical detection.

Red-emitting fluorophores belong to various dye families (e.g., rhodamines and cyanines). As red emission is linked to extensive π-electron conjugation, fluorophores are usually large polycyclic aromatic hydrocarbons, porphyrin-type compounds, or very polar push-pull heteroaromatic compounds, which in turn makes their aqueous solubility an issue. Additionally, due to their structure, red-emitting fluorophores show a tendency towards aggregation due to intermolecular π stacking or attractive dipole-dipole interactions. Aggregation is extremely detrimental to fluorescence, and most red-emitting fluorophores become very weakly emissive, or not emissive at all, at increased concentrations. Thus, the brightness, photostability and aqueous solubility of red fluorophores can suffer when the carbocyclic framework is extended.

Fluorescent dye molecules with improved fluorescence properties (such as fluorescence intensity, maximum emission wavelength) can improve the speed and accuracy of nucleic acid sequencing. Fluorescence signal intensity is particularly important when measurements are made in solvents typically used in nucleic acid sequencing technologies (e.g., water based biological buffers) and at elevated temperature (e.g., 60° C. to 80° C.) as fluorescence of most dyes is significantly lower at such conditions. Optimization of the structure of the fluorescent dyes can improve their fluorescent properties and also improve the efficiency of nucleotide incorporation, reduce the level of sequencing errors and decrease the usage of reagents in, and therefore the costs of, nucleic acid sequencing.

Rhodamines are deaminated xanthene cores with an aryl moiety (e.g., phenyl) at the 9' position and demonstrate thermal and photochemical stability, strongly absorb visible light, and show high fluorescence quantum yields. Rhodamine based compounds have been utilized as industrial dyes, electronic materials, medical devices, bio markers, lighting devices, sensors and photovoltaics. Rhodamine compounds having a carboxyphenyl fragment can exist in three different forms in equilibrium, depending on the pH, temperature, properties of the solvent (e.g., polarity), and the concentration of the solution: cationic (+), zwitterion (±) or lactone:

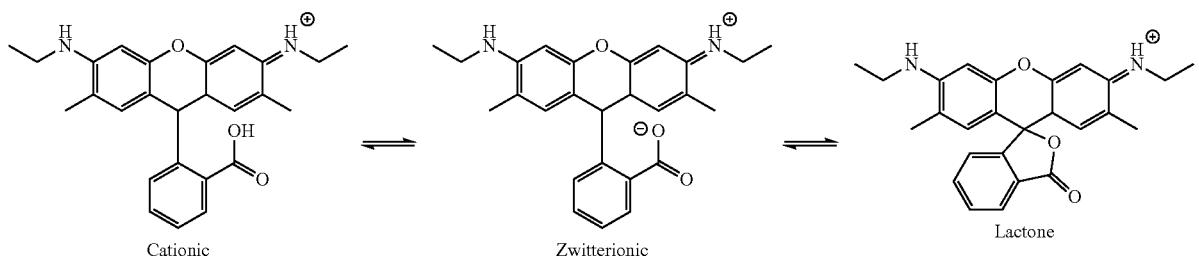 [SMILES: CCNc1cc2c(cc1C)C(c1ccccc1C(=O)O)C1C=C(C)/C(=[NH+]\CC)C=C1O2 ; CCNc1cc2c(cc1C)C(c1ccccc1C(=O)[O-])C1C=C(C)/C(=[NH+]\CC)C=C1O2 ; CCNc1cc2c(cc1C)C1(OC(=O)c3ccccc31)C1C=C(C)/C(=[NH+]\CC)C=C1O2]

| Cationic | Zwitterionic | Lactone |

Each form has its own characteristic spectral-luminescent properties. While rhodamine derivatives in cationic and zwitterionic forms are highly fluorescent molecules, the lactone form is essentially non-fluorescent due to the interruption of conjugation of the chromophore of the zwitterionic form. Consequently, absorption of lactones of rhodamine occurs in the UV spectral region and the fluorescence quantum yield and lifetime are very low. Depending on the desired application, it may be beneficial to limit or eliminate the formation of lactone, non-fluorescent, species by introducing a secondary amine at that ortho position (e.g., [—N—CH$_2$CH$_2$—O—]).

Example 2. Synthesizing Asymmetrical Rhodamine Compounds

Asymmetrical rhodamine compounds are valuable tools for biological applications. The advantages of using asymmetrical rhodamine compounds compared to the symmetrical counterparts are attributed to the asymmetrical nature of the electron clouds of such rhodamine compounds, which exhibit enhanced fluorescence, enable fine-tuning absorption and emission spectra, and improve hydrophilicity (see, e.g., Li et al. Chem. Commun., 2020, 56, 2455-2458). However, the methods of preparation of asymmetrical rhodamine compounds and the scalability thereof pose significant challenges, which prevent their widespread production and utility.

Figure 1B:
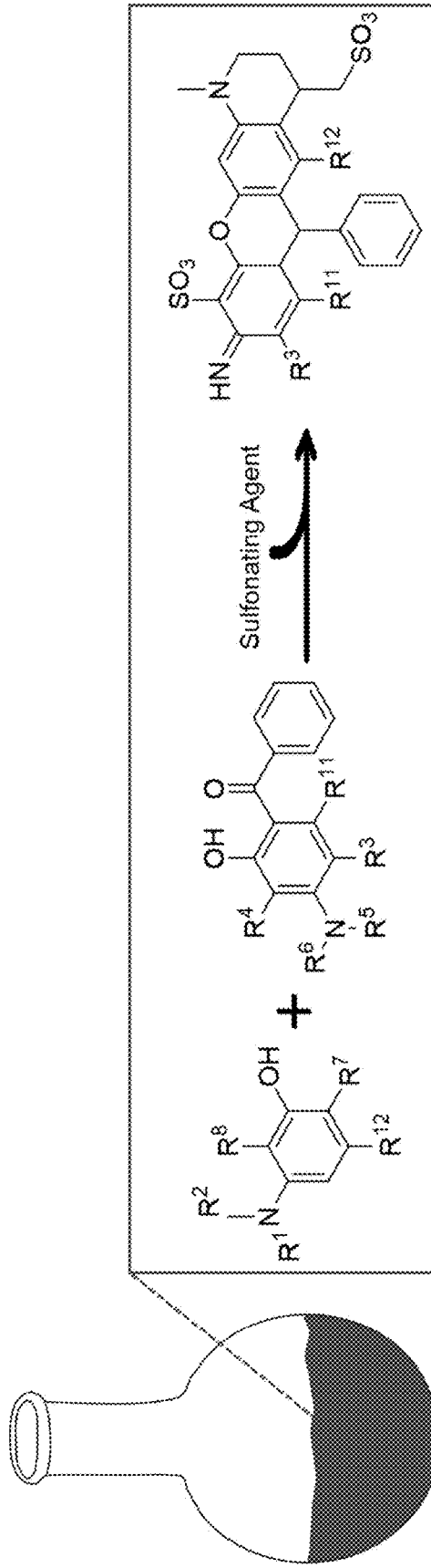
FIG. 1B shows a reaction scheme for generating an asymmetrical rhodamine compound as described herein. The scheme depicts a one-pot method using an aminophenol (e.g., Compound A) in the presence of a benzophenone substituted with hydroxyl and amine moieties (e.g., Compound B) and a sulfonating agent to provide an asymmetrical rhodamine with sulfonate moieties installed adjacent to the carbons bearing the amine moieties and exocyclic to xanthene ring.

Described herein are efficient one-pot protocols for synthesizing sulfonated rhodamine compounds. FIGS. 1A and 1B show reaction schemes for generating an asymmetrical rhodamine compound as described herein. FIG. 1A depicts a one-pot method using an aminophenol (e.g., Compound A) in the presence of a benzophenone substituted with hydroxyl and amine moieties (e.g., Compound B) and a sulfonating agent to provide an asymmetrical rhodamine with sulfonate moieties installed adjacent to the carbons bearing the amine moieties. In a different embodiment, the method described herein could provide an asymmetrical rhodamine with sulfonate moieties installed adjacent to the carbons bearing the amine moieties and exocyclic to xanthene ring as provided in FIG. 1B. Additionally, in yet another embodiment, the methods described herein teach the use of benzyl protecting groups to make asymmetric rhodamine dyes. An advantage of the approach provided herein is the protocols enable the protecting groups to be removed during the dye reaction (e.g., MSA at 120° C.-180° C.), enabling sulfonation (i.e., the addition of one or more SO$_3$H moieties) without the need to isolate the greasy dye, thereby saving time and simplifies the purification of the dye. The advantages of "one pot" rhodamine dye formation, deprotection, and sulfonation include: (i) higher yield and efficiency because three steps are combined into one; (ii) avoids work-up and purification of intermediate non-sulfonated dyes which can be challenging due to limited solubility; and (iii) allows work-up and purification of sulfonated dyes which is easier due to increased water solubility.

Scheme 1. Initial formation of compound A.

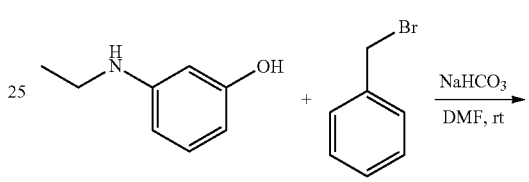

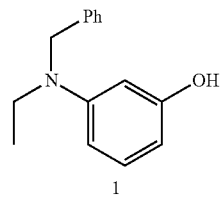

1

3-(Ethylamino)phenol (5.8 g) was dissolved in dry dimethylformamide. Sodium bicarbonate (5.3 g) was added, and the suspension was magnetically stirred. Benzyl bromide (7.2 g) was slowly added dropwise. The reaction progress was monitored by C18, reverse phase HPLC (MeCN/50 mM TEAA, 30 to 100% over 20 min). After one hour the dimethylformamide was evaporated on a rotovap and the residue was dissolved in ether (100 mL) and water (50 mL). The crude product was purified by normal phase Biotage chromatography (hexanes/ethyl acetate, 10 to 20%) to obtain compound 1 as a white solid and confirmed with $^1$H NMR: (500 MHz, CD$_2$Cl$_2$) δ 7.38-7.30 (m, 1H), 7.29-7.20 (m, 1H), 7.02 (dd, J=10.7, 5.5 Hz, 1H), 6.35-6.24 (m, 1H), 6.20-6.08 (m, 1H), 4.89 (s, 1H), 4.51 (s, 1H), 3.47 (q, J=7.1 Hz, 1H). $^{13}$C NMR (125 MHz, CD$_2$Cl$_2$) δ 156.83, 150.12, 139.39, 130.06, 128.54, 126.75, 126.54, 105.07, 102.93, 99.12, 54.02, 45.47, 12.02.

Scheme 2. Formation of a compound A molecule.

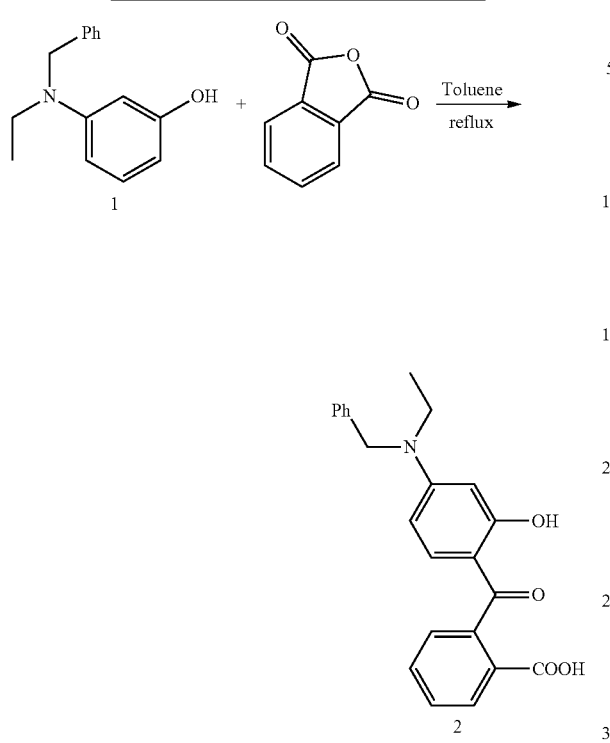

3-[ethyl(phenylmethyl)amino]phenol (946 mg, 4.2 mmol) and phthalic anhydride (617 mg, 4.2 mmol) in dry toluene (8 mL) were refluxed. The reaction mixture was cooled to room temperature and the product was collected by suction filtration. The product 2 was a pink solid (957 mg). The structure was confirmed by LCMS (m/z 374). $^1$H NMR (500 MHz, DMSO) δ 13.10 (s, 1H), 12.52 (s, 1H), 7.97 (dd, J=7.8, 1.0 Hz, 1H), 7.63 (dtd, J=33.9, 7.5, 1.3 Hz, 2H), 7.35 (ddd, J=22.8, 10.5, 4.3 Hz, 3H), 7.27-7.14 (m, 3H), 6.88-6.74 (m, 1H), 6.23 (dd, J=9.2, 2.5 Hz, 1H), 6.10 (d, J=2.4 Hz, 1H), 4.62 (s, 2H), 3.52 (q, J=7.0 Hz, 2H), 1.14 (t, J=7.0 Hz, 3H). $^{13}$C NMR (125 MHz, DMSO) δ 199.19, 167.38, 164.95, 154.69, 140.52, 138.43, 134.68, 132.49, 130.40, 130.14, 129.90, 129.11, 128.12, 127.43, 126.82, 110.34, 104.84, 97.72, 53.25, 45.74, 12.70.

Scheme 3. One pot sulfonation and dye formation.

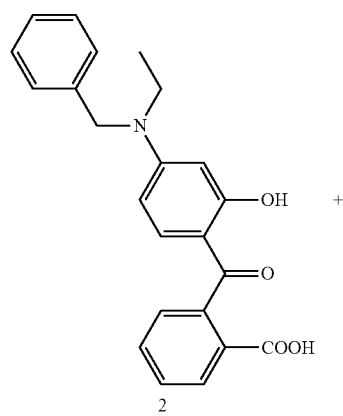

Compound 2 (an example of a compound A molecule) and 3-(ethylamino) phenol (an example of a compound B) were added to a round bottom flask equipped with a magnetic stir bar followed by the addition of methanesulfonic acid. The reaction mixture was heated at 120° C. for 4 hours. The progress of the reaction was monitored by HPLC; 0-100% (B) over 19 minutes; 50 mM TEAA (A) and acetonitrile (B) at lambda max 520 nm; Rt=15.8 min. Formation of the desired product was confirmed by LC-MS analysis; m/z 387. The crude reaction mixture was taken to the next step without purification and fuming sulfuric acid (6 mL) was added to it dropwise at room temperature and stirred for one hour. The progress of the reaction was monitored by HPLC; 0-100% (B) over 19 minutes; 50 mM TEAA (A) and acetonitrile (B) at lambda max 520 nm; Rt=12.4 min. Formation of the desired product, compound 4 was confirmed by LC-MS analysis using 25 mM TEAB and acetonitrile; m/z 545.

The crude dye was concentrated in vacuo and purified using reverse phase (Pursuit 5 C18 250×50.0 mm) with 0% for 5 minutes; 0-35% (B) over 60 minutes in 50 mM TEAB (A) and acetonitrile (B) to give 333.8 mg of compound 4 as red solid.

Scheme 4. Synthetic scheme to functionalize the dye with a linker.

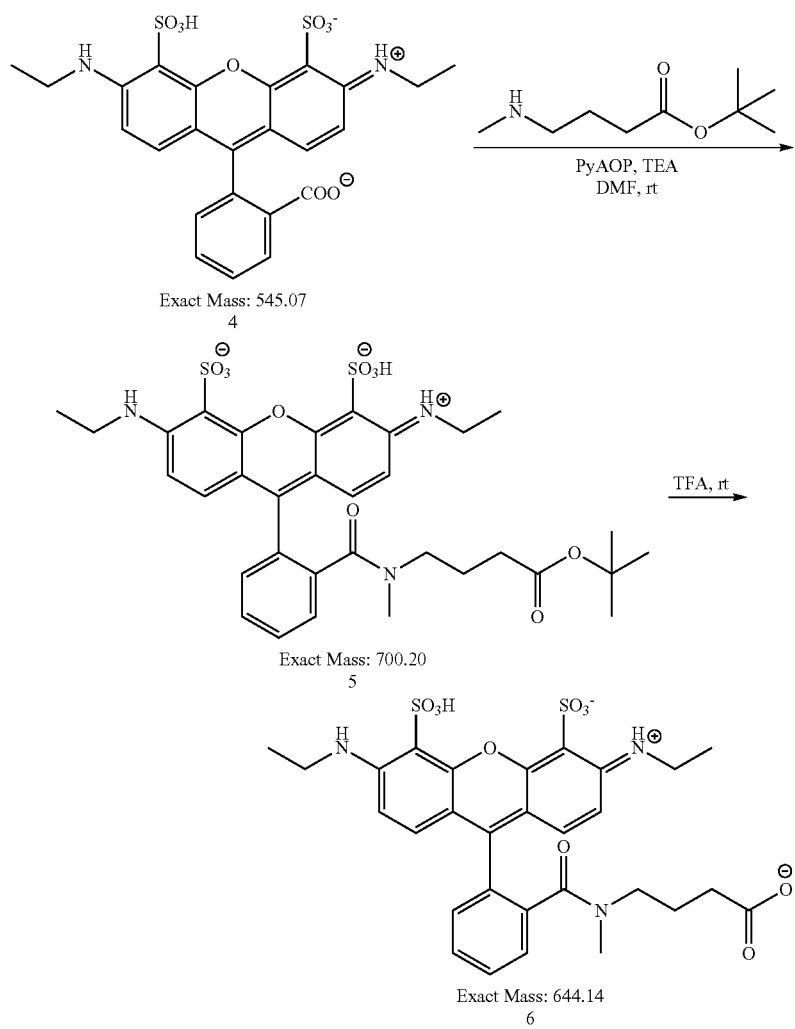

Tert-butyl-4-(methylamino) butanoate was added to a solution of compound 4 in dry DMF. PyAOP and triethyl amine were added to the above solution and stirred for 30 minutes. The progress of the reaction was monitored by HPLC; 0-100% (B) over 19 minutes; 50 mM TEAA (A) and acetonitrile (B) at lambda max 532 nm; Rt=16.28 min. Formation of the desired product was confirmed by LC-MS analysis using 25 mM TEAB and acetonitrile; m/z 700. The crude reaction mixture was purified using reverse phase (Pursuit 5 C18 250×50.0 mm) with 0% for 5 minutes; 0-55% (B) over 60 minutes; 50 mM TEAB (A) and acetonitrile (B) to give 251.7 mg of compound 5 as red solid. Trifluoroacetic acid (2 mL) was added to compound 5 and stirred at room temperature for an hour. The progress of the reaction was monitored by HPLC to give 160.7 mg of compound 6 as red solid. Formation of the desired product was confirmed by LC-MS analysis using 25 mM TEAB and acetonitrile; m/z 644 and $^1$H NMR (500 MHz, MeOD) δ 7.76-7.57 (m, 1H), 7.43 (t, J=8.1 Hz, 1H), 7.27 (dd, J=12.9, 9.5 Hz, 1H), 7.11-6.95 (m, 1H), 3.54-3.39 (m, 1H), 3.14-3.04 (m, 1H), 2.91 (s, 1H), 2.68 (s, 1H), 2.04 (t, J=7.2 Hz, 1H), 1.74 (dd, J=15.2, 7.5 Hz, 1H), 1.61-1.53 (m, 1H), 1.33 (t, J=7.2 Hz, 2H).

The methods provided supra could be applied to a different combinations of Compound A and Compound B. For example, the methods could be applied to generate an asymmetrical sulfonated rhodamine with an isophthalic acid moiety (i.e., benzene-1,3-dicarboxylic acid moiety) as described infra.

Scheme 5. Formation of a compound A molecule using substituted phthalic anhydride.

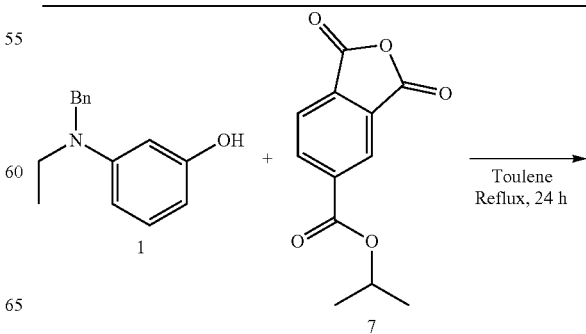

-continued

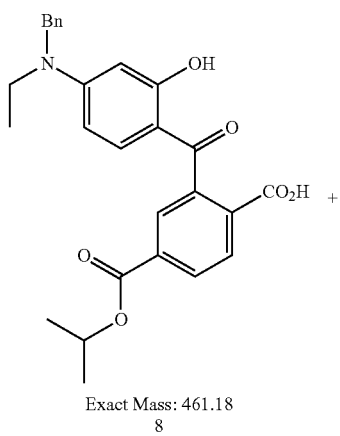

Exact Mass: 461.18
8

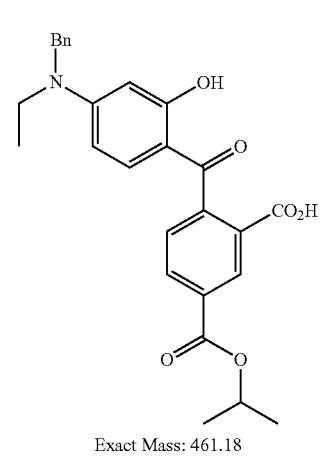

Exact Mass: 461.18
9

To a round bottom flask containing compound 1 (prepared as described supra) was added propan-2-yl 1,3-dioxo-2-benzofuran-5-carboxylate 7 in dry toluene and refluxed for 24 hours to provide a reaction mixture containing two isomers, compounds 8 and 9. The product (compound 9) was isolated via crystallization. The structure was confirmed by LCMS (m/z 461) and $^1$H NMR.

Scheme 6. One pot sulfonation and dye formation.

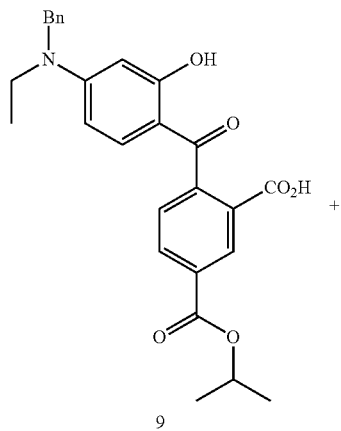

-continued

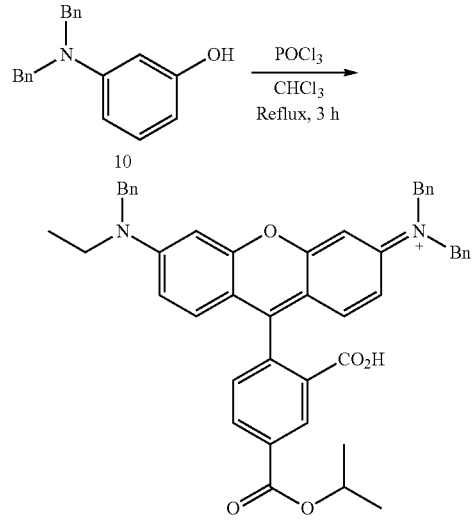

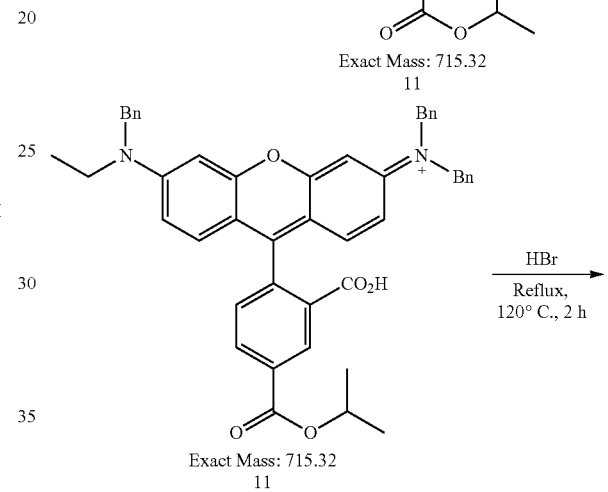

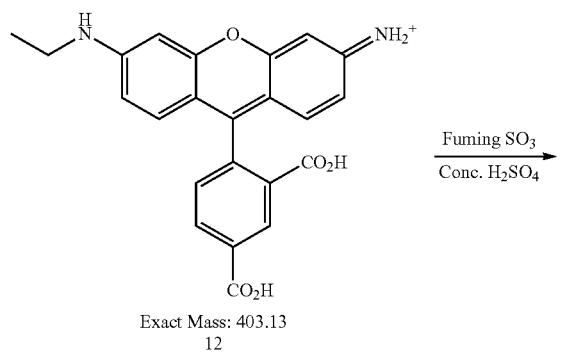

Exact Mass: 403.13
12

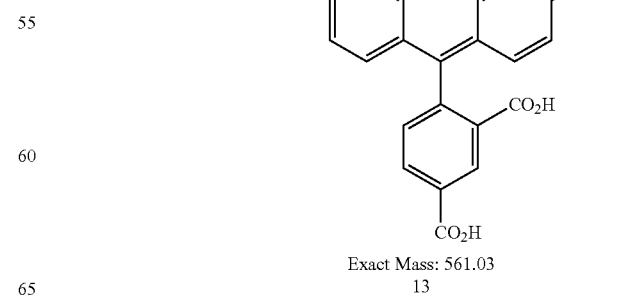

Exact Mass: 561.03
13

Compound 9, 3-(dibenzylamino)phenol 10 (an example of Compound B), and $POCl_3$ were added to a round bottom flask containing anhydrous chloroform and refluxed for 3 hours. The formation of compound 11 was monitored using HPLC, and the desired product was confirmed using LC-MS (m/z 715). The crude reaction mixture was taken to the next step without purification. The crude mixture was heated to 120° C. and refluxed in anhydrous HBr. The formation of compound 12 was monitored via HPLC and confirmed using LC-MS (m/z 403). The crude reaction mixture was taken to the next step without purification and fuming sulfuric acid was added dropwise at room temperature and stirred for one hour. The progress of the reaction was monitored by HPLC, and the desired product, compound 13, was confirmed by LC-MS (m/z 561).

The methods described herein take advantage of the use of protecting groups (e.g., benzyl groups) to mask amine moieties present in the aminophenol (i.e., Compound B) and the compound containing the ketone moiety (i.e., Compound A). The presence of the secondary amines that results from the amine deprotection (which is an example of a dye-intermediate formed during the "one pot" reaction following dye formation and prior to sulfonation) facilitates controlled addition of sulfonate moieties ($—SO_3$) moieties to the carbon adjacent to the amine-bearing carbons (i.e., sulfonation occurs at $R^4$ and/or $R^8$). Additionally, the use of amine protecting groups facilitate efficient generation of Compound A as a major product as shown in Scheme 2. Lastly, the presence of tertiary amines in a dye-intermediate formed during the "one pot" reaction facilitates controlled exocyclic sulfonation (i.e., where the addition of sulfonate groups are added exocyclic relative to the xanthene ring of rhodamine as shown in FIG. 1B).

Example 3. In Vivo and In Vitro Imaging Using Asymmetrical Rhodamine Fluorescent Compounds In vivo and in vitro imaging studies often feature near-IR (NIR) or red-emitting fluorophores because these dyes require excitation wavelengths between 600-900 nm, which do not spectrally overlap with the wavelength(s) absorbed by tissue, proteins, and other biomolecules (See Koide et al., J Am Chem Soc., 2012 Mar. 21; 134(11):5029-31). As a result, these fluorophores facilitate low autofluorescence from intrinsic biomolecules and an improved fluorescence signal from the target biomolecule(s) and background. However, these red-emitting fluorophores are notoriously known to suffer from poor water solubility, low fluorescence quantum yield, and low photostability (See Kolmakov et al., Chemistry. 2010 Jan. 4; 16(1):158-66; Lin et al., J. Mater. Chem. C, 2019, 7, 11515-11521). These photophysical and chemical properties, which are inherent to these fluorophores, compromise the imaging duration and thus, the spatial and temporal resolution of the desired biomolecule (s).

To overcome these aforementioned limitations prevalent to in vivo and in vitro imaging techniques, the compositions and methods of generating thereof as described in Example 2 could also be applied in these applications. Bioconjugation techniques to generate dye-biomolecule conjugates are known in the art. For example, the use of an activating agent, such as N,N,N',N'-Tetramethyl-O—(N-succinimidyl)uronium tetrafluoroborate (abbreviated as TSTU, as described in Kovács et al. ACS Omega. 2023 Jun. 14; 8(25):22836-22843) could be used with a compound described herein to generate an activated substrate for the reaction with an azido-containing amine (e.g., commercially available 3-azido-1-propanamine) to install an azide moiety onto the compound described herein as shown in Scheme 7.

Scheme 7. Activation and functionalization of compound described herein with bioconjugate reactive moiety.

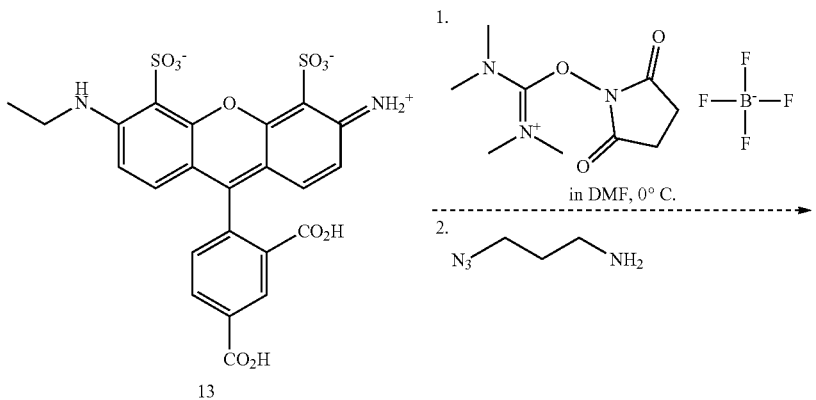

-continued

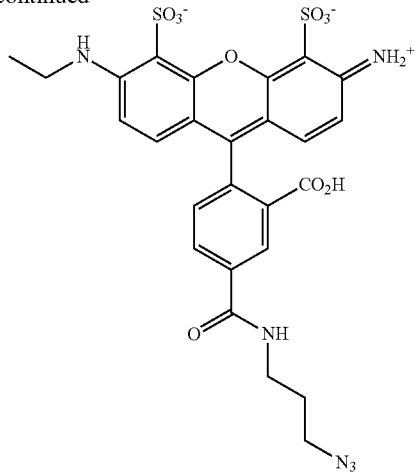

The installment of a bioconjugation reactive moiety onto a biomolecule (e.g., an antibody) used to facilitate the detection of a biomolecule of interest could be achieved by a reaction with a DBCO-containing reagent (e.g., commercially available DBCO-PEG$_5$-NHS) as shown in Scheme 8. The strain inherent to the cyclooctyne ring present in the DBCO-labelled antibody and the high reactivity of the triazine azide present on the compound described herein would enable the bioconjugation step to proceed favorably in a copper-less strain-promoted azide-alkyne cycloaddition reaction (Scheme 9).

Scheme 8. Installation of bioconjugate reactive moiety onto an antibody used to facilitate detection of biomolecules of interest.

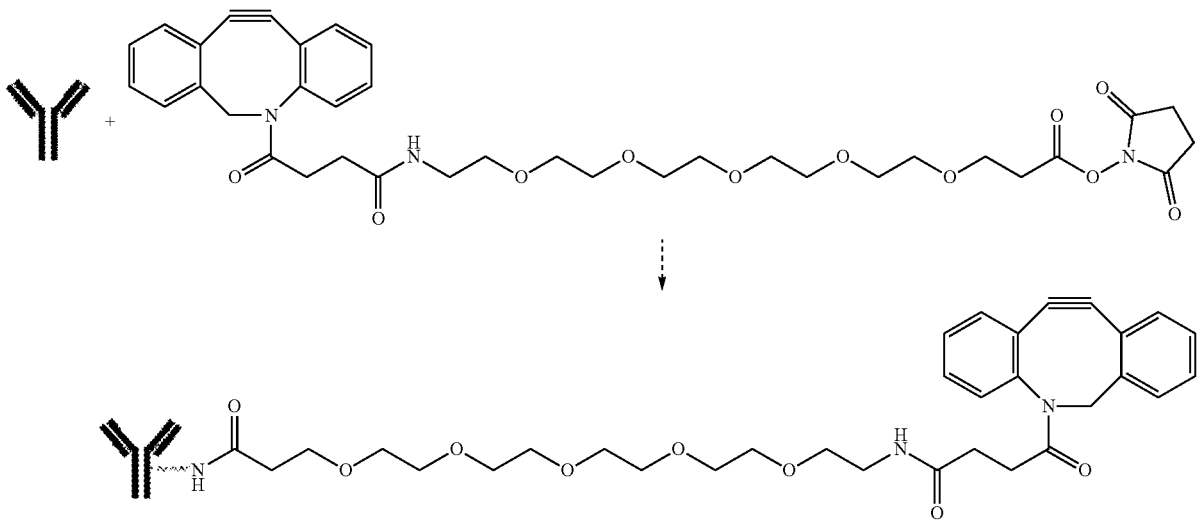

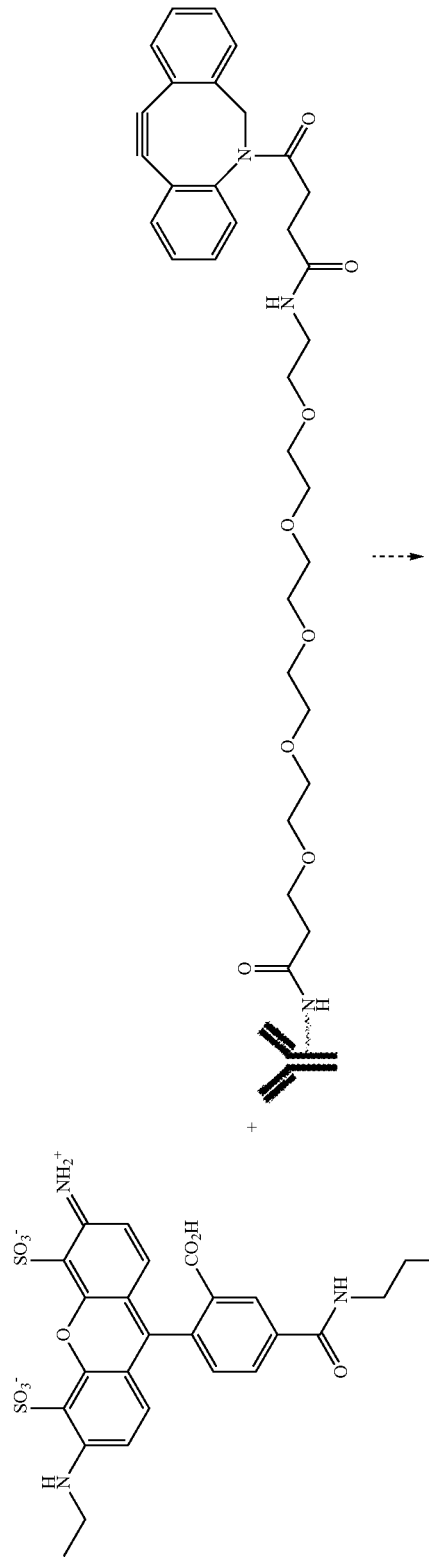
Scheme 9. Bioconjugation of DBCO-labelled antibody and a compound described herein.

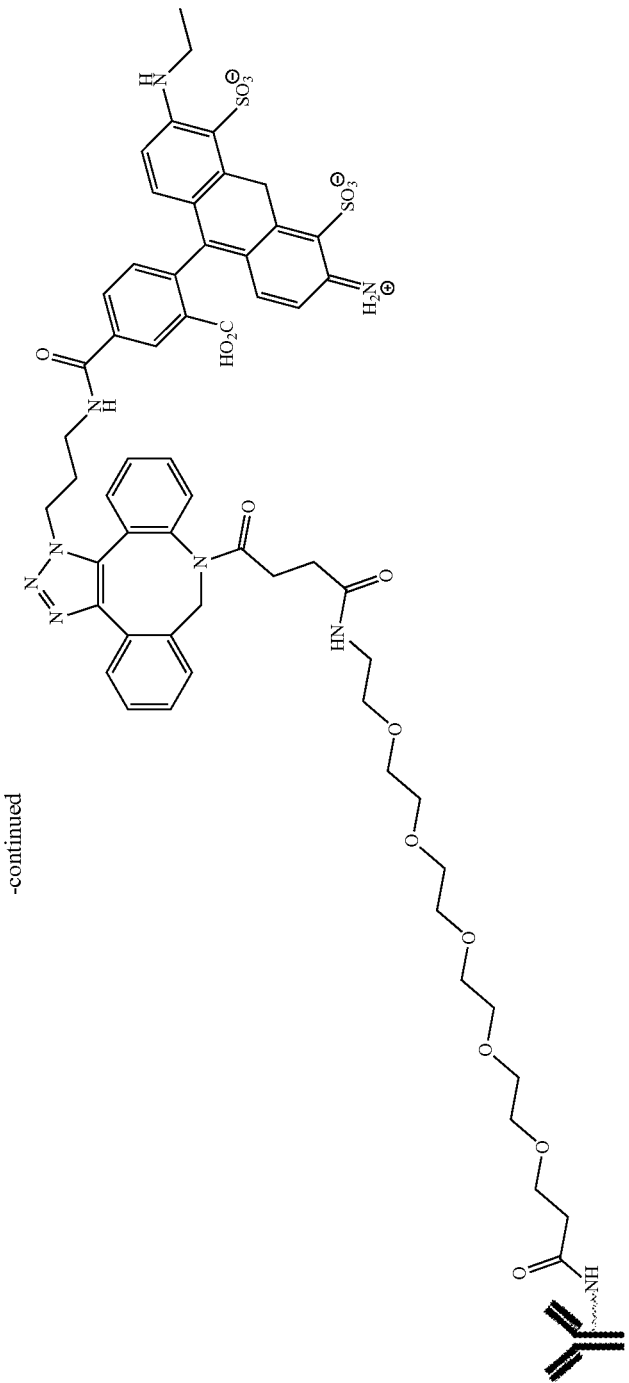
-continued

Other bioconjugates contemplated with the compound described herein includes bioconjugation to a nucleic acid or an oligonucleotide. Using the synthetic strategies discussed supra, a nucleic acid or oligonucleotide functionalized with a nucleophilic moiety could react with a DBCO-containing reagent to provide a DBCO-labelled nucleic acid or oligonucleotide. Scheme 10 provides an example of labelling a thymine with DBCO for bioconjugation to a compound described herein. The resultant DBCO-labelled thymine undergoes a bioconjugation reaction between the compound described herein (activated and functionalized with an azide moiety as discussed supra) to provide an oligonucleotide labeled with the compound described herein for in vitro or in vivo detection of nucleic acid molecules of interest (Scheme 11).

Scheme 10. Installation of bioconjugate reactive moiety onto a nucleic acid used to facilitate detection of biomolecules of interest.

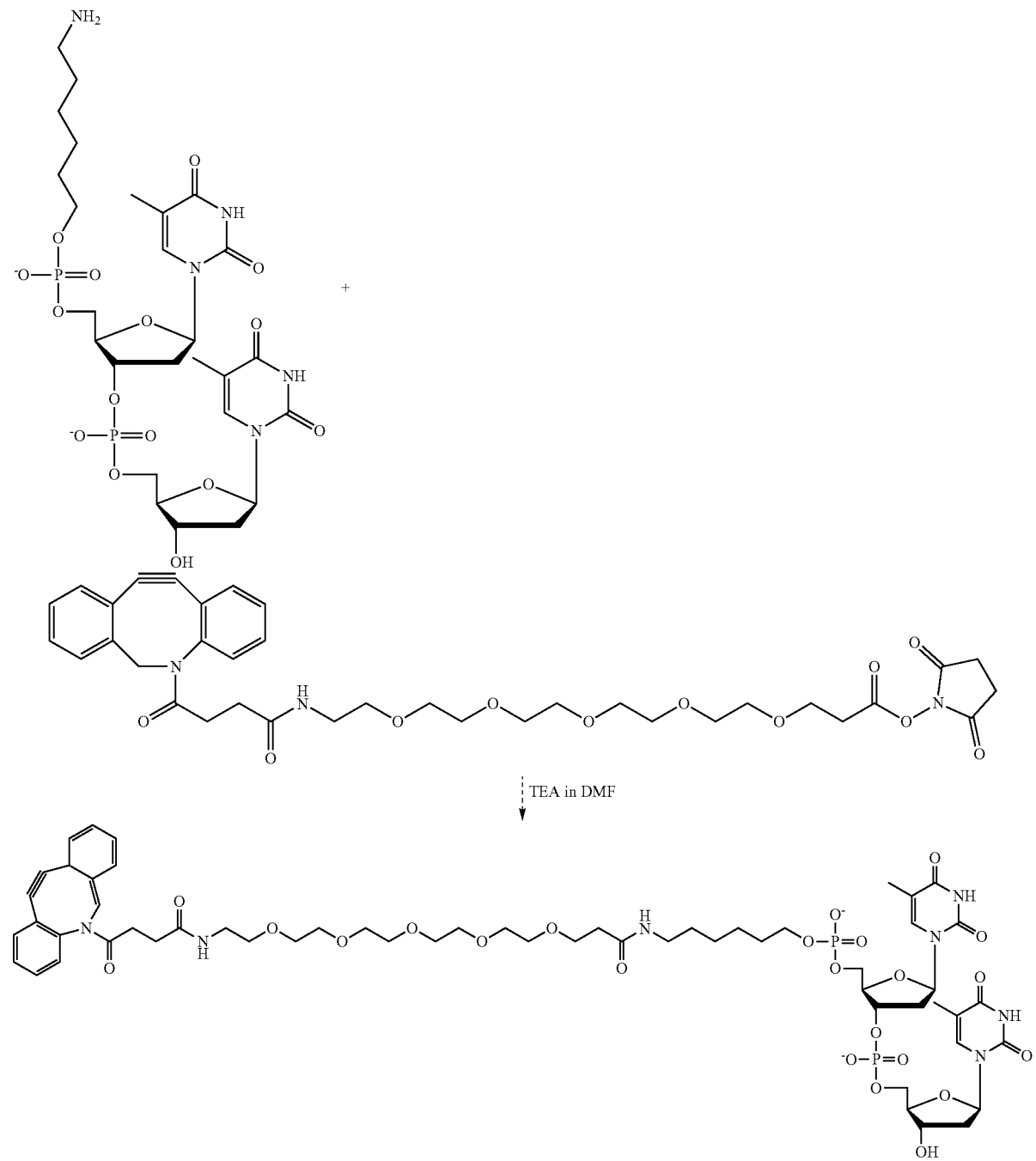

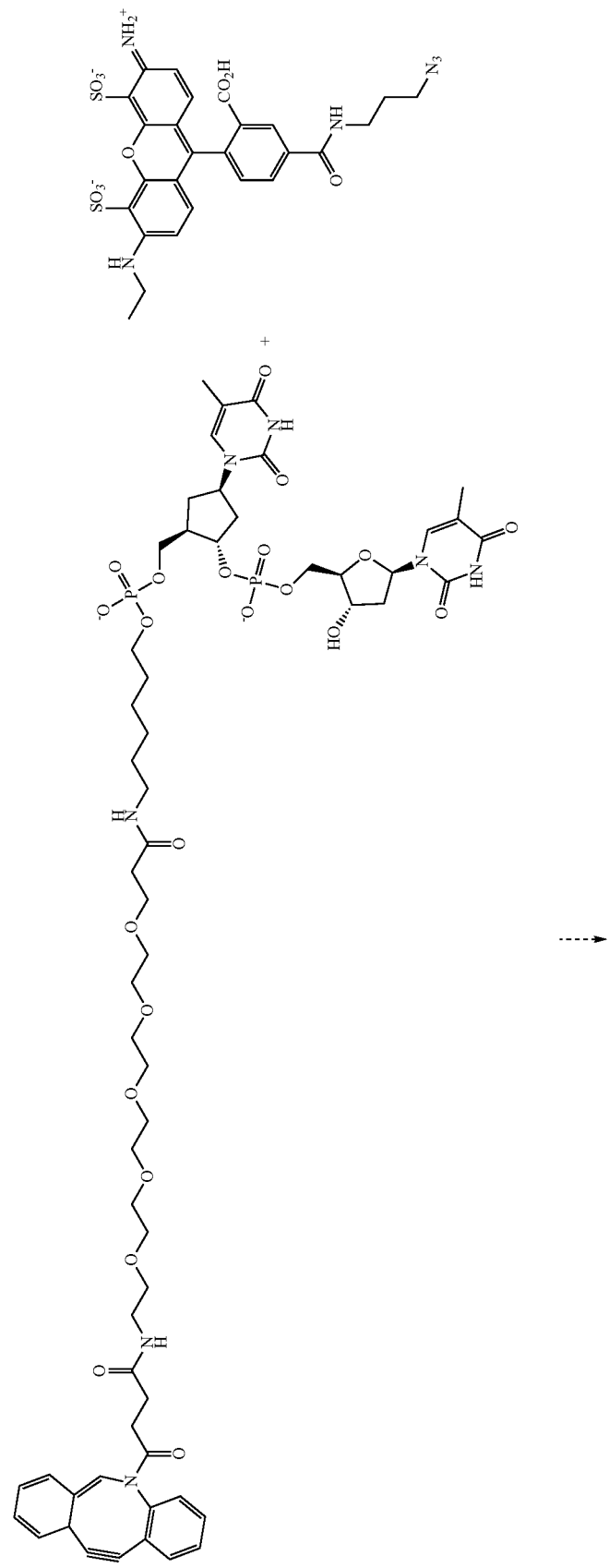
Scheme 11. Bioconjugation of DBCO-labelled nucleic acid and a compound described herein.

-continued
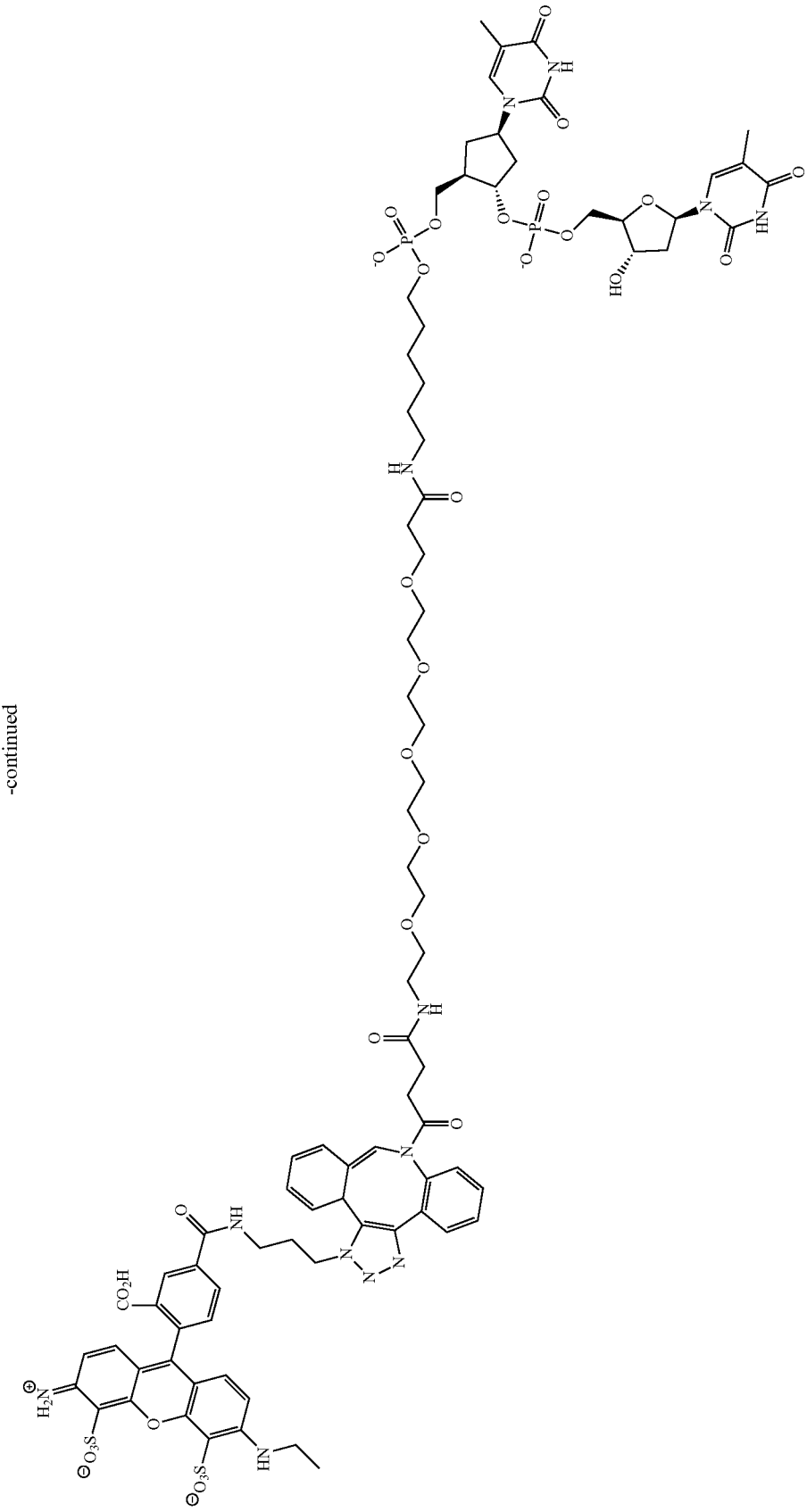

Scheme 12. Generic overview of the synthetic scheme depicting the attachment of a compound to a nucleic acid base via a covalent linker through a reaction involving two bioconjugate reactive moieties reacting to from a bioconjugate linker.
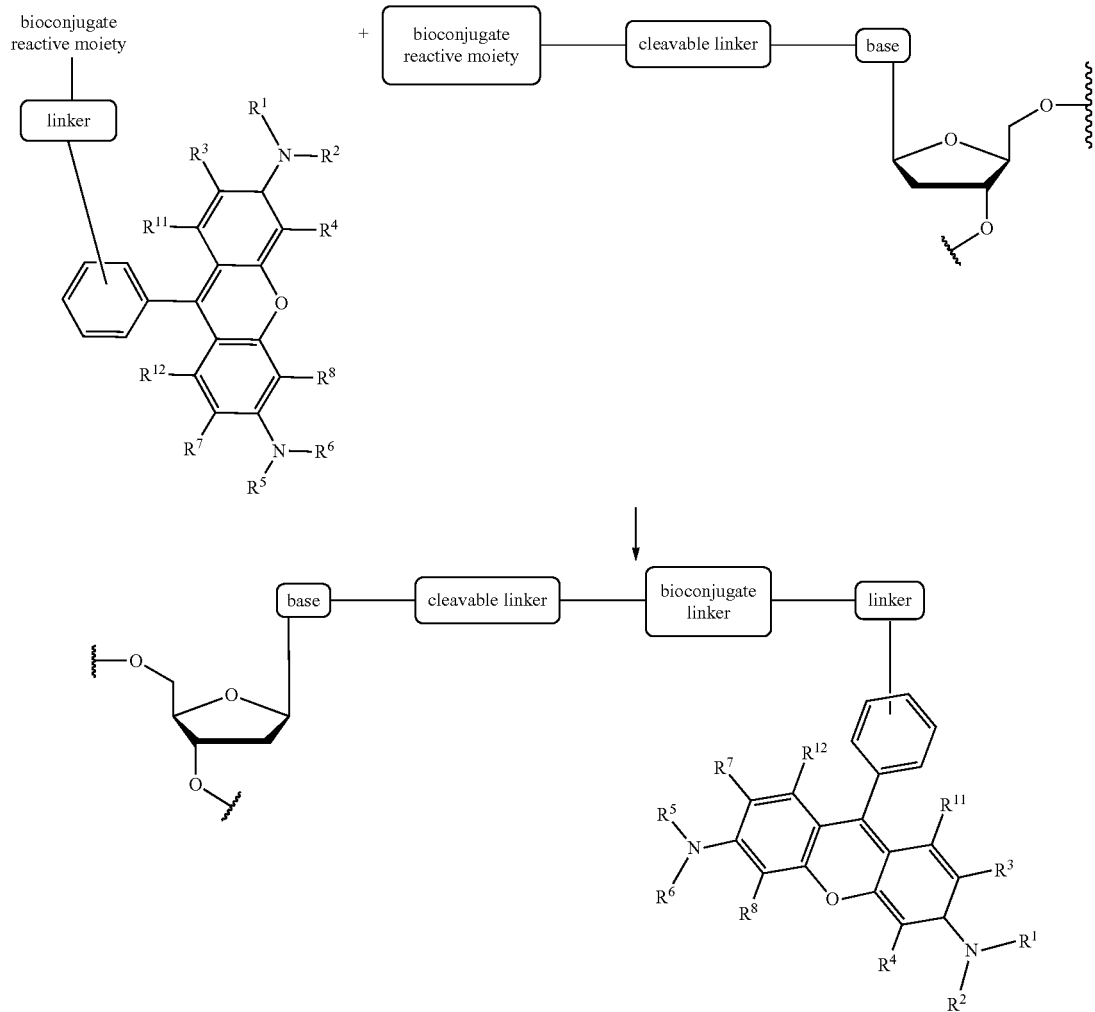
Scheme 13. Synthetic scheme depicting the attachment of a compound to a nucleic acid base via a covalent linker.
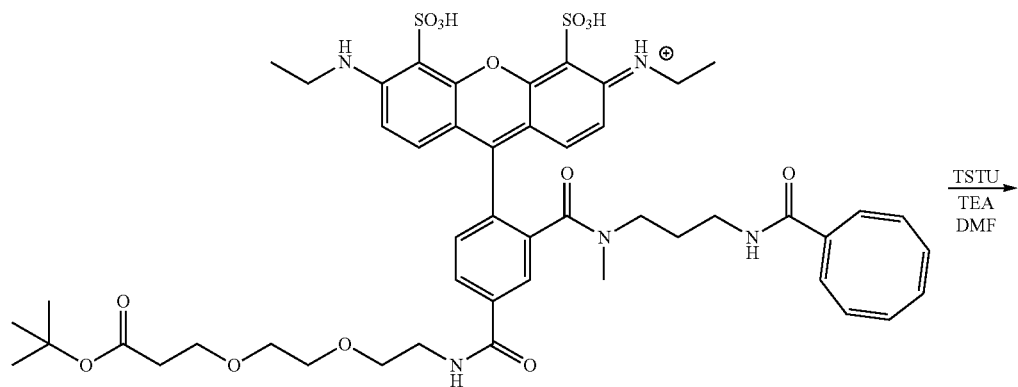

-continued

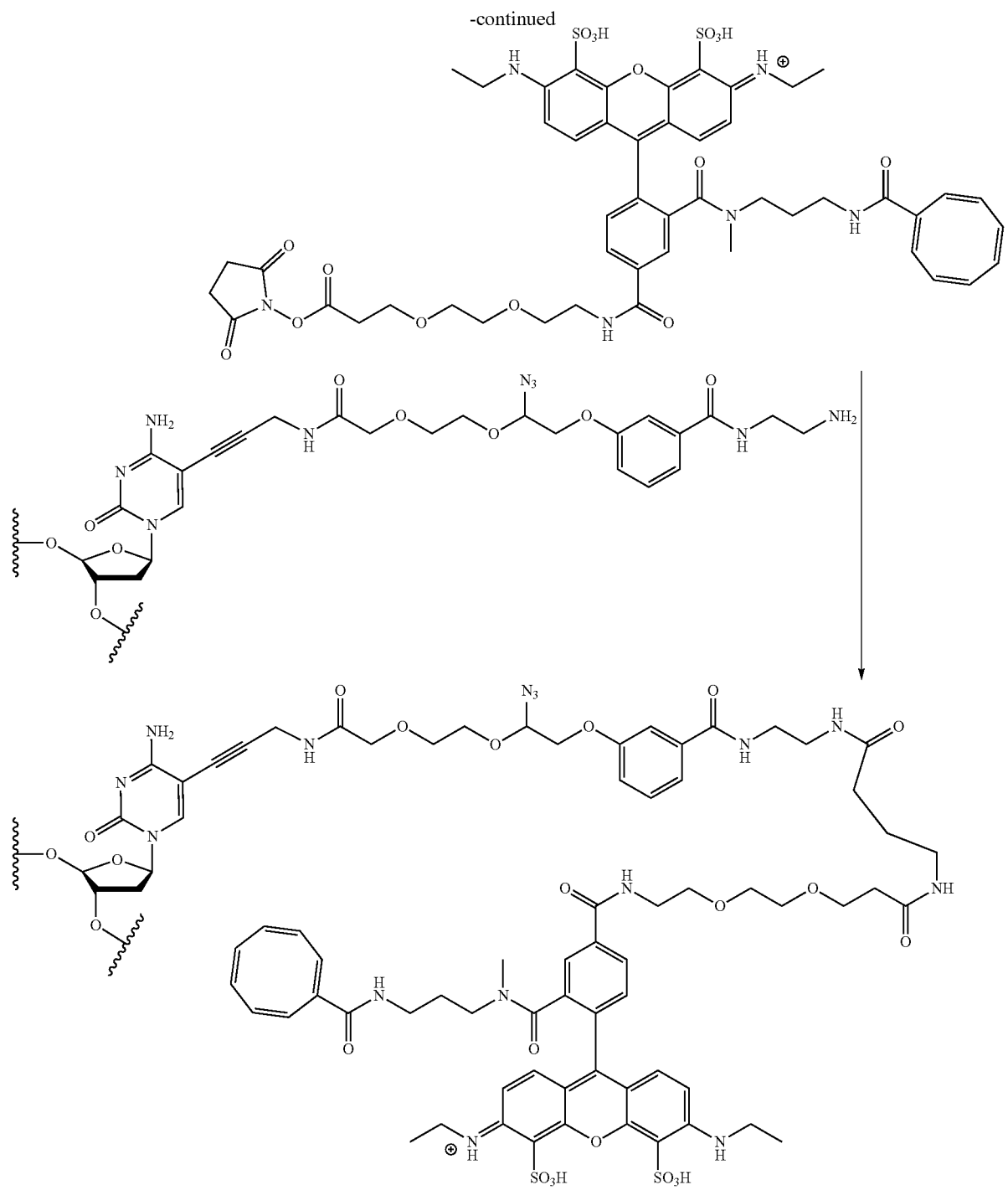

Schemes 12 and 13 are intended to be a representative of the possible linking chemistry to append the dye to a nucleic acid. One having ordinary skill in the art would appreciate the various conjugation strategies to incorporate the dye to a variety of agents (e.g., oligonucleotide (e.g., DNA, RNA, or siRNA), protein (e.g., antibody or antibody fragment), or compound (e.g., small molecule). The symbol ⌇ in scheme 12 and scheme 13 refers to an attachment point to a phosphate (e.g., monophosphate or polyphosphate), a hydrogen, or a reversible terminator moiety as described herein.

Fluorescent dye molecules with improved fluorescence properties (such as fluorescence intensity, maximum emission wavelength) can improve the speed and accuracy of nucleic acid sequencing. Fluorescence signal intensity is particularly important when measurements are made in solvents typically used in nucleic acid sequencing technologies (e.g., water based biological buffers) and at elevated temperature (e.g., 60° C. to 80° C.) as fluorescence of most dyes is significantly lower at such conditions. Optimization of the structure of the fluorescent dyes can improve their fluorescent properties and also improve the efficiency of nucleotide incorporation, reduce the level of sequencing errors and decrease the usage of reagents in, and therefore the costs of, nucleic acid sequencing.

Improving the hydrophilicity of the compounds described herein. Many commercial fluorescent dyes have a polycyclic aromatic nature and are hydrophobic. Those molecules are also prone to minimize exposure to any hydrophilic environment through interactions with nearby hydrophobic surfaces and residues. These interactions include dye-dye interaction and dye-biomolecule (e.g., proteins, lipids, oligonucleotides) interactions. Hydrophobic interactions can cause substantial quenching effect for fluorescent dyes (see, for example, Randolph, J. B.; Waggoner, A. S. Nucleic Acids Res. 1997, 25(14), 2923-2929). One method to overcome this problem is to improve the hydrophilic character of the dye by, for example, introducing a sulfonate substituent into the dye molecule (sulfonated carbocyanine dyes are disclosed in U.S. Pat. No. 5,268,486 and sulfonated xanthene dyes are disclosed in U.S. Pat. No. 6,130,101. Utilizing methods known in the art, and described below in greater detail, the compounds described herein may have improved hydrophilic character through the addition of polar or solubilizing residues (e.g., sulfonate or phosphonate moieties).

For example, sulfonation of the compound (e.g., a compound described herein) is carried out by stirring the dye in fuming sulfuric acid (20-30% $SO_3$ content) or concentrated sulfuric acid at an appropriate temperature. Compounds with electron-donating groups on the aromatic ring are typically sulfonated at room temperature, while compounds having electron-withdrawing groups such as fluorine and chlorine on the aromatic ring are typically sulfonated at an elevated temperature, for example at 100-110° C. Mono-sulfonation of rhodol dyes is carried out by stirring the appropriate dye in fuming sulfuric acid at 0° C. for several hours. Bis-sulfonation of dyes is achieved by stirring the dye in fuming sulfuric acid at room temperature for several hours. Where the compound possesses a vinylic methyl group, sulfonation at the vinylic methyl is accomplished by treatment with concentrated sulfuric acid at room temperature.

The facile one-pot synthesis of the compound described herein could be adapted to generate spectrally distinguishable compounds with hydrophilic properties and synthetic handles for the generation of bioconjugates harboring compounds described herein, which enables the detection of a multitude of biomolecules targeted by various specific binding reagents for various in vitro and in vivo imaging applications.

Example 4. In Situ Sequencing Applications Using Asymmetrical Rhodamine Fluorescent Compounds The emergence of spatial biology enables profiling disease relevant biomolecules, such as mRNA and proteins, in the original context of a cell or tissue section. Formalin-fixed paraffin embedded (FFPE) tissue sections are commonly used with spatial biology techniques (e.g., in situ sequencing) due to the prolonged shelf life of FFPE tissue sections. However, FFPE tissue sections are notorious for exhibiting autofluorescence, resulting from the presence of Schiff based formed between endogenous amines found in the tissue and the formalin used to generate the FFPE tissue block and the presence of intrinsically fluorescent biomolecules, such as collagen, elastin, and flavins, found in the tissue (see, e.g., Croce, A. C. et al. Eur J Histochem. 2014 Oct. 22; 58(4): 2461). Autofluorescence remains a key challenge for spatial biology workflows using FFPE tissue sections as autofluorescence impedes the discrimination of fluorescence derived from fluorescently-labelled biomolecules and background fluorescence. Additionally, autofluorescence limits the detection of lowly expressed biomolecules, especially in tissue sections where such biomolecules display intercellular and intracellular heterogeneity in expression and spatial distribution.

To overcome these aforementioned limitations prevalent spatial biology techniques, the compositions and methods of generating thereof as described in Example 2 could also be applied in these applications. For example, biomolecules of interest in a cell or tissue section are targeted by specific binding reagents, such as antibodies to bind to proteins of interest or oligonucleotide probes to bind to nucleic acids of interest. Aforementioned specific binding reagents are contemplated to include a detectable label, which is detected in situ by sequencing-by-synthesis (i.e., in situ sequencing), where sequencing-by-synthesis includes sequencing the detectable label using fluorescently labeled nucleotides covalently attached to compounds described herein. Methods of generating compounds described herein could be adapted to afford fluorescently labeled nucleotides that are spectrally distinguishable compounds and with spectral emission profiles to facilitate in situ sequencing of various biomolecules of interest directly in a tissue section while bypassing the limitation imposed by autofluorescence. Bioconjugates of the compound described herein prepared using synthetic strategies described in Schemes 7-13 could be utilized for in situ sequencing and detection of protein and/or nucleic acid molecules of interest.

What is claimed is:

1. A method of making a compound of formula I,

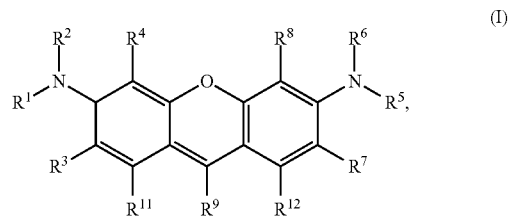

the method comprising mixing compound A and compound B together in a reaction vessel at a first temperature to form a dye-intermediate, and adding oleum to said reaction vessel at a second temperature, wherein compound A has the formula:

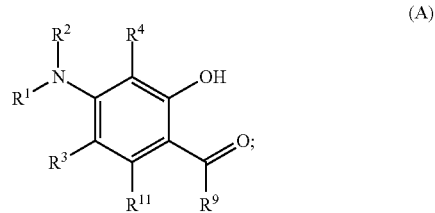

and compound B has the formula:

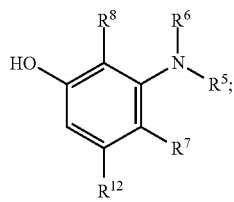

R¹ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁶ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein $R^1$, $R^2$, $R^5$, or $R^6$ is hydrogen;

$R^1$ and $R^2$ substituents bonded to the same nitrogen atom may optionally be joined to form a substituted or unsubstituted heterocycloalkyl, or substituted or unsubstituted heteroaryl;

$R^5$ and $R^6$ substituents bonded to the same nitrogen atom may optionally be joined to form a substituted or unsubstituted heterocycloalkyl, or substituted or unsubstituted heteroaryl;

$R^2$ and $R^4$ substituents may optionally be joined to form a substituted or unsubstituted heterocycloalkyl, or substituted or unsubstituted heteroaryl;

$R^1$ and $R^3$ substituents may optionally be joined to form a substituted or unsubstituted heterocycloalkyl, or substituted or unsubstituted heteroaryl;

$R^6$ and $R^8$ substituents may optionally be joined to form a substituted or unsubstituted heterocycloalkyl, or substituted or unsubstituted heteroaryl;

$R^5$ and $R^7$ substituents may optionally be joined to form a substituted or unsubstituted heterocycloalkyl, or substituted or unsubstituted heteroaryl;

$R^3$, $R^4$, $R^7$, $R^8$, $R^{11}$, and $R^{12}$ are independently hydrogen, —PO₃H, —PO₄H, —SO₂NH₂, —SO₃H, —SO₄H, substituted or unsubstituted alkyl, or substituted or unsubstituted heteroalkyl; wherein $R^3$, $R^4$, $R^7$, or $R^8$ is —SO₃H; and $R^9$ is substituted or unsubstituted aryl.

2. The method of claim 1, wherein said dye-intermediate is not isolated or removed from said reaction vessel prior to adding oleum.

3. The method of claim 1, wherein said reaction vessel comprises a sulfonic acid.

4. The method of claim 1, wherein said reaction vessel comprises difluoroacetic acid, dichloroacetic acid, ethane sulfonic acid, benzene sulfonic acid, toluene sulfonic acid, methanesulfonic acid, dichlorobenzene, trifluoroacetic acid, or polyphosphoric acid.

5. The method of claim 1, wherein said reaction vessel comprises methanesulfonic acid.

6. The method of claim 1, wherein said reaction vessel comprises a Lewis acid, wherein said Lewis acid is selected from aluminum chloride (AlCl₃), boron trifluoride (BF₃), iron(III) chloride (FeCl₃), magnesium chloride (MgCl₂), zinc chloride (ZnCl₂), chromic acid (H₂CrO₄), stannic chloride (SnCl₄), stannous chloride (SnCl₂), titanium(IV) chloride (TiCl₄), and bromotrifluoromethane (CF₃Br).

7. The method of claim 1, wherein said oleum is 20% fuming sulfuric acid.

8. The method of claim 1, wherein said first temperature is about 80° C. to about 130° C., and said second temperature is about 10° C. to about 30° C.

9. The method of claim 1, wherein said first temperature is about 95° C. to about 120° C., and said second temperature is about 15° C. to about 25° C.

10. The method of claim 1, wherein said first temperature is about 100° C., and said second temperature is about 20° C.

11. The method of claim 1, wherein compound A has the formula:

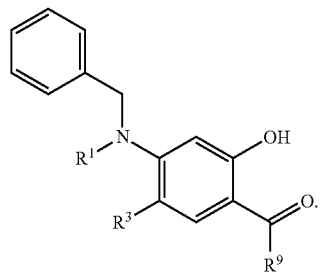

12. The method of claim 1, wherein compound A has the formula:

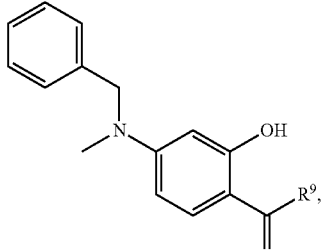

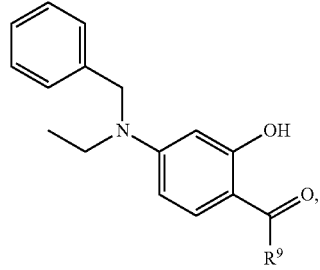

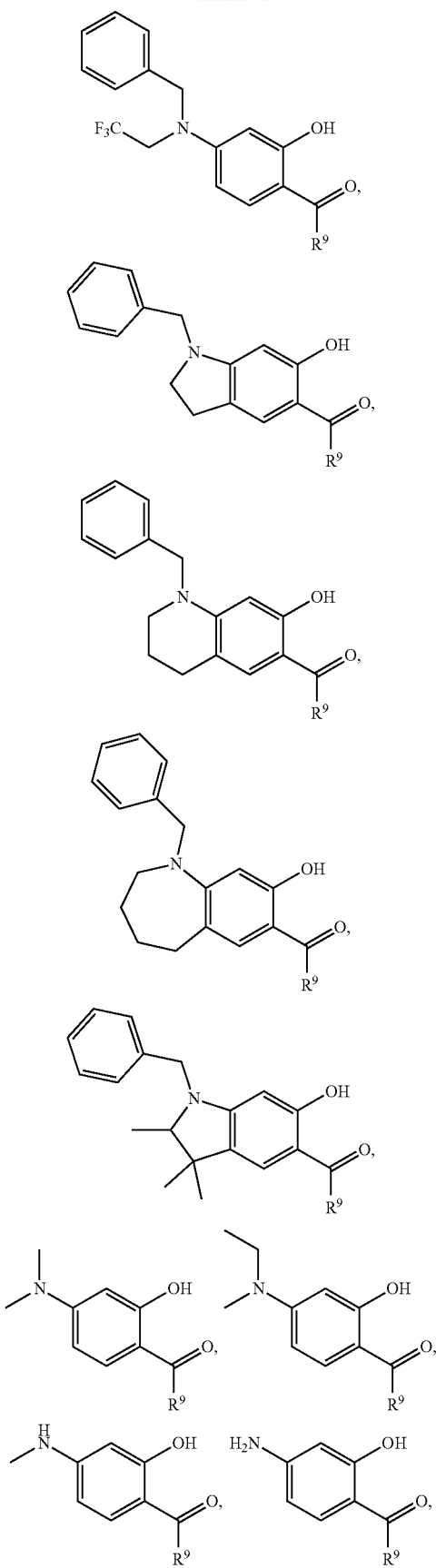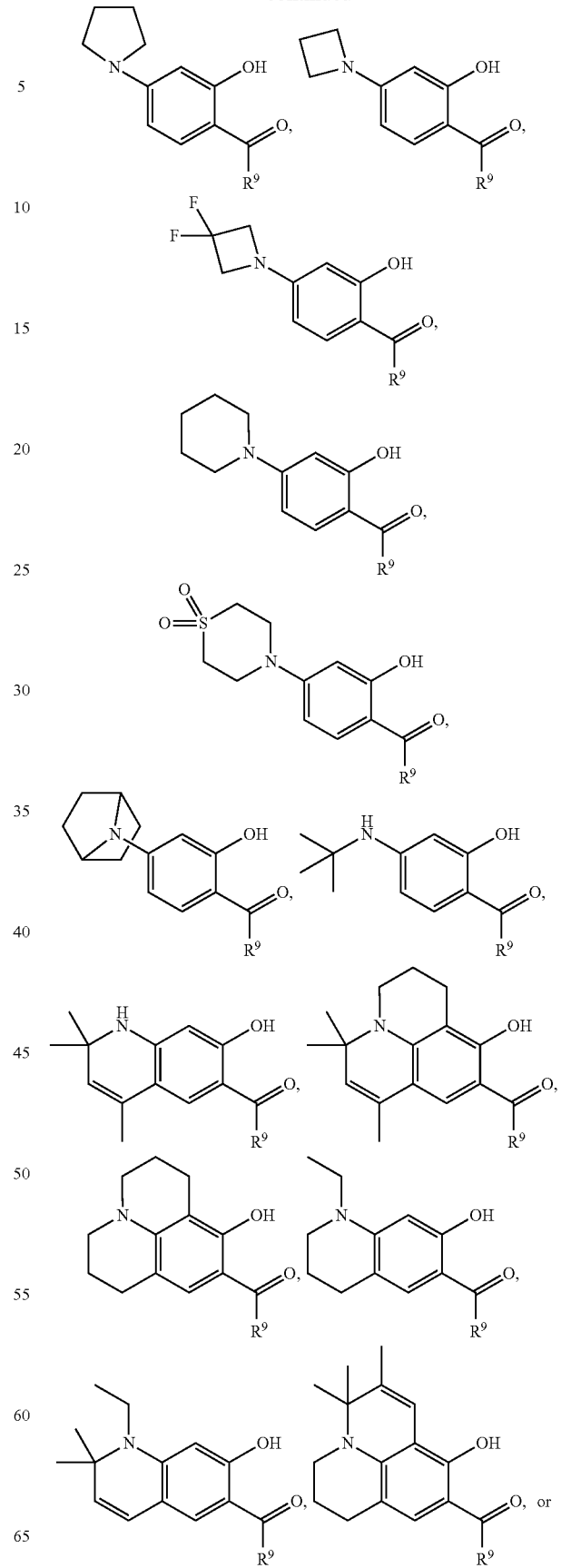

-continued
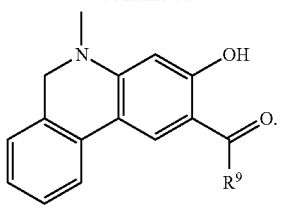
13. The method of claim 1, wherein compound A has the formula:
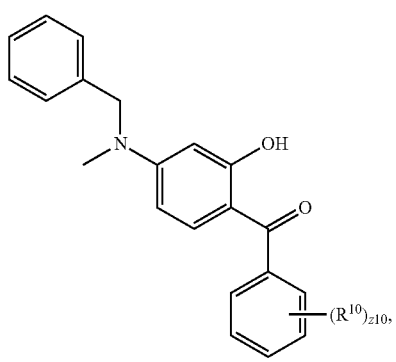
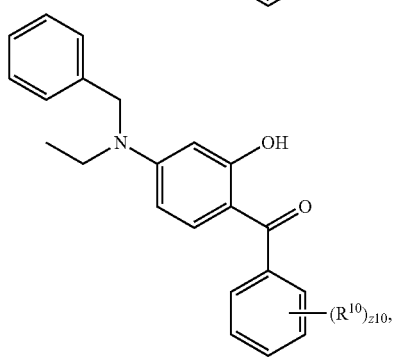
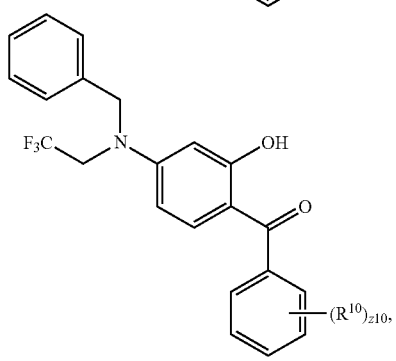
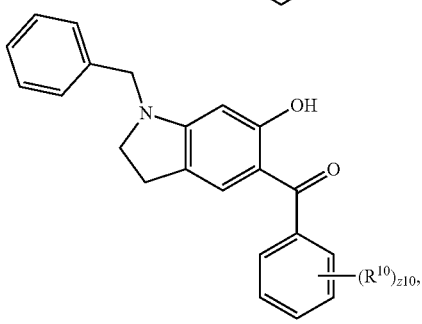
-continued
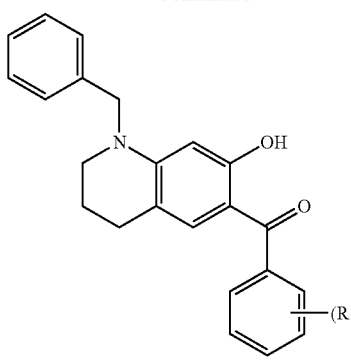
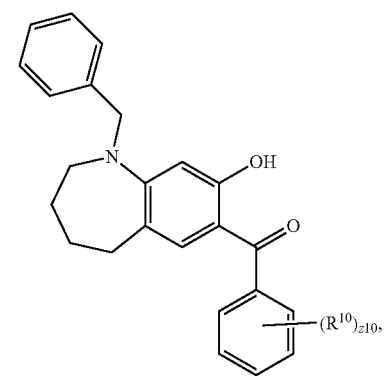
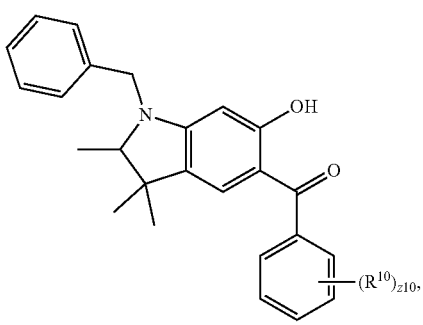
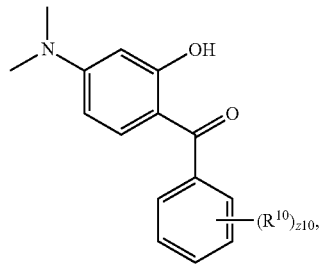
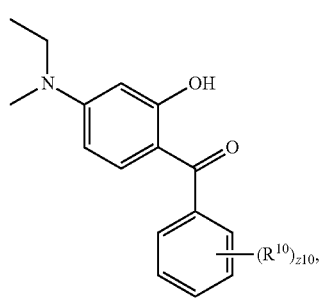

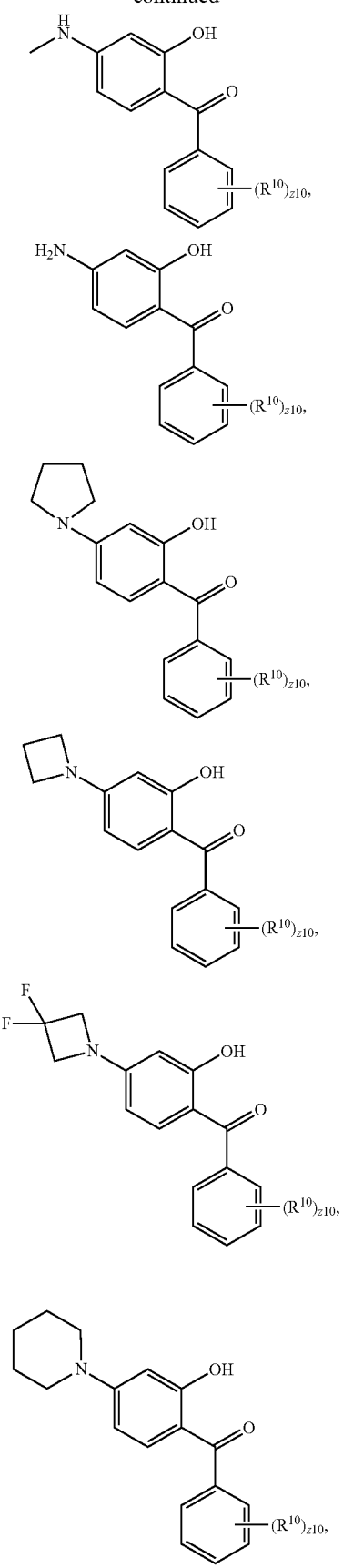
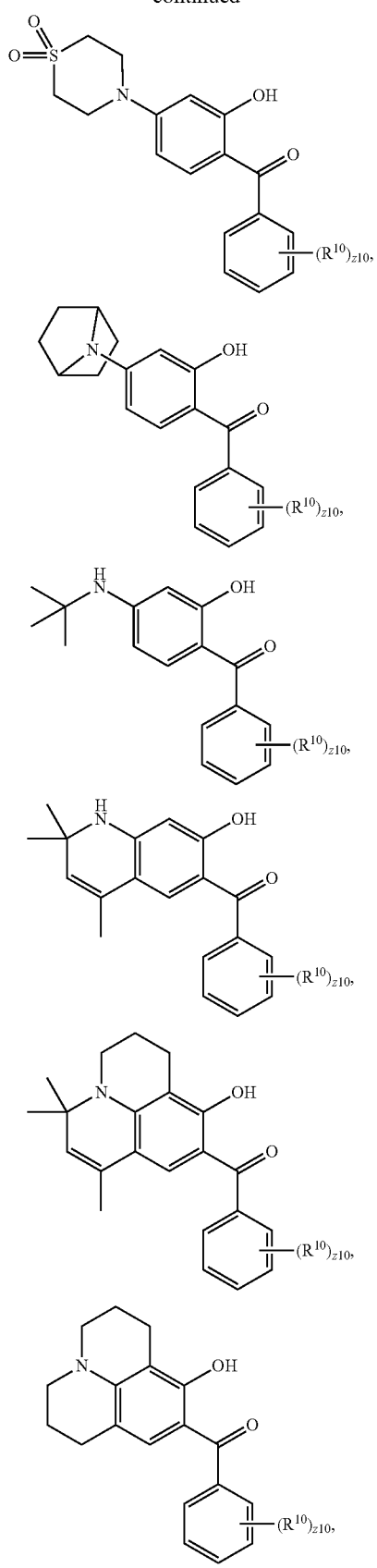

-continued

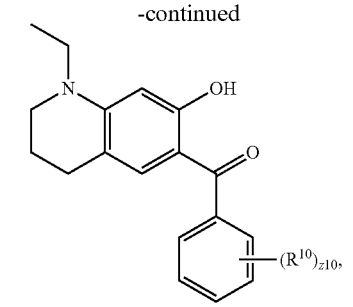

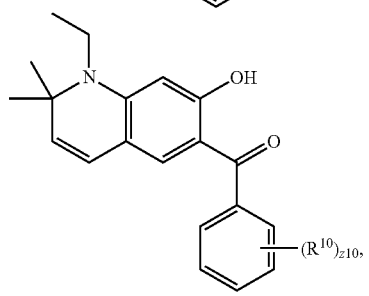

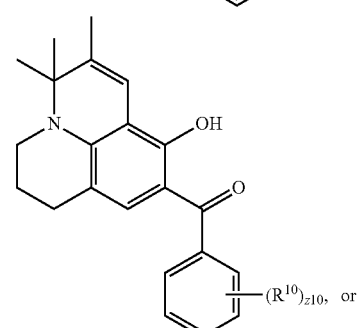

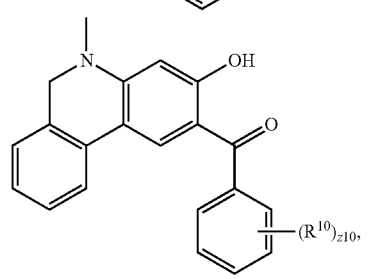

wherein

R$^{10}$ is independently hydrogen, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SF$_5$, —SO$_2$Cl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; and z10 is an integer from 0 to 5.

14. The method of claim 1, wherein compound B has the formula:

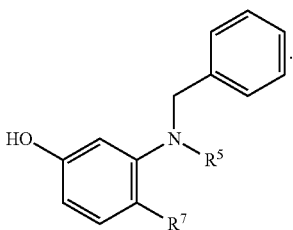

15. The method of claim 1, wherein compound B has the formula:

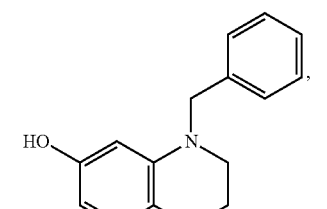

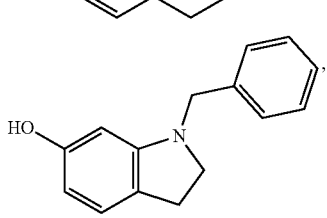

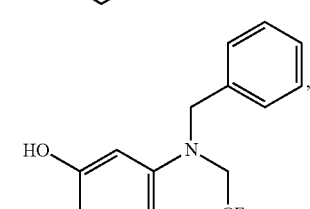

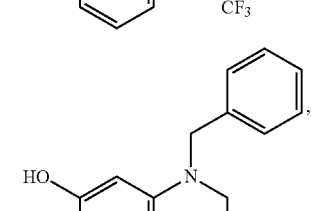

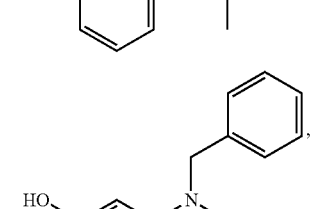

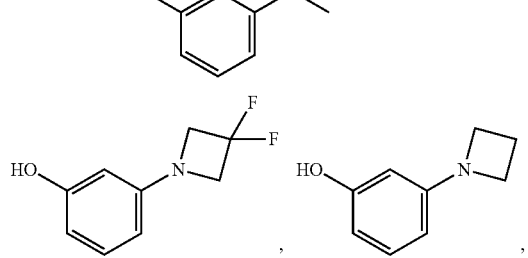

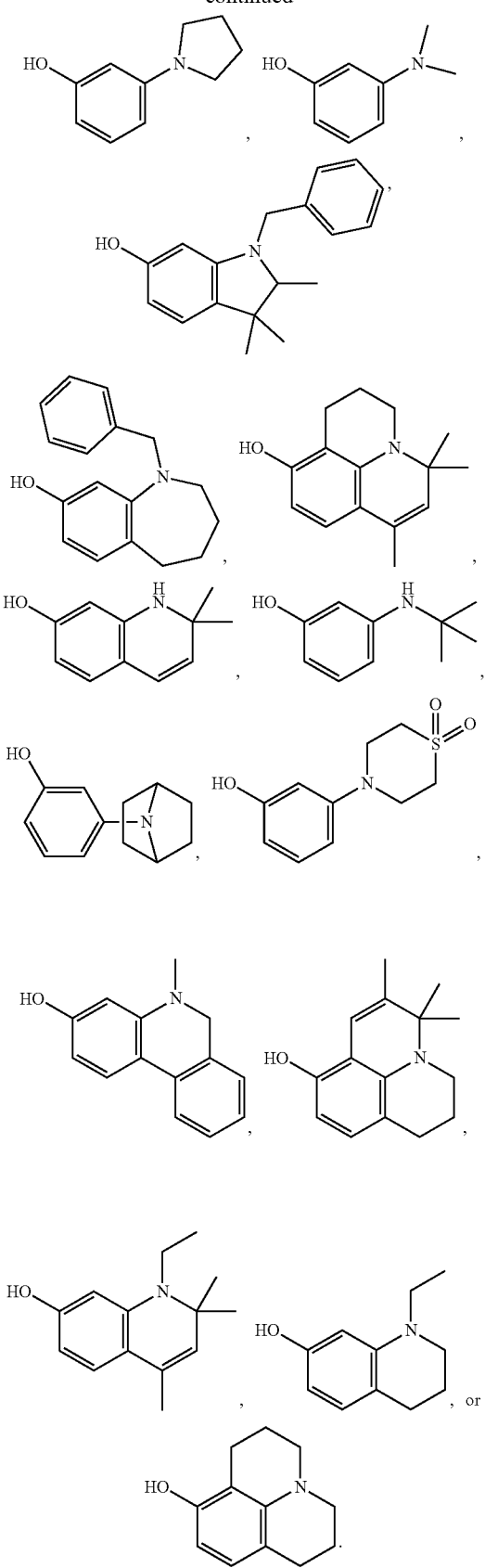
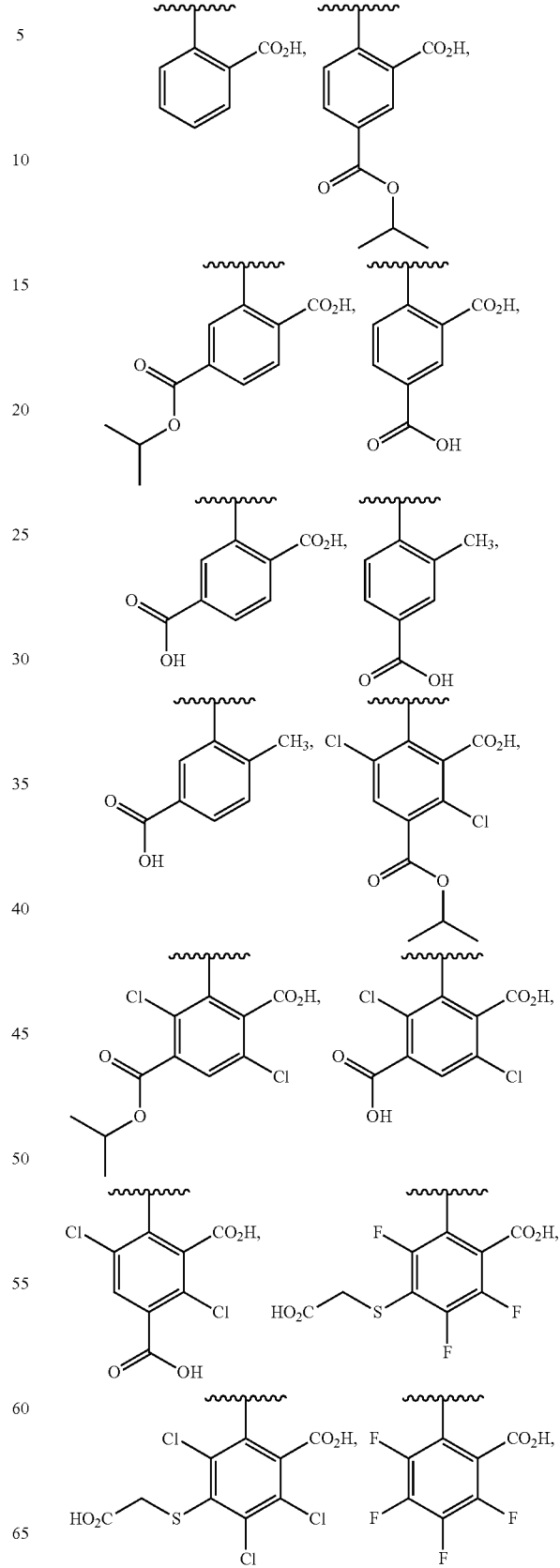
16. The method of claim 1, wherein $R^9$ is:

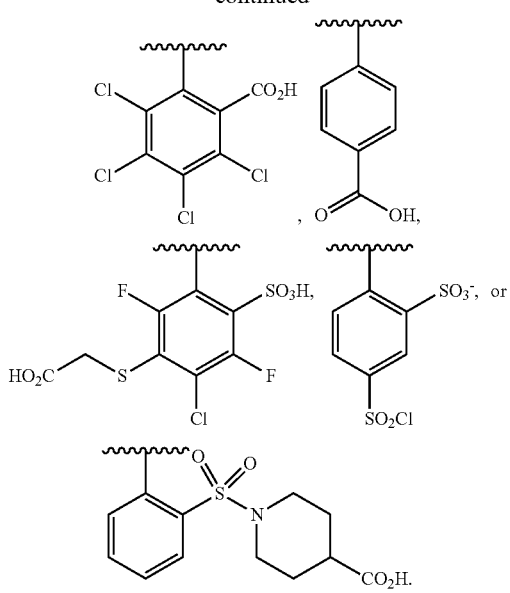
17. The method of claim 1, wherein the compound of formula I has the formula:
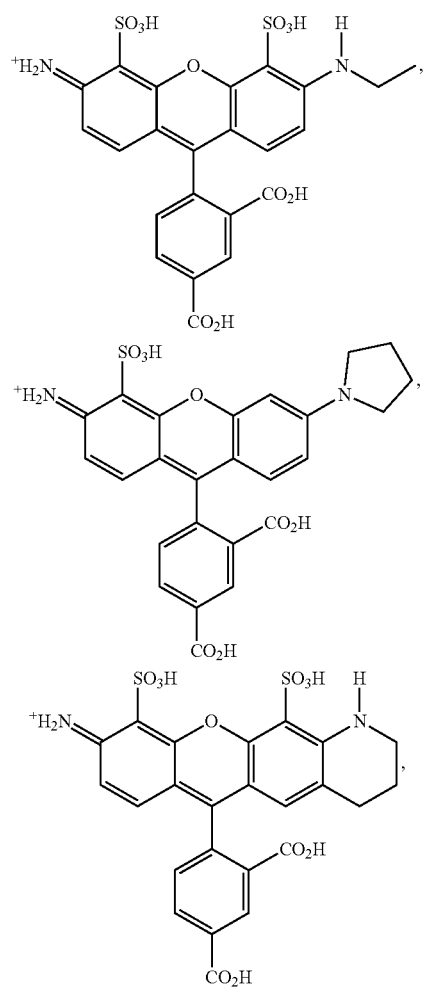
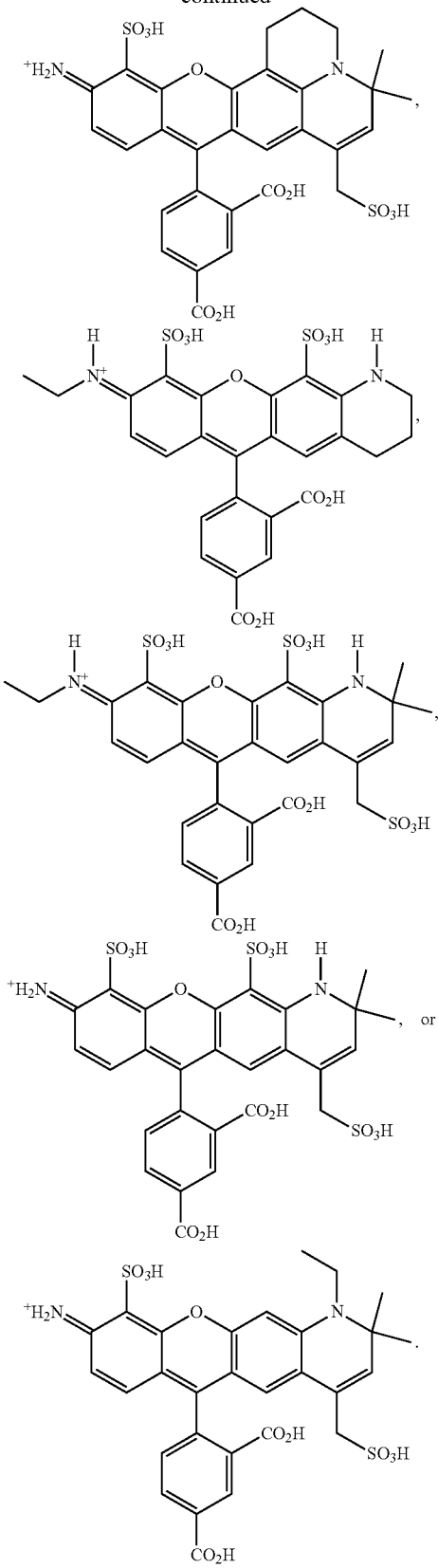
18. A compound made according to claim 1, having the formula:

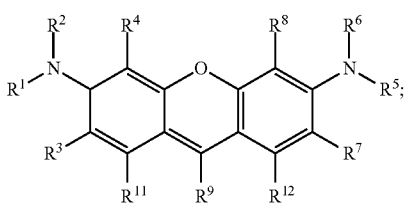

wherein
- $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- wherein $R^1$, $R^2$, $R^5$, or $R^6$ is hydrogen;
- $R^1$ and $R^2$ substituents bonded to the same nitrogen atom may optionally be joined to form a substituted or unsubstituted heterocycloalkyl, or substituted or unsubstituted heteroaryl;
- $R^5$ and $R^6$ substituents bonded to the same nitrogen atom may optionally be joined to form a substituted or unsubstituted heterocycloalkyl, or substituted or unsubstituted heteroaryl;
- $R^2$ and $R^4$ substituents may optionally be joined to form a substituted or unsubstituted heterocycloalkyl, or substituted or unsubstituted heteroaryl;
- $R^1$ and $R^3$ substituents may optionally be joined to form a substituted or unsubstituted heterocycloalkyl, or substituted or unsubstituted heteroaryl;
- $R^6$ and $R^8$ substituents may optionally be joined to form a substituted or unsubstituted heterocycloalkyl, or substituted or unsubstituted heteroaryl;
- $R^5$ and $R^7$ substituents may optionally be joined to form a substituted or unsubstituted heterocycloalkyl, or substituted or unsubstituted heteroaryl;
- $R^3$, $R^4$, $R^7$, $R^8$, $R^{11}$, and $R^{12}$ are independently hydrogen, $-PO_3H$, $-PO_4H$, $-SO_2NH_2$, $-SO_3H$, $-SO_4H$, substituted or unsubstituted alkyl, or substituted or unsubstituted heteroalkyl; wherein $R^3$, $R^4$, $R^7$, or $R^8$ is $-SO_3H$; and
- $R^9$ is substituted or unsubstituted aryl.

19. The compound of claim 18, having the formula:

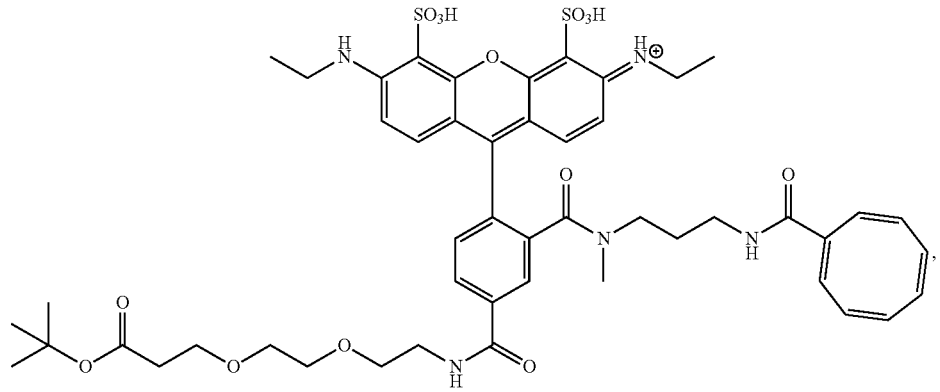

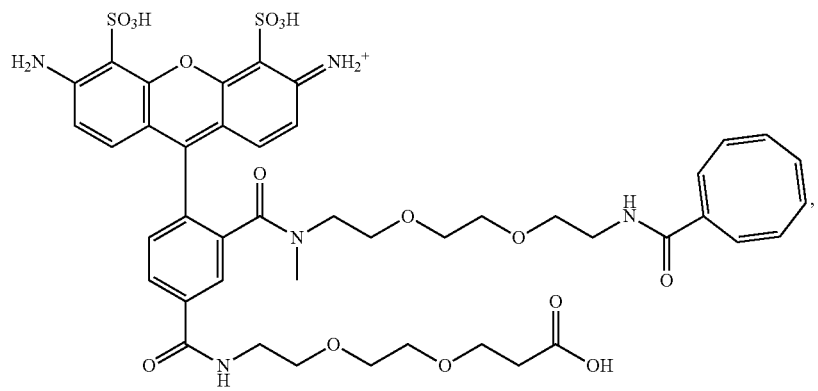

-continued

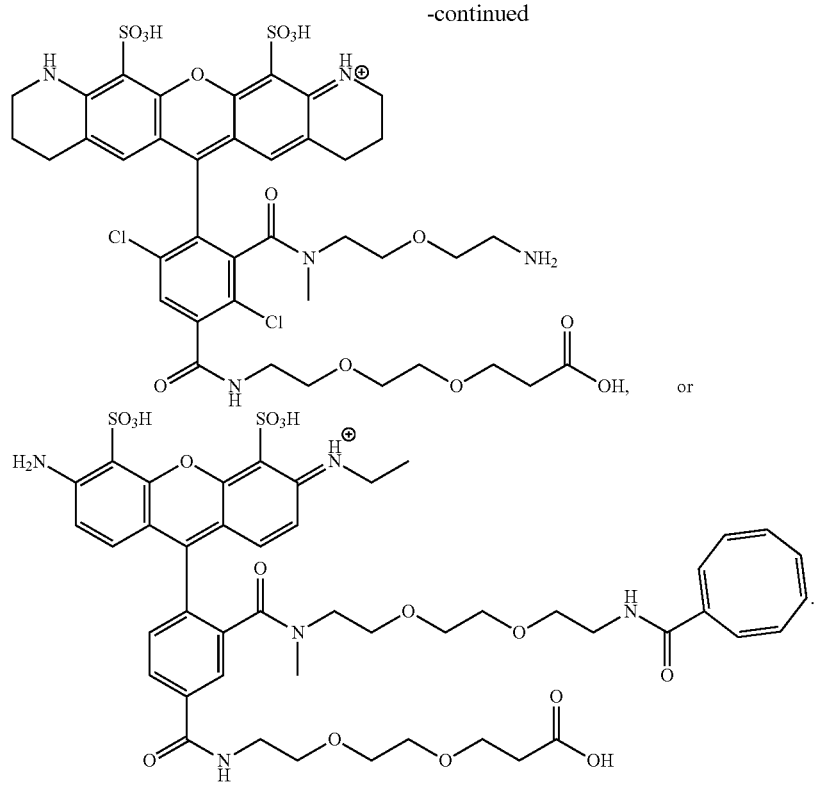

20. A nucleotide comprising a monovalent compound having the formula:

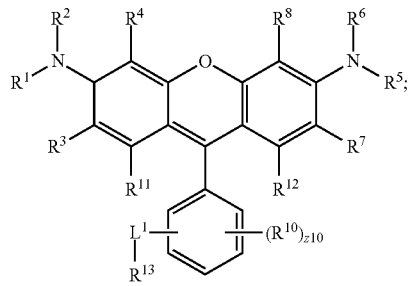

wherein
R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^2$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^5$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R$^6$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein R$^1$, R$^2$, R$^5$, or R$^6$ is hydrogen;
R$^1$ and R$^2$ substituents bonded to the same nitrogen atom may optionally be joined to form a substituted or unsubstituted heterocycloalkyl, or substituted or unsubstituted heteroaryl;
R$^5$ and R$^6$ substituents bonded to the same nitrogen atom may optionally be joined to form a substituted or unsubstituted heterocycloalkyl, or substituted or unsubstituted heteroaryl;
R$^2$ and R$^4$ substituents may optionally be joined to form a substituted or unsubstituted heterocycloalkyl, or substituted or unsubstituted heteroaryl;
R$^1$ and R$^3$ substituents may optionally be joined to form a substituted or unsubstituted heterocycloalkyl, or substituted or unsubstituted heteroaryl;
R$^6$ and R$^8$ substituents may optionally be joined to form a substituted or unsubstituted heterocycloalkyl, or substituted or unsubstituted heteroaryl;
R$^5$ and R$^7$ substituents may optionally be joined to form a substituted or unsubstituted heterocycloalkyl, or substituted or unsubstituted heteroaryl;
R$^3$, R$^4$, R$^7$, R$^8$, R$^{11}$, and R$^{12}$ are independently hydrogen, —PO$_3$H, —PO$_4$H, —SO$_2$NH$_2$, —SO$_3$H, —SO$_4$H, substituted or unsubstituted alkyl, or substituted or unsubstituted heteroalkyl; wherein R$^3$, R$^4$, R$^7$, or R$^8$ is —SO$_3$H;
R$^{10}$ is hydrogen, halogen, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$L^1$ is a covalent linker;
z10 is an integer from 1 to 4; and
$R^{13}$ is a monovalent nucleotide.

\* \* \* \* \*